(12) United States Patent
Dixit et al.

(10) Patent No.: US 9,499,605 B2
(45) Date of Patent: Nov. 22, 2016

(54) MULTIVALENT HETEROMULTIMER SCAFFOLD DESIGN AND CONSTRUCTS

(75) Inventors: Surjit Bhimarao Dixit, Richmond, CA (US); Igor Edmundo Paolo D'Angelo, Port Moody, CA (US); David Kai Yuen Poon, Richmond, CA (US)

(73) Assignee: Zymeworks Inc., Vancouver, British Columbia (CA)

( * ) Notice: Subject to any disclaimer, the term of this patent is extended or adjusted under 35 U.S.C. 154(b) by 0 days.

(21) Appl. No.: 13/411,353

(22) Filed: Mar. 2, 2012

(65) Prior Publication Data

US 2012/0244577 A1 Sep. 27, 2012

Related U.S. Application Data

(60) Provisional application No. 61/449,016, filed on Mar. 3, 2011.

(51) Int. Cl.
| | |
|---|---|
| *C07K 14/76* | (2006.01) |
| *C07K 14/79* | (2006.01) |
| *C07K 14/47* | (2006.01) |
| *C07K 14/485* | (2006.01) |
| *C07K 14/605* | (2006.01) |
| *C07K 14/765* | (2006.01) |
| *C07K 16/28* | (2006.01) |
| *C07K 16/32* | (2006.01) |
| *C07K 19/00* | (2006.01) |

(52) U.S. Cl.
CPC ........... *C07K 14/79* (2013.01); *C07K 14/4721* (2013.01); *C07K 14/485* (2013.01); *C07K 14/605* (2013.01); *C07K 14/76* (2013.01); *C07K 14/765* (2013.01); *C07K 16/283* (2013.01); *C07K 16/32* (2013.01); *C07K 19/00* (2013.01); C07K 2317/622 (2013.01); C07K 2319/00 (2013.01)

(58) Field of Classification Search
CPC ... C07K 14/76; C07K 19/00; C07K 2319/01
See application file for complete search history.

(56) References Cited

U.S. PATENT DOCUMENTS

| | | |
|---|---|---|
| 4,179,337 A | 12/1979 | Davis et al. |
| 4,857,467 A | 8/1989 | Sreekrishna et al. |
| 4,946,778 A | 8/1990 | Ladner et al. |
| 4,980,286 A | 12/1990 | Morgan et al. |
| 5,073,627 A | 12/1991 | Curtis et al. |
| 5,108,910 A | 4/1992 | Curtis et al. |
| 5,258,498 A | 11/1993 | Huston et al. |
| 5,482,858 A | 1/1996 | Huston et al. |
| 5,576,195 A | 11/1996 | Robinson et al. |
| 5,641,670 A | 6/1997 | Treco et al. |
| 5,731,168 A | 3/1998 | Carter et al. |
| 5,780,594 A | 7/1998 | Carter |
| 5,837,846 A | 11/1998 | Huston et al. |
| 5,846,818 A | 12/1998 | Robinson et al. |
| 5,856,456 A | 1/1999 | Whitlow et al. |
| 5,869,620 A | 2/1999 | Whitlow et al. |
| 5,990,275 A | 11/1999 | Whitlow et al. |
| 6,001,606 A | 12/1999 | Ruben et al. |
| 6,077,692 A | 6/2000 | Ruben et al. |
| 6,350,430 B1 | 2/2002 | Dooley et al. |
| 6,492,123 B1 | 12/2002 | Holliger et al. |
| 6,686,179 B2 | 2/2004 | Fleer |
| 6,905,688 B2 | 6/2005 | Rosen |
| 6,926,898 B2 | 8/2005 | Rosen |
| 6,946,134 B1 | 9/2005 | Rosen |
| 6,972,322 B2 | 12/2005 | Fleer |
| 6,987,006 B2 | 1/2006 | Fleer |
| 6,989,365 B2 | 1/2006 | Fleer |
| 6,994,857 B2 | 2/2006 | Rosen |
| 7,041,478 B2 | 5/2006 | Fleer |
| 7,056,701 B2 | 6/2006 | Fleer |
| 7,094,577 B2 | 8/2006 | Fleer |
| 7,138,497 B2 | 11/2006 | Houston et al. |
| 7,141,547 B2 | 11/2006 | Rosen |
| 7,189,690 B2 | 3/2007 | Rosen |
| 7,271,149 B2 | 9/2007 | Glaesner |
| 7,385,032 B2 | 6/2008 | Tschopp et al. |
| 7,410,779 B2 | 8/2008 | Fleer |
| 7,482,013 B2 | 1/2009 | Ballance |

(Continued)

FOREIGN PATENT DOCUMENTS

| | | |
|---|---|---|
| EP | 0201239 | 11/1986 |
| EP | 0251744 | 1/1988 |
| EP | 0258067 | 3/1988 |
| EP | 0322094 | 6/1989 |
| EP | 0394827 | 10/1990 |
| EP | 1088888 | 4/2001 |
| JP | 62-096086 | 5/1987 |
| JP | 07501698 | 2/1995 |
| JP | 2001523971 | 11/2001 |
| WO | WO 86/05807 | 10/1986 |

(Continued)

OTHER PUBLICATIONS

Dockal et al. 2000; Conformational transitions of the three recombinant domains of human serum albumin depending on pH. Journal of Biological Chemistry 275(5): 3042-3050.*

(Continued)

*Primary Examiner* — Karen Cochrane Carlson
(74) *Attorney, Agent, or Firm* — Kilpatrick Townsend & Stockton LLP

(57) ABSTRACT

Provided herein are multifunctional heteromer proteins. In specific embodiments is a heteromultimer that comprises: at least two monomeric proteins, wherein each monomeric protein comprises at least one cargo polypeptide, attached to a transporter polypeptide, such that said monomeric proteins associate to form the heteromultimer. These therapeutically novel molecules comprise monomers that function as scaffolds for the conjugation or fusion of therapeutic molecular entities resulting in the creation of bispecific or multivalent molecular species.

24 Claims, 54 Drawing Sheets

(56) References Cited

U.S. PATENT DOCUMENTS

| | | | |
|---|---|---|---|
| 7,507,413 | B2 | 3/2009 | Rosen |
| 7,507,414 | B2 | 3/2009 | Rosen |
| 7,521,424 | B2 | 4/2009 | Rosen |
| 7,592,010 | B2 | 9/2009 | Rosen |
| 7,708,996 | B2 | 5/2010 | Yu et al. |
| 7,785,599 | B2 | 8/2010 | Ballance et al. |
| 7,799,759 | B2 | 9/2010 | Rosen |
| 7,951,917 | B1 | 5/2011 | Arathoon et al. |
| 7,977,457 | B2 | 7/2011 | Reiter et al. |
| 8,501,185 | B2* | 8/2013 | Heitner Hansen et al. ............ 424/178.1 |
| 8,704,462 | B2 | 4/2014 | Shteynberg et al. |
| 2004/0071696 | A1 | 4/2004 | Adams et al. |
| 2005/0186664 | A1 | 8/2005 | Rosen et al. |
| 2007/0041987 | A1* | 2/2007 | Carter et al. ............ 424/185.1 |
| 2007/0196363 | A1 | 8/2007 | Arathoon et al. |
| 2008/0261877 | A1 | 10/2008 | Ballance |
| 2008/0267962 | A1 | 10/2008 | Ballance et al. |
| 2008/0269125 | A1 | 10/2008 | Ballance |
| 2008/0269126 | A1 | 10/2008 | Ballance |
| 2008/0269127 | A1 | 10/2008 | Ballance |
| 2009/0060721 | A1 | 3/2009 | Davis et al. |
| 2009/0105140 | A1 | 4/2009 | Rosen |
| 2009/0226466 | A1 | 9/2009 | Fong et al. |
| 2010/0093627 | A1 | 4/2010 | Rosen |
| 2010/0166749 | A1 | 7/2010 | Presta et al. |
| 2010/0189686 | A1 | 7/2010 | Rosen |
| 2010/0196265 | A1 | 8/2010 | Adams et al. |
| 2010/0261650 | A1 | 10/2010 | Ballance |
| 2011/0009312 | A1 | 1/2011 | Rosen |
| 2011/0059076 | A1 | 3/2011 | McDonagh et al. |
| 2011/0274691 | A1 | 11/2011 | Arvedson et al. |
| 2011/0287009 | A1 | 11/2011 | Scheer et al. |
| 2012/0149876 | A1 | 6/2012 | Von Kreudenstein et al. |
| 2012/0244577 | A1 | 9/2012 | Dixit et al. |
| 2012/0270801 | A1 | 10/2012 | Frejd et al. |
| 2013/0195849 | A1 | 8/2013 | Spreter Von Kreudenstein et al. |
| 2014/0066378 | A1 | 3/2014 | Dixit et al. |
| 2014/0154253 | A1 | 6/2014 | Ng et al. |
| 2014/0200331 | A1 | 7/2014 | Corper et al. |
| 2016/0207979 | A1 | 7/2016 | Dixit et al. |

FOREIGN PATENT DOCUMENTS

| | | |
|---|---|---|
| WO | WO 87/04462 | 7/1987 |
| WO | WO 89/10036 | 10/1989 |
| WO | WO 89/10404 | 11/1989 |
| WO | WO 90/01063 | 2/1990 |
| WO | WO 91/06657 | 5/1991 |
| WO | WO 93/11162 | 6/1993 |
| WO | WO 94/12650 | 6/1994 |
| WO | WO 95/23857 | 9/1995 |
| WO | WO 96/29411 | 9/1996 |
| WO | WO 96/34891 | 11/1996 |
| WO | WO 97/04658 | 2/1997 |
| WO | WO 97/24445 | 7/1997 |
| WO | WO 00/45835 | 8/2000 |
| WO | WO 01/07608 | 2/2001 |
| WO | WO 01/11046 | 2/2001 |
| WO | WO 01/21658 | 3/2001 |
| WO | 0149866 | 7/2001 |
| WO | WO 03/012069 | 2/2003 |
| WO | 03031464 A2 | 4/2003 |
| WO | WO 03/060071 | 7/2003 |
| WO | 2004029207 A2 | 4/2004 |
| WO | 2004082640 | 9/2004 |
| WO | 2006106905 A1 | 10/2006 |
| WO | 2008131242 A1 | 10/2008 |
| WO | 2009012784 | 1/2009 |
| WO | 2009089004 A1 | 7/2009 |
| WO | 2010027903 | 3/2010 |
| WO | WO 2010/092135 | 8/2010 |
| WO | 2010118169 A2 | 10/2010 |
| WO | 2011047180 | 4/2011 |
| WO | WO 2011/051489 | 5/2011 |
| WO | 2011069090 | 6/2011 |
| WO | 2011028952 A1 | 10/2011 |
| WO | 2011120134 A1 | 10/2011 |
| WO | 2011120135 A1 | 10/2011 |
| WO | 2011143545 A1 | 11/2011 |
| WO | 2011147982 A2 | 12/2011 |
| WO | 2012006635 A1 | 1/2012 |
| WO | 2012058768 A1 | 5/2012 |
| WO | 2012116453 A1 | 9/2012 |
| WO | 2013063702 A1 | 5/2013 |
| WO | 2013166594 A1 | 11/2013 |
| WO | 2013166604 A1 | 11/2013 |
| WO | 2014004586 A1 | 1/2014 |
| WO | 2014012082 A2 | 1/2014 |
| WO | 2014012085 A2 | 1/2014 |
| WO | 2014018572 A2 | 1/2014 |
| WO | 2014082179 A1 | 6/2014 |
| WO | 2014182970 A1 | 11/2014 |
| WO | 2015006749 A2 | 1/2015 |

OTHER PUBLICATIONS

Dockal et al. 2000. Five recombinant fragments of human serum albumin—tools for the characterization of the warfarin binding site. Protein Science. 9: 1455-1465.*

U.S. Appl. No. 13/941,450, "Corrected Notice of Allowability", mailed Jul. 10, 2015, 12 pages.

U.S. Appl. No. 13/941,450, "Corrected Notice of Allowability", mailed Aug. 7, 2015, 7pages.

U.S. Appl. No. 13/941,450, "Corrected Notice of Allowability", mailed Oct. 9, 2015, 12 pages.

U.S. Appl. No. 13/941,450, "Final Office Action", mated Sep. 25, 2014, 15 pages.

U.S. Appl. No. 13/941,450, "Non-Final Office Action", mailed Mar. 6, 2014, 26 pages.

U.S. Appl. No. 13/941,450, "Notice of Allowance", mailed Jun. 23, 2015, 12 pages.

Creighton, Thomas E., *Proteins: Structures and Molecular Properties*, Second ed., W. H. Freeman, New York (1993).

EP12751893.4, "Extended European Search Report", mailed Jan. 19, 2015, 9 pages.

PCT/US2013/050408, "International Search Report and Written Opinion", mailed Feb. 6, 2014.

Atwell, et al., "Stable heterodimers from remodeling the domain interface of a homodimer using a phage display library", J Mol Biol. Jul. 4, 1997;270(1):26-35.

Bohua, et al., "Bispecific antibody to ErbB2 Overcomes Trastuzumab Resistance through Comprehensive Blockade of ErbB2 Heterodimerization", *Cancer Research*. Sep. 17, 2013, V.73 (21), p. 6471-83.

Chames et al., "Therapeutic antibodies: successes, limitations and hopes for the future", British Journal of Pharmacology, vol. 157, No. 2, 2009, pp. 220-223.

Cochlovius et al., "Treatment of human B cell lymphoma xenografts with a CD3 x CD19 diabody and T cells", Journal of Immunology, vol. 165, No. 2, 2000, pp. 888-895.

Davis et al., "SEEDbodies: fusion proteins based on strand-exchange engineered domain (SEED) CH3 heterodimers in an Fc analogue platform for asymmetric binders or immunofusions and bispecific antibodies", Protein Engineering, Design and Selection, vol. 23, No. 4, Feb. 4, 2010, pp. 195-202.

Gunasekaran, et al. Enhancing antibody Fc heterodimer formation through electrostatic steering effects: applications to bispecific molecules and monovalent IgG. J Biol Chem. Jun. 18, 2010;285(25): 19637-46. doi: 10.1074/jbc.M110.117382. Epub Apr. 16, 2010.

Hardy et al., "Valency of Antibody Binding to Enveloped Virus Particles as Determined by Surface Plasmon Resonance", J Viral., vol. 77, No. 2, 2003, pp. 1649-1652.

(56) References Cited

OTHER PUBLICATIONS

Igawa et al., "VH/VL interface engineering to promote selective expression and inhibit conformational isomerization of thrombopoietin receptor against single-chain diabody", Protein Engineering, Design and Selection, vol. 23, No. 8, Aug. 2010, pp. 667-677.
Kang, et al., Engineering multivalent antibodies to target heregulin-induced HER3 signaling in breast cancer cells, MAbs, vol. 6, pp. 340-353, 2013.
Klein et al., "Progress in overcoming the chain association issue in bispecific heterodimeric IgG antibodies", MABS, vol. 4, No. 6, Nov./Dec. 2012, pp. 653-663.
Lewis et al., "Generation of bispecific IgG antibodies by structura-based design of an orthogonal Fab interface", Nature Biotechnology, Jan. 26, 2014.
Lu et al., "Fab-scFv fusion protein: an efficient approach to production of bispecific antibody fragments", Journal of Immunological Methods, vol. 267, No. 2, 2002, pp. 213-226.
McDonagh, et al., "Antitumor activity of a novel bispecific antibody that targets the ErbB2/ErbB3 oncogenic unit and inhibits heregulin-induced activation of ErbB3 ", Mol. Cancer Ther., vol. 11, No. 3, Jan. 2012, pp. 582-593.
Merchant, et al. An efficient route to human bispecific IgG. Nature Biotechnology. 1998; 16(7):677-81.
Moore et al., "A novel bispecific antibody format enables simultaneous bivalent and monovalent co-engagement of distinct target antigens", MAbs, vol. 3, No. 6, 2011, pp. 546-557.
PCT/CA2011/000321, "International Search Report and Written Opinion", Jul. 15, 2011, 15 pages.
PCT/CA2011/000322, "International Search Report and Written Opinion", Jun. 27, 2011, 15 pages.
PCT/CA2011/001238, "International Search Report and Written Opinion", Jan. 26, 2012, 16 pages.
PCT/CA2012/050780, "International Search Report and Written Opinion", Feb. 14, 2013, 17 pages.
PCT/CA2013/000471, "International Search Report and Written Opinion", Aug. 15, 2013, 12 pages.
PCT/CA2013/050358, "International Search Report and Written Opinion", Jul. 30, 2013, 19 pages.
PCT/US2013/047725, "International Search Report and Written Opinion", Nov. 22, 2013, 15 pages.
PCT/US2013/50411, "International Search Report and Written Opinion", Jan. 29, 2014, 19 pages.
PCT/CA2013/050914, "International Search Report and Written Opinion", Feb. 7, 2014, 11 pages.
PCT/CA2014/051140, "International Search Report and Written Opinion", Feb. 18, 2015, 17 pages.
PCT/US2014/037401, "International Search Report and Written Opinion", Oct. 7, 2014, 14 pages.
PCT/US2014/46436, "International Search Report and Written Opinion", Jan. 2, 2015, 15 pages.
PCT/US2014/65546, "Invitation to Pay Additional Fees," Feb. 4, 2015, 2 pages.
PCT/US2014/065571, "International Search Report and Written Opinion", Feb. 19, 2015, 13 pages.
Ridgway et al., "Knobs-into-holes' engineering of antibody CH3 domains for heavy chain heterodimerization", Protein Engineering, vol. 9, No. 7, Jul. 1996, pp. 617-621.
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, 1415-1425.
Shields et al., "High resolution mapping of the binding site on human IgG1 for Fc gamma RI, Fc gamma RII, Fc gamma RIII, and FcRn and design of IgG1 variants with improved binding to the Fc gamma R", Journal of Biological Chemistry, vol. 276, No. 9, Mar. 2, 2001, pp. 6591-6604.
Stanglmaier et al., "Bi20 (FBTA05), A Novel Trifunctional Bispecific Antibody (anti-CD20 3 anti-CD3), Mediates Efficient Killing of B-cell Lymphoma Cells Even With Very Low CD20 Expression Levels", International Journal of Cancer, vol. 123, 2008, pp. 1181-1189.
Troise et al., "Differential binding of human immunoagents and Herceptin to the ErbB2 receptor", FEBS Journal, vol. 275, No. 20, 2008, pp. 4967-4979.
Zhu et al., "Remodeling domain interfaces to enhance heterodimer formation", Protein Science, vol. 6, No. 4, Apr. 1997, pp. 781-788.
PCT/CA2012/050131 International Preliminary Report on Patentability dated Sep. 3, 2013.
U.S. Appl. No. 13/941,450 Final Office action mailed Sep. 25, 2014.
Ahmed, et al. CancerResource: a comprehensive database of cancer-relevant proteins and compound interactions supported by experimental knowledge. Nucleic Acids Res. Jan. 2011;39(Database issue):D960-7.
Altschul, et al. Basic local alignment search tool. J Mol Biol. 1990: 215(3):403-10.
Altschul, et al. Gapped Blast and PSI-BLAST: a new generation of protein database search programs. Nucleic Acids Res. Sep. 1, 1997;25(17):3389-402.
Anzenbacherova, et al., Determination of enzyme (angiotensin convertase) inhibitors based on enzymatic reaction followed by HPLCJ.Pharma Biomed Anal Mar. 2001; 24(5-6): 1151-6.
Bahadhur, et al. The interface of protein-protein complexes: analysis of contacts and prediction of interactions. Cell Mol Life Sci. Apr. 2008;65(7-8):1059-72.
Baker, et al. Insulin-Like Growth Factor I Increases Follicle-Stimulating Hormone (FSH) Content and Gonadotropin-Releasing Hormone-Stimulated FSH Release from Coho Salmon Pituitary Cells In Vitro. Biol Reprod Sep. 2000; 63(3): 865-71.
Batterham, et al. Gut hormone PYY3-36 physiologically inhibits food intake. Nature 2002; 418: 650-654.
Batzer, et al. Enhanced evolutionary PCR using oligonucleotides with inosine at the 3'-terminus. Nucleic Acids Res. Sep. 25, 1991;19(18):5081.
Bebbington et al., High-Level Expression of a Recombinant antibody from Myeloma Cells Using a Glutamine Synthetase Gene as an Amplifiable Selectable Marker. Bio/technology 10:169 (1992).
Biblia and Robinson, In Pursuit of the Optimal Fed-Batch Process for Monoclonal Antibody Production. Biotechnol. Prog. 11:1-13 (1995).
Bigbee, et al. "Bioassayable growth hormone release in rats in response to a single bout of treadmill exercise." Appl Physiol Dec. 2000; 89(6): 2174-8.
Bouchon et al. Cutting Edge: Inflammatory Responses Can Be Triggered by TREM-1, a Novel Receptor Expressed on Neutrophils and Monocytes J Immunol May 15, 2000; 164(10): 4991-5.
Bristow. International Standards for Growth Hormone. Horm Res 1999; 51 Suppl 1: 7-12.
Buchwald, et al. Long-term, continuous intravenous heparin administration by an implantable infusion pump in ambulatory patients with recurrent venous thrombosis. Surgery. Oct. 1980;88(4):507-16.
Cao et al. Further LDL Cholesterol Lowering Through Targeting PCSK9 for Coronary Artery Disease. Endocrine, Metabolic & Immune Disorders—Drug Targets 2008, 8, 238-243.
Carter, et al. Structure of serum albumin. Adv Protein Chem. 1994; 45:153-203.
Chaudhary, et al. The major histocompatibility complex-related Fc receptor for IgG (FcRn) binds albumin and prolongs its lifespan. J Exp Med. Feb. 3, 2003;197(3):315-22.
Dennis, et al. Albumin Binding as a General Strategy for Improving the Pharmacokinetics of Proteins. (2002) J Biol Chem 277, 35035-35043.
Dockal, et al. The three recombinant domains of human serum albumin. Structural characterization and ligand binding properties. J Biol Chem. Oct. 1999 ;274(41):29303-10.
During, et al. Controlled release of dopamine from a polymeric brain implant: in vivo characterization. Ann Neurol. Apr. 1989;25(4):351-6.

(56) References Cited

OTHER PUBLICATIONS

Eichels, et al. Angiotensin converting enzyme inhibitors block mitogenic signalling pathways in rat cardiac fibroblasts. Naunyn-Schmiedeberg's Arch Pharmacol (1999) 359 :394-399.
Epsevik, et al. A highly sensitive cell line, WEHI 164 clone 13, for measuring cytotoxic factor/tumor necrosis factor from human monocytes. Journal of Immunological Methods, 95 (1986) 99-105.
Forrer, et al. Enzyme-Linked Immunosorbent Assay for Measurement of JNK, ERK, and p38 Kinase Activities. Biol. Chem. 379(8-9): (1998) 1101- 1110.
Gao, et al (1999) Sensitivity of an Epstein-Barr virus- positive tumor line, Daudi, to alpha interferon correlates with expression of a GC-rich viral transcript. Mol Cell Biol. 19(11): 7305-13.
Gaylinn, et al. (1993) Molecular Cloning and Expression of a Human Anterior Pituitary Receptor for Growth Hormone-Releasing Hormone. Molecular Endocrinology, vol. 7, 77-84.
Gegg, et al. Probing minimal independent folding units in dihydrofolate reductase by molecular dissection. Protein Science (1997). 6: 1885-1892.
Gillis, et al. (1978) T CELL Growth Factor: Parameters of Production and a Quantitative Microassay for Activity. J. Immunol. 120, 2027.
Gleeson et al. Transformation of the Methylotrophic Yeast *Hansenula polymorpha*. (1986) J. Gen. Microbiol. 132, 3459-3465.
Goodson, in Medical Applications of Controlled Release, Chapter 6: Dental Application. supra, vol. 2, pp. 115-138 (1984).
Gray, et al. Characterization, primary structure, and evolution of lamprey plasma albumin. Protein Sci. Feb. 1992;1(2):289-302.
Hall, et al. The crystal and molecular structures of diferric porcine and rabbit serum transferrins at resolutions of 2.15 and 2.60 A, respectively. Acta Crystallogr D 2002, 58, 70-80.
Heaney-Kieras, et al. Limited Pepsin Digestion of Human Plasma Albumin. (1977) J Biol Chem 252, 4326-4329.
Henikoff, et al. Amino acid substitution matrices from protein blocks. Proc Natl Acad Sci U S A. Nov. 15, 1992;89(22):10915-9.
Hoffman, et al. Isolation and characterization of mutants constitutive for expression of the fbpl gene of Schizosaccharomyces pombe. Genetics. Apr. 1990;124(4):807-16.
Howard, et al. Intracerebral drug delivery in rats with lesion-induced memory deficits. J Neurosurg. Jul. 1989;71(1):105-12.
Hunkapiller, et al. A microchemical facility for the analysis and synthesis of genes and proteins. Nature. Jul. 12-18, 1984;310(5973):105-11.
Ikeda, et al. A novel bioassay based on human growth hormone (hGH) receptor mediated cell proliferation: measurement of 20K-hGH and its modified forms. Growth Hormone & IGF Research 2000, 10, 248-255.
Ishikawa, et al. A Novel Specific Bioassay for Serum Human Growth Hormone.J Clin Endocrinol Metab Nov. 2000; 85(11): 4274-9.
Johnson, B., Ed. Post-Translational Covalent Modification of Proteins. Academic Press, New York, pp. 1-12 (1983).
Joliot, et al. Antennapedia homeobox peptide regulates neural morphogenesis. Proc Natl Acad Sci U S A. Mar. 1, 1991;88(5):1864-8.
Karlin, et al. Applications and statistics for multiple high-scoring segments in molecular sequences. Proc Natl Acad Sci U S A. Jun. 15, 1993;90(12):5873-87.
Kipriyanov, et al. Recent advances in the generation of bispecific antibodies for tumor immunotherapy. Curr Opin Drug Discov Devel. Mar. 2004;7(2):233-42.
Kitamura et al. Establishment and Characterization of a Unique Human Cell Line That Proliferates Dependently on CM-CSF, IL-3, or Erythropoietin. 1989 J.Cell. Physiol. 140: 323.
Koller, et al. Inactivating the beta 2-microglobulin locus in mouse embryonic stem cells by homologous recombination. Proc Natl Acad Sci U S A. Nov. 1989;86(22):8932-5.
Kragh-Hansen, et al. Effect of genetic variation on the thermal stability of human serum albumin. Biochim Biophys Acta. Feb. 14, 2005;1747(1):81-8.
Kratz. Albumin as a drug carrier: design of prodrugs, drug conjugates and nanoparticles. J Control Release. Dec. 18, 2008;132(3):171-83.
Ku, et al. Control of homeostasis of CD8+ memory T cells by opposing cytokines. Science 288: 675-678, 2000.
Kwon et al., TR1, a new member of the tumor necrosis factor receptor superfamily, induces fibroblast proliferation and inhibits osteoclastogenesis and bone resorption. FASEB J. 12: 845-854 (1998).
Langer. New methods of drug delivery. Science, New Series, vol. 249, No. 4976 (Sep. 28, 1990), pp. 1527-1533.
Levy, et al. Of Inhibition calcification of bioprosthetic heart valves by local controlled-release diphosphonate. Science, New Series, vol. 228, No. 4696 (Apr. 12, 1985), pp. 190-192.
Ma, et al. Enzyme dynamics point to stepwise conformational selection in catalysis. Current Opinion in Chemical Biology 2010, 14:652-659.
Maundrell. Nmtl of fission yeast. A highly transcribed gene completely repressed by thiamine. J Biol Chem. Jul. 5, 1990;265(19):10857-64.
Mayo, Molecular Cloning and Expression of a Pituitary-Specific Receptor for Growth Hormone-Releasing Hormone. Mol Endocrinol Oct. 1992; 6(10): 1734-44.
Minchiotti, et al. Mutations and polymorphisms of the gene of the major human blood protein, serum albumin. Hum Mutat. Aug. 2008;29(8):1007-16.
Miraglia, et al. Homogeneous Cell- and Bead-Based Assays for High Throughput Screening Using Fluorometric Microvolume Assay Technology.1999, J. of Biomol. Screen. 4: 193-204.
Miyawaki et al., Inhibition of gastric inhibitory polypeptide signaling prevents obesity. Nat. Medicine, 2002, vol. 8(7): 738-742.
Moore et al., BLyS: Member of the Tumor Necrosis Factor Family and B Lymphocyte Stimulator. Science, New Series, vol. 285, No. 5425 (Jul. 9, 1999), pp. 260-263.
Muller, et al. Bispecific Antibodies for Cancer Immunotherapy. (2010) Biodrugs 24, 89-98.
Murai, et al. Altered Regulation of Cell Cycle Machinery involved in Interleukin-1-induced G1 and G2 Phase Growth Arrest of A375S2 Human Melonoma Cells. J. Biol. Chem. 276: 6797-6806, 2001.
Nardelli, et al. Dendritic cells and MPIF-1: chemotactic activity and inhibition of endogenous chemokine production by IFN-y and CD40 ligation. J. Leukoc. Biol. 65: 822-828 (1999).
Needleman, et al. A general method applicable to the search for similarities in the amino acid sequence of two proteins. J Mol Biol. Mar. 1970;48(3):443-53.
Neumann, et al. Native albumin for targeted drug delivery. Expert Opin Drug Deliv. Aug. 2010; 7(8):915-25.
Osborn, et al."Pharmacokinetic and Pharmacodynamics Studies of a Human Serum Albumin-Interferon-A Fusion Protein in Cynomolgus Monkeys." J Pharamcology and Experiemental Therapeutics 330: 540-548 (2002).
Ohtsuka, et al. An alternative approach to deoxyoligonucleotides as hybridization probes by insertion of deoxyinosine at ambiguous codon positions. J Biol Chem. Mar. 10, 1985; 260(5):2605-8.
PCT/CA2012/050131 International Search Report dated May 23, 2012.
PCT/US2013/050408 International Search Report and Written Opinion dated Feb. 6, 2014.
Pearson, et al. Improved tools for biological sequence comparison. Proc Natl Acad Sci U S A. Apr. 1988;85(8):2444-8.
Phizicky et al., Protein-protein interactions: Methods for Detection and Analysis. Microbiol. Rev. 1995, 59(1):94.
Pontoglio et al., "Defective Insulin Secretion in Hepatocyte Nuclear Factor 1 α-deficient Mice." J Clin Invest May 15, 1998; 101(10): 2215-22.
Poznansky. Enzyme-Albumin Polymers New Approaches to the Use of Enzymes in Medicine. (1984) Appl Biochem Biotechnol 10, 41-56.
Rattan, et al. Protein synthesis, posttranslational modifications, and aging. Ann N Y Acad Sci. Nov. 21, 1992;663: 48-62.
Roopenian, et al. FcRn: the neonatal Fc receptor comes of age. Nat Rev Immunol. Sep. 2007; 7(9):715-25.

(56) References Cited

OTHER PUBLICATIONS

Rosenberg, et al. Biological activity of recombinant human interleukin-2 produced in *Escherichia coli*. Science, New Series, vol. 223, No. 4643 (Mar. 30, 1984), pp. 1412-1415.
Rossolini, et al. Use of deoxyinosine-containing primers vs degenerate primers for polymerase chain reaction based on ambiguous sequence information. Mol Cell Probes. Apr. 1994; 8(2):91-8.
Rubinstein, et al. Convenient assay for Interferons. (1981) Convenient assay for interferons. J. Virol. 37(2): 755-8.
Sarav, et al. Renal FcRn reclaims albumin but facilitates elimination of IgG. J Am Soc Nephrol. Sep. 2009; 20(9):1941-52.
Saudek, et al. A preliminary trial of the programmable implantable medication system for insulin delivery. N Engl J Med. Aug. 31, 1989; 21(9):574-9.
Schecroun, et al. Biological Properties of Salmon Calcitonin IVJ Bone Miner Res Aug. 1999; 14(8): 1425-31.
Seifter, et al. Analysis for protein modifications and nonprotein cofactors. Methods Enzymol. 1990;182:626-46.
Shekhawat, et al. Split-protein systems: beyond binary protein-protein interactions. Curr Opin Chem Biol. Dec. 2011;15(6):789-97.
Smith. Comparison of Biosequences. Advances in Applied Mathematics 2, 482-489 (198 1).
Stains, et al. A general approach for receptor and antibody-targeted detection of native proteins utilizing split-luciferase reassembly. ACS Chem Biol. Oct. 15, 2010;5(10):943-52.
Sung, et al. High-Yield Expression of Fully Bioactive N-Terminal Parathyroid Hormone Analog in *Escherichia coli*. IUBMB Life Feb. 2000; 49(2): 131-5.
Sutherland, et al. Inactivation of glycogen synthase kinase-3fl by phosphorylation: new kinase connections in insulin and growth-factor signalling. Biochem J. Nov. 15, 1993; 296 (Pt 1): 15-19.
Syed, et al. Potent Antithrombin Activity and Delayed Clearance From the Circulation Characterize Recombinant Hirudin Genetically Fused to Albumin. Blood 1997 89: 3243-3252.
Tafelmeyer, et al. Transforming a ($\beta$/$\alpha$)8—barrel enzyme into a split-protein sensor through directed evolution. Chem Biol. May 2004; 11(5):681-9.
Testa, et al., "Assays for hematopoietic growth factors." Balkwill FR (ed) Cytokines, A Practical Approach, pp. 229-244; IRL Press Oxford 1991.
Tijssen, Laboratory Techniques in Biochemistry and Molecular Biology—Hybridization with Nucleic Probes, "Chapter 2: Overview of principles of hybridization and the strategy of nucleic acid assays" (1993), 19-78.
Traunecker, et al. Soluble CD4 molecules neutralize human immunodeficiency virus type 1. Nature. Jan. 7, 1988;331(6151):84-6.
U.S. Appl. No. 13/941,450 Office action mailed Mar. 6, 2014.
Urso, et al. Differences in Signaling Properties of the Cytoplasmic Domains of the Insulin Receptor and Insulin-like Growth Factor Receptor in 3T3-L1 Adopcytes. J. Biol. Chem. 1999, 274:30864-30873.
Varnerin, et al. Production of Leptin in *Escherichia coli*: A Comparison of Methods. Protein Expr Purif Dec. 1998; 14(3): 335-42.
Verhaselt, et al. Bacterial Lipopolysaccharide Stimulates the Production of Cytokines and the Expression of Costimulatory Molecules by Human Peripheral Blood Dendritic Cells. J. Immunol. 158: 2919-2925 (1997).
Waldmann, et al. In Albumin Structure, Function and Uses. Albumin Catabolism. 1977, p. 255-273.
Walz et al., ILA Murine Interleukin-4-Ig Fusion Protein Regulates the Expression of Th1- and Th2-Specific Cytokines in the Pancreas of NOD Mice. Horm Metab Res Oct. 2002; 34(10): 561-9.
Weiner, et al. Human neutrophil interactions of a bispecific monoclonal antibody targeting tumor and human Fc$^\gamma$RIII. Cancer Immunol Immunother (1996) 42: 141-150.
Weinstein et al. Truncation of the c-myb gene by a retroviral integration in an interleukin 3-dependent myeloid leukemia cell line. Proc Natl Acad Sci USA 1986; 83, 5010-4.
Wishart, et al. DrugBank: a knowledgebase for drugs, drug actions and drug targets. Nucleic Acids Res. Jan. 2008;36, W496-W502.
Wu, et al. Receptor-mediated in vitro gene transformation by a soluble DNA carrier system. J Biol Chem. Apr. 5, 1987; 262(10):4429-32.
Wurster, et al. Interleukin 21 is a T Helper (Th) Cell 2 Cytokine that Specifically Inhibits the Differentiation of Naive Th Cells into Interferon $^\gamma$-producing Th1 Cells. J Exp Med Oct. 7, 2002; 196(7): 969-77.
Yeh, et al. Design of yeast-secreted albumin derivatives for human therapy: biological and antiviral properties of a serum albumin-CD4 genetic conjugate. Proc Natl Acad Sci U S A. Mar. 1, 1992; 89(5):1904-8.
Zhou et al. Osteoclast Inhibitory Lectin, a Family of New Osteoclast Inhibitors. J Biol Chem Dec. 13, 2002; 277(50): 48808-15.
Zhu et al. Update of TTD: Therapeutic Target Database Nucleic Acids Res. 2009, 38(1), D787-D791.
Zijlstra, et al. Germ-line transmission of a disrupted $\beta$2-microglobulin gene produced by homologous recombination in embryonic stem cells. Nature. Nov. 23, 1989;342(6248):435-8.
U.S. Appl. No. 15/001,078, Restriction Requirement, Jun. 21, 2016, 13 pages.

\* cited by examiner

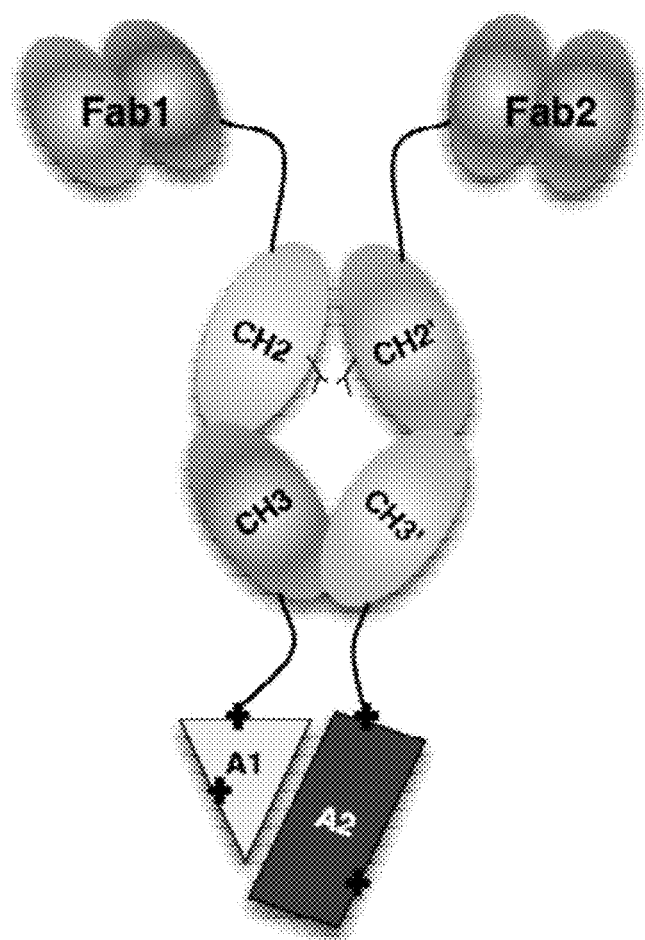

ABH2

Wildtype Albumin

Annexin based Transporter Polypeptide 1: residues 41-186 (gray)
Annexin based Transporter Polypeptide 2: residues 194-344 (black)

FIG. 15 v438: NM32 scFv

TCAAGCGAGCTGACCCAGGACCCCGCCGTGAGCGTCGCACTGGGGCAGACCGTGCCC
ATCACATGCCAGGGAGATAGCCTGCGATCCTACTATGCATCTTGGTACCAGCAGAAG
CCAGGACAGGCACCTGTGCTGGTCATCTATGGGAAAAACAATAGACCATCAGGCATC
CCCGACAGGTTCAGCGGAAGCTCCTCTGGCAACACAGCTTCTCTGACCATTACAGGC
GCACAGGCCGAGGACGAAGCAGATTACTATTGCAACAGTCGGGATAGTTCAGGGAAT
CACGTGGTCTTTGGAGGAGGAACTAAGCTGACCGTGGGAGGAGGATCAGGAGGAGGA
AGCGGAGGAGGCAGCGGAGGAGGATCTGGAGGAGGAAGTGGAGAGGTGCAGCTGGTC
GAAAGCGGAGGAGGAGTGGTCCGACCTGGAGGGTCACTGCGACTGAGCTGTGCAGCT
TCCGGCTTCACATTTGACGATTACGGAATGTCATGGGTGAGACAGGCCCCAGGGAAA
GGACTGGAATGGGTCTCCGGCATCAACTGGAATGGAGCTCTACTGGATACGCCGAC
AGTGTGAAGGGCAGGTTCACCATTTCCCGCGATAACGCTAAAAATTCTCTGTATCTG
CAGATGAACAGTCTGAGGGCCGAGGACACTGCCGTGTACTATTGTGCCCGGGGCAGA
TCCCTGCTGTTTGATTACTGGGGCCAGGGGACACTGGTGACTGTCTCTCGCGGCAGT
GAAAATCTGTATTTTCAG

SSELTQDPAVSVALGQTVPITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG
SGGGSGGGSGGGSGEVQLVESGGGVVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGSENLYFQ

FIG. 15 (cont)

V218: 4D5 scFv

GACATCCAGATGACCCAGTCTCCATCCTCCCTGTCTGCATCTGTAGGAGACAGAGTC
ACCATCACTTGCCGGGCAAGTCAGGACGTTAACACCGCTGTAGCTTGGTATCAGCAG
AAACCAGGGAAAGCCCCTAAGCTCCTGATCTATTCTGCATCCTTTTTGTACAGTGGG
GTCCCATCAAGGTTCAGTGGCAGTCGATCTGGGACAGATTTCACTCTCACCATCAGC
AGTCTGCAACCTGAAGATTTTGCAACTTACTACTGTCAACAGCATTACACTACCCCA
CCCACTTTCGGCCAAGGGACCAAAGTGGAGATCAAAGGTGGTTCTGGTGGTGGTTCT
GGTGGTGGTTCTGGTGGTGGTTCTGGTGGTGGTTCTGGTGAAGTGCAGCTGGTGGAG
TCTGGGGGAGGCTTGGTACAGCCTGGCGGGTCCCTGAGACTCTCCTGTGCAGCCTCT
GGATTCAACATTAAAGATACTTATATCCACTGGGTCCGGCAAGCTCCAGGGAAGGGC
CTGGAGTGGGTCGCACGTATTTATCCACAAATGGTTACACACGGTATGCGGACTCT
GTGAAGGGCCGATTCACCATCTCCGCAGACACTTCCAAGAACACCGCGTATCTGCAA
ATGAACAGTCTGAGAGCTGAGGACACGGCCGTTTATTACTGTTCAAGATGGGGCGGA
GACGGTTTCTACGCTATGGACTACTGGGGCCAAGGGACCCTGGTCACCGTCTCCTCA
GGCAGCGAGAACCTGTATTTTCAG

Protein Sequence
DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSSGSENLYFQ

FIG. 15 (cont)

Base construct # 1:

AGTAGCGAACTGACACAGGACCCCGCAGTGAGCGTCGCACTGGGACAGACAGTGCGA
ATCACTTGCCAGGGGGACTCACTGCGGAGCTACTATGCCTCCTGGTACCAGCAGAAA
CCAGGCCAGGCTCCCGTGCTGGTCATCTATGGCAAGAACAATAGGCCTAGTGGGATT
CCAGATCGCTTTTCAGGGAGCTCCTCTGGAAACACTGCAAGTCTGACCATTACAGGC
GCTCAGGCAGAGGACGAAGCCGATTACTATTGCAACAGCAGGGACAGTTCAGGGAAT
CACGTGGTCTTCGGAGGAGGAACTAAGCTGACCGTGGGAGGAGGCAGCGGAGGAGGA
TCTGGAGGAGGAAGTGGAGGAGGATCAGGAGGAGGAAGCGGAGAGGTGCAGCTGGTC
GAAAGCGGAGGAGGAGTGGTCCGGCCAGGAGGGTCCCTGAGACTGTCTTGTGCCGCT
AGTGGATTCACTTTTGACGATTACGGAATGTCATGGGTCCGGCAGGCACCTGGCAAG
GGACTGGAGTGGGTGAGCGGCATCAACTGGAATGGAGGCTCCACAGGGTACGCTGAT
TCTGTGAAAGGACGCTTTACTATTAGCCGAGACAACGCCAAGAACAGCCTGTATCTG
CAGATGAACTCTCTGAGAGCTGAGGATACCGCAGTGTACTATTGCGCCAGGGGCCGC
TCTCTGCTGTTCGACTACTGGGGACAGGGCACACTGGTGACTGTCTCACGCGGGGGA
AGCGGGGATGCTCACAAGTCCGAGGTCGCACATCGATTCAAAGACCTGGGAGAGGAA
AATTTTAAGGCCCTGGTGCTGATCGCCTTCGCTCAGTATCTGCAGCAGTGCCCTTTT
GAAGACCACGTGAAACTGGTCAACGAGGTGACCGAGTTCGCCAAGACATGCGTGGCC
GACGAGAGTGCTGAAATTGTGATAAATCACTGCATACCTGTTTGGAGATAAGCTG
TGTACCGTGGCCACACTGCGGAGACATACGGCGAAATGGCAGACTGCTGTGCCAAA
CAGGAGCCTGAAAGAAACGAGTGCTTCCTGCAGCACAAGGACGATAACCCCAATCTG
CCTCGACTGGTGCGGCCAGAAGTGGACGTCATGTGTACTGCTTTCCACGATAATGAG
GAAACCTTTCTGAAGAAATACCTGTATGAGATTGCCCGGAGACATCCATACTTTTAT
GCCCCGAACTGCTGTTCTTTGCTAAGCGCTATAAAGCAGCCTTCACCGAGTGCTGT
CAGGCTGCAGATAAGGCCGCTTGCCTGCTGCCAAAACTGGACGAGCTGAGAGATGAA
GGCAAAGCAAGCTCCGCCAAGCAGAGGCTGAAATGTGCAAGCCTGCAGAAGTTCGGC

FIG. 15 (cont)

GAGAGGGCCTTTAAAGCATGGGCCGTGGCTAGACTGTCTCAGAGGTTCCCCAAGGCT
GAGTTTGCAGAAGTCAGTAAGCTGGTGACTGACCTGACCAAAGTGCACACAGAGTGC
TGTCATGGCGACCTGCTGGAATGCGCCGACGATCGCGCCGATTTGGCTAAGTACATC
TGTGAGAACCAGGACTCCATTTCTAGTAAGCTGAAAGAGTGCTGTGAAAAGCCACTG
CTGGAGAAATCTCATTGCATCGCTGAGGTGGAAAATGACGAAATGCCCGCAGATCTG
CCTAGCCTGGCAGCCCACTTCGTCGAGTCCAAGGATGTGTGTAAAAACTATGCCGAG
GCTAAAGATGTGTTTCTGGGAATGTTTCTGTATGAGTATGCAAGAGCATGAGGATCC

Base construct # 1 Protein:

SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG
SGGGSGGGSGGGSGEVQLVESGGGVVRPGGSLRLSCAASGFTFLDYGMSWVRQAPGK
GLEWVSGINWNGGSTGYADSVKGRFTISRDNAKNSLYLQMNSLRAEDTAVYYCARGR
SLLFDYWGQGTLVTVSRGGSGDAHKSEVAHRFKDLGEENFKALVLIAFAQYLQQCPF
EDHVKLVNEVTEFAKTCVADESAENCDKSLHTLFGDKLCTVATLRETYGEMADCCAK
QEPEPNECFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKCASLQKFG
ERAFKAWAVARLSQRFPKAEFAEVSKLVTDLTKVHTECCHGDLLECADDRADLAKYI
CENQDSISSKLKECCEKPLLEKSHCIAEVENDEMPADLPSLAADFVESKDVCKNYAE
AKDVFLGMFLYEYARA

Base construct # 2:

GATGCTCATAAATCTGAGGTCGCTCACCGGTTCAAGGATCTGGGCGAGGAAAACTTT
AAAGCACTGGTGCTGATCGCTTTCGCACAGTACCTGCAGCAGTGCCCCTTTGAGGAC
CACGTGAAGCTGGTCAACGAGGTGACAGAGTTCGCCAAAACTTGCGTCGCCGACGAG
TCTGCTGAAAATTGTGATAAGAGTCTGCATACACTGTTGGAGATAAACTGTGTACT

FIG. 15 (cont)

GTGGCCACCCTGAGAGAGACTTATGGCGAAATGGCAGACTGCTGTGTCAAGCAGGAG
CCTGAAAGGAACGAGTGCTTCCTGCAGCATAAAGACGATAACCCCAATCTGCCTAGG
CTGGTGCGCCCAGAAGTGGACGTCATGTGTACCGCCTTCCACGATAATGAGGAAACA
TTTCTCAAGAAATACCTGTATGAGATTGCCCGGAGACATCCATACTTTTATGCXGCC
GAACTGCTGTTCTTTGCCAAGAGATACAAAGCCGCTTTCACCGAGTGCTGTCAGGCA
GCCGATAAGGCTGCATGCCTGCTGCCAAAACTGGACGAGCTGCGAGATGAAGGGAAG
GCCAGCTCCGCTAAGCAGCGGCTGAAATGTGCTAGCCTGCAGAAGTTCGGAGAGCGA
GCCTTCAAGGCATGGGCTGTGGCACGACTGTCCAGCGGTCCCCAAAGCAGAGTTT
GCCGAAGTCTCTAAGCTGGTGACAGACCTGACTAAAGTGCACACCGAGTGCTGTCAT
GGCGACCTGCTGGAATGCGCCGACGATCGAGCTGATCTGGCAAAGTACATCTGTGAG
AATCAGGACAGCATTTCTAGTAAGCTGAAAGAGTGCTGTGAAAAGCCTCTGCTGGAG
AAATCCACTGCATCGCCGAGGTGGAAAACGACGAAATGCCAGCTGATCTGCCCTCA
CTGGCGCTGACTTTGTCGAGAGCAAGGATGTGTGTAAAAATTATGCCGAAGCTAAG
GATGTGTTCCTGGGCATGTTTCTGTACGAGTATGCAAGGGCAGGAGGGTCCGGAGGC
TCTGGAGGAAGTGGAGGGTCAGGAGGCTCAAGCGAACTGACTCAGGACCCCGCTGTG
AGCGTCGCACTGGGACAGACTGTGAGGATCACCTGCCAGGGGACAGCCTGCGCTCC
TACTATGCATCCTGGTACCAGCAGAAGCCTGGCCAGGCCCCAGTGCTGGTCATCTAT
GGCAAAAACAATCGGCCCTCAGGGATTCCTGATCGGTTCAGCGGGTCCTCTAGTGGA
AACACAGCTTCTCTGACCATTACAGGCGCTCAGGCAGAGGACGAAGTCGATTACTAT
TGCAACAGCCGCGACTCAAGCGGGAATCATGTGGTCTTCGGAGGAGGAACCAAGCTG
ACAGTGGGAGGAGGCTCTGGAGGAGGCAGTGGGGGAGGCTCAGGAGGAGGCAGCGGA
GGAGGCTCCGGAGAGGTCCAGCTGGTGGAAAGCGGAGGAGGACTGGTCCGCCCAGGA
GGATCTCTGCGACTGAGTTGTGCAGCCTCAGGATTCACCTTTGACGATTACGGAATG
AGTTGGGTTCGGCAGGCACCTGGAAAGGGACTGGAGTGGGTGAGCGGCATCAACTGG
AATGGCGGAGCACTGGCTACGCTGATTCCGTGAAGGGAAGATTCACCATTTCCAGG
GACAACGGCAAAAATTCTCTGTATCTGCAGATGAATAGTCTGAGAGCCGAGGACACA

FIG. 15 (cont)
GCTGTGTACTATTGCGGCAGGGGAGGTCTCTGCTGTTCGACTACTGGGGCAGGGC
ACTCTGGTCACTGTGTCAAGATGAGGATCC Base construct # 2 Protein:
DAHKSEVAHRFKDLGEENFKALVLIAFAQYLQQCPFEDHVKLVNEVTEFAKTCVADE
SAENCDKSLHTLFGDKLCTVATLRETYGEMADCCAKQEPERNECFLQHKDDNPNLPR
LVRPEVDVMCTAFHDNEETFLKKYLYEIARRHPYFYAPELLFFAKRYKAAFTECCQA
ADKAACLLPKLDELRDEGKASSAKQRLKCASLQKFGERAFKAWAVARLSQRFPKAEF
AEVSKLVTDLTKVHTECCHGDLLECADDRADLAKYICENQDSISSKLKECCEKPLLE
KSHCIAEVENDEMPADLPSLAADFVESKDVCKNYAEAKDVFLGMFLYEYARRAGGSGG
SGGSGGSGGSSELTQDPAVSVALGQTVRITCQGDSLRSYYASWYQQKPGQAPVLVIY
GKNNRPSGIPDRFSGSSSGNTASLTITGAQAEDEADYYCNSRDSSGNHVVFGGGTKL
TVGGGSGGGSGGGSGGGSGGGSGEVQLVESGGGVVKPGGSLRLSCAASGFTFDDYGM
SWVRQAPGKGLEWVSGINWNGGSTGYADSVKGRFTISRDNAKNSLYLQMNSLRAEDT
AVYYCARGKSLLFDYWGQGTLVTVSR Base construct #3:
TCCTCCGAGCTGACCCAGGACCCTGCCGTGTCCGTGGCTCTGGGACAGACCGTGCGG
ATCACATGCCAGGGAGATAGCCTGAGATCCTACTATGCTAGCTGGTACCAGCAGAAA
CCCGGCCAGGCACCTGTGCTGGTCATCTATGGGAAGAACAATCGCCCATCTGGCATC
CCCGACCCATTCAGTGGAAGCTCCTCTGGCAACACAGCCTCTCTGACTATTACCGGC
GCTCAGGCAGAGGACGAAGCTGATTACTATTGCAACAGCAGGGATAGTTCAGGGAAT
CACGTGGTCTTTGGAGGAGGAACTAAGCTGACCGTGGGAGGAGGATCTGGAGGAGGA
AGTGGCGGGGCATCAGGAGGAGGAAGCGGAGGAGGCAGCGGAGAGGTGCAGCTGGTC
GAAAGCGGAGGAGGAGTGGTCAGACCAGGAGGGTCTCTGAGGCTGAGTTGTGCCGCT
TCAGGCTTCACCTTTGACGATTACGGAATGTCTTGGGTGCGGCAGGCACCTGGAAAG
GGACTGGAGTGGGTGAGTGGCATCAACTGGAATGGAGGCAGCACAGGATACGCAGAC

FIG. 15 (cont)

TCCGTGAAAGGCCGATTCACTATTTCACGGGATAACGCCAAGAATAGCCTGTATCTG
CAGATGAACAGCCTGAGAGCAGAGGACACAGCCGTGTACTATTGTGCCAGGGGCCGC
TCTCTGCTGTTTGATTACTGGGGCCAGGGAACACTGGTGACTGTCAGCCGAGGAGGA
TCTGGAGGAGTGGAGGTCAGGACGAAGCGGAGGGTCCGTGGTCCTGCTGCTGCGA
CTGGCTAAAACTTACGAGACCACACTGGAAAAGTGCTGTGCAGCCGCTGACCCCCAT
GAGTGCTATGCAAAAGTGTTCGATGAGTTCAAGCCTCTGGTCGAGGAACCACAGAAC
CTGATCAAACAGAATTGTGAGCTGTTCGAACAGCTGGGCGAGTACAAGTTTCAGAAC
GCCCTGCTGGTGAGATATACCAAGAAAGTGCCCCAGGTCTCTACACCTACTCTGGTG
GAGGTCAGTAGGAATCTGGGCAAAGTGGGGTCAAAATGCTGTAAGCACCCAGAGGCT
AAGCGCATGCCCTGCGCAGAAGACTACCTGAGCGTGGTCCTGAACCAGCTGTGTGTG
CTGCATGAGAAAACTCCAGTGTCCGATAGGGTCACTAAGTGCTGTACCGAAAGCCTG
GTGAACCGGAGACCTTGCTTCTCCGCCCTGGAGGTGGACGAAACCTATGTCCCAAAA
GAGTTTAATGCCGAAACCTTCACATTTCACGCTGATATCTGTACCCTGTCCGAGAAG
GAACGCCAGATTAAGAAACAGACAGCTCTGGTGGAGCTGGTCAAGCATAAACCCAAG
GCAACAAAGAACAGCTGAAGGCCGTGATGGACGATTTCGCAGCCTTTGTGGAGAAA
TGCTGTAAGGCCGACGATAAGGAAACTTGCTTTGCTGAAGAAGGGAAGAAACTGGTC
GCCCCATCACAGGCTGCTCTGGGACTGTGAGGATCC

Base Construct #3 Protein:

SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG
SGGGSGGGSGGGSGEVQLVESGGGVVRPGGSLRLSCAASGFTFDDYGMSWVRQAPGK
GLEWVSGINWNGSTGYADSVKGRFTISRDNAKNSLYLQMNSLRAEDTAVYYCARGR
SLLFDYWGQGTLVTVSRGGSGGSGGSGGSGGSVVLLRLAKTYETTLEKCCAAADPH
ECYAKVFDEFKPLVEEPQNLIKQNCELFEQLGEYKFQNALLVRYTKKVPQVSTPTLV
EVSRNLGKVGSKCCKHPEAKRMPCAEDYLSVVLNQLCVLHEKTPVSDRVTKCCTESL

FIG. 15 (cont)

VNRRPCFSALEVDETYVPKEFNAETFTFHADICTLSEKERQIKKQTALVELVKHKPK
ATKEQLKAVMDDFAAFVEKCCKADDKETCFAEEGKKLVAASQAALGL

Base construct # 4

AGCGTCGTCCTGCTGCTGAGACTGGCTAAAACATACGAGACCACACTGGAAAAGTGC
TGTGCCGCTGCAGACCCTCACGAGTGCTATGCCAAAGTGTTCGATGAGTTCAAGCCT
CTGGTCGAGGAACCACAGAACCTGATCAAACAGAATTGTGAGCTGTTCGAACAGCTG
GGCGAGTACAAGTTTCAGAACGCCCTGCTGGTGAGGTATACTAAGAAAGTGCCCCAG
GTCAGTACTCCTACCCTGGTGGAGGTCTCACGGAATCTGGGGAAAGTGGGAAGCAAA
TGCTGTAAGCACCCAGAGGCAAAGAGAATGCCCTGCGCCGAAGACTACCTGAGCGTG
GTCCTGAACCAGCTGTGTGTGCTGCATGAGAAAACTCCAGTGAGCGATAGGGTCACA
AAGTGCTGTACTGAATCCCTGGTGAACCGGAGACCTTGCTTCTCTGCCCTGGAGGTG
GACGAAACCTATGTCCCAAAGGAGTTTAATGCTGAAACATTCACTTTTCACGCAGAT
ATCTGTACACTGAGCGAGAAGGAACGCCAGATTAAGAAACAGACTGCCCTGGTGGAG
CTGGTCAAGCATAAACCCAAGGCCACCAAAGAACAGCTGAAGGCTGTGATGGACGAT
TTCGCCGCTTTTGTCGAGAAATGCTGTAAGGCAGACGATAAGGAAACATGCTTCGCC
GAGGAAGGGAAGAAACTGGTGGCAGCAAGCCAGGCTGCACTGGGACTGGGAGGGTCT
GGAGGCAGTGGAGGATCAGGAGGGAGCGGAGGCAGCTCCGAGCTGACCCAGGACCCC
GCTGTGAGCGTCGCACTGGGACAGACCGTGCGCATCACATGTCAGGGCGATTCCCTG
CGATCTTACTATGCTTCCTGGTACCAGCAGAAACCCGGCCAGGCACCTGTGCTGGTC
ATCTATGGAAAGAACAATAGACCAAGTGGCATTCCCGACAGGTTCTCAGGCTCTAGT
TCAGGGAACACCGCCTCCCTGACCATTACAGGCGCACAGGCCGAGGACGAAGCTGAT
TACTATTGCAACTCTCGGGATAGCTCCGGCAATCATGTGGTCTTTGGGGAGGCACT
AAGCTGACCGTGGGGGAGGCAGTGGGGAGGCTCAGGAGGAGGCAGCGGAGGAGGC
TCCGGAGGAGGCTCTGGCGAGGTGCAGCTGGTCGAATCCGGAGGAGGAGTGGTCGA
CCAGGAGGAAGTCTGCGACTGTCATGTGCCGCTAGCGGGTTCACTTTTGACGATTAC

FIG. 15 (cont)
GGAATGAGTTGGGTGCGACAGGCACCTGGAAAGGGACTGGAGTGGGTGTCTGGCATC
AACTGGAATGGCGGGTCCACTGGCTACGCAGACTCTGTGAAAGGGAGGTTTACCATT
AGCCGCGATAACGCCAAGAACAGCCTGTATCTGCAGATGAACAGCCTGCGCGCCGAG
GACACAGCTGTGTACTATTGCGCCCAGGGGGAGGTCACTGCTGTTTGATTACTGGGGG
CAGGGGACTCTGGTCACTGTGTCACGGTGAGGATCC Protein Base Construct #4
SVVLLLRLAKTYETTLEKCCAAADPHECYAKVFDEFKPLVEEPQNLIKQNCELFEQL
GEYKFQNALLVRYTKKVPQVSTPTLVEVSRNLGKVGSKCCKHPEAKRMPCAEDYLSV
VLNQLCVLHEKTPVSDRVTKCCTESLVNRRPCFSALEVDETYVPKEFNAETFTFHAD
ICTLSEKERQIKKQTALVELVKHKPKATKEQLKAVMDDFAAFVEKCCKADDKETCFA
EEGKKLVAASQAALGLGGSGGSGGSGGSGGSSELTQDPAVSVALGQTVRITCQGDSL
RSYYASWYQQKPGQAPVLVIYGKNNRPSGIPDRFSGSSSGNTASLTITGAQAEDEAD
YYCNSRDSSGNHVVFGGGTKLTVGGGSGGGSGGGSGGGSGGGSGEVQLVESGGGVVR
PGGSLRLSCAASGFTFDDYGMSWVRQAPGKGLEWVSGINWNGGSTGYADSVKGRFTI
SRDNAKNSLYLQMNSLPAEDTAVYYCARGRSLLFDYWGQGTLVTVSR Base construct 5
GACATTCAGATGACACAGTCCCCAAGCTCCCTGAGCGCTTCCGTCGGCGATCGAGTG
ACTATCACCTGCCGAGCCTCTCAGGACGTCAACACTGCTGTGGCATGGTACCAGCAG
AAGCCTGGGAAAGCACCAAAGCTGCTGATCTACTCTGCCAGTTTTCTGTATTCTGGA
GTGCCAGTAGATTCTCAGGAAGCAGGTCCGGCACCGATTTACACTGACTATCTCT
AGTCTGCAGCCTGAGGACTTCGCCACATACTATTGCCAGCAGCACTATACCACACCC
CTACATTTGGACAGGGCACTAAAGTGGAAATTAAGGGCGGGTCAGGCGGAGGGAGC
GGAGGAGGGTCCGGAGGAGGGTCTGGAGGAGGGAGTGGAGAGGTGCAGCTGGTCGAA
TCCGGAGGAGGACTGGTGCAGCCTGGAGGCTTACTGAGGCTGAGCTGTGCTGCTTCC
GGCTTCAATATCAAGGATACCTACATTCATTGGGTCAGACAGGCTCCTGGGAAAGGA

FIG. 15 (cont)

CTGGACTGGGTGGCAAGGATCTATCCAACCAATGGGTACACACGGTATGCCGATAGC
GTGAAGGGAAGATTCACTATTCCTGCTGACACTAGTAAAAACACCGCATACCTGCAG
ATGAATAGCCTGAGGGCAGAGGACACCGCCGTGTACTATTGCTCCCGCTGGCGGGA
GACGGCTTTTACGCTATGGATTATTGGGGCCAGGGGACCCTGGTGACAGTCTCAAGC
GGCGGGTCAGGAGATGCACACAAAGCGAGGTCGCCCATCGCTTCAAGGATCTGGGC
GAGGAAAATTTAAAGCCCTGGTGCTGATTGCCTTCGCTCAGTACCTGCAGCAGTGC
CCATTCGAAGACCACGTGAAGCTGGTCAACGAGGTGACCGAATTTGCCAAAACATGC
GTCGCTGACGAGTCCGCAGAAAATTGTGATAAGTCTCTGCATACACTGTTCGGCGAT
AAACTGTGTACTGTGGCCACCCTGCGCGAGACTTATGGGAAATGGCCGACTGCTGT
GCTAAGCAGGAGCCAGAACGAAACGAGTGCTTTCTGCAGCACAAGGACGATAACCCA
AATCTGCCAAGGCTGGTGCGCCCAGAAGTGGACGTCATGTGTACTGCTTTCCACGAT
AATGAGGAAACCTTTCTGAAGAAATACCTGTATGAGATCGCCCGGAGACATCCATAC
TTCTATGCCCCGAACTGCTGTTCTTTGCTAAACGGTACAAGGCAGCCTTTACCGAG
TGCTGTCAGGCTGCAGATAAAGCCGCTTGCCTGCTGCCTAAGCTGGACGAGCTGCGA
GATGAAGGCAAGGCATCCTCTGCCAAACAGCGGCTGAAGTGTGCCAGCCTGCAGAAA
TTCGGGGAGCGGGCTTTTAAGGCATGGGCCGTGGCTCGACTGTCTCAGCGGTTCCCA
AAGGCTGAGTTTGCAGAAGTCAGTAAACTGGTGACAGACCTGACTAAGGTGCACACA
GAGTGCTGTCATGGCGACCTGCTGGAATGCGCCGACGATAGAGCCGATCTGGCTAAG
TACATCTGTGAGAACCAGGACAGCATTAGTTCAAAGCTGAAAGAGTGCTGTGAAAAA
CCTCTGCTGGAGAAGAGCCACTGCATCGCAGAGGTGGAAAATGACGAAATGCCCGCC
GATCTGCCTAGTCTGGCAGCCGACTTCGTCGAGTCAAAAGATGTGTGTAAGAACTAC
GCCGAAGCAAAAGATGTGTTTCTGGGAATGTTTCTGTATGAGTATGCCCGAGCCTGA
GGATCC

FIG. 15 (cont)

Base construct 5 protein

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSSGGSGDAHKSEVAHRFKDLGEENFKALVLIAFAQYLQQC
PFEDHVKLVNEVTEFAKTCVADESAENCDKSLHTLFGDKLCTVATLRETYGEMADCC
AKQEPERNECFLQHKDDNPNLPRLVRPEVDVMCTAFHDNEETFLKKYLYEIARRHPY
FYAPELLFFAKRYKAAFTECCQAADKAACLLPKLDELRDEGKASSAKQRLKCASLQK
FGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNY
AEAKDVFLGMFLYEYARA

Base construct # 6:

GACGCACATAAGTCCGAGGTCGCTCACAGGTTCAAAGATCTGGGCGAGGAAAACTTT
AAGGCCCTGGTGCTGATCGCTTTCGCACAGTACCTGCAGCAGTGCCCATTCGAAGAC
CACGTGAAACTGGTCAACGAAGTGACTGAATTTGCCAAGACCTGCGTCGCCGACGAG
TCCGCTGAAAATTGTGATAAATCTCTGCATACTCTGTTCGGGGATAAGCTGTGTACC
GTGGCCACACTGCGCGAGACCTATGGAGAAATGGCAGACTGCTGTGCCAAACAGGAG
CCAGAACGAAACGAGTGCTTTCTGCAGCATAAGGACGATAACCCAAATCTGCCAAGG
CTGGTGCGCCCAGAAGTGGACGTCATGTGTACCGCCTTCCACGATAATGAGGAAACA
TTTCTGAAGAAATACCTGTATGAGATTGCCCGGAGACATCCATACTTCTATGCCCCC
GAACTGCTGTTCTTTGCTAAGCGCTACAAAGCCGCTTTTACCGAGTGCTGTCAGGCA
GCCGATAAAGCTGCATGCCTGCTGCCTAAGCTGGACGAGCTGAGGGATGAAGGAAAG
GCCAGCTCCGCTAAACAGCGCCTGAAGTGTGCCTCTCTGCAGAAATTCGGCGAGCGG
GCTTTTAAGGCATGGGCTGTCGCACGACTGAGCCAGCGGTTCCCAAAGGCAGAGTTT
GCCGAAGTCTCCAAACTGGTGACTGACCTGACCAAGGTGCACACCGAGTGCTGTCAT

FIG. 15 (cont)

GGCGACCTGCTGGAATGCGGCGACGATAGAGCTGATCTGGCAAAGTACATCTGTGAG
AACCAGGACAGCATTTCTAGTAAGCTGAAAGAGTGCTGTGAAAAACCCCTGCTGGAG
AAGAGTCACTGCATCGCAGAGGTGGAAAACGACGAAATGCCTGCCGATCTGCCAAGT
CTGGCCGCTGACTTCGTCGAGTCAAAAGATGTGTGTAAGAATTATGCCGAAGCTAAG
GATGTGTTCCTGGGCATGTTTCTGTACGAGTATGCACGAGCAGGAGGGAGCGGAGGC
TCCGGAGGATCTGGCGGGAGTGGAGGCGACATCCAGATGACTCAGTCCCCTTCAAGC
CTGAGTGCTTCAGTCGGCGATCGCGTGACTATTACCTGCCGAGCCTCTCAGGACGTC
AATACAGCTGTGGCATGGTACCAGCAGAAGCCCGGCAAAGCTCCTAAGCTGCTGATC
TACAGCGCATCCTTTCTGTATTCAGGGGTGCCCAGCAGATTCTCTGGCAGTAGATCA
GGACAGATTTTACACTGACTATTTCCTCTCTGCAGCCTGAGGACTTCGCCACTTAC
TATTGCCAGCAGCACTATACCACACCCCCTACATTTGGACAGGGCACTAAAGTGGAA
ATCAAGGGAGGCAGCGGAGGAGGATCTGGAGGAGGAAGTGGAGGAGGATCAGGAGGA
GGAAGCGGAGAGGTCCAGCTGGTGGAAAGCGGAGGAGGACTGGTGCAGCCTGGAGGG
TCCCTGAGACTGTCTTGTGCAGCCAGTGGCTTCAACATCAAAGATACCTACATTCAT
TGGGTCAGACAGGCTCCTGGGAAGGGACTGGAGTGGGTGGCAAGGATCTATCCAACA
AATGGATACACTCGGTATGCCGATAGCGTGAAAGGCCGGTTCACCATTTCAGCAGAC
ACCAGCAAGAACACAGCTTACCTGCAGATGAACAGCCTGCGAGCTGAGGACACAGCA
GTGTACTATTGCAGTCGGTGGGGCGGCGATGGCTTTTACGCTATGGACTATTGGGGG
CAGGGGACACTGGTGACTGTGAGTTCTTGAGGATCC

Protein Base construct # 6:
DAHKSEVAHRFKDLGEENFKALVLIAFAQYLQQCPFEDHVKLVNEVTEFAKTCVADE
SAENCDKSLHTLFGDKLCTVATLRETYGEMADCCAKQEPERNECFLQHKDDNPNLPR
LVRPEVDVMCTAFHDNEETFLKKYLYEIARRHPYFYAPELLFFAKRYKAAFTECCQA
ADKAACLLPKLDELRDEGKASSAKQRLKCASLQKFGERAFKAWAVARLSQRFPKAEF
AEVSKLVTDLTKVHTECCHGDLLECADDRADLAKYICENQDSISSKLKECCEKPLLE
KSHCIAEVENDEMPADLPSLAADFVESKDVCKNYAEAKDVFLGMFLYEYARRHPDYSVV

FIG. 15 (cont)

SGGSGGSGGDIQMTQSPSSLSASVGDRVTITCRASQDVNTAVAWYQQKPGKAPKLLI
YSASFLYSGVPSRFSGSRSGTDFTLTISSLQPEDFATYYCQQHYTTPFTFGQGTKVE
IKGGSGGSGGGSGGSGGGSGEVQLVESGGGLVQPGGSLRLSCAASGFNIKDTYIH
WVRQAPGKGLEWVARIYPTNGYTRYADSVKGRFTISADTSKNTAYLQMNSLRAEDTA
VYYCSRWGGDGFYAMDYWGQGTLVTVSS

Base construct # 7:

GACATTCAGATGACACAGAGCCCAAGCTCCCTGTCCGCATCTGTGGGCGACCGAGTC
ACAATCACTTGCCGGGCCTCCCAGGATGTGAACACTGCTGTCGCATGGTACCAGCAG
AAACCAGGGAAGGCTCCCAAACTGCTGATCTACAGTGCATCATTCCTGTATAGTGGC
GTGCCATCAAGGTTTAGCGGCTCCCGATCTGGAACCGACTTCACCCTGACAATCTCT
AGTCTGCAGCCCGAGGATTTTGCCACATACTATTGCCAGCAGCACTATACCACACCC
CCTACTTTCGGCAGGGAACCAAGGTGGAGATCAAGGGAGGGAGCGGAGGAGGGTCC
GGAGGAGGGTCTGGAGGCGGGAGTGGAGGAGGGTCAGGAGAGGTGCAGCTGGTCGAA
AGCGGAGGAGGACTGGTGCAGTCTGGAGGCAGCCTGCGACTGTCCTGTGCCGCTTCT
GGCTTTAACATCAAGGACACCTACATTCATTGGGTGCGGCAGGCACCTGGCAAAGGA
CTGGAGTGGGTGGCTAGAATCTATCCAACTAATGGATACACCAGATATGCTGACAGC
GTGAAGGGCAGGTTTACTATCAGTGCTGATACATCAAAGAACACTGCATACCTGCAG
ATGAATAGCCTGCGCGCCGAGGATACCGCTGTGTACTATTGTAGCCGATGGGGGGA
GACGGCTTCTACGCCATGGATTATTGGGGACAGGGCACCCTGGTGACAGTCTCAAGC
GGAGGGAGTGGAGGCTCAGGAGGAAGCGGAGGGTCCGGAGGCTCTGTGGTCCTGCTG
CTGAGACTGGCTAAGACCTACGAGACTACCCTGGAAAAATGCTGTGCAGCCGCTGAC
CCCCACGAGTGCTATGCAAAGGTGTTCGATGAGTTCAAGCCTCTGGTCGAGGAACCA
CAGAACCTGATCAAGCAGAATTGTGAGCTGTTCGAACAGCTGGGCGAGTACAAGTTT
CAGAACGCCCTGCTGGTGAGGTATACAAAGAAAGTGCCCCAGGTCAGCACTCCTACC
CTGGTGGAGGTCTCCAGGAATCTGGGGAAGGTCGGATCTAAGTGCTGTAAACACCCA
GAGGCAAAACGCATGCCCTGCGCCGAAGACTACCTGTCCGTGGTCCTGAATCAGCTG

FIG. 15 (cont)
TGTGCTGCATGAGAAGACCCCTGTGTCTGATCGAGTCACCAAATGCTGTACAGAA
AGTCTGGTGAACCGGAGACCCTGCTTTTCTGCCCTGGAGGTGGACGAAACATATGTC
CCTAAGGAGTTCAATGCCGAAACATTCACTTTTCACGCTGATATCTGTACACTGTCC
GAGAAGGAACGCCAGATTAAGAAACAGACTGCTCTGGTGGAGCTGGTCAAGCATAAA
CCAAAGGCAACCAAGGAACAGCTGAAAGCCGTGATGGACGATTTCGCAGCCTTTGTC
GAGAAGTGCTGTAAAGCCGACGATAAGGAAACTTGTTTCGCCGAGGAAGGCAAAAAA
CTGGTCGCAGCATCACAGGCAGCACTGGGACTGTGAGGATCC Base construct # 7 Protein:
DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVPQAPGKG
LEWVARIYPTNGYTRYADSVKGRFTISADTSKNTAYLQMNSLRAEDTAVYYCSRWGG
DGFYAMDYWGQGTLVTVSSGGSGGSGGSGGSGGSVVLLLPLAKTYETTLEKCCAAAD
PHECYAKVFDEFKPLVEEPQNLIKQNCELFEQLGEYKFQNALLVRYTKKVPQVSTPT
LVEVSRNLGKVGSKCCKHPEAKRMPCAEDYLSVVLNQLCVLHEKTPVSDRVTKCCTE
SLVNRRPCFSALEVDETYVPKEFNAETFTFHADICTLSEKERQIKKQTALVELVKHK
PKATKEQLKAVMDDFAAFVEKCCKADDKETCFAEEGKKLVAASQAALGL Base construct # 8
TCCGTCGTCCTGCTGCTGAGACTGGCTAAGACCTACGAGACCACACTGGAAAAATGC
TGTGCCGCTGCAGACCCCCACGAGTGCTATGCCAAGGTGTTCGATGAGTTCAAGCCT
CTGGTGGAGGAACCACAGAACCTGATCAAGCAGAATTGTGAGCTGTTCGAACAGTG
GGCGAGTACAAATTTCAGAACGCCCTGCTGGTGAGGTATACAAAGAAAGTGCCCCAG
GTCTCTACACCTACTCTGGTGGAGGTCAGTAGGAATCTGGGCAAGGTCGGGTCAAAA
TGCTGTAAGCACCCAGAGGCCAAACGCATGCCCTGCGCTGAAGACTACCTGTCTGTG
GTCCTGAACCAGCTGTGTGTGCTGCATGAGAAGACCCCTGTGAGCGATCGAGTCACC FIG. 15 (cont)
AAATGCTGTACAGAAAGCCTGCTGAATCGGAGACCTTGCTTTTCCGCTCTGGAGGTG
GACGAAACATATGTCCCTAAGGAGTTCAATGCAGAAACCTTCACATTTCACGCCGAT
ATCTGTACTCTGTCCGAGAAGGAACGTCAGATTAAGAAACAGACCGCCCTGGTGGAG
CTGGTCAAGCATAAACCAAAGGCTACTAAGGAACAGCTGAAAGCAGTGATGGACGAT
TTCGCCGCTTTTGTCGAGAAATGCTGTAAGGCAGACGATAAGGAAACCTGCTTTGCC
GAGGAAGGCAAGAAACTGGTGGCAGCCAGCCAGGCTGCACTGGGACTGGGAGGGTCC
GGAGGCTCTGGAGGAAGTGGAGGGTCAGGAGGCGACATCCAGATGACACAGAGCCCA
AGCTCCCTGTCAGCAAGCGTGGGTGACCGAGTCACTATTACCTGTCGGGCCTCCCAG
GATGTGAATACTGCAGTCGCCTGGTACCAGCAGAAACCAGGAAAGGCTCCCAAACTG
CTGATCTACTCCGCATCTTTCCTGTATAGCGGCGTGCCATCCAGGTTTAGTGGATCA
CGCAGCGGCACAGACTTCACACTGACTATTTCTAGTCTGCAGCCCGAGGATTTTGCC
ACTTACTATTGCCAGCAGCACTATACTACCCCCCCTACCTTCGGACAGGGCACAAAG
GTGGAGATCAAGGGAGGATCTGGAGGAGGAAGTGGAGGAGGATCAGGAGGAGGAAGC
GGAGGAGGCAGCGGAGAGGTGCAGCTGGTCGAATCTGGAGGAGGACTGGTGCAGCCT
GGAGGGTCTCTGCGACTGAGTTGTGCCGCTTCAGGCTTTAACATCAAGGACACCTAC
ATTCATTGGGTGCGGCAGGCACCTGGGAAGGGACTGGAGTGGGTCGCTAGAATCTAT
CCAACTAATGGGTACACCAGATATGCCGACAGCGTGAAGGAAGGTTCACCATTAGC
GCCGATACATCCAAAAACACTGCTTACCTGCAGATGAACAGCCTGCGCGCTGAGGAT
ACAGCAGTGTACTATTGCAGTCGATGGGGCGGCGATGGTTCTACGCAATGGACTAC
TGGGGACAGGGGACTCTGGTCACCGTCAGCAGCTGAGGATCC <u>Base construct # 8 Protein</u>
SVVLLLRLAKTYETTLEKCCAAADPHECYAKVFDEFKPLVEEPQNLIKQNCELFEQL
GEYKFQNALLVRYTKKVPQVSTPTLVEVSRNLGKVGSKCCKHPEAKRMPCAEDYLSV
VLNQLCVLHEKTPVSDRVTKCCTESLVNRRPCFSALEVDETYVPKEFNAETFTFHAD
ICTLSEKERQIKKQTALVELVKHKPKATKEQLKAVMDDFAAFVEKCCKADDKETCFA
EEGKKLVAASQAALGLGGSGGSGGSGGSGGDIQMTQSPSSLSASVGDRVTITCRASQ

FIG. 15 (cont)

DVNTAVAWYQQKPGKAPKLLIYSASFLYSGVPSRFSGSRSGTDFTLTISSLQPEDFA
TYYCQQHYTTPPTPGQGTKVEIKGGGGGSGGGSGGGSGGGSEVQLVESGGGLVQP
GGSLRLSCAASGFNIKDTYIHRVRQAPGKGLEWVARIYPTNGYTRYADSVKGRFTIS
ADTSKNTAYLQMNSLRAEDTAVYYCSRWGGEGFYAMDYWGQGTLVTVSS

Base construct # 9:

TCAAGCGAACTGACTCAGGACCCCGCTGTGAGCGTCGCACTGGGACAGACTGTGCGG
ATCACCTGCCAGGGGGACTCCCTGAGATCTTACTATGCCTCCTGGTACCAGCAGAAA
CCAGGCCAGGCTCCCGTGCTGGTCATCTATGGCAAGAACAATAGACCTTCCGGGATT
CCAGATAGGTTTTCTGGAAGCTCCTCTGGCAACACAGCTAGCCTGACCATTACAGGA
GCCCAGGCTGAGGACGAAGCAGATTACTATTGCAACTCCAGGGACAGTTCAGGCAAT
CACGTGGTCTTCGGCGGGGGAACAAAGCTGACTGTGGGAGGAGGATCAGGAGGAGGA
AGCGGAGGAGGCAGCGGAGGAGGATCTGGAGGAGGAAGTGGAGAGGTGCAGCTGGTC
GAAAGTGGAGGAGGAGTGGTCAGGCCTGGAGGGTCACTGCGACTGAGCTGTGCCGCT
TCCGGATTCACATTTGACGATTACGGAATGTCTTGGGTCCGGCAGGCACCAGGAAAG
GGACTGGAGTGGGTGAGTGGCATCAACTGGAATGGAGGCTCTACAGGGTACGCTGAT
AGTGTGAAAGGACGCTTTACTATTAGTCGAGACAACGCCAAGAACAGCCTGTATCTG
CAGATGAACAGCCTGAGAGCTGAGGATACTGCTGTGTACTATTGTGCCAGGGGCCGC
TCCCTGCTGTTCGACTACTGGGGCCAGGGAACCCTGGTGACAGTCTCTAGGGGGGGA
AGTGGCGATGCTCACAAGAGCGAGGTCGCACATCGCTTCAAAGACCTGGGGGAGGAA
AATTTTAAGGCCCTGGTGCTGATCGCATTCGCCCAGTATCTGCAGCAGTGCCCTTTT
GAAGACCACGTGAAACTGGTCAACGAGGTGACCGAGTTCGCCAAGACATGCGTGGCA
GACGAGTCCGCCGAAAATTGTGATAAATCTCTGCATACTCTGTTTGGGGATAAGCTG
TGTACTGTGGCCACCCTGCGGGAGACCTACGGAGAAATGGCTGACTGCTGTGCAAAA
CAGGAGCCAGAAAGAAACGAGTGCTTCCTGCAGCACAAGGACGATAACCCCAATCTG
CCTCGACTGGTGCGGCCCGAAGTGGACGTCATGTGTACTGCCTTCCACGATAATGAG
GAAACCTTTCTGAAGAAATACCTGTATGAGATTGCCCGGAGACATCCCTACTTTTAT

FIG. 15 (cont)

GCCCCTGAACTGCTGTTCTTTGCTAAGCGGTACAAAGCAGCCTTCACCGAGTGCTGT
CAGGCTGCAGATAAGGCCGCTTGCCTGCTGCCAAAACTGGACGAGCTGCGAGATGAA
GGGAAAGCTAGCTCCGCAAAGCAGAGACTGAAATGTGCAAGCCTGCAGAAGTTCGGC
GAGAGGCCCTTAAAGCTTGGCCAGTGGCCAGACTGACCCAGACGTTCCCCAAGGCC
GAGTTTGCTGAAGTCTCCAAGCTGGTGACAGACCTGACTAAAGTGCACACTGAGTGC
TGTCATGGCGACCTGCTGGAATGCGCCGACGATCGCGCAGATCTGGCCAAATACATC
TGTGAGAACCAGGACTCTATTCTAGTAAGCTGAAAGAGTGCTGTGAAAAGCCTCTG
CTGGAGAAAGCCACTGCATCGCTGAGGTGGAAAACGACGAAATGCCCGCAGATCTG
CCTAGTCTGGCAGCCGACTTTGTCGAGTCAAAGGATGTCTGTAAAAATTATGCTGAA
GCAAAGGATGTCTTCCTGGGCATGTTTCTGTACGAGTATGCACGAGCTGGAGGGAGT
GGAGGCTCAGGAGGAAGCGGCGGGTCCGGAGGCTCAAGCGAACTGACCCAGGACCCC
GCCGTGTCTGTCGCTCTGGGACAGACAGTGAGGATCACTTGCCAGGGCGACTCTCTG
CGCAGTTACTATGCAAGTTGGTATCAGCAGAAGCCTGGCCAGGCCCCTGTCCTGGTC
ATCTATGGCAAGAATAATCGCCCTAGTGGGATTCCAGATCGATTTTCAGGGTCCTCT
AGTGGAAACACAGCTTCTCTGACTATTACCGGCGCACAGGCCGAGGACGAAGCCGAT
TACTATTGCAACAGCAGAGACTCAAGCGGCAATCATGTGGTCTTCGGAGGAGGAACC
AAGCTGACAGTGGGAGGAGGCTCAGGCGGCGGCAGCGGAGGAGGCTCCGGGGGAGGC
TCTGGAGGAGGCAGTGGAGAGGTCCAGCTGGTGGAATCCGGAGGAGGAGTGGTCCCA
CCAGGAGGATCACTGAGACTGTCCTGTGCTGCATCCGGATTCACCTTCGATGATTAC
GGAATGAGCTGGGTCAGGCAGGCACCTGGCAAGGGCCTGGAATGGGTGTCCGGCATC
AACTGGAATGGCGGGTCAACCGGGTACGCTGATAGCGTGAAAGGACGGTTCACAATT
AGCAGGGATAATGCTAAGAACAGCTTATATCTGCAAATGAACAGCCTGCGCGCAGAG
GACACAGCCGTGTACTATTGCGCCCGGGGCGGAGCCTGCTGTTTGATTACTGGGGG
CAGGGCACACTGGTGACCGTCTCTCGGTGAGGATCC

Base construct # 9 protein:

FIG. 15 (cont)

SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGSGGG
SGGGSGGSGGGSSGEVQLVESGGGVVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGESGDAHKSEVAHRFKDLGEENFKALVLIAFAQYLQQCPF
EDHVKLVNEVTEFAKTCVADESAENCDKSLHTLFGDKLCTVATLRETYGEMADCCAK
QEPERNECFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKCASLQKFG
ERAFKAWAVARLSQRFPKAEFAEVSKLVTDLTKVHTECCHGDLLECADDRADLAKYI
CENQDSISSKLKECCEKPLLEKSHCIAEVENDEMPADLPSLAADFVESKDVCKNYAE
AKDVFLGMFLYEYARRAGGSGGSGGSGGSGGSSELTQDPAVSVALGQTVRITCQGDSL
RSYYASWYQQKPGQAPVLVIYGKNNRPSGIPDRFSGSSSGNTASLTITGAQAEDEAD
YYCNSRDSSGNHVVFGGGTKLTVGGSGGGSGGGSGGSGGGSGEVQLVESGGGVVR
PGGSLRLSCAASGFTFDDYGMSWVRQAPGKGLEWVSGINWNGGSTGYADSVKGRFTI
SRDNAKNSLYLQMNSLRAEDTAVYYCARGRSLLFDYWGQGTLVTVSR

Base construct # 10:
AGTAGCGAACTGACCCAGGACCCCGCAGTGAGCGTCGCACTGGGGCAGACAGTGAGA
ATCACTTGCCAGGGAGATTCTCTGAGGAGTTACTATGCCTCCTGGTACCAGCAGAAA
CCCGGCCAGGCTCCTGTGCTGGTCATCTATGGAAGAACAATAGGCCAAGCGGCATC
CCCGACCGCTTCTCCGGCAGCTCCTCTGGAACACAGCTAGCCTGACTATTACCGGC
GCTCAGGCAGAGGACGAAGCAGATTACTATTGCAACTCCAGGGATAGTTCAGGCAAT
CACGTGGTCTTTGGCGGGGGAACAAAGCTGACTGTGGGAGGAGGAAGCGGAGGAGGC
AGCGGAGGGGATCTGGAGGAGGAAGTGGAGGAGGATCAGGAGAGGTGCAGCTGGTC
GAAAGCGGAGGAGGAGTGGTCCGCCCTGGAGGAGCCTGCGACTGTCCTGTGCCGCT
TCTGGCTTCACCTTTGACGATTACGGAATGAGCTGGGTGCGGCAGGCACCAGGAAG
GGACTGGAGTGGGTGTCCGGCATCAACTGGAATGGAGGCTCCACAGATACGCAGAC

FIG. 15 (cont)

TCTGTGAAAGGCCGATTCACTATTTCTCGGGATAACGCCAAGAATAGTCTGTATCTG
CAGATGAACAGCCTGAGAGCTGAGGACACTGCAGTGTACTATTGTGCCAGGGGCCGC
AGCCTGCTGTTTGATTACTGGGGCCAGGGAACCCTGGTGACAGTCTCCAGGGGAGCA
TCAGGAGGAGGGAGGGTCCGGAGGATCTGGAGGAGTGTGGTCCTGCTGCTGGGA
CTGGCTAAAACCTACGAGACCACACTGGAAAAGTGCTGTGCAGCCGCTGACCCTCAT
GAGTGCTATGCCAAAGTGTTCGATGAGTTCAAGCCACTGGTCGAGGAACCCAGAAC
CTGATCAAACAGAATTGTGAGCTGTTCGAACAGCTGGGCGAGTACAAGTTTCAGAAC
GCCCTGCTGGTGCGCTATACCAAGAAAGTGCCTCAGGTCAGCACACCAACTCTGGTG
GAAGTCTCCCGGAATCTGGGGAAAGTGGGATCTAAATGCTGTAAGCACCCCGAGGCT
AAGAGAATGCCTTGCGCAGAAGACTACCTGTCTGTGGTCCTGAACCAGCTGTGTGTG
CTGCATGAGAAAACCCCAGTGAGCGATAGGGTCACCAAGTGCTGTACAGAAAGTCTG
GTGAACCGGAGACCATGTTCTCAGCCCTGGAGGTGGACGAAACATATGTCCCCAAA
GAGTTTAATGCCGAAACCTTCACATTTCACGGTGATATCTGTACTCTGTCCGAGAAG
GAACGCAGATTAAGAAACAGACCGCCTGGTGGAGCTGGTCAAGCATAAACCCAAG
GCAACAAAGAACAGCTGAAGGCCGTGATGGACGATTTCGCAGCCTTTGTCGAGAAA
TGCTGTAAGGCTGACGATAAGGAAACTTGCTTCGCAGAGGAAGGAAAGAAACTGGTG
GCTGCAAGCCAGGCAGCTCTGGGACTGGGAGGCTCAGGAGGAAGCGGCGGGTCCGGA
GGCTCTGGGGGAAGCTCCGAGCTGACCCAGGACCCAGCCGTGCTGTCGCTCTGGGC
CAGACTGTGCGCATCACCTGTCAGGGGATAGTCTGCGATCATACTATGCAAGTTGG
TATCAGCAGAAACCTGGCCAGGCCCAGTCCTGGTCATCTATGGAAGAATAATCGA
CCTTCCGGCATCCCCGACCGGTCTCCGGATCTAGTTCAGGCAACACAGCCTCTCTG
ACTATTACCGGCGCCCAGGCTGAGGACGAAGCTGATTACTATTGCAACAGCAGGGAT
AGCTCCGGAAACCACGTGGTCTTTGGAGGAGGAACTAAGCTGACCGTGGGAGGAGGA
AGTGGCGGGGATCAGGCGGCGGAAGCGGCGGCGGCAGCGGAGGAGGATCTGGCGAA
GTGCAGCTGGTCGAATCTGGCGGAGGAGTGGTCCGGCCAGGAGGGAGTCTGAGACTG
TCATGTGCAGCCAGCGGCTTCACATTCCGATGATTACGGAATGTCTTGGGTGCGGCAG
GCACCTGGAAAGGGCCTGGAATGGGTGAGTGGCATCAACTGGAACGGCGGCAGTACC

FIG. 15 (cont)

GGATACGCTGACTCAGTGAAAGGCAGATTCACAATTTCTAGAGACAATGCTAAGAAT
AGTTTATATCTGCAAATGAACAGCCTGAGAGCAGAGGACACTGCCGTGTACTATTGC
GCCCGGGGGAGGTCACTGCTGTTCGATTACTGGGGGCAGGGCACTCTGGTCACTGTG
TCAAGCTGAGGATCC

Base construct # 10 protein:

SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG
SGGGSGGGSGGGSGEVQLVESGGGVVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGGSGGSGGSGGSGGSVVLLLPLAKTYETTLEKCCAAADPH
ECYAKVFDEFKPLVEEPQNLIKQNCELFEQLGEYKFQNALLVRYTKKVPQVSTPTLV
EVSRNLGKVGSKCCKHPEAKRMPCAEDYLSVVLNQLCVLHEKTPVSDRVTKCCTESL
VNRRPCFSALEVDETYVPKEFNAETFTFHADICTLSEKERQIKKQTALVELVKHKPK
ATKEQLKAVMDDFAAFVEKCCKADDKETCFAEEGKKLVAASQAALGLGGSGGSGGSG
GSGGSSELTQDPAVSVALGQTVRITCQGDSLRSYYASWYQQKPGQAPVLVIYGKNNR
PSGIPDRFSGSSSGNTASLTITGAQAEDEADYYCNSRDSSGNHVVFGGGTKLTVGGG
SGGGSGGGSGGGSGGGSGEVQLVESGGGVVRPGGSLRLSCAASGFTFDDYGMSWVRQ
APGKGLEWVSGINWNGGSTGYADSVKGRFTISRDNAKNSLYLQMNSLRAEDTAVYYC
ARGRSLLFDYWGQGTLVTVSR

Base construct # 11:

GATATTCAGATGACTCAGTCTCCAGCTCCCTGTCAGCTAGCGTCGGCGATCGGGTG
ACAATCACTTGCAGAGCCAGCCAGGACGTCAACACAGCCGTGGCTTGGTACCAGCAG
AAGCCCGGAAAAGCACCTAAGCTGCTGATCTACTCCGCCTCTTTCTGTATTCTGGC
GTCCCAGTAGATTCAGTGGATCAAGGAGCGGCACCGATTTTACCCTGACAATCTCT
AGTCTGCAGCCTGAGGACTTTGCCACATACTATTGCCAGCAGCACTATACCACACCC

FIG. 15 (cont)

CCTACTTTGGGCAGGGAACAAGGTGGAAATCAAAGGCGGGTCAGCGGAGGGAGC
GGAGGAGGGTCCGGAGGAGGGTCTGGAGGAGGGAGTGGAGAGGTGCAGCTGGTGGAA
TCTGGAGGAGGACTGGTGCAGCCAGGAGGCTCACTGCGGCTGAGCTGTGCCGCTCC
GGCTTCAACATCAAAGATACCTACATTCATTGGGTCCGACAGGCACCAGGCAAGGGA
CTGGAGTGGGTGGCTAGAATCTATCCACCAATGGCTACACACGATATGCCGATAGC
GTGAAAGGGCGGTTTACAATTTCTGCAGACACTAGTAAGAACACCGCCTACCTGCAG
ATGAACAGCCTGCGCCTGAGGACACTGCAGTGTACTATTGTAGTCGATGGGGGGGA
GACGGCTTCTACGCCATGGATTATTGGGGACAGGGCACCCTGGTGACAGTCTCAAGC
GGAGGGTCCGGCGATGCACACAAGTCTGAGGTCGCTCATAGATTCAAAGACCTGGGG
GAGGAAAATTTTAAGGCCCTGGTGCTGATTGCATTCGCCCAGTACCTGCAGCAGTGC
CCCTTTGAAGACCACGTGAAACTGGTCAACGAGGTGACAGAGTTCGCCAAGACTTGC
GTCGCCGACGAGAGTGCTGAAAATTGTGATAAATCACTGCATACACTGTTTGGGGAT
AAGCTGTGTACTGTGGCCACCCTGCGGGAGACTTATGGAGAAATGGCAGACTGCTGT
GCCAAACAGGAGCCTGAAAGAAACGAGTGCTTCCTGCAGCACAAGGACGATAACCCT
AATCTGCCAAGGCTGGTGCGCCCAGAAGTGGACGTCATGTGTACTGCCTTCCACGAT
AATGAGGAAACCTTTCTGAAGAAATACCTGTATGAGATCGCCCGGAGACATCCCTAC
TTTTATGCTCCTGAACTGCTGTTCTTTGCAAAACGGTACAAGGCAGCCTTCACCGAG
TGCTGTCAGGCTGCAGATAAGGCCGCTTGCCTGCTGCCCAAACTGGACGAGCTGCGG
GATGAAGGCAAGGCTTCCTCTGCAAAGCAGAGACTGAAATGTGCAAGCCTGCAGAAG
TTCGGGGAGAGGGCCTTTAAAGCTTGGGCAGTCGCACGACTGAGCCAGCGATTCCCT
AAGGCCGAGTTTGCTGAAGTCTCCAAGCTGGTGACAGACCTGACTAAAGTGCACACC
GAGTGCTGTCATGGCGACCTGCTGGAATGCGCCGACGATCGCGCAGATCTGGCCAAG
TACATCTGTGAGAACCAGGACAGCATTAGTTCAAAGCTGAAAGAGTGCTGTGAAAAG
CCACTGCTGGAGAAATCCCACTGCATTGCTGAGGTGGAAAACGACGAAATGCCAGCA
GATCTGCCCAGCCTGGCAGCCGACTTCGTCGAGTCCAAGGATGTGTGTAAAAATTAT
GCTGAAGCAAAGGATGTGTTCCTGGGCATGTTTCTGTACGAGTATGCCAGGGCTGGA
GGCAGTGGAGGATCAGGAGGGAGCGGAGGCTCCGGAGGAGACATCCAGATGACCCAG

FIG. 15 (cont)

ASCDCAAGGTCGCTGTCCGGTTCTGTGGGCGATAGGGTGACTATTACCTGCCGCGCC
TCCCAGGACGTCAATACAGCAGTGGCCTGGTACCAGCAGAAACCTGGGAAGGCTCCA
AAACTGCTGATCTACAGTGCATCATTCCTGTATTCAGGAGTGCCAAGCCGCTTTAGC
GGGTCCCGATCTGGAACTGATTTCACACTGACTATCTCTAGTCTGCAGCCCGAGGAC
TTTGCCACCTATTACTGCCAGCAGCACTACACTACCCACCCACCTTGGGCAGGGA
ACAAAGGTGGAAATCAAAGGGGGTCCGGCGGCGGGTCTGGCGGAGGAGTGGAGGA
GGGTCAGGCGGCGGGAGCGGCGAGGTCCAGCTGGTGGAATCCGGCGGCGGCCTGGTG
CAGCCTGGAGGCTCCCTGCGACTGTCTTGTGCTGCAAGTGGCTTTAACATCAAGGAC
ACTTACATTCATTGGGTCAGGCAGGCTCCTGGCAAGGCCTGGAATGGGTGGCACGA
ATCTATCCAACAAATGGATACACTAGGTACGCCGATAGCGTGAAAGGCAGGTTCACC
ATTTCAGCCGACACCAGCAAGAACACAGCTTACCTGCAAATGAACAGCCTGAGGGCT
GAGGACACAGCAGTGTACTATTGCAGCCGCTGGGGCGGGGACGGGTTCTATGCTATG
GACTATTGGGGGCAGGGCACTCTGGTCACTGTGTCAAGCTGAGGATCC

Base construct # 11 protein:

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSSGGSGDAHKSEVAHRFKDLGEENFKALVLIAFAQYLQQC
PFEDHVKLVNEVTEFAKTCVADESAENCDKSLHTLFGDKLCTVATLRETYGEMADCC
AKQEPERNECFLQHKDDNPNLPRLVRPEVDVMCTAFHDNEETFLKKYLYEIARRHPY
FYAPELLFFAKRYKAAFTECCQAADKAACLLPKLDELRDEGKASSAKQRLKCASLQK
FGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNY
AEAKDVFLGMFLYEYARAGGSGGSGGSGGSGGDIQMTQSPSSLSASVGDRVTITCRA
SQDVNTAVAWYQQKPGKAPKLLIYSASFLYSGVPSRFSGSRSGTDFTLTISSLQPED

FIG. 15 (cont)

FATYYCQQHYTTPPTFGQGTKVEIKGGSGGGSGGGSGGGSGGGSEVQLVESGGGLV
QPGGSLRLSCAASGFNIKDTYIHWVRQAPGKGLEWVARIYPTNGYTRYADSVKGRFT
ISADTSKNTAYLQMNSLRAEDTAVYYCSRWGGDGFYAMDYWGQGTLVTVSS

Base construct # 12:

GACATTCAGATGACTCAGAGCCCAAGCTCCCTGAGCGCATCCGTGGGCGACAGAGTC
ACCATCACATGCAGGGCCTCCCAGGATGTGAACACCGCTGTCGCATGGTACCAGCAG
AAACCTGGGAAGGCTCCAAAACTGCTGATCTACTCTGCAAGTTTCCTGTATAGTGGA
GTCCCATCAAGGTTTTCAGGCAGCCGGTCCGGGACCGACTTCACTCTGACCATCTCT
AGTCTGCAGCCCGAGGATTTCGCCACATACTATTGCCAGCAGCACTATACCACACCC
CCTACCTTTGGCCAGGGGACAAAAGTGGAAATTAAGGGAGGGAGCGGAGGAGGGTCC
GGAGGAGGGTCTGGAGGCGGGAGTGGAGGAGGGTCAGGAGAGGTGCAGCTGGTCGAA
TCCGGAGGAGGACTGGTGCAGCCAGGAGGCAGCCTGCGGCTGTCCTGTGCCGCTTCT
GGCTTCAACATCAAAGACACCTACATTCATTGGGTGCGCCAGGCTCCAGGAAAGGGA
CTGGAGTGGGTCGCACGAATCTATCCCACTAATGGGTACACCCGGTATGCCGATTCC
GTGAAAGGAAGATTCACAATTAGTGCAGATACATCAAAGAACACTGCCTACCTGCAG
ATGAACAGCCTGCGAGCAGAGGATACTGCCGTGTACTATTGTAGTCGGTGGGGGGGA
GACGGCTTTTACGCCATGGATTATTGGGGCAGGGAACCCTGGTGACAGTCTCAAGC
GGAGGGTCAGGAGGCAGCGGAGGCAGCGGAGGGTCTGGAGGCAGTGTGGTCCTGCTG
CTGAGGCTGGCTAAAACCTACGAGACTACCCTGGAAAAGTGCTGTGCAGCCGCTGAC
CCCCACGAGTCCTATGCCAAAGTGTTCGATGAGTTCAAGCCACTGGTCGAGGAACCC
CAGAACCTGATCAAACAGAATTGTGAGCTGTTCGAACAGCTGGGCGAGTACAAGTTT
CAGAACGCCCTGCTGGTGCGCTATACCAAGAAAGTGCCTCAGGTCTCTACACCAACT
CTGGTGGAGGTCAGTAGGAATCTGGGGAAAGTGGGATCAAAGTGCTGTAAACACCCC
GAGGCCAAGCGCATGCCTTGCGCTGAAGACTACCTGTCTGTGGTCCTGAACCAGCTG
TGTGTGCTGCATGAGAAAACCCCCGTGAGCGATCGGGTCACCAAGTGCTGTACAGAA
AGCCTGGTGAACCGGAGACCCTGCTTCTCCGCTCTGGAGGTGGACGAAACATATGTC

FIG. 15 (cont)

CCTAAGGAGTTTAATGCTGAAACCTTCACATTTCATGCAGATATCTGTACACTGTCC
GAGAAGGAAAGACAGATTAAGAAACAGACTGCCCTGGTGGAGCTGGTCAAGCATAAA
CCTAAGGCACAAAGAACAGCTGAAGGCTGTGATGGACGATTCGCAGCCTTTGTC
GAGAAGTGCTGTAAAGCCGACGATAAGGAAACTTGCTTCGCTGAGGAAGGAAAGAAA
CTGGTGGCTGCAAGCCAGGCAGCTCTGGGCCTGGGAGGATCAGGAGGAGTGGAGGC
TCCGGAGGATCTGGAGGGGACATCCAGATGACCCAGTCTCCTTCCTCTCTGTCTGCT
AGTGTGGGCGACCGCGTCACTATTACCTGTCGAGCCAGCCAGGATGTGAATACAGCC
GTCGCTTGGTACCAGCAGAAGCCCGGCAAAGCACCTAAGCTGCTGATCTACTCAGCC
AGCTTTCTGTATAGCGGGGTGCCTTCCCGATTCTCCGGATCTCGGAGTGGCACTGAC
TTTACACTGACTATCAGTTCACTGCAGCCAGAGGATTTCGCCACCTATTACTGCCAG
CAGCACTACACAACTCCACCCACTTTTGGCCAGGGGACCAAAGTGGAAATCAAGGGA
GGCTCTGGAGGAGGCAGTGGAGGAGGCTCAGGAGGAGGCAGCGGAGGAGGCTCCGGC
GAAGTGCAGCTGGTCGAATCTGGCGGCGGCCTGGTCCAGCCAGGAGGATCTCTGAGG
CTGAGTTGTGCAGCCTCAGGCTTCAACATCAAGGATACTTACATTCATTGGGTGCGG
CAGGCACCTGGAAAGGGCCTGGAATGGGTCGCTAGAATCTATCCAACTAATGGCTAC
ACCAGATATGCCGACAGCGTGAAAGGGCGCTTTACCATTAGCGCAGATACATCCAAA
AATACCGCTTACCTGCAGATGAATAGCCTGAGAGCTGAGGATACAGCAGTGTACTAT
TGCTCCAGATGGGGCGGCGATGGTTTTTACGCAATGGACTACTGGGGACAGGGAACA
CTGGTCACCGTCTCTTCTTGAGGATCC

Base construct # 12 protein:
DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSGGSGGSGGSGGSGGSVVLLRLAKTYETTLEKCCAAAD
PHECYAKVFDEFKPLVEEPQNLIKQNCELFEQLGEYKFQNALLVRYTKKVPQVSTPT

FIG. 15 (cont)

LVEVSPNLGKVGSKCCKHPEAKRMPCAEDYLSVVLNQLCVLHEKTPVSDRVTKCCTE
SLVNRRPCFSALEVDETYVPKEFNAETFTFHADICTLSEKERQIKKQTALVELVKHK
PKATKEQLKAVMDDFAAFVEKCCKADDKETCFAEEGKKLVAASQAALGLGGSGGSGG
SGGSGGDIQMTQSPSSLSASVGDRVTITCRASQDVNTAVAWYQQKPGKAPKLLIYSA
SFLYSGVPSRFSGSPSGTDFTLTISSLQPEDFATYYCQQHYTTPPTFGQGTKVEIKG
GSGGSGGGSGGGSGGGSGEVQLVESGGGLVQPGGSLRLSCAASGFNIKDTYIHWVR
QAPGKGLEWVARIYPTNGYTRYADSVKGRFTISADTSKNTAYLQMNSLRAEDTAVYY
CSRWGGDGFYAMDYWGQGTLVTVSS

Base construct # 13:

AGTTCTGAGCTGACCCAGGACCCGCTGTGAGCGTCGCACTGGGACAGACAGTGCGG
ATCACTTGCCAGGGCGACAGCTGAGATCCTACTATGCTAGCTGGTACCAGCAGAAG
CCTGGCCAGGCACCAGTGCTGGTCATCTATGGAAAAACAATAGACTCAGCGGCATT
CCTGATAGGTTCTCCGGGAGCTCCTCTGGAAACACAGCTAGCCTGACTATTACCGGC
GCCAGGCTGAGGACGAAGCCGATTACTATTGCAACAGCAGGACAGTTCAGGGAAT
CACGTGGTCTTTGGAGGAGGAACTAAGCTGACCGTGGGAGGAGGCAGCGGAGGAGGA
TCTGGAGGAGGAAGTGGAGGAGGATCAGGAGGAGGAAGCGGAGAGGTGCAGCTGGTC
GAAAGCGGAGGAGGAGTGGTCAGGCCAGGAGGGTCCCTGCGACTGTCTTGTGCCGCT
AGTGGGTTCACTTTTGACGATTACGGAATGAGTTGGGTCAGGCAGGCACCAGGAAAG
GGACTGGAGTGGGTGAGCGGCATCAACTGGAATGGAGGCAGTACAGGCTACGCTGAT
TCAGTGAAGGGCCGCTTCACTATTTCTCGAGACAACGCCAAAAATAGTCTGTATCTG
CAGATGAACTCACTGCGCGCCGAGGATACAGCTGTGTACTATTGCGCCAGGGGCCGC
TCCCTGCTGTTTGACTACTGGGGCAGGGAACACTGGTGACTGTCTCACGGGGGGA
AGCGGAGATGCACACAAATCTGAGGTCGCCCATAGATTCAAGGACCTGGGCGAGGAA
AATTTTAAAGCCCTGCTGCTGATCGCATTCGCCCAGTATCTGCAGCAGTGCCCTTTC
GAAGACCACGTGAAGCTGGTCAACGAGGTCACAGAATTTGCCAAAACTTGCGTCGCA
GACGAGAGCGCCGAAAATTGTGATAAGTCCCTGCATACCCTGTTCGGCGATAAACTG

FIG. 15 (cont)

TGTACCGTGGCCACACTGAGGGAGACATACGGGGAAATGGCTGACTGCTGTGCAAAG
CAGGAGCCCGACGCAACGAGTGCTTCTGCAGCACAAAGACGATAACCCAAATCTG
CCCCGACTGGTGCGGCCTGAAGTGGACGTCATGTGTACTGCCTTCCACGATAATGAG
GAAACCTTTCTGAAGAATACCTGTATCAGATTGCCCGGAGACATCCTACTTCTAT
GCTCCTGAACTGCTGTTCTTTGCAAAGCGGTACAAAGCAGCCTTTACCGAGTGCTGT
CAGGCTGCAGATAAAGCCGCTTGCCTGCTGCCTAAGCTGGACGAGCTGAGGGATGAA
GGCAAGGCTAGCTCCGCAAAACAGCGCCTGAAGTGTGCTAGCCTGCAGAAATTCGGC
GAGCGGCCTTCAAGGCTTGGGCAGTGGCCAGACTGTCACAGAGGTTCCCAAAGGCC
GAGTTTGCTGAAGTCAGCAAACTGGTGACTGACCTGACCAAGGTGCACACCGAGTGC
TGTCATGGCGACCTGCTGGAATGCGCCGACGATAGAGCAGATCTGGCCAAGTACATC
TGTGAGAACCAGGACTCCATTTCTAGTAAGCTGAAAGAGTGCTGTGAAAAACCCCTG
CTGGAGAAGTCTCATTGCATCGCCGAGCTGGAAAACGACGAAATGCCAGCTGATCTG
CCCTCTCTGGCAGCCGACTTCGTCGAGAGTAAAGATGTGTGTAAGAATTATGCTGAA
GCAAAGGATGTGTTCCTGGGCATGTTTCTGTACGAGTATGCACGAGCTGGAGGGTCT
GGAGGCAGTGGAGGATCAGGAGGGAGCGGAGGCGACATCCAGATGACCCAGTCCCCT
TCAAGCCTGAGTGCTTCAGTCGGCGATCGAGTGACAATTACTTGCCGGGCCTCTCAG
GACGTCAATACAGCAGTGGCTTGGTATCAGCAGAAGCCTGGGAAAGCACCAAAGCTG
CTGATCTACAGCGCCTCCTTTCTGTATTCCGGAGTGCCTTCTCGGTTCTCTGGCAGT
AGATCAGGGACTGATTTTACCCTGACAATTCCTCTCTGCAGCCAGAGGACTTCGCC
ACCTACTATTGCCAGCAGCACTATACCACACCCCCTACCTTTGGCCAGGGGACAAAA
GTGGAAATCAAGGGGGGAAGTGGCGGGGGATCAGGCGGCGGAAGCGGCGGCGGCAGC
GGCGGCGGATCTGGAGAGGTCCAGCTGGTGGAAAGCGGAGGAGGACTGGTGCAGCCA
GGAGGGAGTCTGAGACTGTCATGTGCTGCAAGCGGCTTCAACATCAAGGATACCTAC
ATTCACTGGGTCAGGCAGGCCCCAGGAAAAGGCCTGGAGTGGGTGGCCCGCATCTAT
CCCACCAATGGCTACACACGCTATGCCGATTCCGTGAAGGGACGATTCACAATTTCC
GCCGACACTTCTAAAAACACGGCTTACCTGCAGATGAACAGCCTGCGAGCCGAGGAC

FIG. 15 (cont)
ACTGCTGTGTACTATTGTGTAGAGGGGGGGGGGACGGGTTTTACGCAATGGACTAC
TGGGGCCAGGGACTCTGGTCACTGTCAGCAGCTGAGGATCC

Base construct # 13 protein:
SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG
SGGGSGGGSGGGSGEVQLVESGGGVVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGGSGDAHKSEVAHRFKDLGEENFKALVLIAFAQYLQQCPF
EDHVKLVNEVTEFAKTCVADESAENCDKSLHTLFGDKLCTVATLRETYGEMADCCAK
QEPERNECFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKCASLQKFG
ERAFKAWAVARLSQRFPKAEFAEVSKLVTDLTKVHTECCHGDLLECADDRADLAKYI
CENQDSISSKLKECCEKPLLEKSHCIAEVENDEMPADLPSLAADFVESKDVCKNYAE
AKDVFLGMFLYEYARRHPDYSVVLLLRLAKTYETTLEKCCAAADPHECYAKVFDEF
AKDVFLGMFLYEYARGGSGGSGGSGGSGGDIQMTQSPSSLSASVGDRVTITCRASQ
DVNTAVAWYQQKPGKAPKLLIYSASFLYSGVPSRFSGSRSGTDFTLTISSLQPEDFA
TYYCQQHYTTPPTFGQGTKVEIKGGSGGGSGGGSGGGSGGGSGEVQLVESGGGLVQP
GGSLRLSCAASGFNIKDTYIHWVRQAPGKGLEWVARIYPTNGYTRYADSVKGRFTIS
ADTSKNTAYLQMNSLRAEDTAVYYCSRWGGDGFYAMDYWGQGTLVTVSS Base construct # 14:
GACATTCAGATGACCCAGTCCCCAAGCTCCCTGTCTGCTAGTGTCGGCGATCGGGTC
ACTATCACCTGCAGAGCCTCTCAGGACGTCAACACAGCCGTGGCTTGGTACCAGCAG
AAGCCTGGCAAAGCACCAAAGCTGCTGATCTACTCAGCCAGCTTTCTGTATAGCGGG
GTGCCTTCCAGATTCTCCGGCTCTAGGAGTGGGACTGATTTTACACTGACTATCTCT

FIG. 15 (cont)

```
AGTCTGCAGCCAGAGGACTTCGCCACCTACTATTGCCAGCAGCACTATACCACACCC
CCTACATTTGGGCAGGGAACTAAAGTGGAAATTAAGGGAGGGTCTGGAGGAGGGAGT
GGAGGAGGGTCAGGCGGAGGGAGCGGAGGAGGGTCCGGCGAGGTGCAGCTGGTCGAA
AGCGGAGGAGGACTGGTGCAGCCTGGAGGCTCTCTGAGGCTGAGTGTGCCCGCTTCA
GGCTTCAACATCAAGGATACCTACATTCATTGGGTCCGACAGGCTCCAGGCAAAGGG
CTGGAGTGGGTGGCAAGAATCTATCCCACAAATGGCTACACTAGATATGCCGATAGC
GTGAAGGGGAGGTTCACAATTAGCGCTGACACCTCCAAAAACACAGCATACCTGCAG
ATGAATAGTCTGCGGGCTGAGGACACTGCAGTGTACTATTGTAGCAGATGGGGGGGA
GACGGCTTTTACGCCATGGATTATTGGGGACAGGGCACTCTGGTGACCGTCTCAAGC
GGAGGGAGCGGGATGCACACAAATCCGAGGTCGCCCATGCTTCAAGGACCTGGGA
GAGGAAATTTTAAAGCCCTGGTGCTGATTGCATTCGCCCAGTACCTGCAGCAGTGC
CCCTTCGAAGACCACGTGAAGCTGGTCAACGAGGTGACCGAATTTGCCAAAACATGC
GTGGCCGACGAGTCAGCTGAAAATTGTGATAAGAGCCTGCATACCCTGTTCGGAGAT
AAACTGTGTACAGTGGGCCACTCTGAGGGAGACATATGGCGAAATGGCAGACTGCTGT
GCCAAGCAGGAGCCCGAACGCAACGAGTGCTTTCTGCAGCACAAAGACGATAACCCA
AATCTGCCCAGGCTGGTGCGCCCTGAAGTGGACGTCATGTGTACTGCCTTCCACGAT
AATGAGGAAACCTTTCTGAAGAAATACCTGTATGAGATCGCCCGGAGACATCCCTAC
TTCTATGCCCCTGAACTGCTGTTCTTTGCTAAACGGTACAAGGCAGCCTTTACCGAG
TGCTGTCAGGCTGCAGATAAAGCCGCTTGCCTGCTGCCTAAGCTGGACGAGCTGAGG
GATGAAGGAAAGGCTTCCTCTGCAAAACAGCGCCTGAAGTGTGCCTCCCTGCAGAAA
TTCGGCGAGCGGGCTTTTAAGGCTTGGGCAGTGGCACGACTGTCCCAGCGATTCCCA
AAGGCCGAGTTTGCTGAAGTCTCTAAACTGGTGACCGACCTGACAAAGGTGCACACC
GAGTGCTGTCATGGCGACCTGCTGGAATGCGCCGACGATAGCAGATCTGGCCAAG
TACATCTGTGAGAACCAGGACTCCATTAGTTCAAAGCTGAAAGAGTGCTGTGAAAAA
CCCCTGCTGGAGAAGTCTCACTGCATCGCAGAGGTGGAAAACGACGAAATGCCAGCA
GATCTGCCTTCCCTGGCAGCAGACTTCGTCGAGTCTAAAGATGTGTGTAAGAATTAT
GCTGAAGCAAAGGATGTGTTCCTGGGCATGTTTCTGTACGAGTATGCACGAGCTGGA
```

FIG. 15 (cont)

GGCTCAGGAGGAAGCGGAGGGTCCGGAGGCTCTGGGGGAAGCTTCGAACTGACCCAG
GACCCCGCTGTGAGCGTTGCACTGGGACAGACTGTGCGCATTACTTGCCAGGGAGAC
AGTCTGCGATCATACTATGCTTCCTGGTACCAGCAGAAGCCAGGCAGGCACCCGTG
CTGGTCATCTATGGGAAAAACAATCGACCTTCCGGCATCCCCGATCGGTTCTCTGGA
TCTAGTTCAGGCAACACAGCTAGCCTGACCATCACAGGGGCACAGGCCGAGGACGAA
GCCGATTACTATTGCAACAGCAGAGACAGCTCCGGCAATCATGTGGTCTTTGGAGGA
GGAACTAAGTTGACCGTGGGAGGAGGATCTGGAGGAGGAAGTGGCGGGGGATCAGGA
GGAGGAAGCGGAGGAGGCAGCGGAGAGGTCCAGCTGGTGGAAAGCGGAGGAGGAGTG
GTCAGGCCAGGAGGGTCTCTGCGACTGAGTTGTGCTGCATCAGGCTTCACTTTTGAC
GATTACGGAATGAGCTGGGTCAGGCAGGCACCAGGGAAGGGACTGGAGTGGGTGAGC
GGCATCAACTGGAATGGAGGCTCTACAGGATACGCTGATAGTGTGAAGGGCCGCTTC
ACTATTAGTGCAGACAACGCCAAAAATTCACTGTATCTGCAGATGAATAGCCTGCGC
GCCGAGGACACAGCTGTGTACTATTGCGCCAGAGGAAGGTCACTGCTGTTTGATTAT
TGGGGGCAGGGCACACTGGTCACCGTCTCCCGCTGAGGATCC

Base construct # 14 protein:

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTEPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSSGGSGDAHKSEVAHRFKDLGEENFKALVLIAFAQYLQQC
PFEDHVKLVNEVTEFAKTCVADESAENCDKSLHTLFGDKLCTVATLRETYGEMADCC
AKQEPERNECFLQHKDDNPNLPRLVRPEVDVMCTAFHDNEETFLKKYLYEIARRHPY
FYAPELLFFAKRYKAAFTECCQAADKAACLLPKLDELRDEGKASSAKQRLKCASLQK
FGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNY
AEAKDVFLGMFLYEYARAGGSGGSGGSGGSGGSSELTQDPAVSVALGQTVRITCQGD

FIG. 15 (cont)

SLRSYYASWYQQKPEQAPVLVIYGKNNRPSGIPDRFSGSSSGNTASLTITGAQAEDE
ADYYCNSRDSSGNHVVFGGGTKLTVGGGSGGGSGGGSGGGSGGGSQEVQLVESGGGV
VRPGGSLRLSCAASGFTFDDYGMSWVRQAPGKGLEWVSGINWNGGSTGYADSVKGRF
TISRDNAKNSLYLQMNSLRAEDTAVYYCARGRSLLFDYWGQGTLVTVSP

Base construct # 15:

TCTTCAGAACTGACCCAGGACCCCGCAGTGAGCGTCGCACTGGGCCAGACCGTGAGA
ATCACATGCCAGGGGATTCCCTGAGGTCTTACTATGCTAGCTGGTACCAGCAGAAG
CCAGGCCAGGCACCCGTGCTGGTCATCTATGGCAAAAACAATAGGCCTTCAGGGATT
CCAGACCGCTTTAGCGGAAGCTCCTCTGGCAACACAGCAAGCCTGACAATTACTGGC
GCTCAGGCAGAGGACGAAGCCGATTACTATTGCAACAGCAGGGATAGTTCAGGCAAT
CACGTGGTCTTCGGAGGAGGAACTAAGCTGACCGTGGGAGGAGGATCTGGAGGAGGA
AGTGGCGGGGATCAGGAGGAGGAAGCGGAGGAGGCAGCGGAGAGGTGCAGCTGGTC
GAAAGCGGAGGAGGAGTGGTCCGCCCAGGAGGGTCTCTGCGACTGAGTTGTGCCGCT
TCAGGATTCACCTTTGACGATTACGGAATGTCCTGGGTGAGGCAGGCACCAGGGAAG
GGACTGGAGTGGGTCTCTGGCATCAACTGGAATGGAGGCTCTACAGGGTACGCTGAC
AGTGTGAAGGGACGGTTCACCATTTCCCGGGATAACGCCAAAAATTCTCTGTATCTG
CAGATGAATAGTCTGCGCGCTGAGGACACCGCAGTGTACTATTGTGCCAGGGGCCGC
AGTCTGCTGTTCGATTACTGGGGCCAGGGAACACTGGTGACTGTCAGCCGAGGAGGA
AGTGGAGGGTCAGGAGGCAGCGGAGGCAGCGGAGGGTCTGTGGTCCTGCTGCTGAGA
CTGGCTAAGACATACGAGACCACACTGGAAAAATGCTGTGCAGCCGCTGACCCCCAT
GAGTGCTATGCCAAGGTGTTCGATGAGTTCAAGCCACTGGTCGAGGAACCCCAGAAC
CTGATCAAGCAGAATTGTGAGCTGTTCGAACAGCTGGGCGAGTACAAATTTCAGAAC
GCCCTGCTGGTGCGCTATACCAAGAAAGTGCCTCAGGTCTCAACCCCAACACTGGTG
GAGGTCAGCAGGAATCTGGGCAAGGTCGGGTCCAAATGCTGTAAGCACCCCGAGGCA
AAACGCATGCCTTGCGCCGAAGACTACCTGTCCGTGGTCCTGAACCAGCTGTGTGTG
CTGCATGAGAAGACACCTGTGTCTGATCGGGTCACTAAATGCTGTACCGAATCTCTG

FIG. 15 (cont)

GTGAACCGGAGACCTTGCTTAGTGCCCTGGAGGTGGACGAAACTATGTCCCAAAG
GAGTTCAATGCTGAAACTTTCACCTTTCACGCAGATATCTGTACCCTGAGCGAGAAG
GAAGACAGATTAAGAAACAGACAGCCCTGGTGGAGCTGGTCAAGCATAAACCAAAG
GCCACCAAGGAACAGCTGAAAGCTGTGATGGACGATTTCGCAGCCTTTGTCCAGAAA
TGCTGTAAGGCTGACGATAAGGAAACATGCTTCGCAGAGGAAGGGAAGAAACTGGTG
GCTGCATCCCAGGCAGCTCTGGGACTGGGAGGCAGTGGAGGATCAGGAGGGAGCGGA
GGCTCCGGAGGAGACATCCAGATGACTCAGTCCCCAAGCTCCCTGTCAGCAAGCGTG
GGCGACCGGGTCACAATTACTTGTAGAGCTTCTCAGGATGTGAATACCGCCGTCGCT
TGGTACCAGCAGAAACCCGGCAAGGCCCCTAAACTGCTGATCTACTCCGCTTCTTTC
CTGTATAGCGGAGTGCCATCCCGGTTCAGCGGGTCAAGGAGCGGAACTGACTTCACC
CTGACAATTCTAGTCTGCAGCCTGAGGATTTTGCCACCTACTATTGCCAGCAGCAC
TATACTACCCCCCTACTTTCGGACAGGGCACCAAGGTGGAAATCAAAGGAGGGTCT
GGAGGAGGGAGTGGAGGAGGGTCAGGCGGAGGGAGCGGAGGAGGGTCCGGCGAAGTC
CAGCTGGTCGAATCCGGAGGAGGACTGGTGCAGCCTGGAGGCTCTCTGAGGCTGAGT
TGTGCAGCCTCAGGCTTTACATCAAGGACACCTACATTCATTGGGTGCGGCAGGCA
CCAGGGAAAGGACTGGAGTGGGTGGCCAGAATCTATCCACAAATGGATACACTCGA
TATGCCGACTCTGTGAAGGGCCGGTTCACAATTAGCGCAGATACCTCCAAAAACACA
GCTACCTGCAGATGAACAGCCTGCGCGCCGAGGATACTGCTGTGTACTATTGCAGC
CGATGGGCGGGGACGGCTTCTACGCTATGGACTATTGGGGCAGGGGACTCTGGTG
ACAGTGAGCAGCTGAGGATCC

Base construct # 15 protein:

SSELTQDPAVSVALGQTVRITCQGDSLRSYYASWYQQKPGQAPVLVIYGKNNRPSGI
PDRPSGSSSGNTASLTITGAQAEDEADYYCNSRDSSGNHVVFGGGTKLTVGGGSGGG
SGGGSGGGSGGGSGEVQLVESGGGVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGGSGGSGGSGGSGGSVVLLRLAKTYETTLEKCCAAADPH

FIG. 15 (cont)

ECYAKVFDEFKPLVEEPQNLIKQNCELFEQLGEYKFQNALLVRYTKKVPQVSTPTLV
EVSRNLGKVGSKCCKHPEAKRMPCAEDYLSVVLNQLCVLHEKTPVSDRVTKCCTESL
VNRRPCFSALEVDETYVPKEFNAETFTFHADICTLSEKERQIKKQTALVELVKHKPK
ATKEQLKAVMDDFAAFVEKCCKADDKETCFAEEGKKLVAASQAALGLGGSGGSGGSG
GSGGDIQMTQSPSSLSASVGDRVTITCRASQDVNTAVAWYQQKPGKAPKLLIYSASF
LYSGVPSRFSGSRSGTDFTLTISSLQPEDFATYYCQQHYTTPPTFGQGTKVEIKGGS
GGGSGGGSGGGSGGGSGEVQLVESGGGLVQPGGSLRLSCAASGFNIKDTYIHWVRQA
PGKGLEWVARIYPTNGYTRYADSVKGRFTISADTSKNTAYLQMNSLRAEDTAVYYCS
RWGGDGFYAMDYWGQGTLVTVSS

Base construct # 16:

GATATTCAGATGACCCAGAGCCCAAGCTCCCTGAGTGCATCAGTGGGCGACAGAGTC
ACAATCACTTGCAGGGCTAGCCAGGATGTGAACACAGCTGTCGCATGGTACCAGCAG
AAACCAGGCAAGGCTCCAAAACTGCTGATCTACAGCGCATCCTTCCTGTATTCCGGC
GTGCCCTCTAGGTTTTCTGGGAGTCGCTCAGGAACTGACTTCACCCTGACAATCTCT
AGTCTGCAGCCTGAGGATTTTGCCACCTACTATTGCCAGCAGCACTACACCACACCC
CCTACTTTCGGCCAGGGGACCAAGGTGGAGATCAAGGGCGGGAGTGGAGGCGGGTCA
GGCGGAGGGAGCGGAGGAGGGTCCGGAGGAGGGTCTGGCGAGGTGCAGCTGGTCGAA
AGCGGAGGAGGACTGGTGCAGCCTGGAGGCAGTCTGCGGCTGTCATGTGCCGCTAGC
GGCTTCAACATCAAGGACACCTACATTCATTGGGTGCGCCAGGCACCAGGAAAAGGC
CTGGAGTGGGTCGCCCGAATCTATCCCACCAATGGGTACACAAGATATGCCGACTCC
GTGAAGGGACGCTTTACAATTTCCGCTGATACTTCTAAAAACACCGCATACCTGCAG
ATGAATAGTCTGAGAGCAGAGGATACTGCCGTGTACTATTGTAGCAGATGGGGGGGA
GACGGCTTCTACGCCATGGACTACTGGGGCCAGGGCACTCTGGTGACCGTCTCAAGC
GGAGGGAGCGGAGGCTCCGGAGGATCTGGAGGGAGTGGAGGCTCAGTGGTCCTGCTG
CTGAGGCTGGCTAAGACCTACGAGACTACCCTGGAAAAATGCTGTGCAGCCGCTGAC
CCCACCGAGTGCTATGCCAAGGTGTTCGATGAGTTCAAGCCACTGGTCGAGGAACCC

FIG. 15 (cont)

CAGAAGCTGATCAAGCAGAATTGTGAGCTGTTCGAACAGCTGGGCGAGTACAAATTT
CAGAACGCCCTGCTGGTGGCCTATACAAAGAAAGTGCCTCAGGTCAGTACTCCAACC
CTGGTGGAAGTCTCACGGAATGTGGGAAAGGTCGGCAGCAAGTGCTGTAAACACCCC
GAGGCAAAAGAATGCCTTGCGCCGAAGACTACCTGAGGGTGGTCCTGAATCAGCTG
TGTGTGCTGCATGAGAAGACACCTGTGAGCGATAGGGTCACAAAATGCTGTACTGAA
TCCCTGGTGAACCGGAGACCTTGCTTTTCTGCTCTGGAGGTGGACGAAACTTATGTC
CCAAAGGAGTTCAATGCCGAAACATTCACTTTTCACGCTGATATCTGTACCCTGAGC
GAGAAGGAACGCCAGATTAAGAAACAGACAGCCCTGGTGGAGCTGGTCAAGCATAAA
CCAAAGGCAACTAAGGAACAGCTGAAAGCCGTGATGGACGATTTCGCAGCCTTTGTC
GAGAAGTGCTGTAAAGCCGACGATAAGGAAACCTGCTTTGCTGAGGAAGGCAAGAAA
CTGGTGGCTGCAAGCCAGGCAGCTCTGGGACTGGGAGGAAGCGGAGGGTCCGGAGGC
TCTGGGGAAGTGGAGGGTCCTCTGAGCTGACCCAGGACCCGCTGTGTCCGTCGCA
CTGGGACAGACCGTGCGAATTACATGTCAGGGCGATTCACTGCGGAGCTACTATGCT
TCTTGGTACCAGCAGAAGCCTGGCCAGGCACCAGTGCTGGTCATCTATGGAAAAAAC
AATCGGCCCAGTGGCATTCCTGACAGATTTTCAGGCAGTTCAAGCGGGAACACCGCA
TCCCTGACCATCACAGGCGCCCAGGCTGAGGACGAAGCCGATTACTATTGCAACTCT
AGGGATTCCTCTGGCAATCATGTGGTCTTCGGAGGCGGGACAAAGCTGACTGTGGGA
GGAGGGAGTGGCGGAGGGTCAGCGGCGGGAGCGGCGGCGGGTCCGGCGGCGGGTCT
GGAGAAGTGCAGCTGGTCGAATCCGGAGGAGGAGTGGTCCGCCCAGGAGGCAGTCTG
CGACTGTCATGTGCAGCCAGCGGGTTCACCTTTGACGATTACGGAATGTCCTGGGTG
CGGCAGGCACCAGGCAAGGGACTGGAGTGGGTGTCTGGCATCAACTGGAATGGGGGC
AGCACAGGCTACGCTGACTCTGTGAAGGGGCGATTCACTATTAGCCGGGATAACGCC
AAAAATTCCCTGTATCTGCAGATGAACAGCCTGAGAGCCGAGGACACAGCTGTGTAC
TATTGCGCCAGGGGCGGTCACTGCTGTTTGATTATTGGGGCAGGGAACTCTGGTC
ACTGTCTCTAGGTGAGGATCC

Base construct # 16 protein:

FIG. 15 (cont)

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVRQAPGKG
LEWVARIYPTNGYTRYADSVKGRFTISADTSKNTAYLQMNSLRAEDTAVYYCSRWGG
DGFYAMDYWGQGTLVTVSSGGSGGSGGSGGSGGSVVLLRLAKTYETTLEKCCAAAD
PHECYAKVFDEFKPLVEEPQNLIKQNCELFEQLGEYKFQNALLVRYTKKVPQVSTPT
LVEVSRNLGKVGSKCCKHPEAKRMPCAEDYLSVVLNQLCVLHEKTPVSDRVTKCCTE
SLVNRRPCFSALEVDETYVPKEFNAETFTFHADICTLSEKERQIKKQTALVELVKHK
PKATKEQLKAVMDDFAAFVEKCCKADDKETCFAEEGKKLVAASQAALGLGGSGGGGG
SGGSGGSSELTQDPAVSVALGQTVRITCQGDSLRSYYASWYQQKPGQAPVLVIYGKN
NRPSGIPDRFSGSSSGNTASLTITGAQAEDEADYYCNSRDSSGNHVVFGGGTKLTVG
GGSGGGSGGGSGGGSGGGSGEVQLVESGGGVVRPGGSLRLSCAASGFTFDDYGMSWV
RQAPGKGLEWVSGINWNGGSTGYADSVKGRFTISRDNAKNSLYLQMNSLRAEDTAVY
YCARGRSLLFDYWGQGTLVTVSK

Sequence for v593:

GACATTCAGATGACACAGAGCCCAAGCTCCCTGTCTGCAAGTGTCGGCGATCGAGTG
ACAATCACTTGCCGGGCTTCCAGGACGTCAACACTGCCGTGGCTTGGTACCAGCAG
AAACCTGGGAAGGCCCCAAAACTGCTGATCTACTCAGCTAGCTTTCTGTATAGCGGA
GTGCCCTCCCGGTTCTCCGGATCTAGAAGTGGCACCGATTTTACCCTGACAATCTCT
AGTCTGCAGCCTGAGGACTTCGCCACATACTATTGCCAGCAGCACTATACCACACCC
CCTACCTTTGGGCAGGGAACAAAGGTGGAAATCAAAGGAGGGTCTGGAGGAGGGAGT
GGAGGAGGTCAGCCGGAGGAGCCGAGGAGGGTCCGGCGAGGTGCAGCTGGTCGAA
AGCGGAGGAGGACTGGTGCAGCCTGGAGGCTCTCTGAGGCTGAGTTGTGCCGCTTCA
GGCTTCAACATCAAAGATACCTACATTCATTGGGTCCGCCAGGCTCCAGGCAAGGGA

FIG. 15 (cont)

```
CTGGAGTGGTGGCACGAATCTATCCACAAATGGATACACTGGTATGCCGATTCC
GTGAAAGGCAGATTCACTATTAGCGCTGACACCTCCAAGAACACAGCATACCTGCAG
ATGAATAGTCTGCGAGCAGAGGACACGGCCGTGTACTATTGCTCACGGTGGGCGGGA
GACGGCTTTACGCCATGGATTATTGGGGACAGGGCACTCTGGTGACCGCTCAAGC
GGAGGGAGCGGAGATGCACACAAGTCCGAGGTCGCTCATGCTTCAAAGACCTGGGC
GAGGAAAACTTTAAGGCCCTGGTGCTGATTGCATTCGCCCAGTACCTGCAGCAGTGC
CCATTCGAGGACCACGTGAAACTGGTCAACGAAGTGACTGAATTTGCCAAGACCTGC
GTGGCTGACGAGTCAGCAGAAAATTGTGATAAAAGCCTGCATACACTGTTCGGCGAT
AAGCTGTGTACAGTGGCCACTCTGAGGAGACTTATGGGGAAATGGCCGACTGCTGT
GCTAAACAGGAGCCAGAACGCAACGAGTGCTTTCTGCAGTACAAGGACGATAACCCA
AATCTGCCCAGACTGGTGAGGCCCGAAGTGGACGTCATGTGTACAGCCTTCCACGAT
AATGAGGAAACTTTTCTGAAGAAATACCTGTATGAGATGCTCGGAGACATCCCTAC
TTCTATGCCCTGAACTGCTGTCTTTGCTAAGAGGTACAAAGCAGCCTTTACCGAG
TGCTGTCAGGCTGCAGATAAGGCCGCTTGCTGCTGCCAAAACTGGACGAGCTGAGA
GATGAAGGCAAGGCATCCTCTGCCAAGCAGAGGCTGAAATGTGCCTCCCTGCAGAAG
TTCGGGAGAGGGCTTTTAAAGCTTGGGCAGTGGCACGACTGAGCCAGCGATTCCCA
AAGGCTGAGTTTGCAGAAGTCTCCAAGCTGGTGACCGACCTGACAAAAGTGCACACC
GAGTGCTGTCATGGCGACCTGCTGGAATGCGCCGACGATCGCGCCGATCTGGCTAAG
TACATCTGTGAGAACCAGGACAGCATTAGTTCAAAGCTGAAAGAGTGCTGTGAAAAG
CCTCTGCTGGAGAAATCCCACTGCATTGCAGAGGTGGAAAACGACGAAATGCCAGCA
GATCTGCCTTCCCTGGCAGCAGACTTCGTCGAGTCTAAGGATGTGTGTAAAAATTAC
GCTGAAGCAAAGGATGTGTTCCTGGGCATGTTTCTGTACGAGTATGCCAGGCGCCAC
CCTGACTACAGCGTGGTCCTGCTGCTGCGGCTGGCTAAAACCTATGAGACTACCCTG
GAAAAGTGCTGTGCTGCAGCCGATCCACATGAGTGCTATGCCAAGGTCTTCGACGAG
TTCAAGCCACTGGTGGAGGAACCCCAGAACCTGATCAAACAGAATTGTGAGCTGTTT
GAACAGCTGGGCGAGTACAAGTTCCAGAACGCCCTGCTGGTGAGATATACAAAGAAA
GTCCCTCAGGTGAGTACTCCAACCCTGGTGGAAGTCTCACGGAATCTGGGCAAAGTG
```

FIG. 15 (cont)

GGGAGCAAGTGCTGTAAACACGCCGAGGCAAAGAGAATGCCTTGCGCCGAAGATTAC
CTGTCTGTGGTCCTGAATCAGCTGTGTGTGCTGCATGAGAAACTCCTGTCAGCGAC
CGGGTGACTAAGTGCTGTACCGATCCCTGGTGAACCGACGGCCTTGCTTCTCTGCC
CTGGAGGTCGATGAAACATATGTGCCAAGGAGTTTAATGCAGAAACATTCACTTTT
CACGCCGACATCTGTACTCTGAGCGAGAAGGAAAGACAGATTAAGAAACAGACCGCC
CTGGTCGAGCTGGTGAAGCATAAACCAAAGGCTACCAAGGAACAGCTGAAAGCAGTC
ATGGACGATTTCGCTGCATTTGTGGAGAAGTGCTGTAAAGCAGACGATAAGGAAACA
TGCTTCGCCGAGGAAGGGAAGAAACTGGTGGCAGCTAGCCAGGCAGCACTGGGACTG
GGAGGCTCAGGAGGAAGCGGAGGGTCCGGAGGCTCTGGAGGAAGCTCCGAGCTGACC
CAGGACCCCGCAGTGTCTGTCGCACTGGGACAGACAGTGAGGATTACTTGTCAGGGG
GACAGTCTGCGCTCATACTATGCTAGCTGGTACCAGCAGAAACCAGGCCAGGCACCC
GTGCTGGTCATCTATGGCAAGAACAATCGCCCTTCCGGGATTCCAGATCGATTCTCT
GGGTCTAGTTCAGGAAACACCGCATCTCTGACCATCACAGGCGCCCAGGCTGAGGAC
GAAGCTGATTACTATTGCAACAGCAGAGACAGCTCCGGCAATCACGTGGTCTTTGGA
GGAGGAACTAAGCTGACCGTGGGAGGAGGATCTGGAGGAGGAAGTGGCGGGGGATCA
GGAGGAGGAAGCGGAGGAGGCAGCGGAGAGGTCCAGCTGGTGGAAAGCGGAGGAGGC
GTGGTCAGACCAGGAGGGTCTCTGAGACTGTCCTGTGCTGCATCAGGATTCACCTTT
GACGATTACGGCATGTCTTGGGTCAGGCAGGCACCTGGGAAGGGCCTGGAATGGGTG
AGTGGCATCAACTGGAATGGAGGCTCTACCGGGTACGCCGATAGTGTGAAAGGAAGG
TTCACAATTAGTCGCGACAACGCTAAGAACAGCCTGTATCTGCAGATGAATAGCCTG
CGCGCTGAGGACACAGCAGTGTACTATTGCGCCAGGGGGAGGTCACTGCTGTTTGAT
TATTGGGGCAGGGAACTCTGGTCACTGTCTCACGGTGAGGATCC

Protein Sequence for v593:

DIQMTQSPSSLSASVGDRVTITCRASQDVNTAVAWYQQKPGKAPKLLIYSASFLYSG
VPSRFSGSRSGTDFTLTISSLQPEDFATYYCQQHYTTPPTFGQGTKVEIKGGSGGGS
GGGSGGGSGGGSGEVQLVESGGGLVQPGGSLRLSCAASGFNIKDTYIHWVRQAPGKG

FIG. 15 (cont)

LEWVARIYPTNGYTRYADSVKGRFTISADTSKNTAYLQMNSLRAEDTAVYYCSRWGG
DGFYAMDYWGQGTLVTVSSGGSGDAHKSEVAHRFKDLGEENFKALVLIAFAQYLQQC
PFEDHVKLVNEVTEFAKTCVADESAENCDKSLHTLFGDKLCTVATLRETYGEMADCC
AKQEPERNECFLQHKDDNPNLPRLVRPEVDVMCTAFHDNEETFLKKYLYEIARRHPY
FYAPELLFFAKRYKAAFTECCQAADKAACLLPKLDELRDEGKASSAKQRLKCASLQK
FGERAFKAWAVARLSQRFPKAEFAEVSKLVTDLTKVHTECCHGDLLECADDRADLAK
YICENQDSISSKLKECCEKPLLEKSHCIAEVENDEMPADLPSLAADFVESKDVCKNY
AEAKDVFLGMFLYEYARRHPDYSVVLLLRLAKTYETTLEKCCAAADPHECYAKVFDE
FKPLVEEPQNLIKQNCELFEQLGEYKFQNALLVRYTKKVPQVSTPTLVEVSRNLGKV
GSKCCKHPEAKRMPCAEDYLSVVLNQLCVLHEKTPVSDRVTKCCTESLVNRRPCFSA
LEVDETYVPKEFNAETFTFHADICTLSEKERQIKKQTALVELVKHKPKATKEQLKAV
MDDFAAFVEKCCKADDKETCFAEEGKKLVAASQAALGLGGSGGSGGSGGSGGSSELT
QDPAVSVALGQTVRITCQGDSLRSYYASWYQQKPGQAPVLVIYGKNNRPSGIPDRFS
GSSSGNTASLTITGAQAEDEADYYCNSRDSSGNHVVFGGGTKLTVGGGSGGGSGGGS
GGGSGGGSGEVQLVESGGGVVRPGGSLRLSCAASGFTFDDYGMSWVRQAPGKGLEWV
SGINWNGGSTGYADSVKGRFTISRDNAKNSLYLQMNSLRAEDTAVYYCARGRSLLFD
YWGQGTLVTVSR

Sequence for v594:
AGTAGCGAACTGACCCAGGACCCCGCAGTGAGCGTCGCACTGGGGCAGACAGTGCGA
ATCACTTGCCAGGGAGACAGCCTGCGGTCCTACTATGCTTCCTGGTACCAGCAGAAA
CCTGGCCAGGCACCAGTGCTGGTCATCTATGGAAGAACAATCGGCCCAGCGGCATC
CCCGATAGATTCTCCGGCAGCTCCTCTGGAACACCGCCTCTCTGACAATTACTGGG
GCCCAGGCTGAGGACGAAGCTGATTACTATTGCAACAGCAGGGACAGTTCAGGAAAT
CACGTGGTCTTTGGAGGAGGAACTAAGCTGACCGTGGGAGGAGGCAGCGGAGGAGGA
TCTGGAGGAGGAAGTGGAGGAGGATCAGGAGGAGGAAGCGGAGAGGTGCAGCTGGTC
GAAAGCGGAGGAGGAGTGGTCAGACCTGGAGGGTCCCTGAGGCTGTCTTGTGCCGCT

FIG. 15 (cont)

AGTGGCTTACCTTTGACGATTACGGAATGAGTTGGGTCCGGCAGGCACCAGGAAAG
GGACTGGAGTGGGTGTCAGGCATCAACTGGAATGGAGGCAGTACCGGATACGCCGAT
TCAGTGAAGGCAGGTTCACAATTTCTCGCGACAACGCTAAGAATAGTCTGTATCTG
CAGATGAACTCACTGAGAGCTGAGGATACAGCAGTGTACTATTGCGCCAGAGGCAGG
TCTCTGCTGTTTGACTACTGGGGCAGGGAACACTGGTGACTGTCTCACGAGGACGA
AGCGGCGATGCACACAAGTCCGAGGTCGCTCATAGATTCAAAGACCTGGGGGAGGAA
AATTTTAAGGCCCTGGTGCTGATCGCATTCGCCCAGTATCTGCAGCAGTGCCCATTC
GAGGACCACGTGAAACTGGTCAACGAGGTGACCGAATTTGCCAAGACATGCGTGCCC
GACGAGAGCGCTGAAAATTGTGATAAATCCCTGCATACACTGTTCGGGGATAAGCTG
TGTACCGTGGCCACACTGAGGGAGACTTACGGAGAAATGGCAGACTGCTGTGCCAAA
CACGAGCCAGAACGCAACGAGTGCTTTCTGCAGCACAAGGACGATAACCCAAATCTG
CCACGACTGGTGCGACCAGAAGTGGACGTCATGTGTACAGCCTTCCACGATAATGAG
GAAACTTTTCTGAAGAAATACCTGTATGAGATCGCCCGGAGACATCCCTACTTCTAT
GCTCCTGAACTGCTGTTCTTTGCAAAACGGTACAAGGCAGCCTTTACCGAGTGCTGT
CAGGCTGCAGATAAGGCCGCTTGCCTGCTGCCAAAACTGGACGAGCTGAGAGATGAA
GGCAAGGCAAGCTCCGCCAAGCAGAGGCTGAAATGTGCTAGCCTGCAGAAGTTCGGG
GAGAGGGCCTTCAAGGCTTGGGCAGTGGCACGACTGTCACAGAGATTCCCCAAGGCT
GAGTTTGCAGAAGTCAGCAAGCTGGTGACTGACCTGACCAAAGTGCACACCGAGTGC
TGTCATGGCGACCTGCTGGAATGCGCCGACGATCGCGCCGATCTGGCTAAGTACATC
TGTGAGAACCAGGACAGCATTTCTAGTAAGCTGAAAGAGTGCTGTGAAAAGCCTCTG
CTGGAGAAATCCCACTGCATCGCCGAGGTGGAAAACGACGAAATGCCAGCTGATCTG
CCCTCTCTGGCAGCCGACTTCGTCGAGAGTAAGGATGTGTGTAAAAATTACGCTGAA
GCAAAGGATGTGTTCCTGGGCATGTTTCTGTACGAGTATGCAAGGCGACACCCAGAC
TACTCCGTGGTCCTGCTGCTGCGCTGGCTAAAACCTATGAGACCACACTGGAAAAG
TGCTGTGCTGCAGCCGATCCTCATGAGTGCTATGCCAAGGTCTTCGACGAGTTCAAG
CCACTGGTGGAGGAACCCCAGAACCTGATCAAGCAGAATTGTGAGCTGTTTGAACAG
CTGGGCGAGTACAAGTTCCAGAACGCCCTGCTGGTGAGATATACAAGAAAGTCCCT

FIG. 15 (cont)

CAGGTGTCAACCCAACACTGGTGGAGGTCAGCCGGAATCTGGGAAAGTGGGCAGC
AAATGCTGTAAGCACCCGAGCAAAGAGAATGCCTTGCGCGAAGATTACCTGTCT
GTGGTCCTGAACCAGCTGTGTGCTGCATGAGAAAACTCCTGTCAGTGACAGGGTG
ACCAAGTGCTGTACAGAATCTCTGGTGAACCGACGGCCTTGCTTCAGTGCCCTGGAG
GTCGATGAAACATATGTGCCAAAGGAGTTTAATGCCGAAACTTTCACCTTTCACGCT
GACATCTGTACTCTGAGCGAGAAGGAACGCCAGATTAAGAAACAGACCGCCCTGGTC
GAGCTGGTGAAGCATAAACCAAAGGCAACAAAGGAACAGCTGAAAGCCGTCATGGAC
GATTTCGTGCATTTGTGGAGAAATGCTGTAAGGCCGACGATAAGGAAACTTGCTTC
GCTGAGGAAGGAAAGAAACTGGTGGCAGCTTCCCAGGCAGCACTGGGACTGGGAGGG
TCTGGAGGCAGTGGAGGATCAGGAGGGAGCGGAGGCGACATCCAGATGACCCAGTCC
CCCTCAAGCCTGAGTGCCTCAGTCGGCGATCGCGTGACAATTACTTGTCGAGCTTCT
CAGGACGTCAATACAGCCGTGGCTTGGTATCAGCAGAAGCCTGGAAAGGCACCAAAA
CTGCTGATCTACAGCGCCTCCTTTCTGTATTCCGGCGTGCCCTCTCGATTCTCTGGA
AGTGGTCAGGCACCGATTTTACCCTGACAATTTCCTCTCTGCAGCCTGAGGACTTC
GCCACATACTATTGCCAGCAGCACTATACTACCCCCCCTACTTTTGGCCAGGGGACC
AAGGTGGAAATCAAAGGGGAAGTGGCGGGGGATCAGGCGGCGGAAGCGGCGGCGGC
AGCGGCGGCGGATCTGGAGAGGTCCAGCTGGTGGAAAGCGGAGGAGGACTGGTGCAG
CCTGGAGGGAGTCTGCGACTGTCATGTGCTGCAAGCGGCTTCAACATCAAAGATACC
TACATTCATTGGGTCAGGCAGGCCCCTGGAAAGGGCCTGGAATGGGTGGCACGAATC
TATCCCACTAATGGCTACACCAGATATGCCGATTCCGTGAAAGGCCGCTTCACTATT
TCCGCTGACACATCTAAGAACACTGCATACCTGCAGATGAACAGCCTGCGCGCTGAG
GACACCGCAGTGTACTATTGCTCTCGATGGGGCGGCGACGGCTTCTACGCAATGGAC
TACTGGGGCAGGGACACTGGTGACTGTGAGCAGCTGAGGATCC

Protein Sequence for v594:
SSELTQDPAVSVALGQTVRITCQGDSLRSYYASWYQQKPGQAPVLVIYGKNNRPSGI
PDRFSGSSSGNTASLTITGAQAEDEADYYCNSRDSSGNHVVFGGGTKLTVGGGSGGG

FIG. 15 (cont)

SGGGSGGGSGGGSGEVQLVESGGGVVRPGGSLRLSCAASGFTFDDYGMSWVRQAPGK
GLEWVSGINWNGGSTGYADSVKGRFTISRDNAKNSLYLQMNSLRAEDTAVYYCARGR
SLLFDYWGQGTLVTVSRGGSGDAHKSEVAHRFKDLGEENFKALVLIAFAQYLQQCPF
EDHVKLVNEVTEFAKTCVADESAENCDKSLHTLFGDKLCTVATLRETYGEMADCCAK
QEPERNECFLQHKDDNPNLPRLVRPEVDVMCTAFHDNEETFLKKYLYEIARRHPYFY
APELLFFAKRYKAAFTECCQAADKAACLLPKLDELRDEGKASSAKQRLKCASLQKFG
ERAFKAWAVARLSQRFPKAEFAEVSKLVTDLTKVHTECCHGDLLECADDRADLAKYI
CENQDSISSKLKECCEKPLLEKSHCIAEVENDEMPADLPSLAADFVESKDVCKNYAE
AKDVFLGMFLYEYARRHPDYSVVLLLRLAKTYETTLEKCCAAADPHECYAKVFDEFK
PLVEEPQNLIKQNCELFEQLGEYKFQNALLVRYTKKVPQVSTPTLVEVSRNLGKVGS
KCCKHPEAKRMPCAEDYLSVVLNQLCVLHEKTPVSDRVTKCCTESLVNRRPCFSALE
VDETYVPKEFNAETFTFHADICTLSEKERQIKKQTALVELVKHKPKATKEQLKAVMD
DFAAFVEKCCKADDKETCFAEEGKKLVAASQAALGLGGSGGSGGSGGSGGDIQMTQS
PSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKGGSGGGSGGGSGGG
SGGGSEVQLVESGGGLVQPGGSLRLSCAASGFNIKDTYIHWVRQAPGKGLEWVARI
YPTNGYTRYADSVKGRFTISADTSKNTAYLQMNSLRAEDTAVYYCSRWGGDGFYAMD
YWGQGTLVTVSS

MULTIVALENT HETEROMULTIMER SCAFFOLD DESIGN AND CONSTRUCTS

CROSS-REFERENCE

This patent application claims the benefit of U.S. Provisional Application Ser. No. 61/449,016 filed Mar. 3, 2011, which is incorporated by reference herein in its entirety

SEQUENCE LISTING

The instant application contains a Sequence Listing which has been submitted in ASCII format via EFS-Web and is hereby incorporated by reference in its entirety. Said ASCII copy, created on May 21, 2012, is named Zymeworks-40252-705-201-SeqLst.txt and is 223,779 bytes in size.

FIELD OF INVENTION

The field of the invention is the rational design of a scaffold for custom development of biotherapeutics.

DESCRIPTION OF RELATED ART

In the realm of therapeutic proteins, antibodies with their multivalent target binding features are excellent scaffolds for the design of drug candidates. Advancing these features further, designed bispecific antibodies and other fused multispecific therapeutics exhibit dual or multiple target specificities and an opportunity to create drugs with novel modes of action. The development of such multivalent and multispecific therapeutic proteins with favorable pharmacokinetics and functional activity has been a challenge.

Human serum albumin (HSA, or HA), a protein of 585 amino acids in its mature form is responsible for a significant proportion of the osmotic pressure of serum and also functions as a carrier of endogenous and exogenous ligands. The role of albumin as a carrier molecule and its stable nature are desirable properties for use as a carrier and transporter of polypeptides in vivo.

Human serum albumin possesses many desirable characteristics. HSA is found throughout the body, but more specifically in the interstitial space and in blood at serum concentrations of 40 g/L which is equivalent to 0.7 mM (Yeh et al., Proc. Natl. Acad. Sci. USA, 89:1904-1908 (1992)). HSA is considered to be the most abundant protein of the serum and is responsible for maintaining osmolarity. HSA has favorable pharmacokinetic properties and is cleared very slowly by the liver and kidney displaying in vivo half-lives up to several weeks (Yeh et al., Proc. Natl. Acad. Sci. USA, 89:1904-1908 (1992); Waldmann, T. A., Albumin Structure, Function and Uses, pp. 255-273 (1977); Sarav et al., J Am Soc Nephrol 20:1941-1952 (2009)). HSA lacks enzymatic activity and antigenicity thereby eliminating potentially undesirable side effects. HSA acts as a carrier for endogenous as well as exogenous ligands. Combined, these features can be extended, at least partially, onto albumin based fusion protein. The poor pharmacokinetic properties displayed by therapeutic proteins can then be circumvented.

SUMMARY OF THE INVENTION

Provided herein are multifunctional heteromultimers and methods to design them. In certain embodiments are heteromultimers, each heteromultimer comprising: at least a first monomer unit that comprises at least one cargo molecule, and a first transporter polypeptide; and at least a second monomer unit that comprises at least one cargo molecule and a second transporter polypeptide; wherein at least one transporter polypeptide is derived from a monomeric protein and wherein said transporter polypeptides self-assemble to form a quasi-native structure of said monomeric protein or analog thereof. In certain embodiments, at least one cargo molecule is a drug, or a therapeutic agent. In certain embodiments, at least one cargo molecule is a biomolecule. In an embodiment, the at least one biomolecule is a DNA, RNA, PNA or polypeptide. In an embodiment, at least one cargo molecule is a polypeptide. In certain embodiments, each monomeric transporter polypeptide is unstable and preferentially forms a heteromultimer with at least one other transporter polypeptide. In certain embodiments, each monomeric transporter polypeptide is stable and preferentially forms a heteromultimer with at least one other transporter polypeptide. In certain embodiments, the heteromultimerization interface comprises at least one disulfide bond. In certain embodiments, the heteromultimerization interface does not comprise a disulfide bond.

In specific embodiments is a heteromultimer that comprises: at least two monomers, wherein each monomer comprises at least one cargo molecule attached to a transporter polypeptide, such that said monomers self-assemble to form the heteromultimer. In certain embodiments is a heteromultimer that comprises: at least two monomeric proteins, wherein each monomeric protein comprises at least one cargo polypeptide, attached to a transporter polypeptide, wherein at least one transporter polypeptide is derived from a monomeric protein and wherein said transporter polypeptides self-assemble to form a quasi-native structure of said monomeric protein or analog thereof. In certain embodiments is a heteromultimer that comprises: at least two monomeric proteins, wherein each monomeric protein comprises at least one cargo polypeptide attached to a transporter polypeptide, such that said monomeric proteins self-assemble via the transporter polypeptide to form the heteromultimer, and wherein at least one transporter polypeptide is derived from a monomeric protein and wherein said transporter polypeptides self-assemble to form a quasi-native structure of said monomeric protein or analog thereof. In certain embodiments, the heteromultimer is a heterodimer. In an embodiment, the heteromultimer is bispecific. In an embodiment, the heteromultimer is multispecific. In certain embodiments, the heteromltimer is bivalent. In an embodiment the heteromultimer is multivalent. In an embodiment, the heteromultimer is multifunctional. In certain embodiments, at least one transporter polypeptide is not derived from an antibody. In certain embodiments, the transporter polypeptides are not derived from an antibody. In certain embodiments, the transporter polypeptides are derivatives of albumin. In certain embodiments of the hetermultimer described herein, the transporter polypeptides are derived from human serum albumin (HSA or HA) of SEQ ID No. 1. In certain embodiments of the hetermultimer described herein, the transporter polypeptides are derived from alloalbumins (HAA). In certain embodiments of the hetermultimer described herein, the transporter polypeptides are derived from sequence homologous to the human serum albumin (HSA or HA) of SEQ ID No. 1.

In some embodiments of the heteromultimer described herein, the transporter polypeptides are derivatives of an annexin protein. In an embodiment, the transporter polypeptides are derived from different annexin proteins. In certain embodiments, the transporter polypeptides are derived from the same annexin protein. In an embodiment, at least one transporter polypeptide is derived from Annexin A1 or lipocortin I. In certain embodiments of the heteromultimer, all transporter polypeptides are derived from Annexin A1 of SEQ ID NO: 14. In certain embodiments of the heteromultimer, at least one transporter polypeptides is derived from a sequence homologous to SEQ ID NO: 14. In an embodiment, at least one transporter polypeptide is derived from Annexin A2 or annexin II. In certain embodiments of the heteromultimer, all transporter polypeptides are derived from Annexin A2 or lipocortin II. In an embodiment, at least one transporter polypeptide is derived from Annexin like protein. In certain embodiments of the heteromultimer, all transporter polypeptides are derived from Annexin like protein. In an embodiment, at least one transporter polypeptide is derived from the group comprising Annexin A1-Annexin A7. In an embodiment of the heteromultimer described herein, all transporter polypeptides are derived from the group comprising Annexin A1-Annexin A7. 14. In certain embodiments, the first annexin based transporter polypeptide has a sequence comprising SEQ ID NO:15, and the second annexin based transporter polypeptide has a sequence comprising SEQ ID NO: 16.

In some embodiments of the heteromultimer described herein, the transporter polypeptides are derivatives of transferrin. In an embodiment, at least one transporter polypeptide is derived from transferrin. In certain embodiments of the heteromultimer, at least one transporter polypeptides are derived from transferrin of SEQ ID NO: 19 or analog thereof. In certain embodiments of the heteromultimer, at least one transporter polypeptide is derived from a polypeptide seuquence homologous to the transferrin. In certain embodiments of the heteromultimer described herein, at least one transporter polypeptide is derived from apo-transferrin. In certain embodiments, the first transferrin based transporter polypeptide has a sequence comprising SEQ ID NO:15 and the second transferrin based transporter polypeptide has a sequence comprising SEQ ID NO: 16.

In certain embodiments of the heteromultimer, at least one cargo molecule is a cargo polypeptide. In an embodiment of the heteromultimer described herein, all cargo molecules are cargo polypeptides. In certain embodiments, the cargo polypeptides are therapeutic proteins or fragments or variants thereof. In certain embodiments, the cargo polypeptides are antigens or fragments or variants thereof. In certain embodiments, the cargo polypeptides are antigen receptors or fragments or variants thereof. In some embodiments, the cargo polypeptide is an antibody, an antibody domain, a ligand or a receptor that binds a target polypeptide. In some embodiments, at least one cargo polypeptide is fused to the transporter polypeptide. In certain embodiments, at least one cargo polypeptide is attached to the N-terminus of the transporter polypeptide. In some embodiments, at least one cargo polypeptide is attached to the C-terminus of the transporter polypeptide. In some embodiments, at least one cargo polypeptide is chemically linked to the transporter polypeptide. In some embodiments of the heteromultimers described herein, at least one cargo polypeptide comprises GLP-1 or fragment or variant thereof. In some embodiments, at least one cargo polypeptide comprises glucagon or fragment or variant thereof. In an embodiment, at least one cargo polypeptide comprises an EGF-A like domain.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide. In certain embodiments, the heteromultimer is a heterodimer. In an embodiment, the heteromultimer is multispecific. In an embodiment, the heteromultimer is bispecific. In certain embodiments of the heteromultimer, the transporter polypeptides are derivatives of the same protein. In certain embodiments, the transporter polypeptides are derivatives of albumin. In certain embodiments of the hetermultimer described herein, the transporter polypeptides are derived from human serum albumin of SEQ ID No. 1. In certain embodiments, the transporter polypeptides are derivatives of an annexin. In an embodiment, the transporter polypeptides are derivatives of Annexin A2. In some embodiments, the transporter polypeptides are derivatives of transferrin.

In certain embodiments, are heteromultimers, each heteromultimer comprising: at least a first monomeric protein that comprises at least one cargo polypeptide and a first transporter polypeptide comprising a first segment of human serum albumin; and at least a second monomeric protein that comprises at least one cargo polypeptide, fragment and a second transporter polypeptide comprising a second segment of human serum albumin; wherein said transporter polypeptides self-assemble to form a quasi-native structure of albumin or analog thereof. In certain embodiments, the first and second segments of human serum albumin are from non-overlapping regions of the protein. In certain embodiments, there is an overlap between the sequences of the first and second segments of human serum albumin. In some embodiments, the overlap is a 5% overlap. In an embodiment, the overlap is a 10% overlap. In certain embodiments, the first segment of human serum albumin comprises a sequence of SEQ ID NO:2, and the second segment of human serum albumin comprises a sequence of SEQ ID NO: 3. In certain embodiments, the first segment of human serum albumin comprises a sequence of SEQ ID NO:8, and the second segment of human serum albumin comprises a sequence of SEQ ID NO: 10.

In certain embodiments, are heteromultimers, each heteromultimer comprising: at least a first monomeric protein that comprises at least one cargo polypeptide and a first transporter polypeptide comprising a sequence of SEQ ID NO:2; and at least a second monomeric protein that comprises at least one cargo polypeptide, and a second transporter polypeptide comprising a sequence of SEQ ID NO: 3. In certain embodiments, are heteromultimers, each heteromultimer comprising: at least a first monomeric protein that comprises at least one cargo polypeptide and a first transporter polypeptide comprising a sequence of SEQ ID NO:8; and at least a second monomeric protein that comprises at least one cargo polypeptide and a second transporter polypeptide comprising a sequence of SEQ ID NO: 10. In certain embodiments of the hetermultimer described herein, at least one transporter polypeptide is derived from alloalbumins. In certain embodiments, both transporter polypeptides are derived from alloalbumins. In certain embodiments, all transporter polypeptides are derivatives of the same alloalbumin. In some other embodiments, the transporter polypeptides are derivatives of different alloalbumins. In some embodiments, each transporter polypeptide is an alloalbumin derivative based on an alloalbumin selected from Table 2. In certain embodiments, the first monomeric protein comprises two cargo polypeptides. In some embodiments, the second monomeric protein comprises two cargo polypeptides. In some embodiment, at least one of the monomeric proteins is engineered by introducing mutations. In certain embodiments, the introduced mutations improve the functionality of the monomeric protein as compared to the native, non-mutated form of the monomer. In certain embodiments the introduced mutations improve one or more of the stability, half-life and heteromultimer formation of the transporter polypeptide.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide. In certain embodiments, at least one cargo polypeptide is selected from the proteins listed in Table 2 or fragments, variants or derivatives thereof. In certain embodiments, at least one cargo polypeptide is selected from ligand, receptor, or antibody to one or more proteins listed in Table 2, or fragment, variant or derivative of said ligand, receptor or antibody. In certain embodiments, at least one cargo polypeptide targets a cell surface antigen from the group consisting of CD19, CD20, CD22, CD25, CD30, CD33, CD40, CD56, CD64, CD70, CD74, CD79, CD105, Cd138, CD174, CD205, CD227, CD326, CD340, MUC16, GPNMB, PSMA, Cripto, ED-B, TMEFF2, EphB2, EphA2, FAP, integrin, Mesothelin, EGFR, TAG-72, GD2, CAIX, 5T4. In certain embodiments, are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein at least one at least one cargo polypeptide is an antibody, or fragment or variant thereof. In certain embodiments, all cargo polypeptides are antibodies or fragments or variants thereof. In some embodiments, the cargo polypeptide is an antibody that binds to a protein listed in Table 2. In some embodiments, the antibody fragment comprises antibody Fc or Fab or Fv region. In some embodiment the cargo polypeptide is a non-antibody protein like nanobodies, affibody, maxibody, adnectins, domain antibody, evibody, ankyrin repeat proteins, anticalins, camlids or ligand protein or polypeptide binding to a therapeutically relevant target. In some embodiments, the antibody or its fragment is derived from an immunoglobulin selected from the group consisting of IgG, IgA, IgD, IgE, and IgM. In certain embodiments, the IgG is of subtype selected from IgG1, IgG2a, IgG2b, IgG3 and IgG4. In certain embodiments, the antibody is multispecific.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein at least one cargo polypeptide is a therapeutic antibody. In some embodiments of the heteromultimers described herein, at least one cargo polypeptide is a therapeutic antibody or fragment or variant thereof, wherein the antibody is selected from antibody is selected from abagovomab, adalimumab, alemtuzumab, aurograb, bapineuzumab, basiliximab, belimumab, bevacizumab, briakinumab, canakinumab, catumaxomab, certolizumab pegol, certuximab, daclizumab, denosumab, efalizumab, galiximab, gemtuzumab ozagamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranizumab, reslizumab, rituximab, teplizumab, tocilizumab, tositumomab, trastuzumab, Proxinium, Rencarex, ustekinumab, and zalutumumab. In certain embodiments, the therapeutic antibody binds a disease related target antigen such as cancer antigen, inflammatory disease antigen or a metabolic disease antigen. In certain embodiments, the target antigen could be a protein on a cell surface and the cell could belong to the group of B-cell, T-cell, stromal cell, endothelial cell, vascular cell, myeloid cell, hematopoietic cell or carcinoma cell.

Provided herein are heteromultimers, each heteromultimer comprising: at least a first monomer that comprises at least one cargo molecule, fragment; and at least a second monomer that comprises at least one cargo molecule and a second transporter polypeptide, wherein at least one cargo polypeptide is an enzyme, enzyme inhibitor, hormone, therapeutic polypeptide, antigen, radiotoxin and chemotoxin inclusive of but not restricted to neurotoxins, interferons, cytokine fusion toxins and chemokine fusion toxins, cytokine, antibody fusion protein or variant or fragment thereof. In some embodiments of the heteromultimers described herein, at least one cargo polypeptide comprises GLP-1 or fragment or variant thereof. In some embodiments, at least one cargo polypeptide comprises glucagon or fragment or variant thereof. In an embodiment, at least one cargo polypeptide comprises an EGF-A like domain. In certain embodiments, the toxin is an immunotoxin such as Denileukin diftitox and Anti-CD22 immunotoxin such as CAT-3888 and CAT-8015. In certain embodiments, the toxin is saporin. In some embodiments, the toxin is a mitotoxin. In some embodiments, the toxin is a diphtheria toxin. In some embodiments, the toxin is botulinux toxin type A. In some embodiments, the toxin is ricin or a fragment there of. In some embodiments, the toxin is a toxin from RTX family of toxins.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein the cargo polypeptide is attached to the transporter polypeptide by chemical conjugation, native ligation, chemical ligation, a disulfide bond or direct fusion or fusion via a linker. In certain embodiments, linkers for attaching cargo molecules such as cargo polypeptides to transporter polypeptides are selected from the linkers described in U.S. Pat. Nos. 5,482,858, 5,258,498 and 5,856,456, US2009060721,U.S. Pat. Nos. 6,492,123, 4,946, 778, 5,869,620, 7,385,032, 5,073,627, 5,108,910, 7,977,457, 5,856,456, 7,138,497, 5,837,846, 5,990,275, EP1088888 incorporated by reference herein.

Provided herein are host cells comprising nucleic acid encoding a heteromultimer described herein. In certain embodiments, the nucleic acid encoding the first monomeric protein and the nucleic acid encoding the second monomeric protein are present in a single vector. In certain embodiments, the nucleic acid encoding the first monomeric protein and the nucleic acid encoding the second monomeric protein are present in separate vectors.

Provided herein is a method of making a heteromultimer, wherein said method comprises: culturing a host cell described herein such that the nucleic acid encoding a heteromultimer described herein is expressed; and recovering the heteromultimer from the cell culture. In some embodiments, the host cell is a prokaryotic cell or a eukaryotic cell. In some embodiments, the host cell is *E. coli*. In certain embodiments, the host cell is yeast cell. In some embodiments, the yeast is *S. cerevisiae*. In some embodiments, the yeast is *Pichia*. In a certain embodiment, the yeast is *Pichia pastoris*. In some embodiments, the yeast is glycosylation deficient, and/or protease deficient. In some embodiments, the host cell is a bacterial cell. In some embodiments, the host cell expressing a heteromultimer descried herein is a mammalian cell. In certain embodiments, the mammalian cell is a CHO cell, a BHK cell, NSO cell, COS cell or a human cell.

Provided is a pharmaceutical composition that comprises a heteromultimer described herein and a pharmaceutically acceptable adjuvant. Also provided are methods of treating an individual suffering from a disease or disorder, said method comprising administering to the individual an effective amount of a formulation or pharmaceutical composition described herein. In certain embodiments is a method of treating cancer in a patient, said method comprising administering to the patient a therapeutically effective amount of a heteromultimer described herein. In some embodiments is a method of treating an immune disorder in a patient, said method comprising administering to the patient a therapeutically effective amount of a heteromultimer described herein. Also provided is a method of treating an infectious disease in a patient, said method comprising administering to the patient a therapeutically effective amount of a heteromultimer described herein. In certain embodiments is a method of treating a cardiovascular disorder in a patient, said method comprising administering to the patient a therapeutically effective amount of a heteromultimer described herein. In certain embodiments is a method of treating a respiratory disorder in a patient, said method comprising administering to the patient a therapeutically effective amount of a heteromultimer described herein. In certain embodiments is a method of treating a metabolic disorder in a patient, said method comprising administering to the patient a therapeutically effective amount of a heteromultimer described herein. In certain embodiments is a method of treating one or more of Congenital adrenal hyperplasia, Gaucher's disease, Hunter syndrome, Krabbe disease, Metachromatic leukodystrophy, Niemann-Pick disease, Phenylketonuria (PKU), Porphyria, Tay-Sachs disease, and Wilson's disease in a patient, said method comprising administering to the patient a therapeutically effective amount of a heteromultimer described herein.

Provided is a kit for detecting the presence of a biomarker of interest in an individual, said kit comprising (a) an amount of a heteromultimer described herein, wherein said heteromultimer comprises at least one cargo polypeptide such that said cargo polypeptide is capable of binding to the biomarker of interest; and (b) instructions for use.

Provided herein are heteromultimer proteins that comprise at least two monomeric proteins, wherein each monomeric protein comprises at least one cargo polypeptide, and an albumin based polypeptide, such that said monomeric proteins self-assemble to form the heteromultimer.

In certain embodiments, the cargo polypeptide is fused to the albumin or alloalbumin based transporter polypeptide. In some embodiments, the cargo polypeptide is fused to the transferrin based transporter polypeptide. In certain embodiments, the cargo polypeptide is fused to the annexin based transporter polypeptide. In some embodiments, the fusion is at the N terminus of the transporter polypeptide. In certain embodiments, the fusion is at the C terminus of the transporter polypeptide. In some embodiments, the fusion involves a bridging linker or spacer molecule. In some embodiments, the cargo polypeptide is chemically conjugated to the transporter polypeptide. In certain embodiments, the cargo polypeptide is attached to the transporter polypeptide by means of chemical ligation or a disulfide bond.

Provided herein are heteromultimer proteins that comprise at least two monomeric proteins, wherein each monomeric protein comprises at least one cargo polypeptide, and a transporter polypeptide, such that said transporter polypeptides self-assemble to form the heteromultimer. In some embodiments, each transporter polypeptide is an alloalbumin based polypeptide, such that said alloalbumin based polypeptides self-assemble to form the heteromultimer. In some embodiments, each transporter polypeptide is a transferrin based polypeptide. In some embodiments, each transporter polypeptide is an annexin based polypeptide. In certain embodiments, each monomeric transporter polypeptide is unstable and preferentially forms a heteromultimer with at least one other transporter polypeptide.

In some embodiments, a heteromultimer described herein is a heterodimer. In some embodiments cargo polypeptide is an antibody, enzyme, hormone, therapeutic polypeptide, antigen, chemotoxin, radiotoxin, cytokine or variant or fragment thereof. In some embodiments, the cargo polypeptide of one monomeric protein functions in synergy with the cargo polypeptide of another monomeric protein.

Provided herein are heteromultimer proteins that comprise at least two monomeric proteins, wherein each monomeric protein comprises at least one cargo polypeptide, and an annexin based polypeptide, such that said annexin based polypeptides self-assemble to form the heteromultimer with a quasi-native structure of annexin or analog thereof. In some embodiments, the annexin is Annexin A1. In some embodiments, a heteromultimer described herein is a heterodimer. In some embodiments cargo polypeptide is an antibody, enzyme, hormone, therapeutic polypeptide, antigen, chemotoxin, radiotoxin, cytokine, ligand to a receptor, receptor or variant or fragment thereof. In some embodiments, the cargo polypeptide of one monomeric protein functions in synergy with the cargo polypeptide of another monomeric protein. In some embodiments the cargo polypeptide can be an agonist or antagonist to the cargo polypeptide of another monomeric protein.

Provided herein are heterodimer proteins that comprise at least two monomeric fusion proteins, wherein each monomeric fusion proteins comprises at least one cargo polypeptide fused to an albumin derived polypeptide, such that said albumin derived polypeptides self-assemble to form the multifunctional heterodimer. In certain embodiments are heterodimeric proteins comprising a first monomer which comprises at least one cargo polypeptide fused to an albumin derived polypeptide; and a second monomer that comprises at least one cargo polypeptide fused to an albumin derived polypeptide. In certain embodiments, the at least one cargo polypeptide of the first monomer is different from the at least one cargo polypeptide of the second monomer. In certain embodiments, the at least one cargo polypeptide of the first monomer is the same as the at least one cargo polypeptide of the second monomer.

In certain embodiments are heteromultimer proteins that comprise at least two monomeric fusion proteins, wherein each monomeric fusion proteins comprises at least one cargo polypeptide fused to an alloalbumin derived polypeptide, such that said alloalbumin derived polypeptides self-assemble to form the multifunctional heteromultimer. In certain embodiments are heteromultimer proteins that comprise at least two monomeric fusion proteins, wherein each monomeric fusion proteins comprises at least one cargo polypeptide fused to a transferrin derived polypeptide, such that said transferrin derived polypeptides self-assemble to form the heteromultimer. In certain embodiments are heteromultimer proteins that comprise at least two monomeric fusion proteins, wherein each monomeric fusion proteins comprises at least one cargo polypeptide fused to an annexin derived polypeptide, such that said annexin derived polypeptides self-assemble to form the heteromultimer. In certain embodiments, the annexin is Annexin A2.

In certain embodiments are heteromultimer proteins comprising a first monomer which comprises at least one cargo polypeptide fused to an alloalbumin derived polypeptide; and a second monomer that comprises at least one cargo polypeptide fused to an alloalbumin derived polypeptide. In certain embodiments, the at least one cargo polypeptide of the first monomer is different from the at least one cargo polypeptide of the second monomer. In certain embodiments, the at least one cargo polypeptide of the first monomer is the same as the at least one cargo polypeptide of the second monomer.

Provided herein is a heteromultimer that comprises: at least two monomers, each comprising a transporter polypeptide and optionally at least one cargo molecule attached to said transporter polypeptide, wherein each transporter polypeptide is obtained by segmentation of a whole protein such that said transporter polypeptides self-assemble to form quasi-native whole protein. In certain embodiments, the heteromultimer is multispecific. In certain embodiments, the transporter polypeptides are not derived from an antibody. In some embodiments, each monomer preferentially forms the heteromultimer as compared to a monomer or a homomultimer. In an embodiment of the heteromultimer, at least one cargo molecule is a theraputic agent, or a biomolecule. In some embodiments, at least one cargo molecule is a biomolecule which is selected from a polypeptide, DNA, PNA, or RNA. In some embodiments, each transporter polypeptide is a derivate of albumin or alloalbumin. In an embodiment, each transporter polypeptide is a derivate of annexin. In certain embodiments, each transporter polypeptide is a derivate of transferrin.

In certain embodiments are pharmaceutical formulations that comprise an albumin-based and/or alloalbumin-based heteromultimeric protein described herein and a pharmaceutically acceptable diluent or carrier. In certain embodiments are pharmaceutical formulations that comprise a transferrin-based heteromultimeric protein described herein and a pharmaceutically acceptable diluent or carrier. In certain embodiments are pharmaceutical formulations that comprise an annexin-based heteromultimeric protein described herein and a pharmaceutically acceptable diluent or carrier. In certain embodiments are pharmaceutical formulations that comprise an Annexin-A2 based heteromultimeric protein described herein and a pharmaceutically acceptable diluent or carrier. In certain embodiments, a formulation described herein is provided as part of a kit or container. In certain embodiments, the kit or container is packaged with instructions pertaining to extended shelf life of the therapeutic protein. In some embodiments, a heteromultimer described herein is used in a method of treating (e.g., ameliorating) preventing, or diagnosing a disease or disease symptom in an individual, comprising the step of administering said formulation to the individual.

Provided herein is a method of obtaining fusion protein scaffolds with a known number of conjugation sites based on any transport protein of interest.

Also provided are transgenic organisms modified to contain nucleic acid molecules described herein to encode and express monomeric fusion proteins described herein.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention,

FIG. 5 is a schematic of a bispecific antibody derived from a heterodimeric Fc domain. Albumin or alloalbumin based polypeptides are connected to the C-terminal of the Fc to selectively drive the formation of heterodimers.

FIG. 8A shows Albumin and FIG. 8B shows heteromultimer scaffold ABH1

FIG. 15 shows sequences of multimers comprising transporter polypeptides based on human serum albumin. (FIG. 15 discloses SEQ ID NOS 25-64,respectively, in order of appearance.)

DETAILED DESCRIPTION

Figure 1:
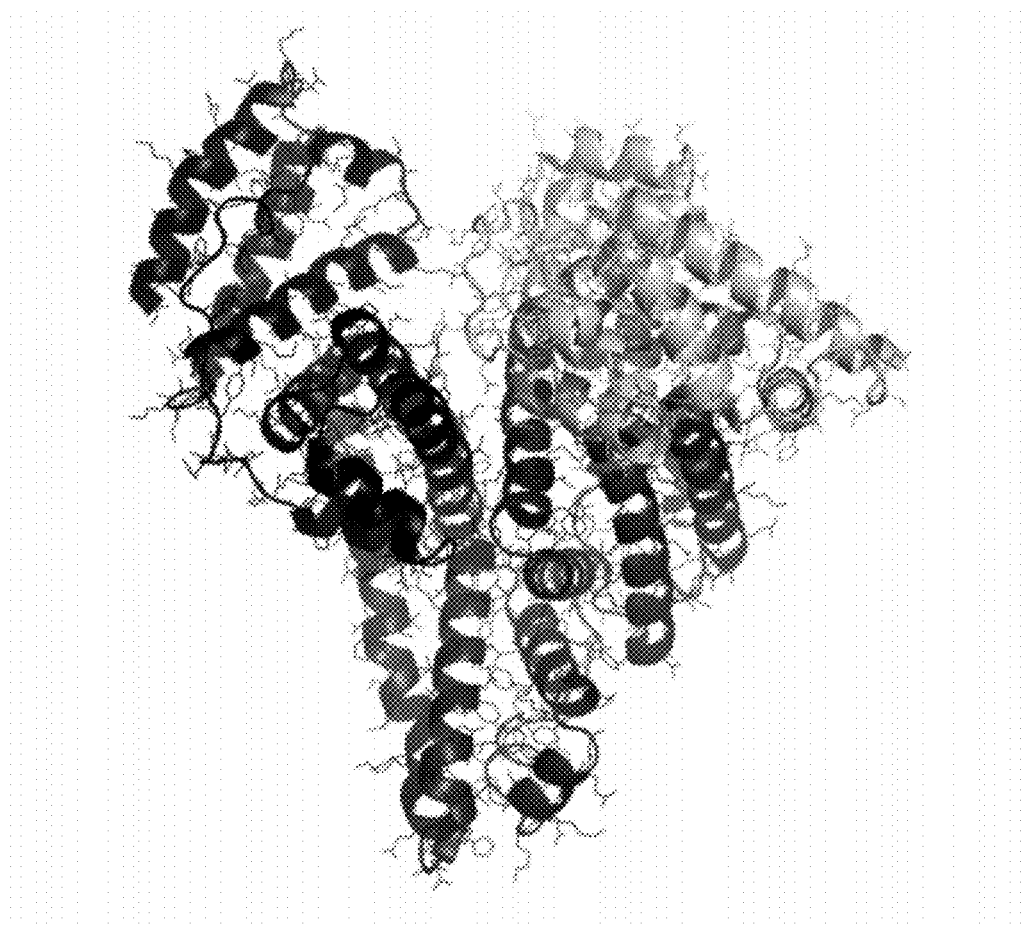
FIG. 1 depicts the structure of the Human Serum Albumin (HSA) molecule. The alpha helical sections of the secondary structure are shown schematically along with the bonds represented as sticks.

In the realm of therapeutic proteins, bispecific molecules exhibit dual target specificities or are able to simultaneously perform multiple functional roles by providing the necessary spatiotemporal organization necessary for drug action. In one aspect, bispecific molecules are particularly interesting when the mode of therapeutic action involves retargeting of effector cells or molecules to a target such as a tumor cell [Muller D. and Kontermann R. E. (2010) *Biodrugs* 24, 89-98]. The development of bispecific therapeutic proteins with favorable pharmacokinetics and functional activity in stable and homogeneous condition has been a challenge. Attempts have been made to assemble bispecific units from multiple antigen binding domains using a number of approaches. These techniques have involved using heterodimeric antibody IgG molecule, using leucine zipper proteins such as the Fos/Jun pair or other scaffolds assembled from the alternate organizations of the light and heavy chains of the variable domains in an antibody. Kipriyanov and Le Gall have reviewed the design of a variety of bispecific constructs [Kipriyanov S. M. & Le Gall F. (2004) *Curr Opin Drug Discov Dev* 7, 233-242]. The use of a heterodimeric antibody IgG molecule wherein mutations are introduced in the CH3 domain of the antibody to achieve the heterodimer and hence introduce the two unique antigen binding sites into one molecule is very attractive because of the natural immunoglobulin like structure of this construct. Further, the Fc portion of the antibody is involved in interactions with the neonatal Fc receptor (FcRn) which mediates an endocytic salvage pathway and this is attributed to improved serum half-life of the antibody molecule [Roopenian D. & Akilesh S. (2007) *Nature Rev Immunol* 7, 715-725]. On the other hand, antibody based bispecific molecules have been problematic in clinical trials because of the strong cytokine responses as a result of the concurrent effector activity induced via the Fc portion of the bispecific antibody [Weiner L. M.; Alpaugh R. K. et al. (1996) *Cancer Immunol Immunother* 42, 141-150]. This highlights the needs for novel scaffolds that can aid in the design of bispecific and immunoconjugate molecules.

The human serum album (HSA) protein is the most abundant component of blood, accounting for close to 60% of the total protein in blood serum at a concentration of about 40 mg/ml. Albumin is also one of the longest-lived proteins in the circulatory system with a half-life of about 19 days. Interestingly, the same endocytic salvage pathway dependent on FcRn molecules that prevents antibody degradation is known to interact with the HSA molecule as well [Chaudhary C.; Mehnaz S. et al. (2003) *J Exp Med* 197, 315-322].

HSA (shown in FIG. 1) is a non-glycosylated 585-residue single polypeptide protein and the 3-dimensional structure of the protein was first observed using X-ray crystallography by Carter and coworkers [reviewed in Carter, D. C. & Ho, J. X. (1994) *Adv Prot Chem* 45, 153-203]. The HSA protein consists of three homologous domains: DI, DII, DIII, attributed to gene duplication, a feature common to the serum albumin in other species as well [Gray J. E. & Doolittle R. F. (1992) Protein Sci 1, 289-302]. Each of the three domains have been expressed and characterized separately and shown to be independently stable [Dockal M., Carter D. C. & Ruker F. (1999) *J Biol Chem* 274, 29303-29310]. Each domain is made up of 10 helical segments and based on the interhelical organization each domain can be further classified into 2 sub-domains comprised of helix 1-6 and 7-10 respectively. HSA has 17 disulphide bonds in total and all these cysteine pairs forming the linkages are within the individual domains. In general, HSA is a very stable due to the large number of disulphide bonds as well as the predominantly helical fold. The sequence identities of albumin molecules across a number of species is quite large, greater than 70% among albumin cDNA derived from humans, horse, bovine, rat, etc. [Carter, D. C. & Ho, J. X. (1994) *Adv Prot Chem* 45, 153-203].

Split protein pairs have been used as sensors to understand protein-protein interactions in the area of functional proteomics. The approach involves identifying suitable segments from a protein that can reconstitute to form an active native-like protein. Generating new split proteins is technically demanding. For a protein to be split in a functionally useful manner, the segmentation site has to yield two segments that efficiently reconstitute into the quasi-native protein when associated to each other. Further, the component protein segments should be soluble enough to stay in solution and selectively associate with the partner segments such that manufacture yields and purification will be economical. Deriving split protein segments that would recombine to form the quasi-native structure is quite challenging [Tafelmeyer P., Johnsson N. & Johnson K. *Chem & Biol* 11, 681-689]. Such split proteins have not been used in the design of protein therapeutics, or as cargo delivery vehicles in the past.

DEFINITIONS

It is to be understood that this invention is not limited to the particular protocols; cell lines, constructs, and reagents described herein and as such may vary. It is also to be understood that the terminology used herein is for the purpose of describing particular embodiments only, and is not intended to limit the scope of the present invention, which will be limited only by the appended claims.

As used herein and in the appended claims, the singular forms "a," "an," and "the" include plural reference unless the context clearly indicates otherwise. Thus, for example, reference to a "HSA", "HA", "albumin", "human serum albumin" and various capitalized, hyphenated and unhyphenated forms is a reference to one or more such proteins and includes variants, derivatives, fragments, equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

A "heteromultimer" or "heteromultimeric polypeptide" is a molecule comprising at least a first monomer comprising a first transporter polypeptide and a second monomer comprising a second transporter polypeptide, wherein the second polypeptide differs in amino acid sequence from the first polypeptide by at least one amino acid residue. The heteromultimer can comprise a "heterodimer" formed by the first and second transporter polypeptides. In certain embodiments, the heteromultimer can form higher order tertiary structures such as, but not restricted to trimers and tetramers. In some embodiments, transporter polypeptides in addition to the first and second transporter polypeptides are present. In certain embodiments, the assembly of transporter polypeptides to form the heteromultimer is driven by surface area burial. In some embodiments, the transporter polypeptides interact with each other by means of electrostatic interactions and/or salt-bridge interactions that drive heteromultimer formation by favoring heteromultimer formation and/or disfavoring homomultimer formation. In some embodiments, the transporter polypeptides inteact with each other by means of hydrophobic interactions that drive heteromultimer formation by favoring heteromultimer formation and/or disfavoring homomultimer formation. In certain embodiments, the transporter polypeptides inteact with each other by means of covalent bond formation. In certain embodiments, the covalent bonds are formed between naturally present or introduced cysteines that drive heteromultimer formation. In certain embodiments of the heteromultimers described herein, no covalent bonds are formed between the monomers. In some embodiments, the transporter polypeptides inteact with each other by means of packing/size-complementarity/knobs-into-holes/protruberance-cavity type interactions that drive heteromultimer formation by favoring heteromultimer formation and/or disfavoring homomultimer formation. In some embodiments, the transporter polypeptides inteact with each other by means of cation-pi interactions that drive heteromultimer formation by favoring heteromultimer formation and/or disfavoring homomultimer formation. In certain embodiments the individual transporter polypeptides cannot exist as isolated monomers in solution. In certain embodiments, the heteromultimer is the preferred state of the individual transporter polypeptides as compared to the monomer.

The term "bispecific" is intended to include any agent, e.g., heteromultimer, monomer, protein, peptide, or protein or peptide complex, which has two different binding specificities. For example, in some embodiments, the molecule may bind to, or interact with, (a) a cell surface target molecule and (b) an Fc receptor on the surface of an effector cell. In certain embodiments of a heteromultimer described herein, at least one monomer is bispecific formed by attaching to the same transporter polypeptide, two cargo molecules with different binding specificities. In certain embodiments of a heteromultimer described herein, the heteromultimer is itself bispecific formed by attaching to the transporter polypeptides, at least two cargo molecules with different specificities. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface target molecule such as but not limited to cell surface antigens, (b) an Fc receptor on the surface of an effector cell, and (c) at least one other component. Accordingly, embodiments of the heteromultimers described herein, are inclusive of, but not limited to, bispecific, trispecific, tetraspecific, and other multispecific molecules. In certain embodiments, these molecules are directed to cell surface antigens, such as CD30, and to other targets, such as Fc receptors on effector cells.

Unless indicated otherwise, the expression "multivalent" is used throughout this specification to denote a heteromultimer comprising at least two sites of attachment for target molecules. The multivalent heteromultimer is designed to have multiple binding sites for desired targets. In certain embodiments, the binding sites are on at least one cargo molecules attached to a transporter polypeptide. In certain embodiments, at least one binding site is on a transporter polypeptide. The expression "bivalent" is used throughout this specification to denote a heteromultimer comprising two target binding sites. In certain embodiments of a bivalent heteromultimer, both binding sites are on the same monomer. The expression "trivalent" is used throughout this specification to denote a heteromultimer comprising three target binding sites. The expression "tetravalent" is used throughout this specification to denote a heteromultimer comprising four target binding sites.

"Fusion proteins" and polypeptides are created by joining two or more genes that originally code for separate polypeptides. Translation of this fusion gene results in a single polypeptide with functional properties derived from each of the original polypeptides. In embodiments of the heteromultimers described herein, at least one monomer may comprise a fusion protein formed by the fusion of at least one cargo polypeptide to the N- or C-terminus of a transporter polypeptide.

The term "substantially purified" refers to a heteromultimer described herein, or variant thereof that may be substantially or essentially free of components that normally accompany or interact with the protein as found in its naturally occurring environment, i.e. a native cell, or host cell in the case of recombinantly produced heteromultimer that in certain embodiments, is substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the heteromultimer or variant thereof is recombinantly produced by the host cells, the protein in certain embodiments is present at about 30%, about 25%, about 20%, about 15%, about 10%, about 5%, about 4%, about 3%, about 2%, or about 1% or less of the dry weight of the cells. When the heteromultimer or variant thereof is recombinantly produced by the host cells, the protein, in certain embodiments, is present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. In certain embodiments, "substantially purified" heteromultimer produced by the methods described herein, has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the protein has been secreted, including medium either before or after a proliferation step. The term also may encompass buffers or reagents that contain host cell lysates, such as in the case where a heteromultimer described herein is produced intracellularly and the host cells are lysed or disrupted to release the heteromultimer.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two monomeric polypeptides which interact with each other and result in the transformation of unfolded or improperly folded polypeptides to native, properly folded polypeptides.

As used herein, the term "modulated serum half-life" means the positive or negative change in circulating half-life of a cargo polypeptide that is comprised by a heteromultimer described herein relative to its native form. Serum half-life is measured by taking blood samples at various time points after administration of heteromultimer, and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of a cargo polypeptide comprised by a heteromultimer described herein, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, praline, serine, threonine, tryptophan, tyrosine, and valine) and pyrrolysine and selenocysteine. Amino acid analogs refers to compounds that have the same basic chemical structure as a naturally occurring amino acid, i.e., an a carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g. α-methyl alanine), D-amino acids, histidine-like amino acids (e.g., 2-amino-histidine, β-hydroxy-histidine, homohistidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and [0139] 8) Cysteine (C), Methionine (M) (see, e.g., Creighton, Proteins: Structures and Molecular Properties (W H Freeman & Co.; 2nd edition (December 1993)

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are known to those of ordinary skill in the art. Optimal alignment of sequences for comparison can be conducted, including but not limited to, by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

One example of an algorithm that is suitable for determining percent sequence identity and sequence similarity are the BLAST and BLAST 2.0 algorithms, which are described in Altschul et al. (1997) Nuc. Acids Res. 25:3389-3402, and Altschul et al. (1990) J. Mol. Biol. 215:403-410, respectively. Software for performing BLAST analyses is publicly available through the National Center for Biotechnology Information available at the World Wide Web at ncbi.nlm.nih.gov. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915) alignments (B) of 50, expectation (E) of 10, M=5, N=−4, and a comparison of both strands. The BLAST algorithm is typically performed with the "low complexity" filter turned off.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, or other nucleic acids, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

As used herein, the term "eukaryote" refers to organisms belonging to the phylogenetic domain Eucarya such as animals (including but not limited to, mammals, insects, reptiles, birds, etc.), ciliates, plants (including but not limited to, monocots, dicots, algae, etc.), fungi, yeasts, flagellates, microsporidia, protists, etc.

As used herein, the term "prokaryote" refers to prokaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the Archaea (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of heteromultimer being administered, which will relieve to some extent one or more of the symptoms of the disease, condition or disorder being treated. Compositions containing the heteromultimer described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

The term "segmentation" refers to a precise internal splice of the original protein sequence which results in "segments" of the protein sequence that preferentially associate as heteromultimers to form a quasi-protein.

Quasi-Native Structure:

With reference to a native protein or its structure, quasi-native proteins and/or 'quasi-native structures' present the native protein like functional and structural characteristics. Proteins are naturally dynamics molecules and display an ensemble of structural configurations although we ascribe a native structure to it, such as the one obtained by X-ray crystallography. The alternate structural configurations observed in the ensemble of geometries of that protein can be deemed to be quasi-native structures relative to each other or relative to the structure observed in the crystal. On a different front, homologous proteins sequences or proteins belonging to common structural families tend to fold into similar structural geometries. The member proteins belonging to this family can be deemed to achieve a quasi-native structure relative to each other. Some of the unique sequences in the protein family could also exhibit similar functional attributes and hence can be referred to as quasi-native proteins relative to each other. In the case of heteromultimers described here comprising of two or more monomeric proteins each of which have a transporter polypeptide component, the transporter polypeptides assemble to form a quasi-native structure. The reference native protein in this case is the protein from which the transporter polypeptide is derived and the reference native structure is the structure of the protein from which the transporter polypeptide is derived. We describe a case where two or more different polypeptides self-assemble to form a heteromultimeric structural and exhibit functional characteristics like a native protein which itself is a monomeric entity. In certain embodiments, we present polypeptide segments derived from albumin that self-assemble to form a heteromultimer that exhibits native albumin like functional characteristics such FcRn binding and structural characteristics. In certain embodiments, we present polypeptide segments derived from transferrin that self-assemble to form a heteromultimer that exhibits native transferrin like structural and functional characteristics. In certain embodiments, we present polypeptide segments derived from annexin that self-assemble to form a heteromultimer that exhibits native annexin like structural and functional characteristics. These heteromultimers are referred to as being quasi-native.

Transporter Polypeptide

As used herein, the term "transporter polypeptide" or "transporter polypeptide" or "transporter peptide" or "transporter" refers to a polypeptide, such that said transporter polypeptide is capable of forming heteromultimeric proteins with other such transporter polypeptides in solution, and wherein said heteromultimeric proteins have a quasi-native structure of a monomeric protein from which at least one transporter polypeptide is derived. In certain embodiments of the heteromultimers described herein, all transporter polypeptides are derived from the same albumin or alloalbumin protein. In certain other embodiments, the heteromultimers are formed by transporter polypeptides derived from various albumin and alloalbumin proteins. In certain embodiments of the heteromultimers described herein, the transporter polypeptides are derived from transferrin. In certain embodiments of the heteromultimers described herein, all transporter polypeptides are derived from annexin proteins. In certain embodiments, the heteromultimers are formed by transporter polypeptides derived from the same annexin protein. In some embodiments, the heteromultimers are formed by transporter polypeptides derived from different annexin proteins. In an embodiment, the heteromultimers are formed by transporter polypeptides derived from annexin A2.

In certain embodiments, transporter polypeptides are segments of a whole protein, wherein said segments are capable of assembling to form a heteromultimer. In certain embodiments, the transporter polypeptides are segments derived from a coiled coil protein. In certain embodiments, the transporter polypeptides are segments derived from a leucine-zipper protein. In an embodiment, the transporter polypeptides are segments from a beta-barrel protein. In an embodiment, transporter polypeptides are segments obtained from a beta-propeller protein. In some embodiments, the transporter polypeptides are segments obtained from a helical bundle protein. In embodiments, the transporter polypeptides are generated from for instance, but not restricted to proteins comprising a zinc finger motif, a helix-turn-helix motif or a beta-hairpin motif. In some embodiments, the transporter polypeptides are segments obtained from non-immunogenic proteins that are structurally stable, and have favorable biological properties.

Albumin

As used herein, "albumin" refers collectively to albumin protein or amino acid sequence, or an albumin segment or variant, having one or more functional activities (e.g., biological activities) of albumin. In particular "albumin" refers to human albumin or segments thereof (see for example, EP 201 239, EP 322 094 WO 97/24445, WO95/23857) especially the mature form of human albumin as shown in FIG. 1, or albumin from other vertebrates, or segments thereof, or analogs or variants of these molecules or fragments thereof. In certain embodiments, albumin refers to a truncated version of albumin.

The term "quasi-albumin" refers to a heteromultimer molecule that has structure and/or function similar to the whole albumin, and wherein said heteromultimer molecule is formed by the assembly of two or more monomeric polypeptides designed based on the sequence of the whole albumin. In certain embodiments, the monomeric polypeptides are "segments" that preferentially associate as heteromultimeric pairs to form a quasi-protein. In some embodiments, the quasi-albumin has 90% of the activity of the whole albumin. In some embodiments, the quasi-albumin has 75% of the activity of whole-albumin. In an embodiment, the quasi-albumin has 50% of the activity of whole albumin. In some embodiments, the quasi-albumin has 50-75% of the activity of whole albumin. In an embodiment, quasi-albumin has 80% of the activity of whole albumin. In some embodiments, the quasi-albumin has 90% of the structure of whole albumin as determined by molecular modeling. In some embodiments, the quasi-albumin has 80% of the structure of whole albumin as determined by molecular modeling. In some embodiments, the quasi-albumin has 70% of the structure of whole albumin as determined by molecular modeling. In some embodiments, the quasi-albumin has 50% of the structure of whole albumin as determined by molecular modeling. In some embodiments, the quasi-albumin has 50%-75% of the structure of whole albumin as determined by molecular modeling.

The terms, human serum albumin (HSA) and human albumin (HA) are used interchangeably herein. The terms, "albumin and serum albumin" are broader, and encompass human serum albumin (and fragments and variants thereof) as well as albumin from other species (and fragments and variants thereof).

In certain embodiments, each albumin-based monomer of the heteromultimeric proteins described herein is based on a variant of normal HA. Each cargo polypeptide portion of the heteromultimeric proteins of the invention may also be variants of the Therapeutic proteins as described herein. The term "variants" includes insertions, deletions and substitutions, either conservative or non conservative, where such changes do not substantially alter one or more of the oncotic, useful ligand-binding and non-immunogenic properties of albumin, or the active site, or active domain which confers the therapeutic activities of the Therapeutic proteins.

In certain embodiments, the heteromultimeric proteins described herein include naturally occurring polymorphic variants of human albumin and fragments of human albumin, for example those fragments disclosed in EP 322 094 (namely HA (Pn), where n is 369 to 419).

In certain embodiments, the albumin is derived from any vertebrate, especially any mammal that includes but is not limited to human, cow, sheep, rat, mouse, rabbit, horse, dog or pig. In certain embodiments, the albumin is derived from non-mammalian albumins including, but are not limited to hen and salmon.

The sequence of human albumin is as shown:

SEQ ID NO: 1
MKWVTFISLLFLFSSAYSRGVFRRDAHKSEVAHRFKDLGEENFKALVLIA

FAQYLQQCPFEDHVKLVNEVTEFAKTCVADESAENCDKSLHTLFGDKLCT

VATLRETYGEMADCCAKQEPERNECFLQHKDDNPNLPRLVRPEVDVMCTA

FHDNEETFLKKYLYEIARRHPYFYAPELLFFAKRYKAAFTECCQAADKAA

CLLPKLDELRDEGKASSAKQRLKCASLQKFGERAFKAWAVARLSQRFPKA

EFAEVSKLVTDLTKVHTECCHGDLLECADDRADLAKYICENQDSISSKLK

ECCEKPLLEKSHCIAEVENDEMPADLPSLAADFVESKDVCKNYAEAKDVF

LGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEV

SRNLGKVGSKCCKHPEAKRMPCAEDYLSVVLNQLCVLHEKTPVSDRVTKC

CTESLVNRRPCFSALEVDETYVPKEFNAETFTFHADICTLSEKERQIKKQ

TALVELVKHKPKATKEQLKAVMDDFAAFVEKCCKADDKETCFAEEGKKLV

AASQAALGL

Alloalbumin

An alloalbumin is a genetic variant of albumin. In certain embodiments the alloalbumin is human alloalbumin (HAA). Alloalbumins that differ in electrophoretic mobility from albumin have been identified through population genetics surveys in the course of clinical electrophoresis, or in blood donor surveys. As markers of mutation and migration, alloalbumins are of interest to geneticists, biochemists, and anthropologists, but most of these alloalbumin are not associated with disease (Minchioti et al. Human Mutations 29(8), 1007-1016 (2008)).

TABLE 1

List of substitutions comprised by various alloalbumins as compared to HA of SEQ ID NO: 1. Thermostability, half-life information and other HAAs are provided in Kroghhansen et al. Biochim Biophys Acta 1747, 81-88(2005); and WO2011051489 incorporated by reference herein.

| Mutation | Thermostability (C) (positive = stabilizing, negative = destabilizing) | Effect on half-life (% change) |
|---|---|---|
| H3Y | N/A | N/A |
| H3Q | N/A | N/A |
| Q32Stop | N/A | N/A |
| E60K | N/A | N/A |
| D63N | 6.07 | N/A |
| L66P | N/A | N/A |
| E82K | 2.03 | N/A |
| R114G | N/A | N/A |
| R114Stop | N/A | N/A |
| E119K | N/A | N/A |
| V122E | 0.57 | N/A |
| H128R | N/A | N/A |
| Y140C | N/A | N/A |
| A175Stop | N/A | N/A |
| C177F | −1.59 | N/A |
| R218H | N/A | N/A |
| R218P | N/A | N/A |
| K225Q* | −4.86 | N/A |
| K240E | N/A | N/A |
| E244Stop | N/A | N/A |
| Q268R | N/A | N/A |
| D269G | 3.67 | N/A |
| K276N | 4.87 | N/A |
| K313N | −7.16 | N/A |
| D314G | −0.38 | N/A |
| D314V | N/A | N/A |
| N318K | N/A | N/A |
| A320T, & −1R | N/A | 6.16 |
| E321K | 1.42 | N/A |
| E333K | −2.56 | N/A |
| E354K | N/A | N/A |
| E358K | N/A | N/A |
| K359K | −6.56 | N/A |

TABLE 1-continued

List of substitutions comprised by various alloalbumins as compared to HA of SEQ ID NO: 1. Thermostability, half-life information and other HAAs are provided in Krogh-hansen et al. Biochim Biophys Acta 1747, 81-88(2005); and WO2011051489 incorporated by reference herein.

| Mutation | Thermostability (C) (positive = stabilizing, negative = destabilizing) | Effect on half-life (% change) |
|---|---|---|
| D365H | 0.89 | N/A |
| D365V | N/A | N/A |
| E368G | N/A | N/A |
| K372E | N/A | N/A |
| D375N | N/A | N/A |
| D375H | -0.09 | N/A |
| E376K | N/A | N/A |
| E376Q | N/A | N/A |
| E382K | N/A | N/A |
| Q385Stop | N/A | N/A |
| Y401Stop | N/A | N/A |
| R410C | N/A | N/A |
| E479K | N/A | N/A |
| D494N | N/A | 0.84 |
| E501K | 0.13 | N/A |
| E505K | 1.87 | N/A |
| I513N | N/A | N/A |
| V533M | N/A | N/A |
| K536E | N/A | N/A |
| K541E | 6.12 | N/A |
| D550G | N/A | N/A |
| D550A | N/A | N/A |
| K560E | 0.70 | N/A |
| D563N | 4.17 | N/A |
| E565K | N/A | N/A |
| E570K | -6.53 | N/A |
| K573E | 2.08 | 2.7 |
| K574N | N/A | N/A |
| L575insertion (TCCCKSSCLR LITSHLKASQPTMRIRERK (SEQ ID NO: 20)) | -5.30 | N/A |
| Frameshift after 567; Stop at 582 | N/A | -5.7% |
| Frameshift after 572; Stop at 578 | N/A | -8.9% |

Annexin:

As used herein, "annexin" refers to a group of cellular proteins found in eukaryotic organisms. Annexin is also known as lipocortin. As used herein "annexin" may refer to any annexin protein, or to specific annexin proteins such as "annexin A1," "annexin A2," and "annexin A5." Annexins are characterized by their calcium dependent ability to bind negatively charged phospholipids (i.e. membrane walls) Annexins are characterized by a repeat protein scaffold limited to 30-50 kDa in size with fairly ubiquitous tissue distribution. The basic structure of an annexin is composed of two domains: a structurally conserved C terminal "core" region and a divergent N terminal domain. The core region binds the phospholipid cellular membrane in a $Ca^{2+}$ dependent manner. The N terminal region binds cytoplasmic proteins Annexins are important in various cellular and physiological processes and provide a membrane scaffold. The C terminal core is composed of four annexin repeats. Annexin is characterized by its flexible repeat-like nature that influences its intrinsic membrane-sensing abilities. For instance, the affinity towards specific biomembranes can be controlled by the number of repeats. With the characteristic phospholipid sensing, annexin can be useful to sense/target intestinal junctions for drug delivery. Another potential application for an annexin is targeting intestinal tight junctions and the Zonula Occludens region (ZO-1), which is known to be particularly difficult to traverse for larger protein therapeutics, significantly impairing drug absorption.

The term "quasi-annexin" refers to a heteromultimer molecule that has structure and/or function similar to the whole annexin, and wherein said heteromultimer molecule is formed by the assembly of two or more monomeric polypeptides designed based on the sequence of the whole annexin. In certain embodiments, the monomeric polypeptides are "segments" that preferentially associate as heteromultimeric pairs to form a quasi-protein. In some embodiments, the quasi-annexin has 90% of the activity of the whole annexin. In some embodiments, the quasi-annexin has 75% of the activity of whole-annexin. In an embodiment, the quasi-annexin has 50% of the activity of whole annexin. In some embodiments, the quasi-annexin has 50-75% of the activity of whole annexin. In an embodiment, quasi-annexin has 80% of the activity of whole annexin. In some embodiments, the quasi-annexin has 90% of the structure of whole annexin as determined by molecular modeling. In some embodiments, the quasi-annexin has 80% of the structure of whole annexin as determined by molecular modeling. In some embodiments, the quasi-annexin has 70% of the structure of whole annexin as determined by molecular modeling. In some embodiments, the quasi-annexin has 50% of the structure of whole annexin as determined by molecular modeling. In some embodiments, the quasi-annexin has 50%-75% of the structure of whole annexin as determined by molecular modeling.

The sequence of Human wild-type Annexin A2 is as shown:

SEQ ID NO: 14
GSAVSPYPTFNPSSDVAALHKAIMVKGVDEATIIDILTKRNNAQRQQIKA

AYLQETGKPLDETLKKALTGHLEEVVLALLKTPAQFDADELRAAMKGLGT

DEDTLIEILASRTNKEIRDINRVYREELKRDLAKDITSDTSGDFRNALLS

LAKGDRSEDFGVNEDLADSDARALYEAGERRKGTDVNVFNTILTTRSYPQ

LRRVFQKYTKYSKHDMNKVLDLELKGDIEKCLTAIVKCATSKPAFFAEKL

HQAMKGVGTRHKALIRIMVSRSEIDMNDIKAFYQKMYGISLCQAILDETK

GDYEKILVALCGGN

Transferrin:

Transferrins are monomeric proteins of about 76 kDa molecular weight present in all vertebrates and function as a iron-binding and transporting protein. Recombinant human transferrin and its fusions is being considered for the management of various diseases including thalassemia, atransferrinemia, age related macular degeneration, type 2 diabetes, during stem cell transplantation and in the treatment of acute infectious disease caused by the anthrax bacteria. Transferrin is stable in the gastrointestinal environment and a number of studies have shown that intact protein-transferrin conjugates can be orally delivered and remain bioactive.

The term "quasi-transferrin" refers to a heteromultimer molecule that has structure and/or function similar to the whole transferrin, and wherein said heteromultimer molecule is formed by the assembly of two or more monomeric polypeptides designed based on the sequence of the whole transferrin. In certain embodiments, the monomeric polypeptides are "segments" that preferentially associate as heteromultimeric pairs to form a quasi-protein. In some embodiments, the quasi-transferrin has 90% of the activity of the whole transferrin. In some embodiments, the quasi-transferrin has 75% of the activity of whole-transferrin. In an embodiment, the quasi-transferrin has 50% of the activity of whole transferrin. In some embodiments, the quasi-transferrin has 50-75% of the activity of whole transferrin. In an embodiment, quasi-transferrin has 80% of the activity of whole transferrin. In some embodiments, the quasi-transferrin has 90% of the structure of whole transferrin as determined by molecular modeling. In some embodiments, the quasi-transferrin has 80% of the structure of whole transferrin as determined by molecular modeling. In some embodiments, the quasi-transferrin has 70% of the structure of whole transferrin as determined by molecular modeling. In some embodiments, the quasi-transferrin has 50% of the structure of whole transferrin as determined by molecular modeling. In some embodiments, the quasi-transferrin has 50%-75% of the structure of whole transferrin as determined by molecular modeling.

The Sequence of Wildtype Human Transferrin is as shown:

SEQ ID NO: 19
MRLAVGALLV CAVLGLCLAV PDKTVRWCAV SEHEATKCQS

FRDHMKSVIP SDGPSVACVK KASYLDCIRA IAANEADAVT

-continued

LDAGLVYDAY LAPNNLKPVV AEFYGSKEDP QTFYYAVAVV

KKDSGFQMNQ LRGKKSCHTG LGRSAGWNIP IGLLYCDLPE

PRKPLEKAVA NFFSGSCAPC ADGTDFPQLC QLCPGCGCST

LNQYFGYSGA FKCLKDGAGD VAFVKHSTIF ENLANKADRD

QYELLCLDNT RKPVDEYKDC HLAQVPSHTV VARSMGGKED

LIWELLNQAQ EHFGKDKSKE FQLFSSPHGK DLLFKDSAHG

FLKVPPRMDA KMYLGYEYVT AIRNLREGTC PEAPTDECKP

VKWCALSHHE RLKCDEWSVN SVGKIECVSA ETTEDCIAKI

MNGEADAMSL DGGFVYIAGK CGLVPVLAEN YNKSDNCEDT

PEAGYFAVAV VKKSASDLTW DNLKGKKSCH TAVGRTAGWN

IPMGLLYNKI NHCRFDEFFS EGCAPGSKKD SSLCKLCMGS

GLNLCEPNNK EGYYGYTGAF RCLVEKGDVA FVKHQTVPQN

TGGKNPDPWA KNLNEKDYEL LCLDGTRKPV EEYANCHLAR

APNHAVVTRK DKEACVHKIL RQQQHLFGSN VTDCSGNFCL

FRSETKDLLF RDDTVCLAKL HDRNTYEKYL GEEYVKAVGN

LRKCSTSSLL EACTFRRP

Cargo Molecule:

A heteromultimer described herein comprises monomers that comprise at least one cargo molecule, and at least one transporter polypeptide, said cargo molecule and transporter polypeptide associated with one another, by means inclusive of, but not restricted to genetic fusion or chemical conjugation. In certain embodiments, at least one cargo molecule is a therapeutic agent. In certain agents, the cargo molecule is a toxin. In certain embodiments, the cargo molecule is an antigen, or analogs thereof. In an embodiment, the cargo molecule is a natural product, analog, or prodrug thereof. In certain embodiments, the cargo molecule is a therapeutic agent such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6mercaptopurine, 6thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In certain embodiment, the cargo molecule is a biomolecule. In an embodiment, the cargo molecule is a natural or synthetic nucleic acid. In some embodiments, at least one cargo molecule is one or more of a DNA, PNA, and/or RNA oligomer. In certain embodiments, a heteromultimer described herein comprises monomeric proteins that comprise at least one cargo polypeptide, or fragments or variants thereof, and at least one transporter polypeptide, said cargo polypeptide and transporter polypeptide associated with one another, by means inclusive of, but not restricted to genetic fusion or chemical conjugation As used herein, "Cargo polypeptide" refers to proteins, polypeptides, antibodies, peptides or fragments or variants thereof, having one or more therapeutic and/or biological activities. Cargo polypeptides encompassed by the invention include but are not limited to, proteins, polypeptides, peptides, antibodies, substrates or ligands to therapeutically relevant target proteins and biologics. (The terms peptides, proteins, and polypeptides are used interchangeably herein.) Specifically the term "Cargo polypeptide" encompasses antibodies and fragments and variants thereof. Thus a heteromultimer described herein may contain at least a fragment or variant of a cargo polypeptide, and/or at least a fragment or variant of an antibody. Additionally, in certain embodiments, the term "Cargo polypeptide" refers to the endogenous or naturally occurring correlate of a cargo polypeptide.

As a non-limiting example, a "Cargo biomolecule" is a biomolecule such as but not restricted to a protein, DNA, or RNA that is useful to treat, prevent or ameliorate a disease, condition or disorder. As a non-limiting example, a "Cargo polypeptide" may be one that binds specifically to a particular cell type (normal (e.g., lymphocytes) or abnormal e.g., (cancer cells)) and therefore may be used to target a compound (drug, or cytotoxic agent) to that cell type specifically.

In another non-limiting example, a "Cargo molecule" is a molecule that has a biological, activity, and in particular, a biological activity that is useful for treating preventing or ameliorating a disease. A non-inclusive list of biological activities that may be possessed by a Cargo molecule, for instance a Cargo polypeptide includes, enhancing the immune response, promoting angiogenesis, inhibiting angiogenesis, regulating hematopoietic functions, stimulating nerve growth, enhancing an immune response, inhibiting an immune response, or any one or more of the biological activities described herein.

Cargo polypeptides corresponding to a cargo polypeptide portion of a heteromultimer protein described herein, such as cell surface and secretory proteins, are often modified, by the attachment of one or more oligosaccharide groups. The modification, referred to as glycosylation, can dramatically affect the physical properties of proteins and can be important in protein stability, secretion, and localization. Glycosylation occurs at specific locations along the polypeptide backbone. There are usually two major types of glycosylation: glycosylation characterized by O-linked oligosaccharides, which are attached to serine or threonine residues; and glycosylation characterized by N-linked oligosaccharides, which are attached to asparagine residues in an Asn-X-Ser/Thr sequence, where X can be any amino acid except proline. N-acetylneuraminic acid (also known as sialic acid) is usually the terminal residue of both N-linked and Blinked oligosaccharides. Variables such as protein structure and cell type influence the number and nature of the carbohydrate units within the chains at different glycosylation sites. Glycosylation isomers are also common at the same site within a given cell type.

Table 2 provides a non-exhaustive list of Cargo polypeptides that correspond to a Cargo polypeptide portion of a heteromultimer described herein. The "Cargo Polypeptide" column discloses Cargo polypeptide molecules followed by parentheses containing scientific and brand names that comprise, or alternatively consist of, that Cargo polypeptide molecule or a fragment or variant thereof. In an embodiment the cargo molecule is a molecule that binds to a protein disclosed in the "Cargo polypeptide" column, or in Zhu et al. (Nucleic Acids Res. 38(1), D787-D791 (2009)); Wishart et al. (Nucleic Acids Res 36, D901-D906 (2008)); Ahmed et al. (Nucleic Acids Res 39, D960-D967 (2011)) incorporated by reference herein, or a protein that belongs in the class of therapeutic target molecules.

"Cargo polypeptide" as used herein may refer either to an individual Cargo polypeptide molecule (as defined by the amino acid sequence obtainable from the CAS and Genbank accession numbers), or to the entire group of Cargo polypeptide associated with a given Cargo polypeptide molecule disclosed in this column, or a Cargo polypeptide that binds to a polypeptide molecule disclosed in this column.

TABLE 2

Non-exhaustive list of Cargo polypeptides that correspond to a Cargo polypeptide portion of a heteromultimer

| Cargo Polypeptide | Biological Activity | Exemplary Activity Assay | Indication |
| --- | --- | --- | --- |
| EPO (Erythropoietin; Epoetin alfa; Epoetin beta; Gene-activated erythropoietin; Darbepoetin-alpha; NESP; Epogen; Procrit; Eprex; Erypo; Espo; Epoimmun; EPOGIN; NEORECORMON; HEMOLINK; Dynepo; ARANESP) | Stimulates cellular differentiation of bone-marrow stem cells at an early stage of erythropoiesis; accelerates the proliferation and maturation of terminally differentiating cells into erythrocytes; and modulates the level of circulating erythrocytes. | Cell proliferation assay using a erythroleukemic cell line TF-1. (Kitamura et al. 1989 J. Cell. Physiol. 140: 323) | Anemia; Anemia in Renal Disease; Anemia in Oncology Patients; Bleeding Disorders; Chronic Renal Failure; Chronic Renal Failure in Pre-Dialysis Patients; Renal Disease; End-Stage Renal Disease; End-Stage Renal Disease in Dialysis Patients; Chemotherapy; Chemotherapy in Cancer Patients; Anemia in zidovudine-treated HIV patients; Anemia in zidovudine-treated patients; Anemia in HIV patients; Anemia in premature infants; Surgical patients (pre and/or post surgery); Surgical patients (pre and/or post surgery) who are anemic; Surgical patients (pre and/or post surgery) who are undergoing elective surgery; Surgical patients (pre and/or post surgery) who are undergoing elective, non-cardiac surgery; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Surgical patients (pre and/or post surgery) who are undergoing elective, non-cardiac, non-vascular surgery; Surgical patients (pre and/or post surgery) who are undergoing elective, non-vascular surgery; Surgical patients (pre and/or post surgery) who are undergoing cardiac and/or vascular surgery; Aplastic anemia; Refractory anemia; Anemia in Inflammatory Bowel Disease; Refractory anemia in Inflammatory Bowel Disease; Transfusion avoidance; Transfusion avoidance for surgical patients; Transfusion avoidance for elective surgical patients; Transfusion avoidance for elective orthopedic surgical patients; Patients who want to Increase Red Blood Cells. |
| G-CSF (Granulocyte colony-stimulating factor; Granulokine; KRN 8601; Filgrastim; Lenograstim; Meograstim; Nartograstim; Neupogen; NOPIA; Gran; GRANOCYTE; Granulokine; Neutrogin; Neu-up; Neutromax) | Stimulates the proliferation and differentiation of the progenitor cells for granulocytes and monocytes-macrophages. | Proliferation of murine NFS-60 cells (Weinstein et al, Proc Natl Acad Sci USA 1986; 83, pp 5010-4) | Chemoprotection; Adjunct to Chemotherapy; Inflammatory disorders; Cancer; Leukemia; Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; Wound Healing; Autoimmune Disease; Transplants; Bone marrow transplants; Acute myelogeneous leukemia; Lymphoma, Non-Hodgkin's lymphoma; Acute lymphoblastic leukemia; Hodgkin's disease; Accelerated myeloid recovery; Glycogen storage disease. |
| GM-CSF (Granulocyte-macrophage colony-stimulating factor; rhuGM-CSF; BI 61012; Prokine; Molgramostim; Sargramostim; GM-CSF/IL 3 fusion; Milodistim; Leucotropin; PROKINE; LEUKOMAX; Interberin; Leukine; Leukine Liquid; Pixykine) | Regulates hematopoietic cell differentiation, gene expression, growth, and function. | Colony Stimulating Assay: Testa, N. G., et al., "Assays for hematopoietic growth factors." Balkwill F R (edt) Cytokines, A practical Approach, pp 229-44; IRL Press Oxford 1991. | Bone Marrow Disorders; Bone marrow transplant; Chemoprotection; Hepatitis C; HIV Infections; Cancer; Lung Cancer; Melanoma; Malignant melanoma; Mycobacterium avium complex; Mycoses; Leukemia; Myeloid Leukemia; Infections; Neonatal infections; Neutropenia; Mucositis; Oral Mucositis; Prostate Cancer; Stem Cell Mobilization; Vaccine Adjuvant; Ulcers (such as Diabetic, Venous Stasis, or Pressure Ulcers); Prevention of neutropenia; Acute myelogenous leukemia; Hematopoietic progenitor cell mobilization; Lymphoma; Non-Hodgkin's lymphoma; Acute Lymphoblastic Leukemia; Hodgkin's disease; Accelerated myeloid recovery; Transplant Rejection; Xenotransplant Rejection. |
| Human growth hormone (Pegvisamont; Somatrem; Somatropin; TROVERT; PROTROPIN; BIO-TROPIN; HUMATROPE; NUTROPIN; NUTROPIN AQ; | Binds to two GHR molecules and Induces signal transduction through receptor dimerization | Ba/F3-hGHR proliferation assay, a novel specific bioassay for serum human growth hormone. J Clin Endocrinol Metab 2000 Nov; 85(11): 4274-9 Plasma growth hormone (GH) immunoassay and | Acromegaly; Growth failure; Growth hormone replacement; Growth hormone deficiency; Pediatric Growth Hormone Deficiency; Adult Growth Hormone Deficiency; Idiopathic Growth Hormone Deficiency; Growth retardation; Prader-Willi Syndrome; Prader-Willi Syndrome in children 2 years or |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| NUTROPHIN; NORDITROPIN; GENOTROPIN; SAIZEN; SEROSTIM) | | tibial bioassay, Appl Physiol 2000 Dec; 89(6): 2174-8 Growth hormone (hGH) receptor mediated cell mediated proliferation, Growth Horm IGF Res 2000 Oct; 10(5): 248-55 International standard for growth hormone, Horm Res 1999; 51 Suppl 1: 7-12 | older; Growth deficiencies; Growth failure associated with chronic renal insufficiency; Osteoporosis; Postmenopausal osteoporosis; Osteopenia, Osteoclastogenesis; burns; Cachexia; Cancer Cachexia; Dwarfism; Metabolic Disorders; Obesity; Renal failure; Turner's Syndrome; Fibromyalgia; Fracture treatment; Frailty, AIDS wasting; Muscle Wasting; Short Stature; Diagnostic Agents; Female Infertility; lipodystrophy. |
| Insulin (Human insulin; Insulin aspart; Insulin Glargine; Insulin lispro; Lys-B28 Pro-B29; lyspro; LY 275585; diarginylinsulin; Des-B26-B30-insulin-B25-amide; Insulin detemir; LABI; NOVOLIN; NOVORAPID; HUMULIN; NOVOMIX 30; VELOSULIN; NOVOLOG; LANTUS; ILETIN; HUMALOG; MACRULIN; EXUBRA; INSUMAN; ORALIN; ORALGEN; HUMAHALE; HUMAHALIN) | Stimulates glucose uptake and promotes glycogenesis and lipogenesis. | Insulin activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Interferon alfa (Interferon alfa-2b; recombinant; Interferon alfa-n1; Interferon alfa-n3; Peginterferon alpha-2b; Ribavirin and interferon alfa-2b; Interferon alfacon-1; interferon consensus; YM 643; CIFN; interferon-alpha consensus; recombinant methionyl consensus interferon; recombinant consensus interferon; CGP 35269; RO 253036; RO 258310; INTRON A; PEG-INTRON; OIF; OMNIFERON; PEG-OMNIFERON; VELDONA; PEG-REBETRON; ROFERON A; WELLFERON; ALFERON N/LDO; REBETRON; ALTEMOL; VIRAFERON PEG; PEGASYS; VIRAFERON; VIRAFON; AMPLIGEN; INFERGEN; INFAREX; ORAGEN) | Confers a range of cellular responses including antiviral, antiproliferative, antitumor and immunomodulatory activities; stimulate production of two enzymes: a protein kinase and an oligoadenylate synthetase. | Anti-viral assay: Rubinstein S, Familletti P C, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Multiple Sclerosis; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, Osteoclastogenesis; Fibromyalgia; Sjogren's Syndrome; Chronic Fatigue Syndrome; Fever; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Hemmorhagic Fever; Viral Hemmorhagic Fevers; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Calcitonin (Salmon Calcitonin (Salcatonin); Calcitonin human-salmon hybrid; Forcaltonin; Fortical; Calcitonin; Calcitonina Almirall; Calcitonina Hubber; Calcimar; Calsynar; Calogen; Miacalcic; Miacalcin; SB205614; Macritonin; Cibacalcin; Cibacalcina; Cibacalcine; Salmocalcin; PowderJect Calcitonin) (CAS-21215-62-3) | Regulates levels of calcium and phosphate in serum; causes a reduction in serum calcium--an effect opposite to that of human parathyroid hormone. | Hypocalcemic Rat Bioassay, bone resorbing assay and the pit assay, CT receptor binding assay, CAMP stimulation assay: J Bone Miner Res 1999 Aug; 14(8): 1425-31 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Interferon beta (Interferon beta-1a; Interferon beta 1b; Interferon-beta-serine; SH 579; ZK 157046; BCDF; beta-2 IF; Interferon-beta-2; rhIL-6; SJ0031; DL 8234; FERON; IFNbeta; BETASERON; AVONEX; REBIF; BETAFERON; SIGOSIX) | Modulates MHC antigen expression, NK cell activity and IFNg production and IL12 production in monocytes. | Anti-viral assay: Rubinstein S, Familletti P C, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Multiple Sclerosis; Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Osteoclastogenesis; Fibromyalgia; Sjogren's Syndrome; Chronic Fatigue Syndrome; Fever; Hemmorhagic Fever; Viral Hemmorhagic Fevers; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Growth hormone releasing factor; Growth hormone releasing hormone (Sermorelin acetate; Pralmorelin; Somatorelin; Somatoliberin; Geref; Gerel; Groliberin) | Acts on the anterior pituitary to stimulate the production and secretion of growth hormone and exert a trophic effect on the gland. | Growth hormone-releasing peptides (GHRPs) are known to release growth hormone (GH) in vivo and in vitro by a direct action on receptors in anterior pituitary cells. Biological activity can be measured in cell lines expressing growth hormone releasing factor receptor (Mol Endocrinol 1992 Oct; 6(10): 1734-44, Molecular Endocrinology, Vol 7, 77-84). | Acromegaly; Growth failure; Growth hormone replacement; Growth hormone deficiency; Pediatric Growth Hormone Deficiency; Adult Growth Hormone Deficiency; Idiopathic Growth Hormone Deficiency; Growth retardation; Prader-Willi Syndrome; Prader-Willi Syndrome in children 2 years or older; Growth deficiencies; Growth failure associated with chronic renal insufficiency; Osteoporosis; Osteopenia, Osteoclastogenesis; Postmenopausal osteoporosis; burns; Cachexia; Cancer Cachexia; Dwarfism; Metabolic Disorders; Obesity; Renal failure; Turner's Syndrome; Fibromyalgia; Fracture treatment; Frailty, AIDS wasting; Muscle Wasting; Short Stature; Diagnostic Agents; Female Infertility; lipodystrophy. |
| IL-2 (Aldesleukin; interleukin-2 fusion toxin; T cell growth factor; PROLEUKIN; IMMUNACE; CELEUK; ONCOLIPIN 2; MACROLIN) | Promotes the growth of B and T cells and augments NK cell and CTL cell killing activity. | T cell proliferation assay "Biological activity of recombinant human interleukin-2 produced in *Escherichia coli*." Science 223: 1412-1415, 1984. natural killer (NK) cell and CTL cytotoxicity assay "Control of homeostasis of CD8+ memory T cells by opposing cytokines. Science 288: 675-678, 2000; CTLL-2 Proliferation: Gillis et al (1978) J. Immunol. 120, 2027 | Cancer; Solid Tumors; Metastatic Renal Cell Carcinoma; Metastatic Melanoma; Malignant Melanoma; Melanoma; Renal Cell Carcinoma; Renal Cancer; Lung Cancer (e.g,. Non-Small Cell Lung Cancer or Small Cell Lung Cancer); Colon Cancer; Breast Cancer; Liver Cancer; Leukemia; Preleukemia; Hematological Malignancies; Hematological Disorders; Acute Myeloid Leukemia; Melanoma; Malignant Melanoma; Non-Hodgkin's Lymphoma; Ovarian Cancer; Prostate Cancer; Brain Cancer; Glioma; Glioblastoma Multiforme; Hepatitis; Hepatitis C; Lymphoma; HIV Infection (AIDS); Inflammatory Bowel Disorders; Kaposi's Sarcoma; Multiple Sclerosis; Arthritis; Rheumatoid Arthritis; Transplant Rejection; Diabetes; Type 1 Diabetes Mellitus; Type 2 Diabetes. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Parathyroid hormone; parathyrin (PTH; Ostabolin; ALX1-11; hPTH 1-34; LY 333334; MN 10T; parathyroid hormone (1-31); FORTEO; PARATHAR) | Acts in conjuction with calcitonin to control calcium and phosphate metabolism; elevates blood calcium level; stimulates the activity of osteocytes; enhances absorption of Ca+/Pi from small intestine into blood; promotes reabsorption of Ca+ and inhibits Pi by kidney tubules. | Adenylyl cyclase stimulation in rat osteosarcoma cells, ovariectomized rat model of osteoporosis: IUBMB Life 2000 Feb; 49(2): 131-5 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Resistin | Mediates insulin resistance in Type II diabetes; inhibits insulin-stimulated glucose uptake | Ability of resistin to influence type II diabetes can be determined using assays known in the art: Pontoglio et al., J Clin Invest 1998 May 15; 101(10): 2215-22. | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| TR6 (DcR3; Decoy Receptor 3; FASTR) | Inhibits Fas Ligand and AIM-2 (TL5, LIGHT) mediated apoptosis. | Cellular apoptosis can be measured by annexin staining, TUNEL staining, measurement of caspase levels. Inhibition of cell growth can also be directly measured, for example by ALOMAR Blue staining. Assay refs: cytotoxicity assay on human fibrosarcoma (Epsevik and Nissen-Meyer, 1986, J. Immunol. methods). | Fas Ligand or LIGHT induced apoptotic disorders: hepatitis; liver failure (including fulminant liver failure); graft versus host disease; graft rejection; myelodysplastic syndrome; renal failure; insulin dependent diabetes mellitus; rheumatoid arthritis; inflammatory bowel disease; autoimmune disease; toxic epidermal necrolysis; multiple sclerosis. |
| DeCAF (D-SLAM; BCM-like membrane protein; BLAME (B lymphocyte activator macrophage expressed))x | Inhibits proliferation and differentiation of B cells; Antagonize BLyS activity | DeCAF activity can be determined using assays known in the art, such as for example, those described in Examples 32-33 of International Publication No. WO0111046. | B cell and/or T cell mediated immune disorders; Immunodeficiency (e.g., Common Variable Immunodeficiency, Selective IgA Deficiency) |
| BLyS (B Lymphocyte Stimulator; Neutrokine alpha; TL7; BAFF; TALL-1; THANK; radiolabeled BLyS) | Promotes proliferation, differentiation and survival of B cells; Promotes immunoglobulin production by B cells. | BLyS activity can be determined using assays known in the art, such as, for example, the costimulatory proliferation assay and other assays disclosed by Moore et al., 1999, Science, 285(5425): 260-3. | B cell and/or T cell mediated immune disorders, particularly immune system disorders associated with low B cell numbers or low serum immunoglobulin; Immunodeficiency (e.g., Common Variable Immunodeficiency, Selective IgA Deficiency). Radiolabeled forms: lymphoma, non-Hodgkins lymphoma, chronic lymphocytic leukemia, multiple myeloma. |
| Anti-BLyS single chain antibody (scFvI116A01, scFvI050B11, scFvI006D08) and others. | Agonize or antagonize BlyS activity. | BLyS agonist or antagonist activity can be determined using assays known in the art, such as, for example, a modified version the costimulatory proliferation assay disclosed by Moore et al., 1999, Science, 285(5425): 260-3, in | B cell and/or T cell mediated immune disorders; Autoimmune disorders, particularly autoimmune diseases associated with the production of autoantibodies; Rheumatoid Arthritis, Systemic Lupus Erythematosus; Sjogren's Syndrome, cancers expressing Blys as an autocrine growth factor, e.g. certain chronic lymphocytic leukemias. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | which BlyS is mixed or preincubated with the anti-BlyS antibody prior to being applied to the responder B lymphocytes. | |
| MPIF-1 (Myeloid Progenitor Inhibitory Factor; CK beta-8; Mirostipen) | Inhibits myeloid progenitor cells; and activates monocytes | MPIF-1 activity can be measured using the myeloprotection assay and chemotaxis assay described in U.S. Pat. No. 6,001,606. | Chemoprotection; Adjunct to Chemotherapy; Inflammatory disorders; Cancer; Leukemia; Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; Wound Healing; Autoimmune Disease; Transplants; Bone marrow transplants; Acute myelogeneous leukemia; Lymphoma, Non-Hodgkin's lymphoma; Acute lymphoblastic leukemia; Hodgkin's disease; Accelerated myeloid recovery; Glycogen storage disease. |
| KDI (Keratinocyte Derived Interferon; Interferon Kappa Precursor) | Inhibits bone marrow proliferation; and shows antiviral activity. | KDI activity can be measured using the antiviral and cell proliferation assays described in Examples 57-63 of International Publication No. WO0107608. | Multiple sclerosis; Hepatitis; Cancer; Viral infections, HIV infections, Leukemia. |
| TNFR2 (p75) (ENBREL) | Binds both TNFα and TNFβ; mediates T-cell proliferation by TNF; reduces signs and structural damage in patients with moderately to severely active rheumatoid arthritis (RA). | T-cell proliferation can be measured using assays known in the art. For example, "Lymphocytes: a practical approach" edited by: S L Rowland, A J McMichael - chapter 6, pages 138-160 Oxford University Press (2000); and "Current Protocols on CD-ROM" section 3.12 Proliferation Assays for T-cell Function John Wiley & Sons, Inc. (1999). | Autoimmune disease; Rheumatoid Arthritis; Psoriatic arthritis; Still's Disease; Ankylosing Spondylitis; Cardiovascular Diseases; Vasulitis; Wegener's granulomatosis; Amyloidosis; Systemic Lupus Erythematosus, Insulin-Dependent Diabetes Mellitus; Immunodeficiency Disorders; Infection; Inflammation; Inflammatory Bowel Disease; Chrohn's Disease; Psoriasis; AIDS; Graft Rejection; Graft Versus Host Disease. |
| Keratinocyte growth factor 2 (Repifermin; KGF-2; Fibroblast Growth Factor-10; FGF-10) | Stimulates epithelial cell growth. | KGF-2 activity can be measured using the wound healing assays and epithelial cell proliferation assays described in U.S. Pat. No. 6,077,692. | Stimulate Epithelial Cell Proliferation; Stimulate Basal Keratinocytes; Wound Healing; Stimulate Hair Follicle Production; Healing Of Dermal Wounds. Wound Healing; Eye Tissue Wounds, Dental Tissue Wounds, Oral Cavity Wounds, Diabetic Ulcers, Dermal Ulcers, Cubitus Ulcers, Arterial Ulcers, Venous Stasis Ulcers, Burns Resulting From Heat Exposure Or Chemicals, or Other Abnormal Wound Healing Conditions such as Uremia, Malnutrition, Vitamin Deficiencies or Complications Associated With Systemic Treatment With Steroids, Radiation Therapy or Antineoplastic Drugs or Antimetabolites; Promote Dermal Reestablishment Subsequent To Dermal Loss; Increase the Adherence |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Of Skin Grafts To A Wound Bed; Stimulate Re-Epithelialization from The Wound Bed; To Promote Skin Strength; Improve The Appearance Of Aged Skin; Proliferate Hepatocytes, Lung, Breast, Pancreas, Stomach, Bladder, Small Intestine, Large Intestine; Sebocytes, Hair Follicles, Type II Pneumocytes, Mucin-Producing Goblet Cells, or Other Epithelial Cells, Endothelial Cells, Keratinocytes, or Basal Keratinocytes (and Their Progenitors) Contained Within The Skin, Lung, Liver, Bladder, Eye, Salivary Glands, or Gastrointestinal Tract; Reduce The Side Effects Of Gut Toxicity That Result From Radiation, Chemotherapy Treatments Or Viral Infections; Cytoprotector, especially of the Small Intestine Mucosa or Bladder; Mucositis (Mouth Ulcers); Regeneration Of Skin; Full and/or Partial Thickness Skin Defects, including Burns, (e.g., Repopulation Of Hair Follicles, Sweat Glands, And Sebaceous Glands); Psoriasis; Epidermolysis Bullosa; Blisters; Gastric and/or Doudenal Ulcers; Reduce Scarring; Inflamamatory Bowel Diseases; Crohn's Disease; Ulcerative Colitis; Gut Toxicity; Lung Damage; Repair Of Alveoli And/or Brochiolar Epithelium; Acute Or Chronic Lung Damage; Emphysema, ARDS; Inhalation Injuries; Hyaline Membrane Diseases; Infant Respiratory Distress Syndrome; Bronchopulmonary Displasia In Premature Infants; Fulminant Liver Failure; Cirrhosis, Liver Damage caused by Viral Hepatitis and/or Toxic Substances; Diabetes Mellitus; Inflammation. |
| TR2 (and TR2sv1, TR2SV2; TNFRSF14; HVEM; Herpes Virus Entry Mediator; ATAR) | Inhibits B cell proliferation, and mediates and inhibits Herpes Simplex Virus (HSV) infection. | Co-stimulation B-cell proliferation assay and Ig production assay (Moore et al., 1999, Science, 285(5425): 260-3.). HSV-1 and HSV-2 Infectivity Assay: International Publication No. WO 97/04658 Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Herpes; immune disorders; autoimmune disease; graft versus host disease; graft rejection; variable immunodeficiency; immunodeficiency syndromes; cancer. |
| Macrophage derived chemokine, MDC (Ckbeta-13) | Chemotactic for monocyte-derived dendritic cells and IL-2-activated natural killer cells. | | Inflammatory diseases; wound healing; angiogenesis; AIDS infection. |
| HAGDG59 (Retinal short-chain dehydrogenase) | Activates MIP1a release in Dendritic Cells. | Dendritic cell assays are well known in the art. For example, J. Immunol. 158: 2919-2925 (1997); J. Leukoc. Biol. 65: 822-828 (1999). | Immune disorders; cancer; viral infection; inflammation; sepsis; arthritis; asthma. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| GnRH (Gonadotropin Releasing Hormone) | Promotes release of follicle-stimulating hormone and luteinizing hormone from anterior pituitary. | GnRH is known to cause the release of follicle stimulating hormone (FSH) and/or luteinizing hormone (LH) in vivo by a direct action on receptors in anterior pituitary gonadotropes. GnRH activity can be determined by measuring FSH levels in the medium of cultured gonadotropes before and after GnRH supplementation. For example, Baker et al. Biol Reprod 2000 Sep; 63(3): 865-71. | Infertility; Kallmann's syndrome or other forms of hypergonadotropic hypergonadism (failure to go through puberty naturally). |
| Teprotide | Inhibits angiotensin converting enzyme (ACE). | Inhibition of ACE can be determined using assays known in the art. For example, Anzenbacherova et al., J. Pharma Biomed Anal 2001 Mar; 24(5-6): 1151-6. | Hypertension; congestive heart failure. |
| Human chemokine HCC-1 (ckBeta-1; HWFBD) | Involved in inflammation, allergy, tissue rejection, viral infection, and tumor biology; enhances proliferation of CD34+ myeloid progenitor cells. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Autoimmune disorders; Immunity; Vascular and Inflammatory disorders; HIV; AIDS; infectious diseases. |
| ACE2 inhibitor (DX512) | Inhibits production of angiotensin II which induces aldosterone production, arteriolar smooth muscle vasoconstriction, and proliferation of cardiac fibroblasts, Induces angiogenesis; an enzyme that converts angiotensin I to angiotensin1-9; also cleaves des-Arg, bradykinin and neurotensin. | Inhibition of angiotensin can be determined using assays known in the art. For example, in vitro using a proliferation assay with rat cardiac fibroblasts as described in Naunyn Schmiedebergs Arch Pharmacol 1999 May; 359(5): 394-9. | Treatment for elevated angiotensin II and/or aldosterone levels, which can lead to vasoconstriction, impaired cardiac output and/or hypertension; Cardiovascular Disease; Cardiac Failure; Diabetes; Type II Diabetes; Proteinuria; Renal disorders, congestive heart failure. |
| TR1 (OCIF; Osteoclastogenesis inhibitory factor; osteoprotegerin, OPG; tumor necrosis factor receptor superfamily member 11B precursor;) | Inhibits osteoclastogenesis and bone resorption, and induces fibroblast proliferation. | Coculture Assay for Osteoclastogenesis, Bone resorption assay using fetal long-bone organ culture system, dentine resorption assay, and fibroblast proliferation assays are each described in Kwon et al., FASEB J. 12: 845-854 (1998). | Osteoporosis; Paget's disease; osteopenia; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration; organ calcification; vascular calcification. |
| Human chemokine Ckbeta-7 | Chemotactic for both activated (CD3+) T cells and nonactivated (CD14−) lymphocytes and (CD4+) and (CD8+) T lymphocytes and (CD45RA+) T cells | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer; Wound healing; Inflammatory disorders; Immmunoregulatory disorders; Atherosclerosis; Parasitic Infection; Rheumatoid Arthritis; Asthma; Autoimmune disorders. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| CKbeta4 (HGBAN46; HE9DR66) | Attracts and activates microbicidal leukocytes; Attracts CCR6-expressing immature dendritic cells and memory/effector T cells; B-cell chemotaxis; inhibits proliferation of myeloid progenitors; chemotaxis of PBMC's. | Chemokine activities can be determined using assays known in the art: Methods in Molecular Biology, 2000, vol. 138: Chemokine Protocols. Edited by: A. E. I. Proudfoot, T. N. C. Wells, and C. A. Power. © Humana Press Inc., Totowa, NJ | Cancer; Solid Tumors; Chronic Infection; Autoimmune Disorders; Psoriasis; Asthma; Allergy; Hematopoiesis; Wound Healing; Bone Marrow Failure; Silicosis; Sarcoidosis; Hyper-Eosinophilic Syndrome; Lung Inflammation; Fibrotic Disorders; Atherosclerosis; Periodontal diseases; Viral diseases; Hepatitis. |
| Leptin | Controls obesity through regulation of appetite, reduction of body weight, and lowering of insulin and glucose level. | in vivo modulation of food intake, reduction in body weight, and lowering of insulin and glucose levels in ob/ob mice, radioimmunoassay (RIA) and activation of the leptin receptor in a cell-based assay. Protein Expr Purif 1998 Dec; 14(3): 335-42 | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); a Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Immunological Disorders; Immunosuppression. |
| IL-1 receptor antagonist (Anakinra; soluble interleukin-1 receptor; IRAP; KINERET; ANTRIL) | Binds IL1 receptor without activating the target cells; inhibits the binding of IL1-alpha and IL1-beta; and neutralizes the biologic activity of IL1-alpha and IL1-beta. | 1) Competition for IL-1 binding to IL-1 receptors in YT-NCI or C3H/HeJ cells (Carter et al., Nature 344: 633-638, 1990); 2) Inhibition of IL-1-induced endothelial cell-leukocyte adhesion (Carter et al., Nature 344: 633-638, 1990); 3) Proliferation assays on A375-C6 cells, a human melanoma cell line highly susceptible to the antiproliferative action of IL-1 (Murai T et al., J. Biol. Chem. 276: 6797-6806, 2001). | Autoimmune Disease; Arthritis; Rheumatoid Arthritis; Asthma; Diabetes; Diabetes Mellitus; GVHD; Inflammatory Bowel Disorders; Chron's Disease; Ocular Inflammation; Psoriasis; Septic Shock; Transplant Rejection; Inflammatory Disorders; Rheumatic Disorders; Osteoporosis; Postmenopausal Osteoporosis; Stroke. |
| TREM-1 (Triggering Receptor Expressed on Monocytes 1) | Mediates activation of neutrophil and monocytes; Stimulates neutrophil and monocyte-mediated inflammatory response; Promotes secretion of TNF, IL-8, and MCP-1; Induces neutrophil degranulation, Ca2+ mobilization and tyrosine phosphorylation of extracellular signal-related kinase 1 (ERK1), ERK2 and phospholipase C-gamma. | Secretion of cytokines, chemokines, degranulation, and cell surface activation markers can be determined using assays described in Bouchon et al, J Immunol 2000 May 15; 164(10): 4991-5. | Inflammation; Sepsis; bacterial infection; autoimmune diseases; GVHD. |
| HCNCA73 | Induces T-cell activation-expression of CD152 marker; Stimulates release of TNF-a and MIP-1a from immature, monocyte-derived dendritic cells; | FMAT can be used to measure T-cell surface markers (CD69, CD152, CD71, HLA-DR) and T-cell cytokine production (e.g., IFNg production). J. of Biomol. Screen. 4: 193-204 (1999). Other T- | Autoimmune disorders; Inflammation of the gastrointestinal tract; Cancer; Colon Cancer; Allergy; Crohn's disease. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | Promotes maturation of dendritic cells. | cell proliferation assays: "Lymphocytes: a practical approach" edited by: S L Rowland, A J McMichael - Chapter 6, pages 138-160 Oxford University Press (2000); WO 01/21658 Examples 11-14, 16-17 and 33. | |
| VEGF-2 (Vascular Endothelial Growth Factor-2; VEGF-C) | Promotes endothelial cell proliferation. | VEGF activity can be determined using assays known in the art, such as those disclosed in International Publication No. WO0045835, for example. | Coronary artery disease; Critical limb ischemia; Vascular disease; proliferation of endothelial cells, both vascular and lymphatic. Antagonists may be useful as anti-angiogenic agents; Cancer. |
| HCHNF25 (jumping translocation breakpoint) | Activates MIP1a Release in Dendritic Cells. | Dendritic cell assays are well known in the art. For example, J. Immunol. 158: 2919-2925 (1997); J. Leukoc. Biol. 65: 822-828 (1999). | Immune disorders; cancer. |
| HLDOU18 (Bone Morphogenic Protein 9 (BMP9); Growth differentiation factor-2 precursor (GDF-2 precursor)) | Activates L6/GSK3 kinase assay. | Assays for activation of GSK3 kinase activity are well known in the art. For example, Biol. Chem. 379(8-9): (1998) 1101-1110.; Biochem J. 1993 Nov 15; 296 (Pt 1): 15-9. | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Glucagon-Like-Peptide 1 (GLP1; Insulinotropin) | Stimulates the synthesis and release of insulin; enhances the sensitivity of adipose, muscle, and liver tissues towards insulin; stimulates glucose uptake; slows the digestive process; suppresses appetite; blocks the secretion of glucagon. | GLP1 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Exendin-4 (AC-2993) | Stimulates the synthesis and release of insulin; enhances the sensitivity of adipose, muscle, and liver tissues towards insulin; stimulates glucose uptake; slows the digestive process; suppresses appetite; blocks the secretion of glucagon. | Exendin-4 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Disorders; Obesity; Vascular Disorders; Suppression of Body Weight; Suppression of Appetite; Syndrome X. |
| T20 (T20 HIV inhibitory peptide, DP178; DP178 HIV inhibitory peptide) | a peptide from residues 643-678 of the HIV gp41 transmembrane protein ectodomain which binds to gp41 in its resting state and prevents transformation to the fusogenic state | Virus inhibition assays as described in Zhang et al., Sep. 26, 2002, Sciencexpress (www.sciencexpress.org). | HIV; AIDS; SIV (simian immunodeficiency virus) infection. |
| T1249 (T1249 HIV inhibitory peptide; T1249 anti-HIV peptide) | a second generation HIV fusion inbitor | Virus inhibition assays as described in Zhang et al., Sep. 26, 2002, Sciencexpress (www.sciencexpress.org). | HIV; AIDS; SIV (simian immunodeficiency virus) infection |
| Interferon Hybrids, specifically preferred: IFNalpha A/D hybrid (BglII version) IFNalpha A/D hybrid (PvuII version) IFNalpha A/F hybrid IFNalpha A/B hybrid IFNbeta 1/alpha D hybrid (IFNbeta-1/alpha-1 hybrid) IFNalpha/beta hybrid | Confers a range of cellular responses including antiviral, antiproliferative, antitumor and immunomodulatory activities; stimulate production of two enzymes: a protein kinase and an oligoadenylate synthetase. Also, modulates MHC antigen expression, NK cell activity and IFNg production and IL12 production in monocytes. | Anti-viral assay: Rubinstein S, Familletti P C, Pestka S. (1981) Convenient assay for interferons. J. Virol. 37(2): 755-8; Anti-proliferation assay: Gao Y, et al (1999) Sensitivity of an epstein-barr virus-positive tumor line, Daudi, to alpha interferon correlates with expression of a GC-rich viral transcript. Mol Cell Biol. 19(11): 7305-13. | Viral infections; HIV Infections; Hepatitis; Chronic Hepatitis; Hepatitis B; Chronic Hepatitis B; Hepatitis C; Chronic Hepatitis C; Hepatitis D; Chronic Hepatitis D; Human Papillomavirus; Herpes Simplex Virus Infection; External Condylomata Acuminata; HIV; HIV Infection; Oncology; Cancer; Solid Tumors; Melanoma; Malignant Melanoma; Renal Cancer (e.g., Renal Cell Carcinoma); Lung Cancer (e.g., Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Bacterial Infections; Chemoprotection; Thrombocytopenia; Multiple Sclerosis; Pulmonary Fibrosis; Age-Related Macular Degeneration; Macular Degeneration; Crohn's Disease; Neurological Disorders; Arthritis; Rheumatoid Arthritis; Ulcerative Colitis; Osteoporosis, Osteopenia, Osteoclastogenesis; Fibromyalgia; Sjogren's Syndrome; Chronic Fatigue Syndrome; Fever; Hemmorhagic Fever; Viral Hemmorhagic Fevers; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Disorders; Obesity; Vascular Disorders; Suppression of Body Weight; Suppression of Appetite; Syndrome X. |
| B-type natriuretic peptide (BNP, brain natriuretic peptide) | stimulates smooth muscle relaxation and vasodilation, natriuresis, and suppression of renin-angiotensin and endothelin. | Inhibition of angiotensin can be determined using assays known in the art, for example using an in vitro proliferation assay with rat cardiac fibroblasts as described in Naunyn Schmiedebergs Arch Pharmacol 1999 May; 359(5): 394-9. Vasodilation can be measured in animals by measuring the myogenic responses of small renal arteries in an isobaric arteriograph system (see Am J Physiol Regul Integr Comp Physiol 2002 Aug; 283(2): R349-R355). Natriuesis is determined by measuring the amount of sodium in the urine. | Congestive heart failure; cardiac volume overload; cardiac decompensation; Cardiac Failure; Left Ventricular Dysfunction; Dyspnea |
| α-defensin, including alpha 1 defensin, alpha 2 defensin, alpha 3 defensin (myeloid-related defensin; DEFA1; neutrophil-specific defensin; CAF) | Suppression of HIV replication; active against bacteria, fungi, and enveloped viruses. | Virus inhibition assays as described in Zhang et al., Sep. 26, 2002, Sciencexpress (www. sciencexpress.org). | HIV, AIDS; ARC. |
| Phosphatonin (matrix extracellular phosphoglycoprotein; MEPE) | Regulation of phosphate metabolism. | Blood phosphate levels can be measured using methods known in the art such as the Hypophosphatemic Rat Bioassay. Zoolog Sci 1995 Oct; 12(5): 607-10. | Hyperphosphatemia; Hyperphosphatemia in chronic renal failure; hypophosphatemia; Osteomalacia; Rickets; X-linked dominant hypophosphatemic rickets/osteomalacia (XLH); autosomal dominant hypophosphatemic rickets/osteomalacia (ADHR); tumor-induced rickets/osteomalacia (TIO). |
| P1pal-12 (pepducin, PAR1-based pepducin) | Regulation of protease-activated receptor (PAR) signal transduction and thrombin-mediated aggregation of human platelets. | Platelet aggregation can be measured using methods known in the art such as described in Nature Medicine 2002 Oct; 8(10): 1161-1165. | Protection against systemic platelet activation, thrombus, heart attack, stroke, and/or coagulation disorders. |
| P4pal-10 (pepducin, PAR4-based pepducin) | Regulation of protease-activated receptor (PAR) signal transduction and thrombin-mediated aggregation of human platelets. | Platelet aggregation can be measured using methods known in the art such as described in Nature Medicine 2002 Oct; 8(10): 1161-1165. | Protection against systemic platelet activation, thrombus, heart attack, stroke, and/or coagulation disorders. |
| HRDFD27 | Involved in the proliferation of T cells; Production of TNFgamma. | T-cell proliferation can be measured using assays known in the art. For example, "Lymphocytes: a practical approach" edited by: S L Rowland, A J McMichael - chapter 6, pages 138-160 Oxford University Press (2000); and "Current Protocols on CD-ROM" section 3.12 Proliferation Assays for T-cell Function John Wiley & Soncs, Inc. (1999). | Chemoprotection; Adjunct to Chemotherapy; Inflammatory disorders; Cancer; Leukemia; Myelocytic leukemia; Neutropenia, Primary neutropenias (e.g.; Kostmann syndrome); Secondary neutropenia; Prevention of neutropenia; Prevention and treatment of neutropenia in HIV-infected patients; Prevention and treatment of neutropenia associated with chemotherapy; Infections associated with neutropenias; Myelopysplasia; Autoimmune disorders; Psoriasis; Mobilization of hematopoietic progenitor cells; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| HWHGZ51 (CD59; Metastasis-associated GPI-adhered protein homolog) | Stimulates an immune response and induces inflammation by inducing mononuclear cell, eosinophil and PMN infiltration; Inhibits growth of breast cancer, ovarian cancer, leukemia, and melanoma; Overexpressed in colon, lung, breast and rectal tumors; Regulates glucose and/or FFA update by adipocytes and skeletal muscle; Induces redifferentiation of chondrocytes | The ability to affect chondrocyte differentiation can be measured using methods known in the art, such as described in Bone (1995) Sep; 17(3): 279-86. | Wound Healing; Autoimmune Disease; Transplants; Bone marrow transplants; Acute myelogeneous leukemia; Lymphoma, Non-Hodgkin's lymphoma; Acute lymphoblastic leukemia; Hodgkin's disease; Accelerated myeloid recovery; Glycogen storage disease Skeletal diseases and disorders; Musculoskeletal diseases and disorders; Bone fractures and/or breaks; Osteoporosis (postmenopausal, senile, or idiopathic juvenile); Gout and/or pseudogout; Paget's disease; Osteoarthritis; Tumors and/or cancers of the bone (osteochondromas, benign chondromas, chondroblastomas, chondromyxoid fibromas, osteoid osteomas, giant cell tumors, multiple myelomas, osteosarcomas, fibrosarcomas, malignant fibrous histiocytomas, chondrosarcomas, Ewing's tumors, and/or malignant lymphomas); Bone and joint infections (osteomyelitits and/or infectious arthritis); Charcot's joints; Heel spurs; Sever's disease; Sport's injuries; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Kidney diseases and disorders; Shonlein-Henoch purpura, Berger disease, celiac disease, dermatitis herpetiformis, Chron disease; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Hyperinsulinemia; Hypoinsulinemia; Immunological disorders (e.g. arthritis, asthma, immunodeficiency diseases, AIDS, rheumatoid arthritis, |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | granulomatous disease, inflammatory bowl disease, sepsis, acne, neutropenia, neutrophilia, psoriasis, hypersensitivities, T-cell mediated cytotoxicity, host-versus-graft disease, autoimmunity disorders, demyelination, systemic lupus erythematosis, drug induced hemolytic anemia, rheumatoid arthritis, Sjorgren's disease, scleroderma) |
| C17 (cytokine-like protein C17) | Inhibits glucose and/or FFA uptake by adipocytes; Induces proliferation of kidney mesangial cells; Regulation of cytokine production and antigen presentation | Proliferation of kidney mesangial cells can be assayed using techniques described in J. Investig. Med. (1998) Aug; 46(6): 297-302. | Kidney diseases and disorders; Shonlein-Henoch purpura, Berger disease, celiac disease, dermatitis herpetiformis, Chron disease; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Hyperinsulinemia; Hypoinsulinemia; Hematopoietic disorders; Immunological diseases and disorders; Developmental diseases and disorders; Hepatic diseases and disorders; Cancer (particularly leukemia); Immunological disorders (e.g. arthritis, asthma, immunodeficiency diseases, AIDS, rheumatoid arthritis, granulomatous disease, inflammatory bowel disease, sepsis, acne, neutropenia, neutrophilia, psoriasis, hypersensitivities, T-cell mediated cytotoxicity, host-versus-graft disease, autoimmunity disorders, demyelination, systemic lupus erythematosis, drug induced hemolytic anemia, rheumatoid arthritis, Sjorgren's disease, scleroderma) |
| HDPBQ71 | Regulates production and secretion of IFNgamma; Activation of myeloid cells and/or hematopoietic cells | Such assays that may be used or routinely modified to test immunomodulatory activity of polypeptides of the invention (including antibodies and agonists or antagonists of the invention) include the assays disclosed in Miraglia et al., J Biomolecular Screening 4: 193-204 (1999); Rowland et al., ""Lymphocytes: a practical approach"" Chapter 6: 138-160 (2000); Gonzalez et al., J Clin. Lab Anal 8(5): 225-233 (1995); Billiau et al., | Blood disorders and infection (e.g., viral infections, tuberculosis, infections associated with chronic granulomatosus disease and malignant osteoporosis); Autoimmune disease (e.g., rheumatoid arthritis, systemic lupus erythematosis, multiple sclerosis); Immunodeficiency, boosting a T cell-mediated immune response, and suppressing a T cell-mediated immune response; Inflammation and inflammatory disorders; Idiopathic pulmonary fibrosis; Neoplastic diseases (e.g., leukemia, lymphoma, melanoma); Neoplasms and cancers, such as, for example, leukemia, lymphoma, melanoma, and prostate, breast, lung, colon, pancreatic, esophageal, stomach, brain, liver and |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | Ann NY Acad Sci 856: 22-32 (1998); Boehm et al., Annu Rev Immunol 15: 749-795 (1997), and Rheumatology (Oxford) 38(3): 214-20 (1999) | urinary cancer;. Benign dysproliferative disorders and pre-neoplastic conditions, such as, for example, hyperplasia, metaplasia, and/or dysplasia; Anemia; Pancytopenia; Leukopenia; Thrombocytopenia; Hodgkin's disease; Acute lymphocytic anemia (ALL); Plasmacytomas; Multiple myeloma; Burkitt's lymphoma; Arthritis; AIDS; Granulomatous disease; Inflammatory bowel disease; Sepsis; Neutropenia; Neutrophilia; Psoriasis; Suppression of immune reactions to transplanted organs and tissues; Hemophilia; Hypercoagulation; Diabetes mellitus; Endocarditis; Meningitis; Lyme Disease; Asthma; Allergy |
| Oscar (osteoclast-associated receptor isoform-3) | Regulator of osteoclast differentiation; regulator of innate and adaptive immune responses | Assay to detect osteoclast differentiation is described in J. Exp. Med. (2002) Jan 21; 195(2): 201-9. | Skeletal diseases and disorders; Musculoskeletal diseases and disorders; Bone fractures and/or breaks; Osteoporosis (postmenopausal, senile, or idiopathic juvenile); Gout and/or pseudogout; Paget's disease; Osteoarthritis; Tumors and/or cancers of the bone (osteochondromas, benign chondromas, chondroblastomas, chondromyxoid fibromas, osteoid osteomas, giant cell tumors, multiple myelomas, osteosarcomas, fibrosarcomas, malignant fibrous histiocytomas, chondrosarcomas, Ewing's tumors, and/or malignant lymphomas); Bone and joint infections (osteomyelitits and/or infectious arthritis); Charcot's joints; Heel spurs; Sever's disease; Sport's injuries |
| Tumstatin (T5, T7 or T8 peptide; α3(IV)NC1) | Inhibits angiogenesis; Inhibits tumor growth; Inhibits protein synthesis | A tumor cell proliferation assay is described in J. Biol. Chem. (1997) 272: 20395-20401. Protein synthesis can be measured as described in Science (2002) Jan 4; 295(5552): 140-3. | Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer) Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; Bone Marrow Disorders; Bone Disorders; Hairy Cell Leukemia; Chronic Myelogeonus Leukemia; Hematological Malignancies; Hematological Disorders; Multiple Myeloma; Angiogenesis |
| CNTF (Ciliary neurotrophic factor) | Enhances myelin formation; Reduces photoreceptor degradation; Regulates calcium currents | Regulation of myelin formation can be assayed as described in J. Neurosci. (2002) Nov. 1; 22(21): 9221-7. | Neurological and neural diseases and disorders, particularly diseases and disorders associated with myelin and demyelination, such as, for example, ALS, multiple sclerosis, Huntington's disease; Neuronal and spinal cord injuries; Disorders of the eye, such as, for example, retinitis pigmentosa, blindness, color-blindness, macular degeneration. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Somatostatin (Octreotide; octreotide acetate; Sandostating LAR ®) | Inhibits growth hormone, glucagons and insulin; Suppresses LF response to GnRH; Decreases splanchnic blood flow; Inhibits release of serotonin, gastrin, vasoactive intestinal peptide, secretin, motilin, and pancreatic polypeptide. | Inhibition of growth hormone release in humans by somatostatin can be measured as described in J. Clin. Endocrinol. Metab. (1973) Oct; 37(4): 632-4. Inhibition of insulin secretion by somatostatin can be measured as described in the Lancet (1973) Dec. 8; 2(7841): 1299-1301. | Cancer; Metastatic carcinoid tumors; Vasoactive Intestinal Peptide secreting adenomas; Diarrhea and Flushing; Prostatic disorders and cancers; Breast cancer; Gastrointestinal disorders and cancers; Cancers of the endocrine system; Head and neck paragangliomas; Liver disorders and cancers; Nasopharyngeal cancers; Thyroid disorders and cancers; Acromegaly; Carcinoid Syndrome; Gallbladder disorders, such as gallbladder contractility diseases and abnormal bile secretion; Psoriasis; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Kidney disorders; Neurological disorders and diseases, including Alzheimers Disease, Parkinson's disease and dementia; Neuropsychotic disorders, including Bipolar affective disorder; Rheumatoid arthritis; Hypertension; Intracranial hypertension; Esophageal varices; Graves' disease; Seizures; Epilepsy; Gastritis; Angiogenesis; |
| IL-22 (IL22, interleukin-22; IL17D, IL27) | Stimulates glucose uptake in skeletal muscle cells; increases skeletal muscle insulin sensitivity. | IL-22 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| HCE1P80 | Stimulates glucose uptake in; increases insulin sensitivity, | HCE1P80 activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| HDRMI82 | Stimulates glucose uptake; increases insulin sensitivity. | HDRMI82 activity may be assayed in vitro using a [3-H]-glucose uptake assay. (J Biol Chem 1999 Oct 22; 274(43): 30864-30873). | Disorders; Obesity; Vascular Disorders; Suppression of Body Weight; Suppression of Appetite; Syndrome X. Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| HDALV07 (adiponectin; gelatin-binding 28k protein precursor; adipose most abundant gene transcript; APM-1; GBP28; ACRP30; ADIPOQ) | Modulates insulin action | Insulin activity may be assayed in vitro using a [3-H]-glucose uptake assay. (J Biol Chem 1999 Oct 22; 274(43): 30864-30873). | Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Hyperglycemia; Familial combined hyperlipidemia; Metabolic syndrome; Inflammatory disorders; Atherogenic disorders |
| C Peptide | An insulin precursor involved in insulin regulation | C-peptide concentrations can be measured using assays well known in the art, such as the one described in PNAS (1970) Sep; 67(1): 148-55 | Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Hyperglycemia; Familial combined hyperlipidemia; Metabolic syndrome |
| HCBOG68 (enteric adipokine; Fat SID; proline rich acidic protein) | Controls proliferation/ differentiation or metabolism/ physiology/pathology/ of adipocytes and adipose tissue in response to dietary conditions. | Activation of cAMP-mediated transcription in adipocytes can be assayed using methods known in the art (Berger et al., Gene 66: 1-10 (1998); Cullen and Malm, Methods in Enzymol 216: 362-368 (1992); Henthorn et al., Proc Natl Acad Sci USA | Treatment of Obesity; treatment of Diabetes; suppression of body weight gain; suppression of appetite. Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | 85: 6342-6346 (1988); Reusch et al., Mol Cell Biol 20(3): 1008-1020 (2000); and Klemm et al., J Biol Chem 273: 917-923 (1998)). | (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies and/or antagonists, include treatment of weight loss; treatment of AIDS wasting; appetite stimulant; treatment of cachexia. |
| PYY (Peptide YY), including PYY$_{3-36}$ (amino acid residues 31-64 of full length PYY, amino acid residues 3-36 of mature PYY) | Decreases appetite; increases satiety; decreases food intake. | Appetite and food intake can be can be measured by methods known in the art (Batterham et al. Nature 2002; 418: 650654) | Most preferred: Treatment of Obesity; treatment of Diabetes; suppression of body weight gain; suppression of appetite. Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies, antagonists: treatment of weight loss; treatment of AIDS wasting; appetite stimulant; treatment of cachexia. |
| WNT10b | Inhibits adipogenesis. | WNT10b activity can be measured using adipogenesis inhibition assays (Ross et al., Science 2000; 289(5481): 950-953 | Most preferred: Treatment of Obesity; suppression of body weight gain; suppression of appetite. Other indications: Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM). |
| WNT11 | Promotes cardiogenesis. | WNT11 activity can be measured using assays known in the art, including cardiogenesis assays (Eisenberg et al., Dev Dyn 1999 Sep; 216(1): 45-58). | Treatment of Cardiovascular disorders; Congestive Heart Failure; Myocardial Infarction. |
| Herstatin | Inhibits cancer proliferation. | Herstatin activity can be measured using cell proliferation assays known in the art (Doherty et al., PNAS 1999; 96(19): 10869-10874. | Oncology; Cancer; Solid Tumors; Melanoma; Malignant Melanoma; Renal Cancer (e.g., Renal Cell Carcinoma); Lung Cancer (e.g,. Non-Small Cell Lung Cancer or Small Cell Lung Cancer); Colon Cancer; Breast Cancer; Liver Cancer; Prostate Cancer; Bladder Cancer; Gastric Cancer; Sarcoma; AIDS-Related Kaposi's Sarcoma; Lymphoma; T Cell Lymphoma; Cutaneous T-Cell Lymphoma; Non-Hodgkin's Lymphoma; Brain Cancer; Glioma; Glioblastoma Multiforme; Cervical Dysplasia; Leukemia; Preleukemia; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Adrenomedullin | stimulates vasodilation; promotes bone growth. | Vasodilation can be measured using assays known in the art (Ashton et al. Pharmacology 2000; 61(2): 101-105. The promotion of bone growth can be measured using assays known in the art, such as the osteoblast proliferation assay (Cornish et al. Am J Physiol 1997 Dec; 273(6 Pt 1): E1113-20). | Hairy Cell Leukemia; Chronic Myelogeonus Leukemia; Hematological Malignancies; Hematological Disorders; Multiple Myeloma. Treatment of Congestive Heart Failure; Hypertension; Myocardial Infarction; Septic Shock; Osteoporosis; Postmenopausal osteoporosis; Osteopenia. |
| Nogo Receptor | Receptor for the axon growth inhibitor, Nogo. | The promotion of axon regeneration and growth can be measured using assays known in the art (Fournier et al. Nature 2001; 409(6818): 341-346). | Treatment of Central Nervous System Damage; Spinal Cord Injury; Peripheral Nerve Damage; Neurodegenerative Diseases; Parkinson's Disease; Alzheimer's Disease; Huntington's Disease; Amyotrophic Lateral Sclerosis; Progressive Supranuclear Palsy; Creutzfeld-Jacob Disease; Motor Neuron Disease. |
| CART (Cocaine- and Amphetamine-Regulated Transcript) | Inhibits food intact and fat storage; promotes lipid oxidation. | Appetite and food intake can be can be measured by methods known in the art (Batterham et al. Nature 2002; 418: 650654) | Most preferred: Treatment of Obesity; suppression of body weight gain; suppression of appetite. Other indications: Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM). |
| RegIV (Colon Specific Gene; Colon Specific Protein) | Stimulates glucose uptake; increases insulin sensitivity. | RegIV activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. |
| Cosyntropin (Cortrosyn) (CAS-16960-16-0) | Synthetic corticotropin; stimulates the release of cortisol. | The activity of cosyntropin can be assessed in vivo by measuring serum cortisol levels. (Frank et al. J. Am. Vet. Med. Assoc. 1998 212(10): 1569-71). | Endocrine; Addison's disease; Cushing's syndrome; pituitary dysfunction; acute adrenal crisis |
| Pexiganan Acetate (CAS-172820-23-4) | Disrupts bacterial membranes. | Pexiganan acetate activity can be assessed using in vitro antibacterial assays known in the art. (Zasloff et al., Antimicrobial Agents and Chemotherapy 1999, 43: 782-788). | Treatment of Infectious Diseases; Treatment of Bacterial Infections. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Pramlintide (Amylin) (CAS-151126-32-8) | Slows gastric emptying; decreases food intake. | Appetite and food intake can be can be measured by methods known in the art (Batterham et al. Nature 2002; 418: 650654) | Treatment of Obesity; treatment of Diabetes; suppression of body weight gain; suppression of appetite; treatment of endocrine disorders; Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X. Other indications for antibodies, antagonists: treatment of weight loss; treatment of AIDS wasting; appetite stimulant; treatment of cachexia. |
| Teriparatide (CAS-52232-67-4) | Acts in conjuction with calcitonin to control calcium and phosphate metabolism; elevates blood calcium level; stimulates the activity of osteocytes; enhances absorption of Ca+/Pi from small intestine into blood; promotes reabsorption of Ca+ and inhibits Pi by kidney tubules. | Adenylyl cyclase stimulation in rat osteosarcoma cells, ovariectomized rat model of osteoporosis: IUBMB Life 2000 Feb; 49(2): 131-5 | Bone Disorders; Fracture prevention; Hypercalcemia; Malignant hypercalcemia; Osteoporosis; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Terlipressin (triglycyl lycine vasopressin) (CAS-14636-12-5) | Analog of vasopressin; induces vasoconstriction. | Terlipressin activity can be measured using assays of vasoconstriction, such as the isolated arterial ring preparation. (Landstrom et al., Hum Reprod 1999 Jan; 14(1): 151-5). | Variceal hemorrhage; cirrhosis; portal hypertension; hepatorenal syndrome; Blood-related disorders |
| Ularitide (CAS-118812-69-4) | Stimulates natriuresis, diuresis, and vasodilation. | Ularitide activity can be assessed by measuring cGMP accumulation in rat renal cells. (Valentin et al., Hypertension 1993 Apr; 21(4): 432-8). | Excretory disorders; Acute renal failure; asthma; congestive heart failure; hypertension; pulmonary hypertension; cardiovascular disorders |
| Aprotinin (Trasylol) (CAS-9087-70-1; CAS-11061-94-2; CAS-12407-79-3) | Serine protease inhibitor; attenuates Systemic Inflammatory Response, fibrinolysis and thrombin-induced platelet aggregation. | Inhibition of thrombin-induced platelet aggregation can be measured using methods known in the art. (Poullis et al., J Thorac Cardiovasc Surg 2000 Aug; 120(2): 370-8). | Inhibition of fibrinolysis; reduction of blood loss during surgery; Treatment of Inflammation and Immune Disorders. |
| Aspartocin (CAS-4117-65-1; CAS-1402-89-7) | Antibacteria | Aspartocin activity can be assessed using in vitro antibacterial assays known in the art. (Zasloff et al., Antimicrobial Agents and Chemotherapy 1999, 43: 782-788). | Treatment of Infectious Diseases; treatment of bacterial infections. |
| Calcitonin (Calcimar) (CAS-21215-62-3) | Regulates levels of calcium and phosphate in serum; causes a reduction in serum calcium--an effect | Hypocalcemic Rat Bioassay, bone resorbing assay and the pit assay, CT receptor binding assay, CAMP stimulation | Musculoskeletal; Osteoporosis; Paget's disease; hypercalcemia; Bone Disorders; Fracture prevention; Malignant hypercalcemia; Osteopenia, Osteoclastogenesis; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | opposite to that of human parathyroid hormone. | assay: J Bone Miner Res 1999 Aug; 14(8): 1425-31 | osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone disorders; bone healing and regeneration. |
| Carperitide (HANP; recombinant human atrial natriuretic peptide) (CAS-89213-87-6) | Stimulates natriuresis, diuresis, and vasodilation. | Carperitide activity can be assessed in vitro by measuring cGMP accumulation in a number of cell lines, including PC12 cells and cultured human glomerular cells. (Medvede et al., Life Sci 2001 Aug 31; 69(15): 1783-90; Green et al., J Am Soc Nephrol 1994 Oct; 5(4): 1091-8). | Treatment of Heart Failure; Cardiovascular disorders; Respiratory disorders; Acute respiratory distress syndrome. |
| Desirudin (recombinant hirudin; Revasc) (CAS-120993-53-5) | Inhibits thrombin; inhibits blood clotting. | Desirudin activity can be assessed using blood clotting assays known in the art, such as in vitro platelet aggragation assays. (Glusa, Haemostasis 1991; 21 Suppl 1: 116-20). | Blood-related disorder; Thrombosis; thrombocytopenia; hemorrhages. |
| Emoctakin (interleukin 8) (CAS-142298-00-8) | proinflammatory cytokine | | Treatment of Inflammation, Immune disorders, RSV infection. |
| Felypressin (CAS-56-59-7) | Derivative of Vasopressin; Stimulates vasoconstriction; Induces local anesthesia. | Felypressin vasoconstriction activity can be measured using assays of vasoconstriction, such as the isolated arterial ring preparation. (Landstrom et al., Hum Reprod 1999 Jan; 14(1): 151-5). | Treatment of pain; to induce local anesthesia. |
| Glucagon (CAS-16941-32-5) | Induces hyperglycemia. | Glucagon activity may be assayed in vitro using a [3-H]-glucose uptake assay. (J Biol Chem 1999 Oct 22; 274(43): 30864-30873). | Hypoglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; Metabolic Disorders; Immune Disorders; Obesity; Vascular Disorders; Suppression of Body Weight; Suppression of Appetite; Syndrome X; Endocrine disorders. |
| Nagrestipen (CAS-166089-33-4) | | | Inflammation; Immune |
| Pentigetide (Pentyde) (CAS-62087-72-3) | | | Respiratory; Allergy; Immune |
| Proinsulin (CAS-67422-14-4) | Stimulates glucose uptake and promotes glycogenesis and lipogenesis. | Insulin activity may be assayed in vitro using a [3-H]-glucose uptake assay. (J Biol Chem 1999 Oct 22; 274(43): 30864-30873). | Hyperglycemia; Diabetes; Diabetes Insipidus; Diabetes mellitus; Type 1 diabetes; Type 2 diabetes; Insulin resistance; Insulin deficiency; Hyperlipidemia; Hyperketonemia; Non-insulin dependent Diabetes Mellitus (NIDDM); Insulin-dependent Diabetes Mellitus (IDDM); A Condition Associated With Diabetes Including, But Not Limited To Obesity, Heart Disease, Hyperglycemia, Infections, Retinopathy, And/Or Ulcers; |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| | | | Metabolic Disorders; Immune Disorders; Obesity; Vascular Disorders; Suppression of Body Weight; Suppression of Appetite; Syndrome X. |
| Becaplermin (Regranex; recombinant PDGF-BB) (CAS-165101-51-9) | Promotes wound healing. | Becaplermin activity can be assessed using animal wound healing models known in the art. (Saba et al., Ann Plast Surg 2002 Jul; 49(1): 62-6). | Stimulate Epithelial Cell Proliferation; Stimulate Basal Keratinocytes; Promote Wound Healing; Stimulate Hair Follicle Production; Healing Of Dermal Wounds. Wound Healing; Eye Tissue Wounds, Dental Tissue Wounds, Oral Cavity Wounds, Diabetic Ulcers, Dermal Ulcers, Cubitus Ulcers, Arterial Ulcers, Venous Stasis Ulcers, Burns Resulting From Heat Exposure Or Chemicals, or Other Abnormal Wound Healing Conditions such as Uremia, Malnutrition, Vitamin Deficiencies or Complications Associated With Systemic Treatment With Steroids, Radiation Therapy or Antineoplastic Drugs or Antimetabolites; Promote Dermal Reestablishment Subsequent To Dermal Loss; Increase the Adherence Of Skin Grafts To A Wound Bed; Stimulate Re-Epithelialization from The Wound Bed; To Promote Skin Strength; Improve The Appearance Of Aged Skin; Proliferate Hepatocytes, Lung, Breast, Pancreas, Stomach, Bladder, Small Intestine, Large Intestine; Sebocytes, Hair Follicles, Type II Pneumocytes, Mucin-Producing Goblet Cells, or Other Epithelial Cells, Endothelial Cells, Keratinocytes, or Basal Keratinocytes (and Their Progenitors) Contained Within The Skin, Lung, Liver, Bladder, Eye, Salivary Glands, or Gastrointestinal Tract; Reduce The Side Effects Of Gut Toxicity That Result From Radiation, Chemotherapy Treatments Or Viral Infections; Cytoprotector, especially of the Small Intestine Mucosa or Bladder; Mucositis (Mouth Ulcers); Regeneration Of Skin; Full and/or Partial Thickness Skin Defects, including Burns, (e.g., Repopulation Of Hair Follicles, Sweat Glands, And Sebaceous Glands); Psoriasis; Epidermolysis Bullosa; Blisters; Gastric and/or Doudenal Ulcers; Reduce Scarring; Inflamamatory Bowel Diseases; Crohn's Disease; Ulcerative Colitis; Gut Toxicity; Lung Damage; Repair Of Alveoli And/or Brochiolar Epithelium; Acute Or Chronic Lung Damage; Emphysema, ARDS; Inhalation Injuries; Hyaline Membrane Diseases; Infant Respiratory Distress Syndrome; Bronchopulmonary Displasia In Premature Infants; Fulminant Liver Failure; Cirrhosis, Liver Damage caused by Viral Hepatitis and/or Toxic Substances; Diabetes Mellitus; Inflammation; Cancer; Digestive disorders. |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| Ghrelin (Genbank Accession No. AB029434) | Stimulates release of growth hormone from anterior pituitary. Stimulates appetite and reduces fat burning. | Appetite and food intake can be can be measured by methods known in the art (Batterham et al. Nature 2002; 418: 650654) | Endocrine; loss of body weight; loss of body weight associated with cancer or anorexia nervosa; loss of appetite; excessive appetite; body weight gain; Obesity; Diabetes; Acromegaly; Growth failure; Growth hormone deficiency; Growth failure and growth retardation Prader-Willi syndrome in children 2 years or older; Growth deficiencies; Growth failure associated with chronic renal insufficiency; Postmenopausal osteoporosis; burns; cachexia; cancer cachexia; dwarfism; metabolic disorders; obesity; renal failure; Turner's Syndrome, pediatric and adult; fibromyalgia; fracture treatment; frailty, AIDS wasting |
| Ghrelin - binding antibody including antibody fragment, or dominant-negative form of Ghrelin | Inhibits growth hormone release in response to Ghrelin; inhibits increase in appetite. | Appetite and food intake can be can be measured by methods known in the art (Batterham et al. Nature 2002; 418: 650654) | Endocrine; Obesity; Diabetes; body weight gain; excessive appetite; loss of appetite; loss of body weight. |
| receptor NOGO-66 peptide fragment (Genbank Accession No. NP_08939 (amino acids 62-101)) | | | Neurodegenerative disorders; spinal cord injury; neuronal injury; brain trauma; stroke; multiple sclerosis; demyelinating disorders; neural activity and neurological diseases; neural cell (e.g., neuron, glial cell, and schwann cell) regeneration and/or growth |
| Gastric inhibitory polypeptide (GIP), including GIP fragments (Genbank Accession No. NM_004123) | Increases nutrient uptake and tryglyceride accumulation in adipocytes, which leads to obesity and insulin resistance. | Nutrient uptake and tryglyceride accumulation can be measured by methods described in Miyawaki et al., Nat. Medicine, 2002, Vol 8(7): 738-742. | Most preferred: loss of body weight, AIDS wasting, cachexia, and loss of appetite. Other: Obesity; Diabetes; insulin resistance; body weight gain; excessive appetite. |
| Gastric inhibitory polypeptide antibody, or antibody fragments | Increased use of fat as predominant energy source; decreased accumulation of fat in adipocytes. | Fat utilization as an energy source can be measured as described in Miyawaki et al., Nat. Medicine, 2002, Vol 8(7): 738-742. | Obesity; Diabetes; Insulin resistance; body weight gain. |
| Gastric inhibitory peptide receptor or receptor fragments or variants including soluble fragments or variants (Genbank Accession Number NM_000164) | Increased use of fat as predominant energy source; decreased accumulation of fat in adipocytes. | Fat utilization as an energy source can be measured as described in Miyawaki et al., Nat. Medicine, 2002, Vol 8(7): 738-742. | Most preferred: Obesity; Diabetes; body weight gain; excessive appetite; insulin resistance. Other: loss of body weight, AIDS wasting, loss of appetite. |
| POMC (proopiomelanocortin), including fragments or variants (such as, for example, alpha-melanocyte stimulating hormone, αMSH, gamma melanocyte stimulating hormone, γMSH, beta-melanocyte | Activity of POMC-derived fragments are diverse, and well-known in the art. See, for example, Hadley et al., Ann N Y Acad Sci 1999 Oct 20; 885: 1-21; Dores, Prog Clin Biol Res 1990; 342: 22-7; Blalock, Ann N Y Acad | | Preferred: resistance to stress; anti-inflammatory activity; analgesic activity; increased skin pigmentation; increased protein catabolism; increased gluconeogenesis; obesity; diabetes. Other: decreased protein catabolism, decreased skin pigmentation, Addison's disease, Cushing's syndrome |

TABLE 2-continued

Non-exhaustive list of Cargo polypeptides that correspond to a Cargo polypeptide portion of a heteromultimer

| Cargo Polypeptide | Biological Activity | Exemplary Activity Assay | Indication |
|---|---|---|---|
| stimulating hormone, βMSH, adrenocorticotropin, ACTH, beta-endorphin, met-enkephalin) (Genbank Accession No. NM_000930) | Sci. 1999 Oct 20; 885: 161-72). | | |
| HP 467, HP228 (U.S. Pat. No. 6,350,430) | See U.S. Pat. No. 6,350,430 | See U.S. Pat. No. 6,350,430 | Resistance to stress; anti-inflammatory activity; analgesic activity; increased skin pigmentation; increased protein catabolism; increased gluconeogenesis. |
| NDP (U.S. Pat. No. 6,350,430) | See U.S. Pat. No. 6,350,430 | See U.S. Pat. No. 6,350,430 | Resistance to stress; anti-inflammatory activity; analgesic activity; increased skin pigmentation; increased protein catabolism; increased gluconeogenesis. |
| Interleukin-21 (IL-21) | Immunomodulator; inhibits interferon gamma production by Th1 cells, | IL-21 activity can be assessed by measuring interferon gamma production in Th1 cells. (Wurster et al.,: J Exp Med 2002 Oct 7; 196(7): 969-77) | Autoimmune disorders; Inflammatory disorders; Treatment of Psoriasis; Rheumatoid Arthritis; Inflammatory bowel disease. |
| Interleukin-4 (IL-4) | Immunomodulator; promotes the differentiation of T cells into Th2 phenotype. | IL-4 activity can be assessed by measuring Th1/Th2 cytokine responses of isolated spleen cells in vitro. (Waltz et al., Horm Metab Res 2002 Oct; 34(10): 561-9). | Treatment of Psoriasis; Autoimmune disorders; Rheumatoid Arthritis; Inflammatory bowel disease; Inflammatory disorders. |
| Osteoclast Inhibitory Lectin (OCIL) | Inhibits osteoclast formation. | Osteoclast Inhibitory Lectin activity can be assessed using osteoclast formation assays known in the art. (Zhou et al., J Biol Chem 2002 Dec 13; 277(50): 48808-15) | Treatment of Bone Disorders; Osteoporosis; Fracture prevention; Hypercalcemia; Malignant hypercalcemia; Paget's disease; Osteopenia, Osteoclastogenesis; osteolysis; osteomyelitis; osteonecrosis; periodontal bone loss; osteoarthritis; rheumatoid arthritis; osteopetrosis; periodontal, lytic, or metastatic bone disease; osteoclast differentiation inhibition; bone healing and regeneration. |
| PCSK9 Inhibitor | Inhibits the interaction of PCSK9 with LDL Receptor. | Further LDL lowering through targeting PCSK9 for coronary artery disease. (Cao et al. Endocrine, Metabolic & Immune Disorders-Drug Targets 2008, 8, 238-243) | Treatment of coronary heart disease. |

Functional Activity:

"A polypeptide having functional activity" refers to a polypeptide capable of displaying one or more known functional activities associated with the full-length, pro-protein, and/or mature form of a cargo polypeptide. Such functional activities include, but are not limited to, biological activity, antigenicity [ability to bind (or compete with a polypeptide for binding) to an anti-polypeptide antibody], immunogenicity (ability to generate antibody which binds to a specific polypeptide described herein), ability to form multimers with polypeptides described herein, and ability to bind to a receptor or ligand for a polypeptide. In certain embodiments, the functional activity includes the ability to improve the expression and stability of a partner protein.

"A polypeptide having biological activity" refers to a polypeptide exhibiting activity similar to, but not necessarily identical to, an activity of a therapeutic protein described herein, including mature forms, as measured in a particular biological assay, with or without dose dependency. In the case where dose dependency does exist, it need not be identical to that of the polypeptide, but rather substantially similar to the dose-dependence in a given activity as compared to the polypeptide described herein (i.e., the candidate polypeptide will exhibit greater activity or not more than about 25-fold less, or not more than about tenfold less activity, or not more than about three-fold less activity relative to a polypeptide described herein, or presented in Table 2).

In certain embodiments, a heteromultimer described herein has at least one biological and/or therapeutic activity associated with the cargo molecule when said cargo molecule is not linked to the transporter polypeptide. In certain embodiments, a heteromultimer described herein has at least one biological and/or therapeutic activity associated with the cargo polypeptide when said cargo polypeptide is not linked to the transporter polypeptide. In certain embodiments, a heteromultimeric protein described herein has at least one biological and/or therapeutic activity associated with the cargo polypeptide portion (or fragment or variant thereof) when said cargo polypeptide is not linked to the albumin or alloalbumin based polypeptide.

The heteromultimeric proteins described herein can be assayed for functional activity (e.g., biological activity) using or routinely modifying assays known in the art, as well as assays described herein. Additionally, one of skill in the art may routinely assay fragments of a protein corresponding to a cargo protein portion of an albumin or alloalbumin based monomeric polypeptide, for activity using assays referenced in its corresponding row of Table 2 (e.g., in column 3 of Table 2). In certain embodiments, are assay of fragments of an albumin protein corresponding to an albumin protein portion of a heteromultimer, for activity using assays known in the art and/or as described in the Examples section below.

For example, in one embodiment where one is assaying for the ability of a heteromultimeric protein described herein to bind or compete with a Cargo polypeptide for binding to an anti-Cargo polypeptide antibody and/or anti-albumin antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In certain embodiments, where a binding partner (e.g., a receptor or a ligand) is identified for a cargo molecule comprised by a heteromultimer described herein, binding to that binding partner by a heteromultimer described herein is assayed, e.g., by means well-known in the art, such as, for example, reducing and non-reducing gel chromatography, protein affinity chromatography, and affinity blotting. See generally, Phizicky et al., Microbiol. Rev. 59:94-123 (1995). In another embodiment, the ability of physiological correlates of a heteromultimeric protein to bind to a substrate(s) of polypeptides corresponding to the cargo protein portion of the heteromultimer can be routinely assayed using techniques known in the art.

Biological Activities

In certain embodiments, heteromultimers described herein, are used in assays to test for one or more biological activities. If a heteromultimer exhibits an activity in a particular assay, it is likely that at least one cargo protein comprised by one or more monomers of the heteromultimer is implicated in the diseases associated with the biological activity. Thus, the heteromultimer is of use in a treatment of the associated disease.

In certain embodiments, provided is a method of treating a disease or disorder comprising administering to a patient in which such treatment, prevention or amelioration is desired, a heteromultimer described herein, in an amount effective to treat, prevent or ameliorate the disease or disorder.

Provided herein are monomeric albumin or alloalbumin based fusion proteins produced by a cell, wherein said proteins are encoded by polynucleotides, wherein said monomeric proteins comprise at least one cargo protein, and an albumin or alloalbumin derived polypeptide, such that said monomers form heteromultimers in solution. In certain embodiments, when the polynucleotides are used to express the encoded protein from a cell, the cell's natural secretion and processing steps produces a protein that lacks at least one signal sequence. The specific amino acid sequence of the signal sequence is well known in the art.

In certain embodiments, heteromultimers described herein are used in the diagnosis, prognosis, prevention and/or treatment of diseases and/or disorders of the endocrine system. In some embodiments, heteromultimers described herein are used in the diagnosis, prognosis, prevention and/or treatment of diseases and/or disorders of the nervous system.

In certain embodiments, heteromultimers described herein are used in the diagnosis, prognosis, prevention and/or treatment of diseases and/or disorders of the immune system. In certain embodiments, heteromultimers described herein are used in the diagnosis, prognosis, prevention and/or treatment of diseases and/or disorders of the respiratory system.

In certain embodiments, heteromultimers described herein are used in the diagnosis, prognosis, prevention and/or treatment of diseases and/or disorders of the cardiovascular system. In some embodiments, heteromultimers described herein are used in the diagnosis, prognosis, prevention and/or treatment of diseases and/or disorders of the reproductive system.

In certain embodiments, heteromultimers described herein are used in the diagnosis, prognosis, prevention and/or treatment of diseases and/or disorders of the digestive system. In certain embodiments, heteromultimer proteins described herein are used in the diagnosis, prognosis, prevention and/or treatment of diseases or disorders relating to the blood.

In certain embodiments, heteromultimers described herein are used in the diagnosis and/or prognosis of diseases and/or disorders associated with at least one tissue(s) in which at least one gene of interest is expressed, wherein a heteromultimer described herein comprises a cargo molecule that binds said at least one gene of interest.

In some embodiments, heteromultimers described herein and/or polynucleotides encoding the albumin/alloalbumin based monomers that associate to form heteromultimers described herein, are used in the diagnosis, detection and/or treatment of diseases and/or disorders associated with activities that include, but are not limited to, prohormone activation, neurotransmitter activity, cellular signaling, cellular proliferation, cellular differentiation, and cell migration.

Therapeutic Uses:

In an aspect, heteromultimers described herein are directed to antibody-based therapies which involve administering heteromultimers described comprising cargo polypeptide(s) which is an antibody, a fragment or variant of an antibody, to a patient for treating one or more of the disclosed diseases, disorders, or conditions. Therapeutic compounds described herein include, but are not limited to, heteromultimers described herein, nucleic acids encoding heteromultimers described herein.

In a specific embodiment, are antibody-based therapies which involve administering heteromultimers described herein comprising at least a fragment or variant of an antibody to a patient for treating one or more diseases, disorders, or conditions, including but not limited to: neural disorders, immune system disorders, muscular disorders, reproductive disorders, gastrointestinal disorders, pulmonary disorders, cardiovascular disorders, renal disorders, proliferative disorders, and/or cancerous diseases and conditions, and/or as described elsewhere herein.

A summary of the ways in which the heteromultimer proteins of the invention comprising at least a fragment or variant of an antibody are used therapeutically includes binding locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the heteromultimers described herein for diagnostic, monitoring or therapeutic purposes without undue experimentation.

The heteromultimers described herein, comprising at least a fragment or variant of an antibody may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in an embodiment, human antibodies, fragments derivatives, analogs, or nucleic acids, are administered to a human patient for therapy or prophylaxis.

Gene Therapy:

In a specific embodiment, nucleic acids comprising sequences encoding heteromultimer proteins described herein are administered to treat, inhibit or prevent a disease or disorder associated with aberrant expression and/or activity of a protein, by way of gene therapy. Gene therapy refers to therapy performed by the administration to a subject of an expressed or expressible nucleic acid. In this embodiment of the invention, the nucleic acids produce their encoded protein that mediates a therapeutic effect. Any of the methods for gene therapy available in the art can be used.

Demonstration of Therapeutic or Prophylactic Activity:

The heteromultimers or pharmaceutical compositions described herein are tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a heteromultimer, and the effect of such heteromultimer upon the tissue sample is observed.

Therapeutic/Prophylactic Administration and Composition

Provided are methods of treatment, inhibition and prophylaxis by administration to a subject of an effective amount of a heteromultimer or pharmaceutical composition described herein. In an embodiment, the heteromultimer is substantially purified (e.g., substantially free from substances that limit its effect or produce undesired side-effects). In certain embodiments, the subject is an animal, including but not limited to animals such as cows, pigs, horses, chickens, cats, dogs, etc., and in certain embodiments, a mammal, and most preferably human.

Various delivery systems are known and can be used to administer a heteromultimer formulation described herein, e.g., encapsulation in liposomes, microparticles, microcapsules, recombinant cells capable of expressing the compound, receptor-mediated endocytosis (see, e.g., Wu and Wu, J. Biol. Chem. 262:4429-4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, in certain embodiments, it is desirable to introduce the heteromultimer compositions described herein into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it is desirable to administer the heteromultimers, or compositions described herein locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the heteromultimers or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the heteromultimers or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, e.g., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment comprising a nucleic acid encoding a heteromultimer described herein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

Also provided herein are pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heteromultimer is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a Therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

Methods of Recombinant and Synthetic Production of Heteromultimer Proteins:

In certain embodiments are heteromultimers produced as recombinant molecules by secretion from yeast, a microorganism such as a bacterium, or a human or animal cell line. In embodiments, the polypeptides are secreted from the host cells.

Embodiments include a cell, such as a yeast cell transformed to express a heteromultimer protein described herein. In addition to the transformed host cells themselves, are provided culture of those cells, preferably a monoclonal (clonally homogeneous) culture, or a culture derived from a monoclonal culture, in a nutrient medium. If the polypeptide is secreted, the medium will contain the polypeptide, with the cells, or without the cells if they have been filtered or centrifuged away. Many expression systems are known and may be used, including bacteria (for example *E. coli* and *Bacillus subtilis*), yeasts (for example *Saccharomyces cerevisiae, Kluyveromyces lactis* and *Pichia pastoris*, filamentous fungi (for example *Aspergillus*), plant cells, animal cells and insect cells.

A heteromultimer described herein is produced in conventional ways, for example from a coding sequence inserted in the host chromosome or on a free plasmid. The yeasts are transformed with a coding sequence for the desired protein in any of the usual ways, for example electroporation. Methods for transformation of yeast by electroporation are disclosed in Becker & Guarente (1990) Methods Enzymol. 194, 182.

Successfully transformed cells, i.e., cells that contain a DNA construct of the present invention, can be identified by well known techniques. For example, cells resulting from the introduction of an expression construct can be grown to produce the desired polypeptide. Cells can be harvested and lysed and their DNA content examined for the presence of the DNA using a method such as that described by Southern (1975) J. Mol. Biol. 98, 503 or Berent et al. (1985) Biotech. 3, 208. Alternatively, the presence of the protein in the supernatant can be detected using antibodies.

Useful yeast plasmid vectors include pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, 7RP1, LEU2 and URA3. Plasmids pRS413-416 are Yeast Centromere plasmids (Ycps).

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary honmopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase 1, enzymes that remove protruding, -single-stranded termini with their 3' 5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

Exemplary genera of yeast contemplated to be useful in the practice of the present invention as hosts for expressing the albumin, fusion proteins are Pichua (formerly classified as *Hansenula*), Saccharomyces, Kluyveromyces, *Aspergillus, Candida, Torulopsis, Toruluspora, Schizosaccharomyces, Citeromyces, Pachysolen, Zygosaccharomyces, Debaromyces, Trichoderma, Cephalosporium, Humicola, Mucor, Neurospora, Yarrowia, Metschunikowia, Rhodosporidium, Leucosporidium, Botryoascus, Sporidiobolus, Endomycopsis*, and the like. Preferred genera are those selected from the group consisting of *Saccharomyces, Schizosaccharomyces, Kluyveromyces, Pichia* and *Torulaspora*. Examples of *Saccharomyces* spp. are *S. cerevisiae, S. italicus* and *S. rouxii.*

Examples of *Kluyveromyces* spp. are *K. fragilis, K. lactis* and *K. marxianus*. A suitable *Torulaspora* species is *T. delbrueckii*. Examples of *Pichia* (*Hansenula*) spp. are *P. angusta* (formerly *H. polymorpha*), *P. anomala* (formerly *H. anomala*) and *P. pastoris*. Methods for the transformation of *S. cerevisiae* are taught generally in EP 251 744, EP 258 067 and WO 90/01063, all of which are incorporated herein by reference.

Preferred exemplary species of *Saccharomyces* include *S. cerevisiae, S. italicus, S. diastaticus*, and *Zygosaccharomyces rouxii*. Preferred exemplary species of *Kluyveromyces* include *K. fragilis* and *K. lactis*. Preferred exemplary species of *Hansenula* include *H. polymorpha* (now *Pichia angusta*), *H. anomala* (now *Pichia anomala*), and *Pichia capsulata*. Additional preferred exemplary species of *Pichia* include *P. pastoris*. Preferred exemplary species of *Aspergillus* include *A. niger* and *A. nidulans*. Preferred exemplary species of *Yarrowia* include *Y. lipolytica*. Many preferred yeast species are available from the ATCC. For example, the following preferred yeast species are available from the ATCC and are useful in the expression of albumin fusion proteins: *Saccharomyces cerevisiae*, Hansen, teleomorph strain BY4743 yap3 mutant (ATCC Accession No. 4022731); *Saccharomyces cerevisiae* Hansen, teleomorph strain BY4743 hsp150 mutant (ATCC Accession No. 4021266); *Saccharomyces cerevisiae* Hansen, teleomorph strain BY4743 pmt1 mutant (ATCC Accession No. 4023792); *Saccharomyces cerevisiae* Hansen, teleomorph (ATCC Accession Nos. 20626; 44773; 44774; and 62995); *Saccharomyces diastaticus* Andrews et Gilliland ex van der Walt, teleomorph (ATCC Accession No. 62987); *Kluyveromyces lactis* (Dombrowski) van der Walt, teleomorph (ATCC Accession No. 76492); *Pichia angusta* (Teunisson et al.) Kurtzman, teleomorph deposited as *Hansenula polymorpha* de Morais et Maia, teleomorph (ATCC Accession No. 26012); *Aspergillus niger* van Tieghem, anamorph (ATCC Accession No. 9029); *Aspergillus niger* van Tieghem, anamorph (ATCC Accession No. 16404); *Aspergillus nidulans* (Eidam) Winter, anamorph (ATCC Accession No. 48756); and *Yarrowia lipolytica* (Wickerham et al.) van der Walt et von Arx, teleomorph (ATCC Accession No. 201847).

Suitable promoters for *S. cerevisiae* include those associated with the PGKI gene, GAL1 or GAL10 genes, CYC1, PH05, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, alpha-mating factor pheromone, [a mating factor pheromone], the PRBI promoter, the GUT2 promoter, the GPDI promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe* are the thiamine-repressible promoter from the nmt gene as described by Maundrell (1990) J. Biol. Chem. 265, 10857-10864 and the glucose repressible jbp1 gene promoter as described by Hoffman & Winston (1990) Genetics 124, 807-816.

Methods of transforming *Pichia* for expression of foreign genes are taught in, for example, Cregg et al. (1993), and various Phillips patents (e.g. U.S. Pat. No. 4,857,467, incorporated herein by reference), and *Pichia* expression kits are commercially available from Invitrogen BV, Leek, Netherlands, and Invitrogen Corp., San Diego, Calif. Suitable promoters include AOX1 and AOX2. Gleeson et al. (1986) J. Gen. Microbiol. 132, 3459-3465 include information on *Hansenula* vectors and transformation, suitable promoters being MOX1 and FMD1; whilst EP 361 991, Fleer et al. (1991) and other publications from Rhone-Poulenc Rorer teach how to express foreign proteins in *Kluyveromyces* spp., a suitable promoter being PGKI.

The transcription termination signal is preferably the 3' flanking sequence of a eukaryotic gene which contains proper signals for transcription termination and polyadenylation. Suitable 3' flanking sequences may, for example, be those of the gene naturally linked to the expression control sequence used, i.e. may correspond to the promoter.

Alternatively, they may be different in which case the termination signal of the *S. cerevisiae* ADHI gene is preferred.

In certain embodiments, the desired heteromultimer protein is initially expressed with a secretion leader sequence, which may be any leader effective in the yeast chosen. Leaders useful in *S. cerevisiae* include that from the mating factor alpha polypeptide (MFα-1) and the hybrid leaders of EP-A-387 319. Such leaders (or signals) are cleaved by the yeast before the mature albumin is released into the surrounding medium. Further such leaders include those of *S. cerevisiae* invertase (SUC2) disclosed in JP 62-096086 (granted as 911036516), acid phosphatase (PH05), the pre-sequence of MFα-1, 0 glucanase (BGL2) and killer toxin; *S. diastaticus* glucoarnylase I1; *S. carlsbergensis* α-galactosidase (MEL1); *K. lactis* killer toxin; and *Candida* glucoarnylase.

Provided are vectors containing a polynucleotide encoding a heteromultimer protein described herein, host cells, and the production of the heteromultimer proteins by synthetic and recombinant techniques. The vector may be, for example, a phage, plasmid, viral, or retroviral vector. Retroviral vectors may be replication competent or replication defective. In the latter case, viral propagation generally will occur only in complementing host cells.

In certain embodiments, the polynucleotides encoding heteromultimer proteins described herein are joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In certain embodiments, the polynucleotide insert is operatively linked to an appropriate promoter, such as the phage lambda PL promoter, the *E. coli* lac, trp, phoA and rac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418, glutamine synthase, or neomycin resistance for eukaryotic cell culture, and tetracycline, kanamycin or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, NSO, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A; pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

In one embodiment, polynucleotides encoding a heteromultimer protein described herein are fused to signal sequences that will direct the localization of a protein of the invention to particular compartments of a prokaryotic or eukaryotic cell and/or direct the secretion of a protein of the invention from a prokaryotic or eukaryotic cell. For example, in *E. coli*, one may wish to direct the expression of the protein to the periplasmic space. Examples of signal sequences or proteins (or fragments thereof) to which the heteromultimeric proteins are fused in order to direct the expression of the polypeptide to the periplasmic space of bacteria include, but are not limited to, the pelB signal sequence, the maltose binding protein (MBP) signal sequence, MBP, the ompA signal sequence, the signal sequence of the periplasmic *E. coli* heat-labile enterotoxin B-subunit, and the signal sequence of alkaline phosphatase. Several vectors are commercially available for the construction of fusion proteins which will direct the localization of a protein, such as the pMAL series of vectors (particularly the pMAL-.rho. series) available from New England Biolabs. In a specific embodiment, polynucleotides albumin fusion proteins of the invention may be fused to the pelB pectate lyase signal sequence to increase the efficiency of expression and purification of such polypeptides in Gram-negative bacteria. See, U.S. Pat. Nos. 5,576,195 and 5,846,818, the contents of which are herein incorporated by reference in their entireties.

Examples of signal peptides that are fused to a heteromultimeric protein in order to direct its secretion in mammalian cells include, but are not limited to, the MPIF-1 signal sequence (e.g., amino acids 1-21 of GenBank Accession number AAB51134), the stanniocalcin signal sequence (MLQNSAVLLLLVISASA(SEQ ID NO: 21)), and a consensus signal sequence (MPTWAWWLFLVLLLALWA-PARG(SEQ ID NO: 22)). A suitable signal sequence that may be used in conjunction with baculoviral expression systems is the gp67 signal sequence (e.g., amino acids 1-19 of GenBank Accession Number AAA72759).

Vectors which use glutamine synthase (GS) or DHFR as the selectable markers can be amplified in the presence of the drugs methionine sulphoximine or methotrexate, respectively. An advantage of glutamine synthase based vectors are the availability of cell lines (e.g., the murine myeloma cell line, NSO) which are glutamine synthase negative. Glutamine synthase expression systems can also function in glutamine synthase expressing cells (e.g., Chinese Hamster Ovary (CHO) cells) by providing additional inhibitor to prevent the functioning of the endogenous gene. A glutamine synthase expression system and components thereof are detailed in PCT publications: WO87/04462; WO86/05807; WO89/10036; WO89/10404; and WO91/06657, which are hereby incorporated in their entireties by reference herein. Additionally, glutamine synthase expression vectors can be obtained from Lonza Biologics, Inc. (Portsmouth, N.H.). Expression and production of monoclonal antibodies using a GS expression system in murine myeloma cells is described in Bebbington et al., Bio/technology 10:169 (1992) and in Biblia and Robinson Biotechnol. Prog. 11:1 (1995) which are herein incorporated by reference.

Also provided are host cells containing vector constructs described herein, and additionally host cells containing nucleotide sequences that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. A host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the nucleic acids and nucleic acid constructs of the invention into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., the coding sequence corresponding to a Cargo polypeptide is replaced with a heteromultimer protein corresponding to the Cargo polypeptide), and/or to include genetic material. The genetic material operably associated with the endogenous polynucleotide may activate, alter, and/or amplify endogenous polynucleotides.

In addition, techniques known in the art may be used to operably associate heterologous polynucleotides (e.g., polynucleotides encoding an albumin protein, or a fragment or variant thereof) and/or heterologous control regions (e.g., promoter and/or enhancer) with endogenous polynucleotide sequences encoding a Therapeutic protein via homologous recombination (see, e.g., U.S. Pat. No. 5,641,670, issued Jun. 24, 1997; International Publication Number WO 96/29411; International Publication Number WO 94/12650; Koller et al., Proc. Natl. Acad. Sci. USA 86:8932-8935 (1989); and Zijlstra et al., Nature 342:435-438 (1989), the disclosures of each of which are incorporated by reference in their entireties).

Heteromultimer proteins described herein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, hydrophobic charge interaction chromatography and lectin chromatography. Most preferably, high performance liquid chromatography ("HPLC") is employed for purification.

In certain embodiments the heteromultimer proteins of the invention are purified using Anion Exchange Chromatography including, but not limited to, chromatography on Q-sepharose, DEAE sepharose, poros HQ, poros DEAF, Toyopearl Q, Toyopearl QAE, Toyopearl DEAE, Resource/Source Q and DEAE, Fractogel Q and DEAE columns.

In specific embodiments the proteins described herein are purified using Cation Exchange Chromatography including, but not limited to, SP-sepharose, CM sepharose, poros HS, poros CM, Toyopearl SP, Toyopearl CM, Resource/Source S and CM, Fractogel S and CM columns and their equivalents and comparables.

In addition, heteromultimer proteins described herein can be chemically synthesized using techniques known in the art (e.g., see Creighton, 1983, Proteins: Structures and Molecular Principles, W. H. Freeman & Co., N.Y and Hunkapiller et al., Nature, 310:105-111 (1984)). For example, a polypeptide corresponding to a fragment of a polypeptide can be synthesized by use of a peptide synthesizer. Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4diaminobutyric acid, alpha-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

Provided are heteromultimers which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH$_4$; acetylation, formylation, oxidation, reduction; metabolic synthesis in the presence of tunicamycin; etc.

Additional post-translational modifications encompassed herein include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The heteromultimer proteins are modified with a detectable label, such as an enzymatic, fluorescent, isotopic or affinity label to allow for detection and isolation of the protein.

Examples of suitable enzymes include horseradish peroxidase, alkaline phosphatase, beta-galactosidase, or acetylcholinesterase; examples of suitable prosthetic group complexes include streptavidin biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include iodine, carbon, sulfur, tritium, indium, technetium, thallium, gallium, palladium, molybdenum, xenon, fluorine.

In specific embodiments, heteromultimer proteins or fragments or variants thereof are attached to macrocyclic chelators that associate with radiometal ions.

As mentioned, the heteromultimer described herein is modified by either natural processes, such as post-translational processing, or by chemical modification techniques which are well known in the art. It will be appreciated that the same type of modification may be present in the same or varying degrees at several sites in a given polypeptide. Polypeptides of the invention may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth. Enzymol. 182:626-646 (1990); Rattan et al., Ann. N.Y. Acad. Sci. 663:48-62 (1992)).

In certain embodiments, heteromultimeric proteins may also be attached to solid supports, which are particularly useful for immunoassays or purification of polypeptides that are bound by, that bind to, or associate with albumin fusion proteins of the invention. Such solid supports include, but are not limited to, glass, cellulose, polyacrylamide, nylon, polystyrene, polyvinyl chloride or polypropylene.

In embodiments where the heteromultimeric protein comprises only the VH domain of an antibody, it may be necessary and/or desirable to coexpress the protein with the VL domain of the same antibody, such that the VH-albumin fusion protein and VL protein will associate (either covalently or non-covalently) post-translationally.

In embodiments where the heteromultimeric protein comprises only the VL domain of an antibody, it may be necessary and/or desirable to coexpress the fusion protein with the VH domain of the same antibody, such that the VL-albumin fusion protein and VH protein will associate (either covalently or non-covalently) post-translationally.

Also provided herein are chemically modified derivatives of the heteromultimeric proteins which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The proteins may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a Therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 105,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

The presence and quantity of heteromultimer proteins described herein may be determined using ELISA, a well known immunoassay known in the art. In one ELISA protocol that would be useful for detecting/quantifying heteromultimers described herein, comprises the steps of coating an ELISA plate with an anti-human serum albumin antibody, blocking the plate to prevent non-specific binding, washing the ELISA plate, adding a solution containing the protein described herein (at one or more different concentrations), adding a secondary anti-cargo polypeptide specific antibody coupled to a detectable label (as described herein or otherwise known in the art), and detecting the presence of the secondary antibody. In an alternate version of this protocol, the ELISA plate might be coated with the anti-cargo polypeptide specific antibody and the labeled secondary reagent might be the anti-human albumin specific antibody.

Provided herein are multifunctional heteromultimers that comprise: at least two monomers, wherein at least one monomer comprises at least one cargo molecule attached to a transporter polypeptide, such that said monomers associate to form the heteromultimer; wherein at least one transporter polypeptide is derived from a monomeric protein and wherein said transporter polypeptides self-assemble to form a quasi-native structure of said monomeric protein or analog thereof. In certain embodiments, the cargo molecule is a biomolecule. In specific embodiments is a heteromultimer that comprises: at least two monomeric proteins, wherein each monomeric protein comprises at least one cargo polypeptide, attached to a transporter polypeptide, such that said monomeric proteins self-assemble to form the heteromultimer. In certain embodiments, the heteromultimer is a heterodimer. In an embodiment, the heteromultimer is bispecific. In an embodiment, the heteromultimer is multispecific. In certain embodiments, at least one transporter polypeptide is not derived from an antibody. In certain embodiments, the transporter polypeptides are not derived from an antibody. In an embodiment, the heteromultimer is multifunctional. In certain embodiments, the transporter polypeptides are derivatives of albumin. In certain embodiments of the heteromultimer described herein, the transporter polypeptides are derived from human serum albumin of SEQ ID No. 1. In certain embodiments of the heteromultimer described herein, the transporter polypeptides are derived from alloalbumins. In certain embodiments, the cargo polypeptides are therapeutic proteins described herein, or fragments or variants thereof. In some embodiments, at least one cargo polypeptide is fused to the transporter polypeptide. In certain embodiments, at least one cargo polypeptide is attached to the N-terminus of the transporter polypeptide. In some embodiments, at least one cargo polypeptide is attached to the C-terminus of the transporter polypeptide.

Provided herein are heteromultimers, each heteromultimer comprising: at least a first monomer that comprises at least one cargo molecule, and a first transporter polypeptide; and at least a second monomer that comprises at least one cargo molecule and a second transporter polypeptide wherein at least one transporter polypeptide is derived from a monomeric protein and wherein said transporter polypeptides self-assemble to form a quasi-native structure of said monomeric protein or analog thereof. In certain embodiments, at least one cargo molecule is a therapeutic agent described herein. In certain embodiments, at least one cargo molecule is a biomolecule described herein. Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide. In certain embodiments, the heteromultimer is a heterodimer. In certain embodiments, the heteromultimer is multivalent. In an embodiment, the heteromultimer is bivalent. In some embodiments, the heteromultimer is multispecific. In an embodiment, the heteromultimer is bispecific. In certain embodiments, the transporter polypeptides are derivatives of albumin. In certain embodiments of the heteromultimer described herein, the transporter polypeptides are derived from human serum albumin of SEQ ID No. 1.

In certain embodiments, are heteromultimers, each heteromultimer comprising: at least a first monomeric protein that comprises at least one cargo polypeptide and a first transporter polypeptide comprising a sequence of SEQ ID NO:2; and at least a second monomeric protein that comprises at least one cargo polypeptide and a second transporter polypeptide comprising a sequence of SEQ ID NO: 3. In certain embodiments of the heteromultimer described herein, at least one transporter polypeptide is derived from alloalbumins. In certain embodiments, both transporter polypeptides are derived from alloalbumins. In certain embodiments, all transporter polypeptides are derivatives of the same alloalbumin. In some other embodiments, the transporter polypeptides are derivatives of different alloalbumins. In some embodiments, each transporter polypeptide is an alloalbumin derivative based on an alloalbumin selected from Table 2. In certain embodiments, the first monomeric protein comprises two cargo polypeptides. In some embodiments, the second monomeric protein comprises two cargo polypeptides.

In some embodiments of the heteromultimer described herein, the transporter polypeptides are derivatives of an annexin protein. In an embodiment, the transporter polypeptides are derived from different annexin proteins. In certain embodiments, the transporter polypeptides are derived from the same annexin protein. In an embodiment, at least one transporter polypeptide is derived from Annexin A1 or lipocortin I. In certain embodiments of the heteromultimer, all transporter polypeptides are derived from Annexin A1 of SEQ ID NO: 14. In certain embodiments of the heteromultimer, at least one transporter polypeptides is derived from a sequence homologous to SEQ ID NO: 14. In an embodiment, at least one transporter polypeptide is derived from Annexin A2 or annexin II. In certain embodiments of the heteromultimer, all transporter polypeptides are derived from Annexin A2 or lipocortin II. In an embodiment, at least one transporter polypeptide is derived from Annexin like protein. In certain embodiments of the heteromultimer, all transporter polypeptides are derived from Annexin like protein. In an embodiment, at least one transporter polypeptide is derived from the group comprising Annexin A1-Annexin A7. In an embodiment of the heteromultimer described herein, all transporter polypeptides are derived from the group comprising Annexin A1-Annexin A7. 14. In certain embodiments, the first annexin based transporter polypeptide has a sequence comprising SEQ ID NO:15, and the second annexin based transporter polypeptide has a sequence comprising SEQ ID NO: 16.

In some embodiments of the heteromultimer described herein, the transporter polypeptides are derivatives of transferrin. In an embodiment, at least one transporter polypeptide is derived from transferrin. In certain embodiments of the heteromultimer, at least one transporter polypeptides are derived from transferrin of SEQ ID NO: 19 or analog thereof. In certain embodiments of the heteromultimer, at least one transporter polypeptide is derived from a polypeptide seuqence homologous to the transferrin. In certain embodiments of the heteromultimer described herein, at least one transporter polypeptide is derived from apo-transferrin. In certain embodiments, the first transferrin based transporter polypeptide has a sequence comprising SEQ ID NO:15 and the second transferrin based transporter polypeptide has a sequence comprising SEQ ID NO: 16. Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein said cargo polypeptides are selected from the proteins listed in Table 2, and wherein at least one transporter polypeptide is derived from a monomeric protein and wherein said transporter polypeptides self-assemble to form a quasi-native structure of said monomeric protein or analog thereof. In certain embodiments, are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein at least one at least one cargo polypeptide is an antibody, or fragment or variant thereof. In certain embodiments, all cargo polypeptides are antibodies or fragments or variants thereof. In certain embodiments, at least one cargo molecule attached to the first transporter polypeptide is the same as at least one cargo molecule attached to the second transporter polypeptide. In certain embodiments, the cargo molecules attached to the first transporter polypeptide are different from the cargo molecule on the second transporter polypeptide. In certain embodiments, there are at least two cargo molecules attached to the first transporter polypeptide and at least two cargo molecule attached to the second transporter polypeptide. In certain embodiments the cargo molecules attached to the first transporter polypeptide are the same. In certain embodiments at least two cargo molecules attached to the first transporter polypeptide are different from each other. In certain embodiments at least two cargo molecules attached to the second transporter polypeptide are the same. In certain embodiments at least two cargo molecules attached to the second transporter polypeptide are different. In some embodiments, the antibody fragment comprises antibody Fc region. In some embodiments, the antibody is an immunoglobulin selected from the group consisting of IgG, IgA, IgD, IgE, and IgM. In certain embodiments, the IgG is of subtype selected from IgG1, IgG2a, IgG2b, IgG3 and IgG4. In certain embodiments, the antibody is a multi-specific antibody. In some embodiments, the multispecific antibody is a bispecific antibody.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein at least one cargo polypeptide is a therapeutic antibody. In some embodiments of the heteromultimers described herein, at least one cargo polypeptide is a therapeutic antibody or fragment or variant thereof, wherein the antibody is selected from antibody is selected from abagovomab, adalimumab, alemtuzumab, aurograb, bapineuzumab, basiliximab, belimumab, bevacizumab, briakinumab, canakinumab, catumaxomab, certolizumab pegol, certuximab, daclizumab, denosumab, efalizumab, galiximab, gemtuzumab ozagamicin, golimumab, ibritumomab tiuxetan, infliximab, ipilimumab, lumiliximab, mepolizumab, motavizumab, muromonab, mycograb, natalizumab, nimotuzumab, ocrelizumab, ofatumumab, omalizumab, palivizumab, panitumumab, pertuzumab, ranizumab, reslizumab, rituximab, teplizumab, toclizumab, tositumomab, trastuzumab, Proxinium, Rencarex, ustekinumab, and zalutumumab. In certain embodiments, the therapeutic antibody binds a cancer antigen.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein at least one cargo polypeptide is an enzyme, hormone, therapeutic polypeptide, antigen, chemotoxin, radiotoxin, cytokine or variant or fragment thereof.

Provided herein are heteromultimers, each heteromultimer comprising: at least a first monomeric protein that comprises at least one cargo polypeptide and a first transporter polypeptide; and at least a second monomeric protein that comprises at least one cargo polypeptide and a second transporter polypeptide, wherein the cargo polypeptide is attached to the transporter polypeptide by chemical conjugation, native ligation, chemical ligation, a disulfide bond or fusion.

Provided herein are host cells comprising nucleic acid encoding a heteromultimer described herein. In certain embodiments, the nucleic acid encoding the first monomeric protein and the nucleic acid encoding the second monomeric protein are present in a single vector. In certain embodiments, the nucleic acid encoding the first monomeric protein and the nucleic acid encoding the second monomeric protein are present in separate vectors.

Provided herein is a method of making a heteromultimer, wherein said method comprises: culturing a host cell described herein such that the nucleic acid encoding a heteromultimer described herein is expressed; and recovering the heteromultimer from the cell culture. In some embodiments, the host cell is a prokaryotic cell or a eukaryotic cell. In certain embodiments, the host cell is yeast cell. In some embodiments, the yeast is *S. cerevisiae*. In some embodiments, the yeast is glycosylation deficient, and/or protease deficient. In some embodiments, the host cell is a bacterial cell. In some embodiments, the host cell expressing a heteromultimer descried herein is a mammalian cell. In certain embodiments, the mammalian cell is a CHO cell, a BHK cell, NSO cell, COS cell or a human cell.

Provided is a pharmaceutical composition that comprises a heteromultimer described herein and a pharmaceutically acceptable adjuvant. Also provided are methods of treating an individual suffering from a disease or disorder, said method comprising administering to the individual an effective amount of a formulation or pharmaceutical composition described herein. In certain embodiments is a method of treating cancer in a patient, said method comprising administering to the patient a therapeutically effective amount of a heteromultimer described herein. In some embodiments is a method of treating an immune disorder in a patient, said method comprising administering to the patient a therapeutically effective amount of a heteromultimer described herein. Also provided is a method of treating an infectious disease in a patient, said method comprising administering to the patient a therapeutically effective amount of a heteromultimer described herein. In certain embodiments is a method of treating a cardiovascular disorder in a patient, said method comprising administering to the patient a therapeutically effective amount of a heteromultimer described herein. In certain embodiments is a method of treating a respiratory disorder in a patient, said method comprising administering to the patient a therapeutically effective amount of a heteromultimer described herein.

Provided is a kit for detecting the presence of a biomarker of interest in an individual, said kit comprising (a) an amount of a heteromultimer described herein, wherein said heteromultimer comprises at least one cargo polypeptide such that said cargo polypeptide is capable of binding to the biomarker of interest; and (b) instructions for use.

Provided herein are heteromultimer proteins that comprise at least two monomeric proteins, wherein each monomeric protein comprises at least one cargo polypeptide, and an albumin based polypeptide, such that said monomeric proteins self-assemble to form the heteromultimer.

In certain embodiments, the cargo polypeptide is fused to the albumin or alloalbumin based polypeptide. In some embodiments, the cargo polypeptide is chemically conjugated to the albumin or alloalbumin based polypeptide. In certain embodiments, the cargo polypeptide is attached to the albumin or alloalbumin based polypeptide by means of chemical ligation or a disulfide bond.

Provided herein are heteromultimer proteins that comprise at least two monomeric proteins, wherein each monomeric protein comprises at least one cargo polypeptide, and an alloalbumin based polypeptide, such that said alloalbumin based polypeptides self-assemble to form the heteromultimer with a quasi-native structure of said alloalbumin or analog thereof. In some embodiments, a heteromultimer described herein is a heterodimer. In some embodiments cargo polypeptide is an antibody, enzyme, hormone, therapeutic polypeptide, antigen, chemotoxin, radiotoxin, cytokine or variant or fragment thereof. In some embodiments, the cargo polypeptide of one monomeric protein functions in synergy with the cargo polypeptide of another monomeric protein.

In an aspect described herein is a method to derive protein segments from a protein of interest that can efficiently fold and selectively associate together to form an active quasi-native protein like structure.

Provided herein is a strategy for creating polypeptides based on a monomeric protein such as but not restricted to human serum albumin (HSA) that yield a quasi-native monomeric protein like structure and function when associated with each other. In embodiments described herein, this strategy is also used to design heteromultimers comprising monomeric polypeptides that comprise transporter polypeptides that are derivatives of HSA variants, alloalbumins other homologous albumin molecules from other species and also Annexin and Transferrin. The monomers described herein can be engineered using a variety of strategies to improve biophysical characteristics such as the stability of the individual transporter polypeptides or their associated complex.

In an embodiment is a scaffold for the development of bispecific or other multispecific or multifunctional protein molecules based on fragments derived from HSA.

Provided is a transporter polypeptide which is a HAS, HAA, Annexin or Transferrin derived scaffold that can be conjugated or fused with cargo polypeptides such as other functional domains such as antigen binding protein units, target substrates or inhibitors or payloads such as chemotoxins, radiotoxins, cytokines, etc. to achieve a multispecific or multifunctional therapeutic protein.

Described herein are fusions of heterodimeric Fc with transporter polypeptides based on HSA to yield bispecific antibody based therapeutics with sufficient purity and stability for pharmaceutical applications.

In an aspect, described herein is a method of deriving a multispecific or multifunctional protein comprising self-assembling monomers that comprise transporter polypeptides based on HSA, such that, the protein has a number of favorable pharmacokinetic properties including improved half-life, improved stability, low immunogenicity, etc.

Provided herein are heterodimer proteins that comprise at least two monomeric fusion proteins, wherein each monomeric fusion proteins comprises at least one cargo polypeptide fused to an albumin derived polypeptide, such that said albumin derived polypeptides self-assemble to form the multifunctional heterodimer with a quasi-native structure of albumin or an analog thereof.

In certain embodiments are heterodimer proteins that comprise at least two monomeric fusion proteins, wherein each monomeric fusion proteins comprises at least one cargo polypeptide fused to an alloalbumin derived polypeptide, such that said alloalbumin derived polypeptides self-assemble to form the multifunctional heterodimer.

In certain embodiments described herein are heteromultimer proteins that comprise at least two monomeric fusion proteins, wherein each monomeric fusion proteins comprises at least one cargo polypeptide fused to an alloalbumin derived polypeptide, such that said alloalbumin derived polypeptides self-assemble to form the multifunctional heterodimer. In certain embodiments are heterodimeric proteins comprising a first monomer which comprises at least one cargo polypeptide fused to an alloalbumin derived polypeptide; and a second monomer that comprises at least one cargo polypeptide fused to an alloalbumin derived polypeptide. In certain embodiments, the at least one cargo polypeptide of the first monomer is different from the at least one cargo polypeptide of the second monomer.

Provided herein is a heteromultimer that comprises: at least two monomers, each comprising a transporter polypeptide and optionally at least one cargo molecule attached to said transporter polypeptide, wherein each transporter polypeptide is obtained by segmentation of a whole protein such that said transporter polypeptides self-assemble to form quasi-native whole protein. In certain embodiments, the heteromultimer is multispecific. In certain embodiments, the transporter polypeptides are not derived from an antibody. In some embodiments, each monomer preferentially forms the heteromultimer as compared to a monomer or a homomultimer. In an embodiment of the heteromultimer, at least one cargo molecule is a theraputic agent, or a biomolecule. In some embodiments, at least one cargo molecule is a biomolecule which is selected from a polypeptide, DNA, PNA, or RNA. In some embodiments, each transporter polypeptide is a derivate of albumin or alloalbumin. In an embodiment, each transporter polypeptide is a derivate of annexin. In certain embodiments, each transporter polypeptide is a derivate of transferrin.

In certain embodiments are pharmaceutical formulations that comprise an albumin-based and/or alloalbumin-based heteromultimeric protein described herein and a pharmaceutically acceptable diluent or carrier. In certain embodiments, a formulation described herein is provided as part of a kit or container. In certain embodiments, the kit or container is packaged with instructions pertaining to extended shelf life of the therapeutic protein. In some embodiments, a heteromultimer described herein is used in a method of treating (e.g., ameliorating) preventing, or diagnosing a disease or disease symptom in an individual, comprising the step of administering said formulation to the individual.

Also provided are transgenic organisms modified to contain nucleic acid molecules described herein to encode and express monomeric fusion proteins described herein.

Various publications are cited herein, the disclosures of which are incorporated by reference in their entireties.

EXAMPLES

Example 1

The Protein Splitting Method

Figure 6A:
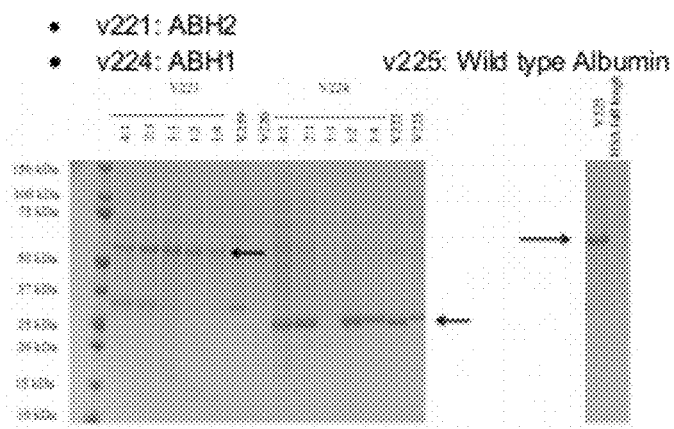
FIGS. 6A-6C show native gel electrophoresis profiles of full-length HSA and heterodimer scaffolds Albumin-based heteromultimer-1 (ABH1) and Albumin-based heteromultimer-2 (ABH2) formed by coexpression of HSA based transporter polypeptides.
Figure 6B:
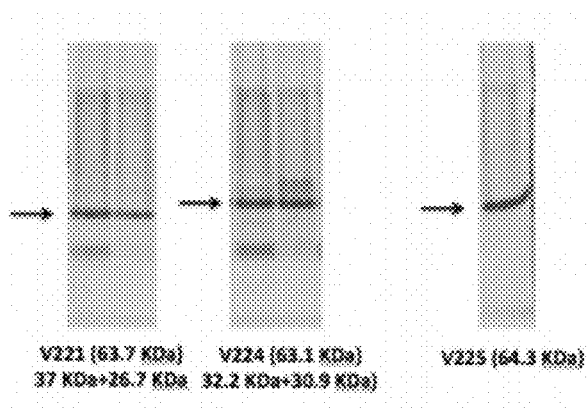

Specific protein-protein association is driven by strong surface complementarity between interacting partners and the accompanying structural and thermodynamic changes. The surface complementarity provides an opportunity to form contacts that support the creation of favorable electrostatic and hydrophobic interactions. Electrostatic interactions involve the formation of salt bridges, hydrogen bonds and the pervasive dispersion interactions. Solvent exclusion and reorganization around non-polar atomic groups at the interface and its associated entropic effects play a role in the hydrophobic component of the binding thermodynamics. Residues with geometries that are optimized for hydrophobic interaction with one another will form contacts (i.e. stacking, pi-pi, cation-pi contacts favorable for stabilizing a protein-protein interface). Similar thermodynamic effects control multi-step protein folding processes that involve the pre-organization of secondary structural units and tertiary domains, which is followed by their association to form the folded quaternary state of the protein. An alternate mechanism to protein folding and binding involves a coupled protein folding and binding process that ultimately results in the quaternary state of the protein. In the context of protein association, the individual protein components need to be co-expressed or be present in the same medium and each of the components or monomers will stably fold into its final structural state only on association with its obligate partner. (FIG. 6)

Generation of a split protein involves recognizing a segmentation site in the native protein, using information from sequence, secondary structure and fold that will yield at least two transporter polypeptides that efficiently form the quasi-native protein structure by self-assembling to form a heteromultimer together. For example, these split protein transporter polypeptides selectively self-assemble and form the quasi-native state when co-expressed. While generating a split protein complementary pair of transporter polypeptides, in a way, the attempt is to emulate a number of naturally occurring obligate protein-protein complexes that exhibit their functionality as a complex while being non-functional in their uncomplexed state. A successful implementation of the strategy results in polypeptides that selectively self-assemble to form heteromultimers with each other, are soluble as individual entities and for functional relevance, do not impair the folding, binding and activity of other components in the environment. The intrinsic nature of the polypeptides to reconstitute with each other has applications in area of creating heteromultimeric fusion entities out of cargo molecules that are not efficient at forming multimers by themselves. The functional role of the split protein segments is to act as transporter polypeptides that drive heteromultimerization.

Example 2

Preparation of HA/Alloalbumin Based Heteromultimer Proteins

Figure 2:
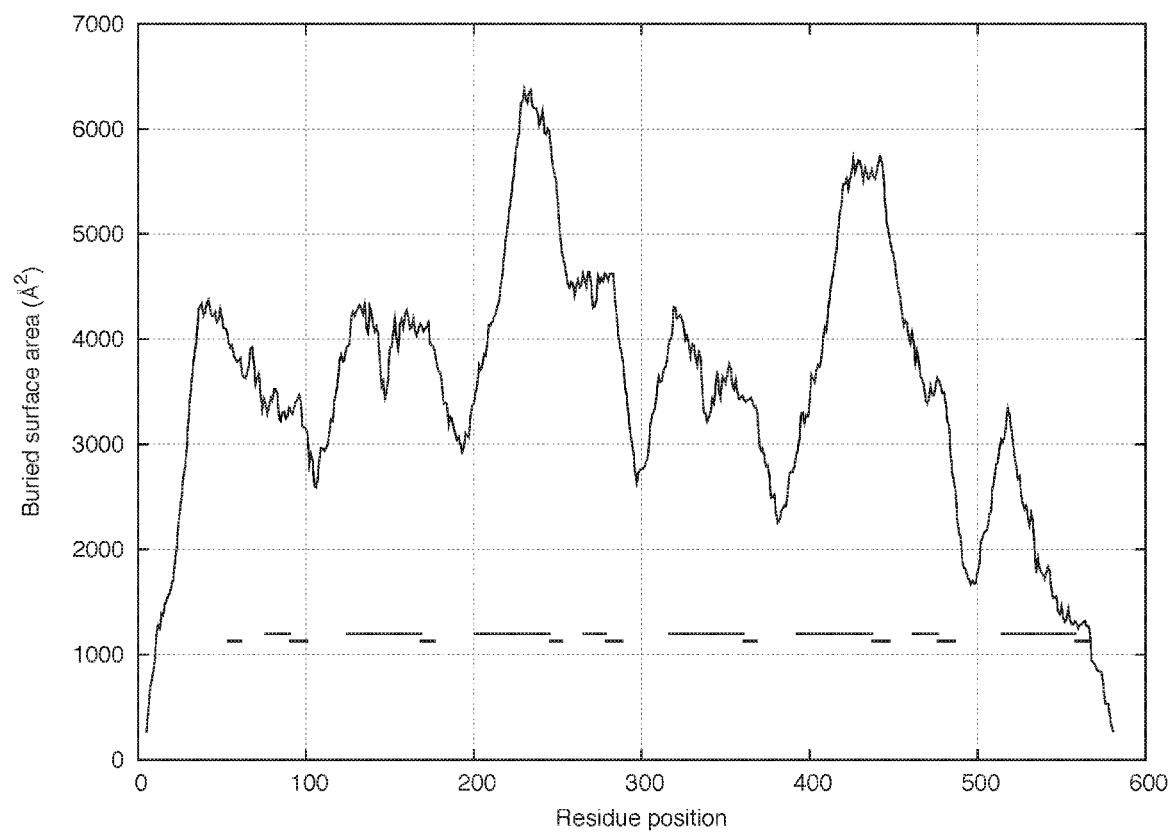
FIG. 2 is a plot of buried solvent accessible surface area at the interface of two albumin-based polypeptides.
Figure 3:
FIG. 3 depicts two albumin-based polypeptides expressed separately. The two polypeptides are shown in light and dark grey respectively. Each polypeptide comprises two fusion sites for functional cargo proteins and these sites are represented as spheres. The disulphide residues in structure are shown as sticks.

Shown is a method to determine the segmentation site along the HSA sequence and structure that will yield monomeric polypeptide chains that stably fold and fuse to form a quasi-native quaternary structure of the original protein. One of the critical requirements for such stable association is the formation of a large buried area of surface complementarity at the interface between the polypeptide chains. The native fold of the original protein provides indication of the natural complementarity of regions within the protein. FIG. 2 shows the solvent accessible surface area buried at the interface of two albumin-based polypeptides that would ideally fold into the quasi-native structure of HSA, when the segmentation point is moved along the protein sequence. The analysis indicates that a large surface area, of the order of about 2000 $\text{Å}^2$ is buried when the split segmentation is introduced anywhere between residues 30 and 520 with a few exceptions. Albumin has an exceptionally large number of disulphides bridges that contributes to the stability of the native protein structure. Section of the protein near residues 110, 190, 300, 390 and 500 provide sites for segmentation that do not split the residues involved in a disulphide link across the two transporter polypeptides. Segmentation in other regions would result in heterodimers with a cross linking disulphide bond between the two transporter polypeptide pairs. FIG. 3 presents a model representation of one such quasi-native albumin structure derived by removal of loop from residues 294 to 303 in the HSA sequence. The total buried surface area for the two albumin based polypeptides of SEQ ID No. 2, and SEQ ID No: 3 shown herein is approximately 2500 $\text{Å}^2$. This is within the average of 1910-3880 $\text{Å}^2$ observed in a number of protein-protein heterodimeric and homodimeric co-complex structures [Bahadhur R. P. & Zacharias M. (2008) *Cell Mol Life Sci* 65, 1059-1072]. This suggests that there is a strong likelihood for the two polypeptides to selectively associate with each other if the folding pathway of the two polypeptides is fairly independent of each other.

Figure 4:
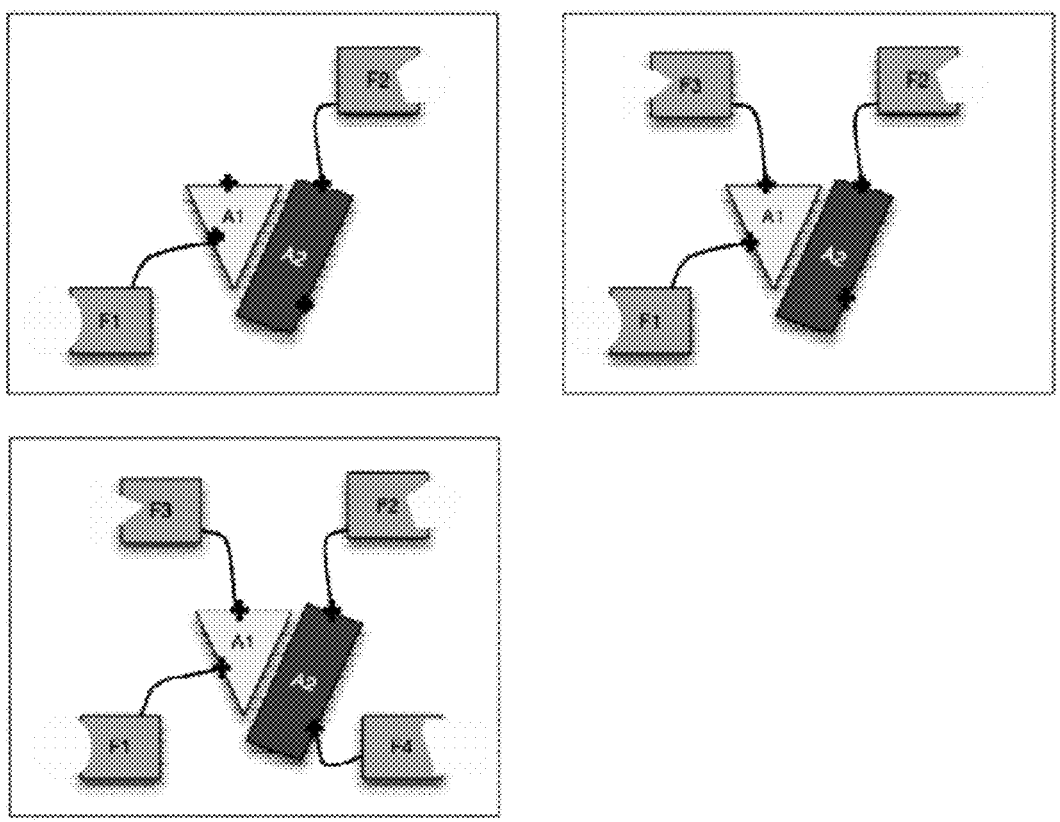
FIG. 4 is a schematic representation of bispecific and other multifunctional therapeutics based on the multispecific heteromultimer described herein. The albumin-based, or alloalbumin-based polypeptides are denoted A1 and A2. Multifunctional heteromultimers are obtained by conjugating antigen binding motifs, cytokines and other forms of signaling molecules, chemotoxin, radiotoxins or other functionally relevant immunoconjugates to N and/or C terminal sites on A1 and A2 and this is represented by the + symbol.

In an aspect of this invention, selective formation of a stable quasi-native structure with the two polypeptides (the pair formed by SEQ ID No. 2 and SEQ ID No. 3 or the transporter pair formed by SEQ ID No. 8 and SEQ ID No. 10) gives us the opportunity to employ these polypeptides to drive the formation of bispecific or other multifunctional molecules after fusing the appropriate cargo proteins of interest to the N or C terminus of the albumin based polypeptides employed as transporter polypeptides. A number of other alternate segmentation patterns resulting in transportation polypeptide pair heterodimer can be designed. The fused cargo proteins can be antigen binding domains or other payloads such as chemotoxins, radiotoxins or cytokines (as represented in FIG. 4). The resulting heterodimers have many of the favorable properties intrinsic to HSA including properties like improved half-life, stability and low immunogenicity. Traditional linkers such as $(Gly_4Ser)_x$ can be used for the association of the cargo protein with the transporter polypeptide.

In another aspect of this invention, each of the HSA based transporter polypeptides is fused independently to the C-terminus of two heavy chains in a bispecific Fc molecule (as represented in FIG. 5). The strong and selective pairing of the two transporter polypeptides (such as SEQ ID No. 2, and SEQ ID No. 3) drives the selectively heterodimerization of the Fc and also contribute to its stability and other valuable pharmacokinetic properties.

Serum albumin preprotein NP_000468.1 GI 4502027 mRNA sequence from NM_000477.5, Consensus CDS (CCDS) ID 3555.1

SEQ ID No. 4: Residue 1-24 (EFATMAVMAPRTLV-LLLSGALALTQTWAG) is the N-terminal export signal sequence region that gets cleaved. This sequence fulfills the same role as the natural signal sequence but it's optimized for mammalian and CHO cell lines.

```
SEQ ID No. 65: gi|4502027|ref|NP_000468.1|
serum albumin preproprotein [Homo sapiens]
EFATMAVMAPRTLVLLLSGALALTQTWAGDAHKSEVAHRFKDLGEENFKA

LVLIAFAQYLQQCPFEDHVKLVNEVTEFAKTCVADESAENCDKSLHTLFG

DKLCTVATLRETYGEMADCCAKQEPERNECFLQHKDDNPNLPRLVRPEVD

VMCTAFHDNEETFLKKYLYEIARRHPYFYAPELLFFAKRYKAAFTECCQA

ADKAACLLPKLDELRDEGKASSAKQRLKCASLQKFGERAFKAWAVARLSQ

RFPKAEFAEVSKLVTDLTKVHTECCHGDLLECADDRADLAKYICENQDSI

SSKLKECCEKPLLEKSHCIAEVENDEMPADLPSLAADFVESKDVCKNYAE

AKDVFLGMFLYEYARRHPDYSVVLLLRLAKTYETTLEKCCAAADPHECYA

KVFDEFKPLVEEPQNLIKQNCELFEQLGEYKFQNALLVRYTKKVPQVSTP

TLVEVSRNLGKVGSKCCKHPEAKRMPCAEDYLSVVLNQLCVLHEKTPVSD

RVTKCCTESLVNRRPCFSALEVDETYVPKEFNAETFTFHADICTLSEKER

QIKKQTALVELVKHKPKATKEQLKAVMDDFAAFVEKCCKADDKETCFAEE

GKKLVAASQAALGL

SEQ ID No. 5: Human serum albumin nucleotide
CCDS Sequence (1852 nt)
GAATTCGCCACTATGGCTGTGATGGCCCCTAGGACCCTGGTGCTGCTGC

TGTCCGGAGCTCTGGCTCTGACTCAGACCTGGGCTGGAGATGCACACAAG

AGTGAGGTTGCTCATCGGTTTAAAGATTTGGGAGAAGAAAATTTCAAAGC

CTTGGTGTTGATTGCCTTTGCTCAGTATCTTCAGCAGTGTCCATTTGAAG

ATCATGTAAAATTAGTGAATGAAGTAACTGAATTTGCAAAAACATGTGTT

GCTGATGAGTCAGCTGAAAATTGTGACAAATCACTTCATACCCTTTTTGG

AGACAAATTATGCACAGTTGCAACTCTTCGTGAAACCTATGGTGAAATGG

CTGACTGCTGTGCAAAACAAGAACCTGAGAGAAATGAATGCTTCTTGCAA
```

-continued
CACAAAGATGACAACCCAAACCTCCCCCGATTGGTGAGACCAGAGGTTGA

TGTGATGTGCACTGCTTTTCATGACAATGAAGAGACATTTTTGAAAAAAT

ACTTATATGAAATTGCCAGAAGACATCCTTACTTTTATGCCCCGGAACTC

CTTTTCTTTGCTAAAAGGTATAAAGCTGCTTTTACAGAATGTTGCCAAGC

TGCTGATAAAGCTGCCTGCCTGTTGCCAAAGCTCGATGAACTTCGGGATG

AAGGGAAGGCTTCGTCTGCCAAACAGAGACTCAAGTGTGCCAGTCTCCAA

AAATTTGGAGAAAGAGCTTTCAAAGCATGGGCAGTAGCTCGCCTGAGCCA

GAGATTTCCCAAAGCTGAGTTTGCAGAAGTTTCCAAGTTAGTGACAGATC

TTACCAAAGTCCACACGGAATGCTGCCATGGAGATCTGCTTGAATGTGCT

GATGACAGGGCGGACCTTGCCAAGTATATCTGTGAAAATCAAGATTCGAT

CTCCAGTAAACTGAAGGAATGCTGTGAAAAACCTCTGTTGGAAAAATCCC

ACTGCATTGCCGAAGTGGAAAATGATGAGATGCCTGCTGACTTGCCTTCA

TTAGCTGCTGATTTTGTTGAAAGTAAGGATGTTTGCAAAAACTATGCTGA

GGCAAAGGATGTCTTCCTGGGCATGTTTTTGTATGAATATGCAAGAAGGC

ATCCTGATTACTCTGTCGTGCTGCTGCTGAGACTTGCCAAGACATATGAA

ACCACTCTAGAGAAGTGCTGTGCCGCTGCAGATCCTCATGAATGCTATGC

CAAAGTGTTCGATGAATTTAAACCTCTTGTGGAAGAGCCTCAGAATTTAA

TCAAACAAAATTGTGAGCTTTTTGAGCAGCTTGGAGAGTACAAATTCCAG

AATGCGCTATTAGTTCGTTACACCAAGAAAGTACCCCAAGTGTCAACTCC

AACTCTTGTAGAGGTCTCAAGAAACCTAGGAAAAGTGGGCAGCAAATGTT

GTAAACATCCTGAAGCAAAAGAATGCCCTGTGCAGAAGACTATCTATCC

GTGGTCCTGAACCAGTTATGTGTGTTGCATGAGAAAACGCCAGTAAGTGA

CAGAGTCACCAAATGCTGCACAGAATCCTTGGTGAACAGGCGACCATGCT

TTTCAGCTCTGGAAGTCGATGAAACATACGTTCCCAAAGAGTTTAATGCT

GAAACATTCACCTTCCATGCAGATATATGCACACTTTCTGAGAAGGAGAG

ACAAATCAAGAAACAAACTGCACTTGTTGAGCTCGTGAAACACAAGCCCA

AGGCAACAAAAGAGCAACTGAAAGCTGTTATGGATGATTTCGCAGCTTTT

GTAGAGAAGTGCTGCAAGGCTGACGATAAGGAGACCTGCTTTGCCGAGGA

GGGTAAAAAACTTGTTGCTGCAAGTCAAGCTGCCTTAGGCTTATGA

The protein and nucleotide sequence of albumin based polypeptides useful as transporter polypeptides are as follows:

Albumin based heteromultimer 1:

Albumin based Transporter polypeptide 1-Ver 1:
SEQ ID No. 2:
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPERN

ECFLQHKDDNPNLPRLVRPEVDVMCTAFHDNEETFLKKYLYEIARRHPYF

YAPELLFFAKRYKAAFTECCQAADKAACLLPKLDELRDEGKASSAKQRLK

CASLQKFGERAFKAWAVARLSQRFPKAEFAEVSKLVTDLTKVHTECCHGD

LLECADDRADLAKYICENQDSISSKLKECCEKPLLEKSHCIAEV

-continued
Nucleotide sequence encoding Albumin based
Transporter polypeptide 1-Ver 1:
SEQ ID No. 6:
GATGCACACAAGAGTGAGGTTGCTCATCGGTTTAAAGATTTGGGAGAAG

AAAATTTCAAAGCCTTGGTGTTGATTGCCTTTGCTCAGTATCTTCAGCAG

TGTCCATTTGAAGATCATGTAAAATTAGTGAATGAAGTAACTGAATTTGC

AAAAACATGTGTTGCTGATGAGTCAGCTGAAAATTGTGACAAATCACTTC

ATACCCTTTTTGGAGACAAATTATGCACAGTTGCAACTCTTCGTGAAACC

TATGGTGAAATGGCTGACTGCTGTGCAAAACAAGAACCTGAGAGAAATGA

ATGCTTCTTGCAACACAAAGATGACAACCCAAACCTCCCCCGATTGGTGA

GACCAGAGGTTGATGTGATGTGCACTGCTTTTCATGACAATGAAGAGACA

TTTTTGAAAAAATACTTATATGAAATTGCCAGAAGACATCCTTACTTTTA

TGCCCCGGAACTCCTTTTCTTTGCTAAAAGGTATAAAGCTGCTTTTACAG

AATGTTGCCAAGCTGCTGATAAAGCTGCCTGCCTGTTGCCAAAGCTCGAT

GAACTTCGGGATGAAGGGAAGGCTTCGTCTGCCAAACAGAGACTCAAGTG

TGCCAGTCTCCAAAAATTTGGAGAAAGAGCTTTCAAAGCATGGGCAGTAG

CTCGCCTGAGCCAGAGATTTCCCAAAGCTGAGTTTGCAGAAGTTTCCAAG

TTAGTGACAGATCTTACCAAAGTCCACACGGAATGCTGCCATGGAGATCT

GCTTGAATGTGCTGATGACAGGGCGGACCTTGCCAAGTATATCTGTGAAA

ATCAAGATTCGATCTCCAGTAAACTGAAGGAATGCTGTGAAAAACCTCT

GTTGGAAAAATCCCACTGCATTGCCGAAGTGTGA

Albumin based Transporter polypeptide 2-Ver 1:
SEQ ID No. 3:
SLAADFVESKDVCKKYASAKDVFLGMFLYEYARRHPDYSVVLLLRLAKT

YETTLEKCCAAADPHECYAKVFDEFKPLVEEPQNLIKQNCELFEQLGEYK

FQNALLVRYTKKVPQVSTPTLVEVSRNLGKVGSKCCKHPEAKRMPCAEDY

LSVVLNQLCVLHEKTPVSDRVTKCCTESLVNRRPCFSALEVDETYVPKEF

NAETFTFHADICTLSEKERQIKKQTALVELVKHKPKATKEQLKAVMDDFA

AFVEKCCKADDKETCFAEEGKKLVAASQAALGL

Nucleotide sequence encoding Albumin based
Transporter polypeptide 2-Ver 1: SEQ ID No. 7:
TCATTAGCTGCTGATTTTGTTGAAAGTAAGGATGTTTGCAAAAACTATG

CTGAGGCAAAGGATGTCTTCCTGGGCATGTTTTTGTATGAATATGCAAGA

AGGCATCCTGATTACTCTGTCGTGCTGCTGCTGAGACTTGCCAAGACATA

TGAAACCACTCTAGAGAAGTGCTGTGCCGCTGCAGATCCTCATGAATGCT

ATGCCAAAGTGTTCGATGAATTTAAACCTCTTGTGGAAGAGCCTCAGAAT

TTAATCAAACAAAATTGTGAGCTTTTTGAGCAGCTTGGAGAGTACAAATT

CCAGAATGCGCTATTAGTTCGTTACACCAAGAAAGTACCCCAAGTGTCAA

CTCCAACTCTTGTAGAGGTCTCAAGAAACCTAGGAAAAGTGGGCAGCAAA

TGTTGTAAACATCCTGAAGCAAAAGAATGCCCTGTGCAGAAGACTATCT

ATCCGTGGTCCTGAACCAGTTATGTGTGTTGCATGAGAAAACGCCAGTAA

GTGACAGAGTCACCAAATGCTGCACAGAATCCTTGGTGAACAGGCGACCA

TGCTTTTCAGCTCTGGAAGTCGATGAAACATACGTTCCCAAAGAGTTTAA

TGCTGAAACATTCACCTTCCATGCAGATATATGCACACTTTCTGAGAAGG

```
AGAGACAAATCAAGAAACAAACTGCACTTGTTGAGCTCGTGAAACACAAG

CCCAAGGCAACAAAAGAGCAACTGAAAGCTGTTATGGATGATTTCGCAGC

TTTTGTAGAGAAGTGCTGCAAGGCTGACGATAAGGAGACCTGCTTTGCCG

AGGAGGGTAAAAAACTTGTTGCTGCAAGTCAAGCTGCCTTAGGCTTATGA
```

Albumin Based Heteromultimer 2:

```
Albumin based Transporter polypeptide 1-Ver 2:
SEQ ID No. 8:
DAHKSEVAHRFKDLGEENFKALVLIAFAQYLQQCPFEDHVKLVNEVTEF

AKTCVADESAENCDKSLHTLFGDKLCTVATLRETYGEMADCCAKQEPERN

ECFLQHKDDNPNLFRLVRPEVDVMCTAFHDNEETFLKKYLYEIARRHPYF

YAPELLFFAKRYKAAFTECCQAADKAACLLPKLDELRDEGKASSAKQRLK

CASLQKFGERAFKAWAVARLSQRFPKAEFAEVSKLVTDLTKVHTECCHGD

LLECADDRADLAKYICENQDSISSKLKECCEKPLLEKSHCIAEVENDEMP

ADLPSLAADFVESKDVCKNYAEAKDVFLGMFLYEYARA

Nucleotide sequence encoding Albumin based
Transporter polypeptide 1-Ver 2: SEQ ID No. 9:
GATGCACACAAGAGTGAGGTTGCTCATCGGTTTAAAGATTTGGGAGAAG

AAAATTTCAAAGCCTTGGTGTTGATTGCCTTTGCTCAGTATCTTCAGCAG

TGTCCATTTGAAGATCATGTAAAATTAGTGAATGAAGTAACTGAATTTGC

AAAAACATGTGTTGCTGATGAGTCAGCTGAAAATTGTGACAAATCACTTC

ATACCCTTTTGGAGACAAATTATGCACAGTTGCAACTCTTCGrGAAACC

TATGGTGAAATGGCTGACTGCTGTGCAAAACAAGAACCTGAGAGAAATGA

ATGCTTCTTGCAACACAAAGATGACAACCCAAACCTCCCCCGATTGGTGA

GACCAGAGGTTGATGTGATGTGCACTGCTTTTCATGACAATGAAGAGACA

TTTTTGAAAAAATACTTATATGAAATTGCCAGAAGACATCCTTACTTTTA

TGCCCCGGAACTCCTTTTCTTTGCTAAAAGGTATAAAGCTGCTTTTACAG

AATGTTGCCAAGCTGCTGATAAAGCTGCCTGCCTGTTGCCAAAGCTCGAT

GAACTTCGGGATGAAGGGAAGGCTTCGTCTGCCAAACAGAGACTCAAGTG

TGCCAGTCTCCAAAAATTTGGAGAAAGAGCTTTCAAAGCATGGGCAGTAG

CTCGCCTGAGCCAGAGATTTCCCAAAGCTGAGTTTGCAGAAGTTTCCAAG

TTAGTGACAGATCTTACCAAAGTCCACACGGAATGCTGCCATGGAGATCT

GCTTGAATGTGCTGATGACAGGGCGGACCTTGCCAAGTATATCTGTGAAA

ATCAAGATTCGATCTCCAGTAAACTGAAGGAATGCTGTGAAAAACCTCTG

TTGGAAAAATCCCACTGCATTGCCGAAGTGGAAATGATGAGATGCCTGC

TGACTTGCCTTCATTAGCTGCTGATTTTGTTGAAAGTAAGGATGTTTGCA

AAAACTATGCTGAGGCAAAGGATGTCTTCCTGGGCATGTTTTTGTATGAA

TATGCAAGAGCATGA

Albumin based Transporter polypeptide 2-Ver 2:
SEQ ID No. 10:
SVVLLLRLAKTYETTLEKCCAAADPHECYAKVFDEFKPLVEEPQNLIKQ

NCELFEQLGEYKFQNALLVRYTKKVPQVSTPTLVEVSRNLGKVGSKCCKH

PEAKRMPCAEDYLSVVLNQLCVLHEKTPVSDRVTKCCTESLVNRRPCFSA

LEVDETYVPKEFNAETFTFHADICTLSEKERQIKKQTALVELVKHKPKAT

KEQLKAVMDDFAAFVEKCCKADDKETCFAEEGKKLVAASQAALGL

Nucleotide sequence encoding Albumin based
Transporter polypeptide 2-Ver 2: SEQ ID No. 11:
TCTGTCGTGCTGCTGCTGAGACTTGCCAAGACATATGAAACCACTCTAG

AGAAGTGCTGTGCCGCTGCAGATCCTCATGAATGCTATGCCAAAGTGTTC

GATGAATTTAAACCTCTTGTGGAAGAGCCTCAGAATTTAATCAAACAAAA

TTGTGAGCTTTTTGAGCAGCTTGGAGAGTACAAATTCCAGAATGCGCTAT

TAGTTCGTTACACCAAGAAAGTACCCCAAGTGTCAACTCCAACTCTTGTA

GAGGTCTCAAGAAACCTAGGAAAAGTGGGCAGCAAATGTTGTAAACATCC

TGAAGCAAAAAGAATGCCCTGTGCAGAAGACTATCTATCCGTGGTCCTGA

ACCAGTTATGTGTGTTGCATGAGAAAACGCCAGTAAGTGACAGAGTCACC

AAATGCTGCACAGAATCCTTGGTGAACAGGCGACCATGCTTTTCAGCTCT

GGAAGTCGATGAAACATACGTTCCCAAAGAGTTTAATGCTGAAACATTCA

CCTTCCATGCAGATATATGCACACTTTCTGAGAAGGAGAGACAAATCAAG

AAACAAACTGCACTTGTTGAGCTCGTGAAACACAAGCCCAAGGCAACAAA

AGAGCAACTGAAAGCTGTTATGGATGATTTCGCAGCTTTTGTAGAGAAGT

GCTGCAAGGCTGACGATAAGGAGACCTGCTTTGCCGAGGAGGGTAAAAAA

CTTGTTGCTGCAAGTCAAGCTGCCTTAGGCTTATGA
```

Generation and Expression of HA or HAA Based Heteromultimers

The genes encoding the full length WT HA and the HA based transporter polypeptide monomers were constructed via gene synthesis using codons optimized for human/mammalian expression. The constructs were designed from known full-length Human Serum Albumin Preprotein (GENEBANK: NP_000468.1), after exclusion of the signal sequence EFATMAVMAPRTLVLLLSGALALTQTWAG (SEQ ID NO: 4). The final gene products were subcloned into the mammalian expression vector pTT5 (NRC-BRI, Canada) (Durocher et al). High level and high-throughput recombinant protein production by transient transfection of suspension-growing human CHO-3E7 was performed. See Table 3 for construct boundaries of the two scaffolds described here: Albumin based heteromultimer 1 (ABH1) and Albumin based heteromultimer 2 (ABH2). Albumin based heteromultimer 2 comprises one disulfide bond between the two transporter polypeptides, while Albumin based heteromultimer 1 is formed entirely by non-covalent interactions. FIG. 6A provides SDS-PAGE (non-reducing) gel analysis of the two heteromultimer constructs (ABH1 and ABH2), after co-expression (different DNA transfection ratios are shown). WT full-length HSA is shown as control. As expected, ABH2 retains the disulfide linkage in non-reducing SDS-PAGE, with a MW roughly double the non-disulfide linked ABH1. FIG. 6B provides Native gel analysis of the two Albumin based heteromultimer constructs (ABH1 and ABH2), after co-expression (1:1 DNA level). WT full-length HSA is shown as control. ABH1 and ABH2 both form a complex of expected mass, comparable to the full-length WT HSA. Furthermore, upon expression, neither the transporter polypeptides forming ABH1 nor the ones forming ABH2 homodimerize; rather they preferably form a stable hetercomplex. See Table 3 below for details.

TABLE 3

Albumin based heteromultimer constructs

| Construct | Segment Boundaries* | MW (KDa) |
|---|---|---|
| Wild Type HA | 1:585 (SEQ ID NO: 1) | 64.3 |
| ABH1 | 1:293 (SEQ ID NO: 2) | 32.2 |
|  | 304:585 (SEQ ID NO: 3) | 30.9 |
| ABH2 | 1:337 (SEQ ID NO: 8) | 37 |
|  | 342:585 (SEQ ID NO: 10) | 26.7 |

WT-HSA and the two Albumin based heteromultimers (ABH1 and ABH2) were expressed in CHO-3E7 cell line grown in suspension in FreeStyle F17 medium (Invitrogen) supplemented with 0.1% w/v pluronic and 4 mM glutamine. The day of transfection cell density should be around 1.5-2 million cells/ml and viability must be greater than 97%. Transfection is done according to patent application WO 2009/137911 using a mixture of plasmid DNA made of 5% pTTo-GFP plasmid (green fluorescent protein to determine transfection efficiency, Table 4), 15% pTT22-AKT plasmid, 21% HSA plasmids (10.63% of each), 68.37% of Salmon Sperm DNA. Following transfection, the shake flask containing cells is then placed on an orbital shaker set to 120 rpm in a humidified incubator with 5% $CO_2$ at 37° C. Twenty-four hours post-transfection, 1% w/v TN1 and 0.5 mM VPA (Valproic acid) are added to the cultures. The cultures are then transferred on an orbital shaker (120 rpm) placed in a humidified incubator with 5% CO2 set at 32° C. At 24-48 hours, GFP positive cells should be between 30-60% as determined by flow cytometry. Cells were harvested 7 days post-transfection and spun at 4,000 rpm for 20 minutes. The supernatant was filter-sterilized (clarified) using a 0.45 μm filter (Millipore). Keep the supernatant at 4° C. for short period storage and at −80° C. for long period storage. Prior to purification, the frozen supernatant was thawed at 37° C., re-filtered and degassed through a 0.45 μm membrane filter under vacuum for 5-10 minutes.

TABLE 4

Cell viability at different stages of expression for WT and ABH1 construct.

| HSA scaffold | % GFP 48 hrs post-transfection | % viability 48 hrs post-transfection | % viability 48 hrs post-transfection |
|---|---|---|---|
| Wild Type HSA | 67 | 94.6 | 72.3 |
| ABH2 | 66.3 | 93.6 | 77.1 |

Purification of HSA and Heteromultimers ABH1 and ABH2

Figure 6C:
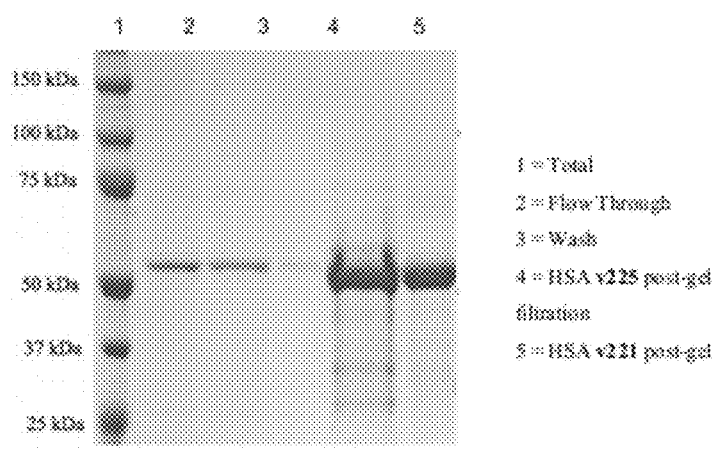

Purification was performed by gravity flow using a benchtop QIAGEN-tip 500 column packed with a Blue Sepharose matrix (GE Healthcare). The Blue Sepharose matrix was equilibrated with 20 ml of PBS pH 7.2. The sample was loaded at a flow rate of 5 ml/min and subsequently washed with 20 ml of PBS. The protein was eluted with 0.1 M Na2HPO4 pH 7.2 supplemented with 1 M NaCl and collected in 1 ml fractions (20 ml total). Fractions containing HSA (as per Bradford protein assay) were pooled, and applied on a HiLoad 16/60 Superdex 200 prep grade gel filtration column coupled to an AKTA Express system (GE Healthcare) using a flow rate of 1 ml/ml. Protein with a purity of >85% was collected; fractions containing pure sample were pooled and concentrated by centrifugation using an Amicon Ultra membrane with a cutoff weight of 10 000 MWCO. FIG. 6C shows SDS-PAGE (non-reducing) analysis of the ABH2 heteromultimer and WT HSA, both after the final stage of purification. Both constructs show the expected MW.

Stability determination of Albumin based Heteromultimers using Differential Scanning Calorimetry (DSC)

Figure 7:
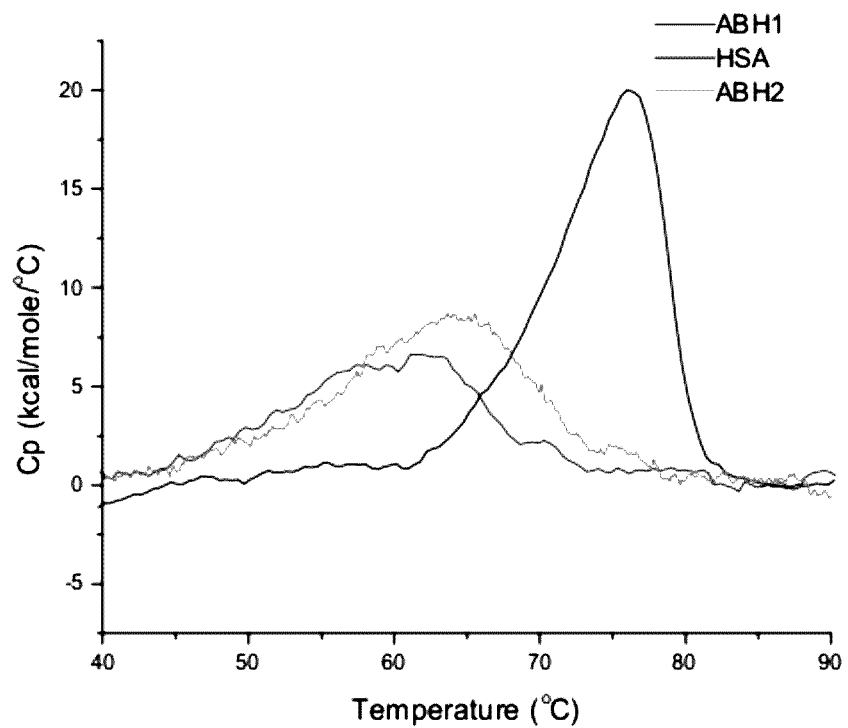
FIG. 7 shows stability of wild type HSA and heterodimer scaffolds ABH1 and ABH2 stuided using Differential Scanning calorimetry

All DSC experiments were carried out using a GE or MicroCal VP-Capillary instrument. The proteins were buffer-exchanged into PBS (pH 7.4) and diluted to 0.3 to 0.7 mg/mL with 0.137 mL loaded into the sample cell and measured with a scan rate of 1° C./min from 20 to 100° C. Data was analyzed using the Origin software (GE Healthcare) with the PBS buffer background subtracted. See Table 5 and FIG. 7 for resulting melting temperature determined.

TABLE 5

Melting temperature for Albumin based heteromultimers

| Molecule | Measured Mass (Da) | Theoretical MW (Da) | Tm° C. |
|---|---|---|---|
| HSA Wild Type | 66620 | 66470 | 75 |
| ABH2 | 66100 | 65880 | 63 |

Evaluation of FcRn Binding of HSA and ABH2 using Surface Plasmon Resonance

Figure 8A:
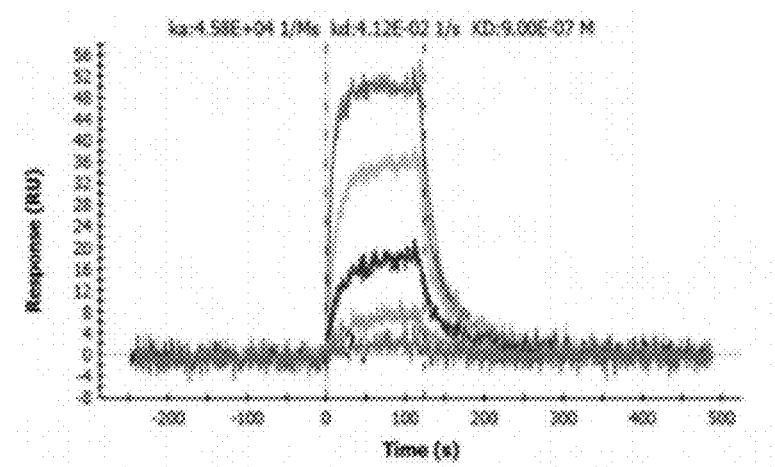
FIGS. 8A-8B show equilibrium binding isotherms 3000 nM FcRN 3× dilution series over 3000 RUs.
Figure 8B:
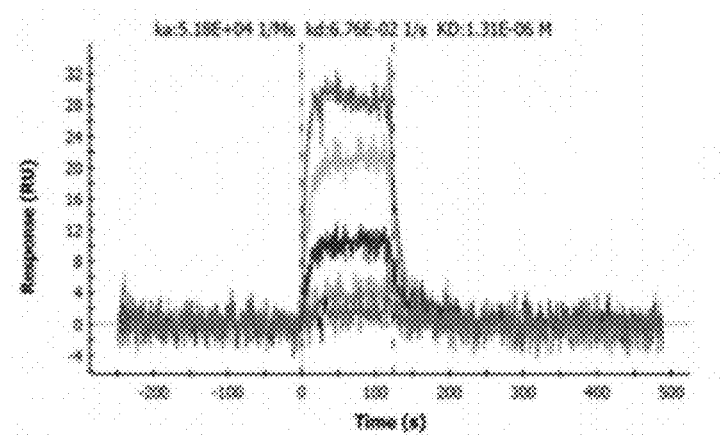

As seen in FIGS. 8A-B, when HSA and a HSA-based heteromultimer are immobilized on the SPR surface, affinity towards FcRn appears to be comparable between the full length WT HSA and ABH2, indicating FcRn binding functionality of albumin is retained by the heteromultimer formed by the self-assembly of albumin based transporter polypeptides. The following Table 6 illustrates FcRn binding data. Values in parenthesis refer to standard deviation.

TABLE 6

Kinetic and Equilibrium fit of FcRn Binding of HSA and ABH2 using Surface Plasmon Resonance

|  | Ka (1/Ms) Grouped Fitted | Kd (1/s) Grouped Fitted | KD (M) Grouped Fitted |  |
|---|---|---|---|---|
| HAS | 5.3E+04 (7E+03) | 7.0E−02 (2.0E−02) | 1.4E−06 (6.0E−07) | Kinetic fit |
| ABH2 | 5.0E+04 (4E+03) | 4.2E−02 (8.0E−03) | 8.0E−07 (2.0E−07) | Kinetic fit |
| HAS |  |  | 9.0E−07 (1.0E−07) | Equilibrium Fit |
| ABH2 |  |  | 9.0E−07 (1.0E−07) | Equilibrium Fit |

Example 3

Generation and Expression of Albumin Based Heteromultimers with Mono- and Tetravalency Comprising Anti-Her2/Neu and Anti-Cd16 scFv Bioactive Fusions Multivalent heteromultimer ABH2 was generated by expressing its single monomeric transporter polypeptides, SEQ ID NO: 8 and SEQ ID NO: 10, fused at one or both termini to cargo polypeptides that are either antiHer2scFv (4D5) and/or anti-CD16 scFv (NM3E). These form a set of 8 base construct monomers based off transporter polypeptide 1 and 8 base construct monomers based off transporter polypeptide 2. Different combinations of these base constructs were combined upon co-expression to form heteromultimers displaying all combination of the two cargo polypeptides at any of the four terminal positions of the two transporter polypeptides, ranging from monovalent to tetravalent.

Figure 9:
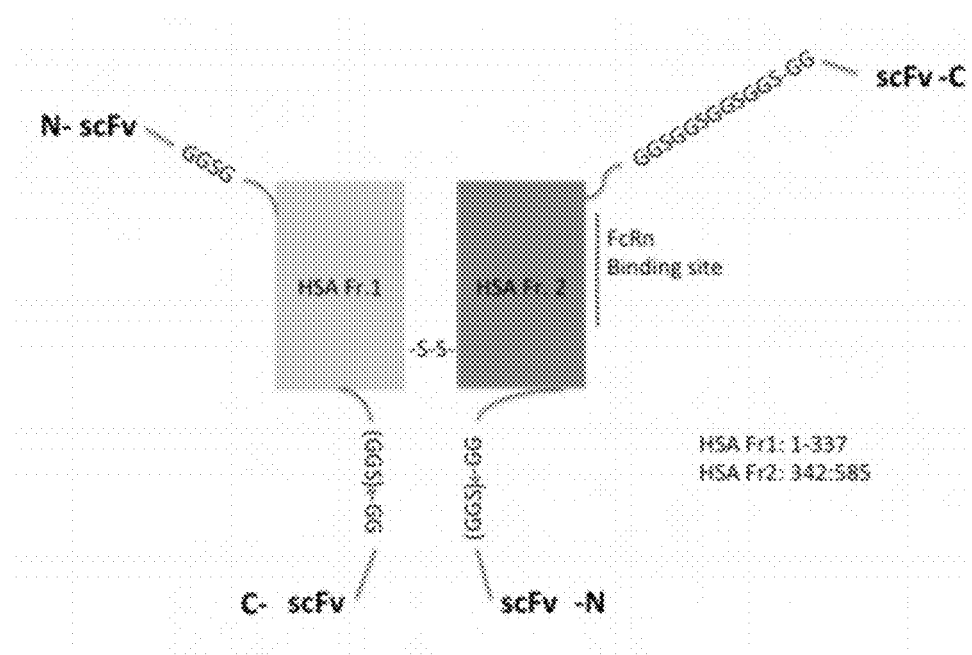
FIG. 9 shows scheme for multivalent Albumin based heteromultimers comprising anti-Her2/neu and anti-CD16 scFv bioactive fusions (FIG. 9 discloses "GGSG" and "$(GGS)_4$-GG" as SEQ ID NOS 23 and 24, respectively.)

As shown in FIG. 9, the bioactive cargo polypeptides were fused to the heteromultimer transporter polypeptides via a GGSG linker (SEQ ID NO: 23), for the N terminus of one monomer and a longer (GGS)4GG linker (SEQ ID NO: 24) for all other termini in the other monomer.

Table 7 illustrates the 16 base constructs (Base construct #1-Base construct #16) that were generated by fusing the 4D5 and NM3 cargo polypeptides to either N or C terminus of transporter polypeptide 1 (F1) or transporter polypeptide 2 (F2). F1: corresponds to SEQ ID 8 and F2 corresponds to SEQ ID 10.

| Single fusions | | |
|---|---|---|
| # | Fusion 1 | Fusion 2 |
| 1 | NM3E2 | F1 |
| 2 | F1 | NM3E2 |
| 3 | NM3E2 | F2 |
| 4 | F2 | NM3E2 |
| 5 | 4D5 | F1 |
| 6 | F1 | 4D5 |
| 7 | 4D5 | F2 |
| 8 | F2 | 4D5| |

| Double fusions | | | |
|---|---|---|---|
| # | Fusion 1 | Fusion 2 | Fusion 3 |
| 9 | NM3E2 | F1 | NM3E2 |
| 10 | NM3E2 | F2 | NM3E2 |
| 11 | 4D5 | F1 | 4D5 |
| 12 | 4D5 | F2 | 4D5 |
| 13 | NM3E2 | F1 | 4D5 |
| 14 | 4D5 | F1 | NM3E2 |
| 15 | NM3E2 | F2 | 4D5 |
| 16 | 4D5 | F2 | NM3E2 |

Figure 10A:
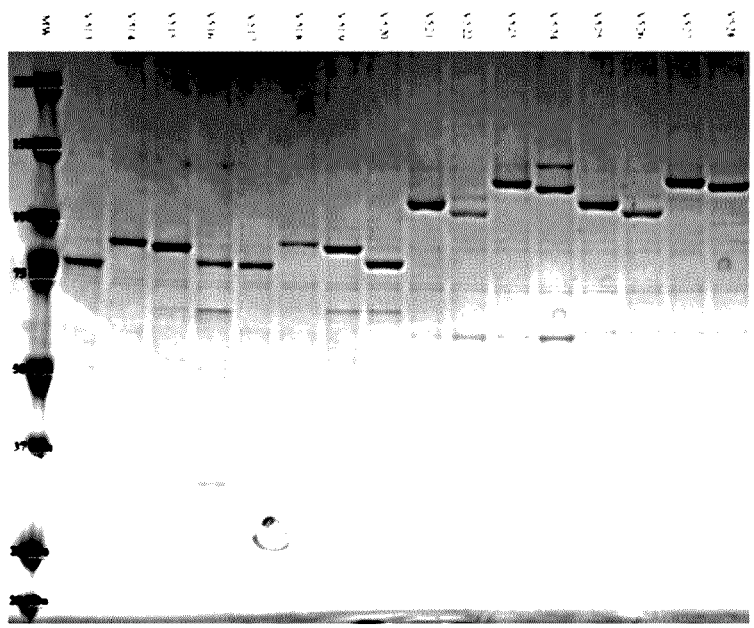
FIGS. 10A-10B contain a non-reducing SDS PAGE analysis of the heteromultimer ABH2 fusions described in table 8. The gel indicates all constructs form the correct complex with expected MW.
Figure 10B:
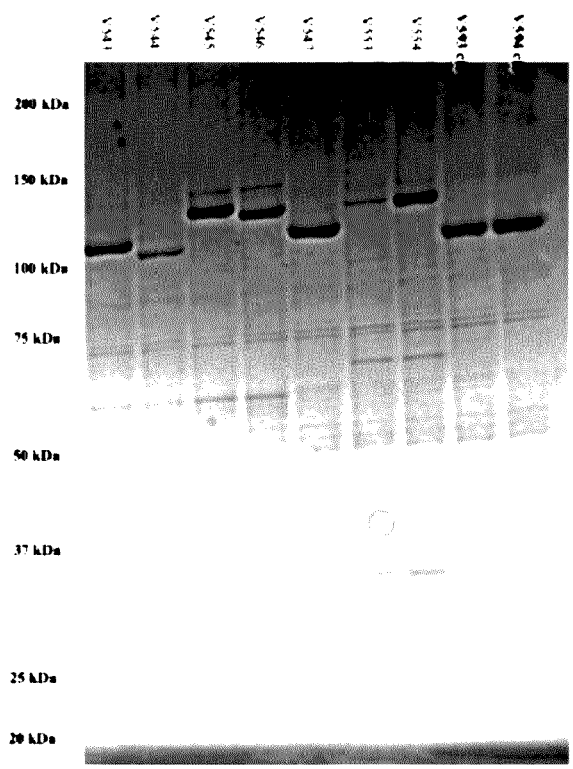

Multivalent constructs were generated as outlined in Example 2 using heteromultimer ABH2. The final gene products were subcloned into the mammalian expression vector pTT5 (NRC-BRI, Canada) (Durocher et al). High level and high-throughput recombinant protein production by transient transfection of suspension-growing human CHO-3E7 was performed. Purification was performed by application of the cellular supernatant with exopressed protein to a QIAGEN-tip 500 column packed with Blue Sepharose matrix (GE Healthcare) coupled to an AKTA Express system (GE Healthcare) using a flow rate of 1 ml/ml. The column was equilibrated with equilibrated with sample buffer composed of 20 ml of PBS pH 7.2, 300 mM NaCl. The sample was loaded at a flow rate of 5 ml/min and subsequently washed with sample buffer. The protein was eluted by applicatuion of NaCl gradient ranging from 300 mM to 2000 mM. Fractions eluting in higher salt concentration were the purest and were pooled, concentrated and subsequently applied to a HiLoad 16/60 Superdex 200 prep grade gel filtration column coupled to an AKTA Express system (GE Healthcare) using a flow rate of 1 ml/ml. Protein with a purity of >85% was collected; fractions containing pure sample were pooled and concentrated by centrifugation using an Amicon Ultra membrane with a cutoff weight of 10 000 MWCO. FIGS. 10A-10B shows SDS-PAGE (non-reducing) analysis of the ABH2 heteromultimer fused to different cargo polypeptides. The position of those polypeptides in the heteromultimer relative to the transporter polypeptides is outlined in table 8 below. All constructs showed the expected molecular weight.

TABLE 8

Monovalent, multivalent, and multispecific constructs that were generated by fusing the 4D5 and NM3 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency |
|---|---|---|---|---|---|
| 513 | NM3E | | | | monovalent |
| 514 | | NM3E | | | monovalent |
| 515 | | | NM3E | | monovalent |
| 516 | | | | NM3E | monovalent |
| 517 | 4D5 | | | | monovalent |
| 518 | | 4D5 | | | monovalent |
| 519 | | | 4D5 | | monovalent |
| 520 | | | | 4D5 | monovalent |
| 521 | NM3E | | NM3E | | bivalent |
| 522 | NM3E | | | NM3E | bivalent |
| 523 | | NM3E | NM3E | | bivalent |
| 524 | | NM3E | | NM3E | bivalent |
| 525 | 4D5 | | 4D5 | | bivalent |
| 526 | 4D5 | | | 4D5 | bivalent |
| 527 | | 4D5 | 4D5 | | bivalent |
| 528 | | 4D5 | | 4D5 | bivalent |
| 529 | NM3E | NM3E | | | bivalent |
| 530 | | | NM3E | NM3E | bivalent |
| 531 | 4D5 | 4D5 | | | bivalent |
| 532 | | | 4D5 | 4D5 | bivalent |
| 543 | NM3E | | 4D5 | | bispecific |
| 544 | NM3E | | | 4D5 | bispecific |
| 545 | | NM3E | 4D5 | | bispecific |
| 546 | | NM3E | | 4D5 | bispecific |
| 547 | 4D5 | | NM3E | | bispecific |
| 548 | | 4D5 | NM3E | | bispecific |
| 549 | 4D5 | | | NM3E | bispecific |
| 550 | | 4D5 | | NM3E | bispecific |

TABLE 8-continued

Monovalent, multivalent, and multispecific constructs that were generated by fusing the 4D5 and NM3 cargo polypeptides to either N or C terminus of transporter polypeptide 1 or transporter polypeptide 2 of ABH2.

| Variant | N terminus-transporter polypeptide 1 (SEQ ID No: 8) | C terminus-transporter polypeptide 1 (SEQ ID No: 8) | N terminus-transporter polypeptide 2 (SEQ ID No: 10) | C terminus-transporter polypeptide 2 (SEQ ID No: 10) | Valency |
|---|---|---|---|---|---|
| 551 | NM3E | 4D5 | | | bispecific |
| 552 | 4D5 | NM3E | | | bispecific |
| 553 | | | NM3E | 4D5 | bispecific |
| 554 | | | 4D5 | NM3E | bispecific |
| 593 | 4D5 | | | NM3E | bispecific |
| 594 | NM3E | | | 4D5 | bispecific |

SPR Binding of Monovalent ABH2 Fused to a Single AntiCD16scFv

Purified heteromultimer ABH2 fused to a single antiCD16scFv to the N terminus of transporter polypeptide SEQ ID 2 (construct v515) was used in a binding experiment using Surface Plasmon Resonance (SPR). Soluble CD16 was covalently immobilized onto a CM5 surface and ABH2 fused to antiCD16scFv was captured and binding kinetics were determined.

SPR supplies. GLM sensorchips, the Biorad ProteOn amine coupling kit (EDC, sNHS and ethanolamine), and 10 mM sodium acetate buffers were purchased from Bio-Rad Laboratories (Canada) Ltd. (Mississauga, ON). Recombinant Her-2 protein was purchased from eBioscience (San Diego, Calif.). HEPES buffer, EDTA, and NaCl were purchased from from Sigma-Aldrich (Oakville, ON). 10% Tween 20 solution was purchased from Teknova (Hollister, Calif.).

SPR biosensor assays. All surface plasmon resonance assays were carried out using a BioRad ProteOn XPR36 instrument (Bio-Rad Laboratories (Canada) Ltd. (Mississauga, ON)) with HBST running buffer (10 mM HEPES, 150 mM NaCl, 3.4 mM EDTA, and 0.05% Tween 20 pH 7.4) at a temperature of 25° C. The CD16 capture surface was generated using a GLM sensorchip activated by a 1:5 dilution of the standard BioRad sNHS/EDC solutions injected for 300 s at 30 µL/min in the analyte (horizontal) direction. Immediately after the activation, a 4.0 µg/mL solution of CD16 in 10 mM NaOAc pH 4.5 was injected in the ligand (vertical) direction at a flow rate of 25 µL/min until approximately 3000 resonance units (RUs) were immobilized. Remaining active groups were quenched by a 300 s injection of 1M ethanolamine at 30 µL/min in the analyte direction, and this also ensures mock-activated interspots are created for blank referencing.

A 500 nM 3-fold dilution series of V515 was injected over 3000 RUs CD16aWT (L6) compared to blank (L5). Flow rate 50 uL/min for 120 s, with a 240 s disassociation phase. Injections were repeated in standard running buffer (DPBS/ 3.4 mM EDTA/0.05% Tween20) and running buffer with an additional 350 mM NaCl. Sensorgrams were aligned and double-referenced using the buffer blank injection and interspots, and the resulting sensorgrams were analyzed using ProteOn Manager software v3.0. Typically, $K_D$ values were determined from binding isotherms using the Equilibrium Fit model. For high affinity interactions with slow off-rates, kinetic and affinity values were additionally determined by fitting the referenced sensorgrams to the 1:1 Langmuir binding model using local $R_{max}$, and affinity constants ($K_D$ M) were derived from the resulting rate constants ($k_d s^{-1}$/$k_a M^{-1} s^{-1}$). All $K_D$ values are reported as the mean and standard deviation from three independent runs.

As shown in Table 9, ABH2 heteromultimer fused to a single antiCD16scFv has full activity and binds its target with good reproducibility and KD similar to the free anti CD16 scFv (NM3E).

TABLE 9

SPR data for monovalent ABH2 fused to a single antiCD16scFv.

| | Injection #1 | | | Injection #2 | | | | |
|---|---|---|---|---|---|---|---|---|
| | ka 1/Ms | kd 1/s | KD M | ka 1/Ms | kd 1/s | KD M | KD (M) Ave | KD SD |
| NM3E | 5.37E+04 | 5.76E−03 | 1.07E−07 | 5.89E+04 | 5.03E−03 | 1.02E−07 | 1.05E−07 | 4.E−09 |
| V515 Dec | 6.11E+04 | 6.71E−03 | 1.10E−07 | | | | | |
| V515 Jan | 5.56E+04 | 7.30E−03 | 1.31E−07 | | | | | |

Example 4

Preparation of HA or HAA Based Heteromultimer Proteins Wherein Cargo Protein(s) Comprise One or More EGF-A Like Domain The peptide sequence of the EGF-A domain in PCSK9 protein or another polypeptide sequence homologous to the EGF-A domain, capable of specifically binding the low density lipoprotein receptor (LDL-R) is derived by sequencing or from a database such as GenBank. The cDNA for the cargo polypeptide comprising EGF-A like domain is isolated by a variety of means including but not exclusively, from cDNA libraries, by RT-PCR and by PCR using a series of overlapping synthetic oligonucleotide primers, all using standard methods. In certain examples, the cargo protein is engineered to improve stability, target binding features or other biophysical or therapeutically relevant properties. The polypeptide is employed as the cargo protein in the creation of a heteromultimer with application in the treatment of hypercholesterolemia. The first and second monomeric fusion polypeptide sequence is derived by fusing the cargo protein sequence directly or with an intermediate linker peptide to the N-terminus and/or C-terminus of HA or HAA based transporter polypeptide such as SEQ ID No: 2, SEQ ID NO: 3, SEQ ID NO: 8 or SEQ ID NO: 10. This monomeric fusion protein sequence is reverse translated to its corresponding DNA sequence to be introduced in an expression vector, sequence optimized for expression in a particular cell line of interest. The first and second monomeric fusion proteins are transfected and coexpressed in the cell line of interest. In certain cases, the transfection is in 1:1 ratio for the two vectors. In some examples, the ratio is selected from 1.5:1, 2:1, 1:1.5, 1:2 etc.

Example 5

Preparation of HA or HAA Based Heteromultimeric Proteins Wherein Cargo Protein(s) are the GLP-1 and/or Glucagon The peptide sequence of GLP-1 or another polypeptide sequence homologous to this peptide, capable of specifically binding the GLP-1 receptor or acting as a GLP-1 agonist is derived by sequencing or from a database such as GenBank. Alternately, the peptide sequence of Glucagon or another polypeptide sequence homologous to this peptide, capable of specifically binding the Glucagon receptor or acting as a Glucagon receptor agonist is derived by sequencing or from a database such as GenBank. The cDNA for each cargo polypeptide comprising GLP-1 or Glucagon is isolated by a variety of means including but not exclusively, from cDNA libraries, by RT-PCR and by PCR using a series of overlapping synthetic oligonucleotide primers, all using standard methods. In certain examples, these GLP-1 or Glucagon based cargo polypeptides are engineered to improve stability, target binding features or other biophysical or therapeutically relevant properties. These GLP-1 and Glucagon based polypeptides are employed as one or more cargo molecules in the creation of a heteromultimer with application in the treatment of type-2 diabetes or another disease related to glucose metabolism. The first and second monomeric fusion polypeptide sequence is derived by fusing the cargo protein sequence directly or with an intermediate linker peptide to the N-terminus and/or C-terminus of HA or HAA based transporter polypeptide such as SEQ ID No: 2, SEQ ID NO: 3, SEQ ID NO: 8 or SEQ ID NO: 10. The fusion proteins can be monospecific with either GLP-1 or Glucagon like polypeptides or be bispecific (coagonist) with both the GLP-1 and Glucagon like polypeptides. Each monomeric fusion protein sequence is reverse translated to its corresponding DNA sequence to be introduced in an expression vector, sequence optimized for expression in a particular cell line of interest. The first and second monomeric fusion proteins are transfected and coexpressed in the cell line of interest. In certain cases, the transfection is in 1:1 ratio for the two vectors. In some examples, the ratio is selected from 1.5:1, 2:1, 1:1.5, 1:2 etc Sequence of Cargo Molecule GLP-1

SEQ ID No: 12:
HAEGTFTSDVSSYLEGQAAKEFIAWLVKGRG

Sequence of Cargo Molecule Glucagon

SEQ ID NO: 13:
HSQGTFTSDYSKYLDSRRAQDFVQWLMNT

Example 6

Annexin Protein Repeat as Membrane-Sensing Multivalent Scaffold

Figure 11:
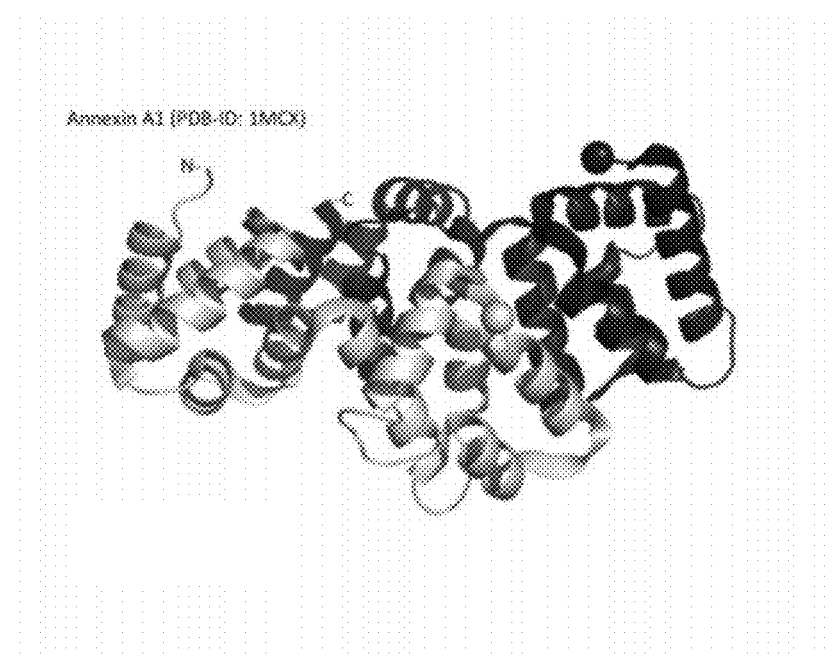
FIG. 11 shows structure of Annexin molecule based on the PDB structure 1MCX. The two monomers that will be derived by splitting the Annexin molecule are color coded as light and dark grey units. The sites of fusion for the cargo protein are represented as spheres.

Annexin is split with an extensive interface to generate a multivalent heteromultimer scaffold comprising two transporter polypeptides Annexin is a 346 residue protein (PDB ID 1MCX). Heteromultimer comprising two transporter polypeptides based on annexin split in the region between residue 186 and 194 is show in FIG. 11. When co-expressed in solution, the large interfacial area between the two transporter polypeptides leads to self-assembly of the heterodimer. The self-assembly of the two units allows for the design of multivalent construct with transporter polypeptides based on the annexin core. Two structures are available, Pig and Human. The two structures are superimposable with an rmsd of 0.6 A. The following stretch of sequence can be removed from the human Annexin sequence DRSEDF (residues 160 through 165). The truncation does not break any secondary structure element and does not involve introducing or removing any Proline residue.

Human annexin WT Sequence

SEQ ID NO: 14:
GSAVSPYPTFNPSSDVAALHKAIMVKGVDEATIIDILTKRNNAQRQQIKA

AYLQETGKPLDETLKKALTGHLEEVVLALLKTPAQFDADELRAAMKGLGT

DEDTLIEILASRTNKEIRDINRVYREELKRDLAKDITSDTSGDFRNALLS

LAKGDRSEDFGVNEDLADSDARALYEAGERRKGTDVNVFNTILTTRSYPQ

LRRVFQKYTKYSKHDMNKVLDLELKGDIEKCLTAIVKCATSKPAFFAEKL

HQAMKGVGTRHKALIRIMVSRSEIDMNDIKAFYQKMYGISLCQAILDETK

GDYEKILVALCGGN

Sequence of Annexin Based Transporter Polypeptide-1:

SEQ ID NO: 15:
SAVSPYPTFNPSSDVAALHKAIMVKGVDEATIIDILTKRNNAQRQQIKAA

YLQETGKPLDETLKKALTGHLEEVVLALLKTPAQFDADELRAAMKGLGTD

EDTLIEILASRTNKEIRDINRVYREELKRDLAKDITSDTSGDFRNALLSL

AKG

Sequence of Annexin Based Transporter Polypeptide-2:

SEQ ID NO: 16:
GVNEDLADSDARALYEAGERRKGTDVNVFNTILTTRSYPQLRRVFQKYTK

YSKHDMNKVLDLELKGDIEKCLTAIVKCATSKPAFFAEKLHQAMKGVGTR

HKALIRIMVSRSEIDMNDIKAFYQKMYGISLCQAILDETKGDYEKILVAL

CGGN

Figure 12:
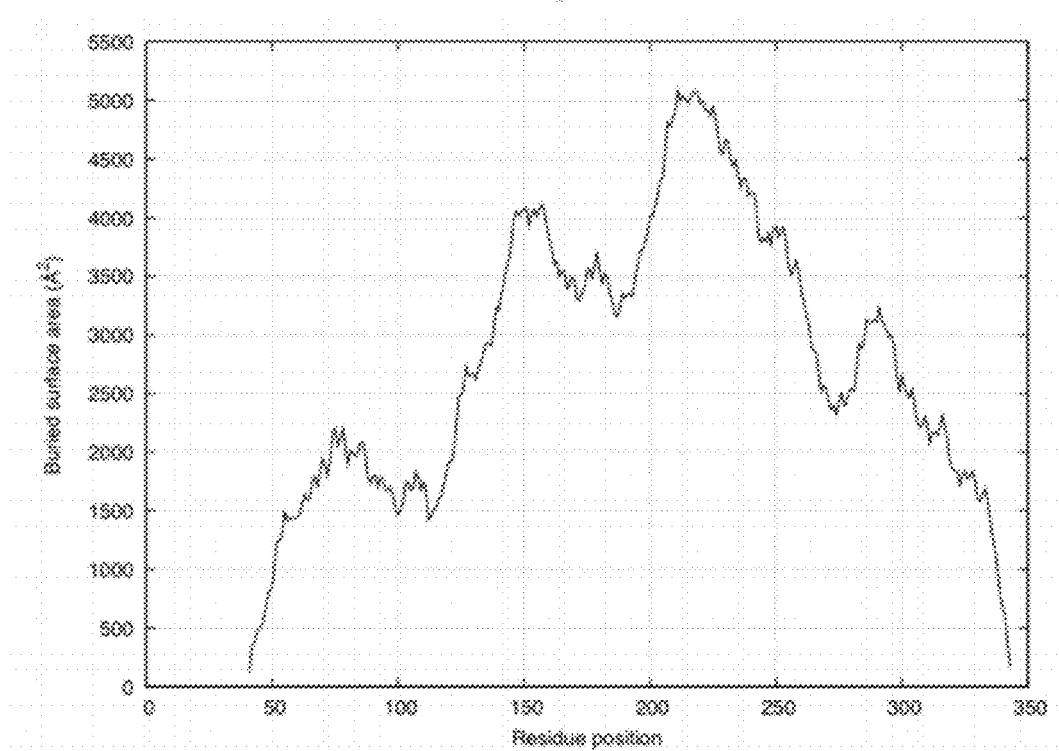
FIG. 12 shows a plot of the buried solvent accessible surface area at the interface of Annexin based tranporter polypeptide-1, and Annexin based tranporter polypeptide-2.

FIG. 12 shows a plot of the buried solvent accessible surface area at the interface of Annexin based tranporter polypeptide-1 (ABT-1), and Annexin based tranporter polypeptide-2 (ABT-2). A split annexin near residue position 186 forms a heterodimer with about 3200 Å$^2$ of buried surface area. The transporter polypeptides such as ABT-1 and ABT-2 based on Annexin can be used to attach cargo biomolecules using the same methods as described above for albumin based transporter polypeptides.

Example 7

Transferrin as a Multivalent Scaffold

Figure 13:
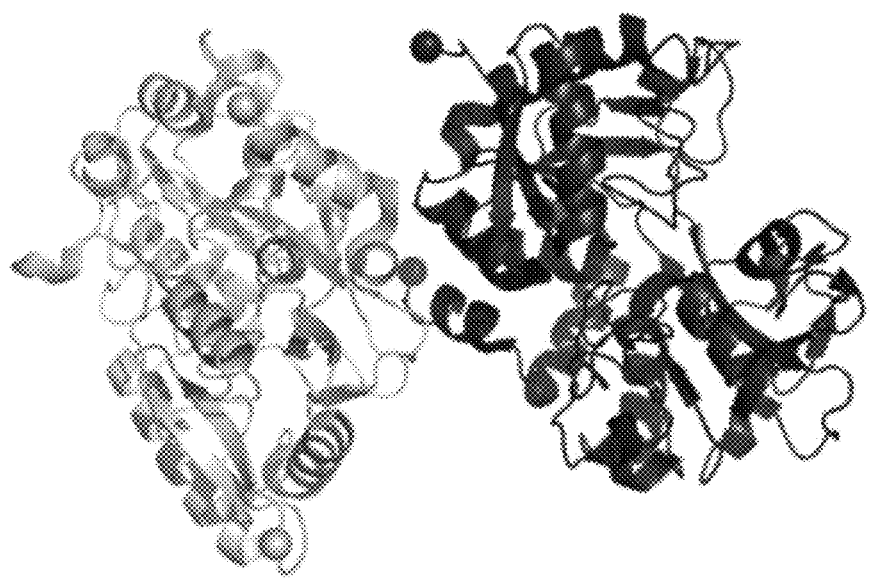
FIG. 13 shows structure of transferrin molecule based on the PDB structure 1H76. The two monomers derived by splitting the transferrin molecule are color coded as light and dark grey units. The sites of fusion for the cargo protein are represented as spheres.

Based on the large number of therapeutically relevant properties of transferrin, this protein presents itself as an interesting scaffold molecule for the design of multivalent protein fusion drugs following the creation of a self-assembling protein and its split component parts. The structure of transferrin is shown in FIG. 13 based on the crystal structure (1H76) available in the protein data bank [Hall D R et al. Acta Crystallogr D 2002, 58, 70-80]. The transferrin molecule is composed of two structurally similar lobes, the N and C terminal lobes, connected by a short peptide linker between residues 333 and 342.

A heterodimer is designed based on transferrin protein, said heterodimer comprising a first transporter polypeptide involving residues 1-333 of transferrin and a second transporter polypeptide composed of residues from 342 to the C-terminus of the original transferrin sequence. When coexpressed, the two transporter polypeptides fold independently and pair to form a quasi-transferrin scaffold capable of maintaining its therapeutically relevant properties. Furthermore, such a Transferrin scaffold allows for the production of multivalent fusion molecules, e.g. a multivalent GLP-1 fusion with trasnsporter polypeptides based on transferring. These fusions can be similar to the GLP-1-fusion polypeptides with Albumin based transporter polypeptides.

Figure 14:
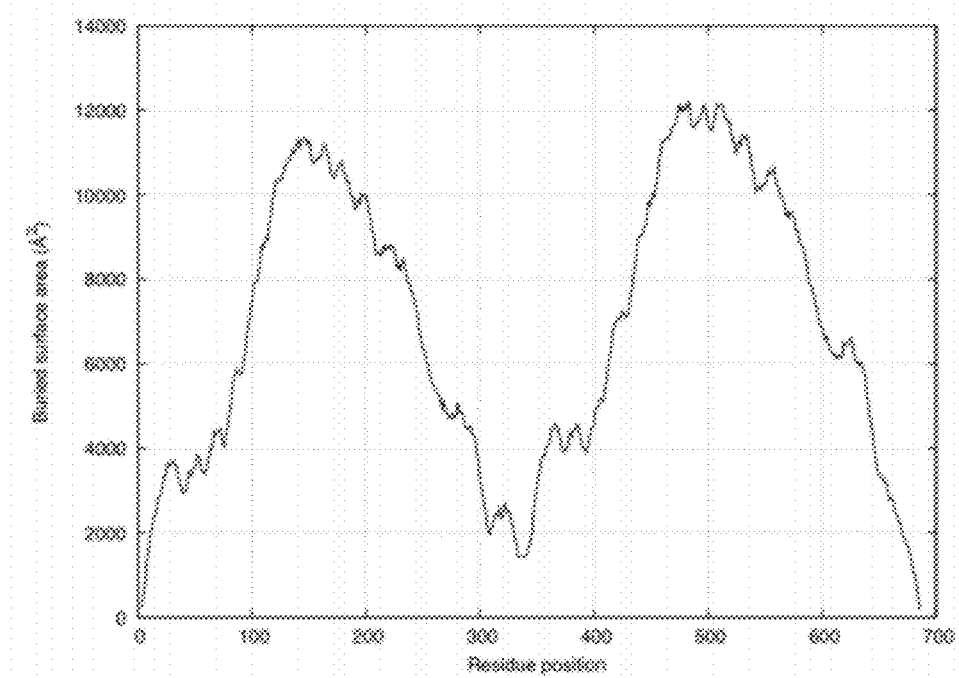
FIG. 14 shows a plot of the buried solvent accessible surface area at the interface of two transferrin based transporter polypeptides described herein. A split transferrin near residue position 330 as designed herein, forms a heterodimer with about 1800 $Å^2$ of buried surface area.

FIG. 13 provides structure of transferrin molecule based on the PDB structure 1H76. The two monomering transporter polypeptides derived by splitting the transferrin molecule are color coded as light and dark grey units. The sites of fusion for the cargo molecules are represented as spheres. FIG. 14 shows a plot of the buried solvent accessible surface area at the interface of two transferrin based polypeptides. A split transferrin near residue position 330 such as the two transporter polypeptides shown below, forms a heterodimer with about 1800 Å$^2$ of buried surface area.

Sequence of Transferrin Based Transporter Polypeptide-1:

```
SEQ ID NO: 17:
MRLAVGALLV CAVLGLCLAV PDKTVRWCAV SEHEATKCQS

FRDHMKSVIP SDGPSVACVK KASYLDCIRA IAANEADAVT

LDAGLVYDAY LAPNNLKPVV AEFYGSKEDP QTFYYAVAVV

KKDSGFQMNQ LRGKKSCHTG LGRSAGWNIP IGLLYCDLPE

PRKPLEKAVA NFFSGSCAPC ADGTDFPQLC QLCPGCGCST

LNQYFGYSGA FKCLKDGAGD VAFVKHSTIF ENLANKADRD

QYELLCLDNT RKPVDEYKDC HLAQVPSHTV VARSMGGKED

LIWELLNQAQ EHFGKDKSKE FQLFSSPHGK DLLFKDSAHG

FLKVPPRMDA KMYLGYEYVT AIRNLREG.
```

Sequence of Transferrin Based Transporter Polypeptide-2:

```
SEQ ID NO: 18:
ECKPVKWCALSHHE RLKCDEWSVN SVGKIECVSA ETTEDCIAKI

MNGEADAMSL DGGFVYIAGK CGLVPVLAEN YNKSDNCEDT

PEAGYFAVAV VKKSASDLTW DNLKGKKSCH TAVGRTAGWN

IPMGLLYNKI NHCRFDEFFS EGCAPGSKKD SSLCKLCMGS

GLNLCEPNNK EGYYGYTGAF RCLVEKGDVA FVKHQTVPQN

TGGKNPDPWA KNLNEKDYEL LCLDGTRKPV EEYANCHLAR

APNHAVVTRK DKEACVHKIL RQQQHLFGSN VTDCSGNFCL

FRSETKDLLF RDDTVCLAKL HDRNTYEKYL GEEYVKAVGN

LRKCSTSSLL EACTFRRP.
```

Example 9

Multiple Cargo Proteins

The heteromultimer proteins described herein (e.g., containing a cargo polypeptide (or fragment or variant thereof) fused to transporter albumin segment or variant thereof) may additionally be fused to other proteins to generate "multifusion proteins". These multifusion proteins can be used for a variety of applications. For example, fusion of the proteins described herein to His-tag IgG domains, and maltose binding protein facilitates purification. (See e.g EPA 394,827; Traunecker et al., Nature 331:84-86 (1988)). Nuclear localization signals fused to the polypeptides can target the protein to a specific subcellular localization. Furthermore, the fusion of additional protein sequences to proteins described herein may further increase the solubility and/or stability of the heteromultimer. The heteromultimer proteins described above can be made using or routinely modifying techniques known in the art and/or by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian or yeast expression vector.

For example, if pC4 (ATCC Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide encoding a heteromultimeric protein described herein (generated and isolated using techniques known in the art), is ligated into this BamHI site. Note that the polynucleotide encoding the fusion protein of the invention is cloned without a stop codon; otherwise an Fc containing fusion protein will not be produced.

If the naturally occurring signal sequence is used to produce the heteromultimeric protein described herein, pC4 does not need a second signal peptide. Alternatively, if the naturally occurring signal sequence is not used, the vector can be modified to include a heterologous signal sequence. (See, e.g., International Publication No. WO 96/34891.)

What is claimed:

1. A heteromultimer comprising a first monomeric protein that comprises (i) a first transporter polypeptide comprising a first segment of albumin; and (ii) at least one cargo polypeptide and a second monomeric protein that comprises (iii) a second transporter polypeptide comprising a second segment of albumin and (iv) at least one cargo polypeptide; wherein said first segment of albumin and said second segment of albumin are derived from an albumin by segmentation of the albumin to remove a loop, said first transporter polypeptide is different from said second transporter polypeptide, and said transporter polypeptides self-assemble to form a quasi-native albumin structure.

2. The heteromultimer of claim 1, wherein said heteromultimer is a heterodimer.

3. The heteromultimer of claim 1 wherein said albumin is human serum albumin having a sequence of SEQ ID NO: 1 or analog or variant thereof.

4. The heteromultimer of claim 1, wherein said first transporter polypeptide has a sequence comprising SEQ ID NO:2 or an analog or variant thereof, and wherein said second transporter polypeptide has a sequence comprising SEQ ID NO:3 or an analog or variant thereof.

5. The heteromultimer of claim 1, wherein said first transporter polypeptide has a sequence comprising SEQ ID NO:8 or an analog or variant thereof, and wherein said second transporter polypeptide has a sequence comprising SEQ ID NO:10 or an analog or variant thereof.

6. The heteromultimer of claim 1, wherein at least one transporter polypeptide is an allo-albumin derivative.

7. The heteromultimer according to claim 1, wherein the transporter polypeptides are derived from the same albumin.

8. The heteromultimer of claim 7, wherein said first transporter polypeptide and said second transporter polypeptide are derived from the same alloalbumin.

9. The heteromultimer according to claim 1, wherein the transporter polypeptides are derived from different albumins.

10. The heteromultimer of claim 9, wherein one of said first transporter polypeptide and said second transporter polypeptide is derived from human serum albumin and the other is derived from an alloalbumin.

11. The heteromultimer of claim 1, wherein at least one cargo polypeptide is an antibody, or a fragment or variant thereof.

12. The heteromultimer of claim 1 wherein the at least one cargo polypeptide of said first monomeric protein binds a target antigen, and the at least one cargo polypeptide of said second monomeric protein comprises a toxin moiety.

13. The heteromultimer of claim 1, wherein said at least one cargo polypeptide binds a target antigen, wherein said target antigen is at least one of alpha-chain (CD25) of IL-2R, Amyloid beta, anti-EpCAM, anti-CD3, CD16, CD20, CD22, CD23, CD3, CD4, CD52, CD80, CTLA-4, EGFR, EpCAM, F protein of RSV, G250, glycoprotein IIB/IIIa R, HER2, HSP90, IgE antibody, IL-12, IL-23, IL-1 beta, IL-5, IL-6, RANKL, TNF alpha, TNFR, VEGF-A, glucagon receptor, GLP receptor, and LDL receptor.

14. The heteromultimer of claim 1 wherein at least one cargo polypeptide is an enzyme, hormone, therapeutic polypeptide, antigen, chemotoxin, radiotoxin, cytokine or a variant or fragment thereof.

15. The heteromultimer of claim 1, wherein said first monomeric protein and said second monomeric protein comprise the same cargo polypeptide.

16. The heteromultimer of claim 1, wherein the cargo polypeptide is attached to the transporter polypeptide by chemical conjugation, native ligation, chemical ligation, a disulfide bond, or direct fusion or fusion via a linker.

17. The heteromultimer of claim 16, wherein the linker is a GGSG linker or a (GGSG)$_4$GG linker.

18. The heteromultimer of claim 1, wherein the heteromultimer binds to FcRn.

19. The heteromultimer of claim 1, wherein the first segment of albumin and the second segment of albumin form a complementary pair of transporter polypeptides.

20. The heteromultimer of claim 1, wherein said first transporter polypeptide and said second transporter polypeptide are derived from a mammalian albumin.

21. The heteromultimer of claim 1, wherein said first transporter polypeptide and said second transporter polypeptide are derived from a non-mammalian albumin.

22. A host cell comprising nucleic acid encoding the heteromultimer of claim 1.

23. The host cell of claim 22, wherein the nucleic acid encoding the first monomeric-protein and the nucleic acid encoding the second monomeric protein are present in a single vector.

24. The host cell of claim 22, wherein the nucleic acid encoding the first monomeric protein and the nucleic acid encoding the second monomeric protein are present in separate vectors.

* * * * *

SEQUENCE LISTING

<160> NUMBER OF SEQ ID NOS: 65

<210> SEQ ID NO 1
<211> LENGTH: 609
<212> TYPE: PRT
<213> ORGANISM: Homo sapiens

<400> SEQUENCE: 1

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365
```

```
Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 2
<211> LENGTH: 293
<212> TYPE: PRT
<213> ORGANISM: Homo sapiens

<400> SEQUENCE: 2

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val
    290

<210> SEQ ID NO 3
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ser Leu Ala Ala Asp Phe Val Glu Ser Lys Asp Val Cys Lys Asn Tyr
1               5                   10                  15

Ala Glu Ala Lys Asp Val Phe Leu Gly Met Phe Leu Tyr Glu Tyr Ala
            20                  25                  30

Arg Arg His Pro Asp Tyr Ser Val Val Leu Leu Leu Arg Leu Ala Lys
        35                  40                  45

Thr Tyr Glu Thr Thr Leu Glu Lys Cys Cys Ala Ala Ala Asp Pro His
    50                  55                  60

Glu Cys Tyr Ala Lys Val Phe Asp Glu Phe Lys Pro Leu Val Glu Glu
65                  70                  75                  80

Pro Gln Asn Leu Ile Lys Gln Asn Cys Glu Leu Phe Glu Gln Leu Gly
                85                  90                  95

Glu Tyr Lys Phe Gln Asn Ala Leu Leu Val Arg Tyr Thr Lys Lys Val
            100                 105                 110

Pro Gln Val Ser Thr Pro Thr Leu Val Glu Val Ser Arg Asn Leu Gly
        115                 120                 125

Lys Val Gly Ser Lys Cys Cys Lys His Pro Glu Ala Lys Arg Met Pro
130                 135                 140

Cys Ala Glu Asp Tyr Leu Ser Val Val Leu Asn Gln Leu Cys Val Leu
145                 150                 155                 160

His Glu Lys Thr Pro Val Ser Asp Arg Val Thr Lys Cys Cys Thr Glu
                165                 170                 175

Ser Leu Val Asn Arg Arg Pro Cys Phe Ser Ala Leu Glu Val Asp Glu
            180                 185                 190

```
Thr Tyr Val Pro Lys Glu Phe Asn Ala Glu Thr Phe Thr Phe His Ala
        195                 200                 205

Asp Ile Cys Thr Leu Ser Glu Lys Glu Arg Gln Ile Lys Lys Gln Thr
    210                 215                 220

Ala Leu Val Glu Leu Val Lys His Lys Pro Lys Ala Thr Lys Glu Gln
225                 230                 235                 240

Leu Lys Ala Val Met Asp Asp Phe Ala Ala Phe Val Glu Lys Cys Cys
                245                 250                 255

Lys Ala Asp Asp Lys Glu Thr Cys Phe Ala Glu Gly Lys Lys Leu
                260                 265                 270

Val Ala Ala Ser Gln Ala Ala Leu Gly Leu
                275                 280

<210> SEQ ID NO 4
<211> LENGTH: 29
<212> TYPE: PRT
<213> ORGANISM: Homo sapiens

<400> SEQUENCE: 4

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly
            20                  25

<210> SEQ ID NO 5
<211> LENGTH: 1845
<212> TYPE: DNA
<213> ORGANISM: Homo sapiens

<400> SEQUENCE: 5
gaattcgcca ctatggctgt gatggcccct aggaccctgg tgctgctgct gtccggagct      60
ctggctctga ctcagacctg gctggagat gcacacaaga gtgaggttgc tcatcggttt     120
aaagatttgg gagaagaaaa tttcaaagcc ttggtgttga ttgcctttgc tcagtatctt     180
cagcagtgtc catttgaaga tcatgtaaaa ttagtgaatg aagtaactga atttgcaaaa     240
acatgtgttg ctgatgagtc agctgaaaat tgtgacaaat cacttcatac ccttttttgga    300 gacaaattat gcacagttgc aactcttcgt gaaacctatg gtgaaatggc tgactgctgt     360
gcaaaacaag aacctgagag aaatgaatgc ttcttgcaac acaaagatga acccaaaac     420 ctcccccgat tggtgagacc agaggttgat gtgatgtgca ctgcttttca tgacaatgaa     480
gagacatttt tgaaaaaata cttatatgaa attgccagaa gacatcctta cttttatgcc     540
ccggaactcc ttttctttgc taaaaggtat aaagctgctt ttacagaatg ttgccaagct     600
gctgataaag ctgcctgcct gttgccaaag ctcgatgaac ttcgggatga agggaaggct     660
tcgtctgcca aacagagact caagtgtgcc agtctccaaa aatttggaga aagagctttc     720
aaagcatggg cagtagctcg cctgagccag agatttccca agctgagtt tgcagaagtt     780 tccaagttag tgacagatct taccaaagtc cacacggaat gctgccatgg agatctgctt     840
gaatgtgctg atgacagggc ggaccttgcc aagtatatct gtgaaaatca agattcgatc     900
tccagtaaac tgaaggaatg ctgtgaaaaa cctctgttgg aaaaatccca ctgcattgcc     960
gaagtggaaa atgatgagat gcctgctgac ttgccttcat agctgctga ttttgttgaa    1020 agtaaggatg tttgcaaaaa ctatgctgag gcaaaggatg tcttcctggg catgttttg    1080 tatgaatatg caagaaggca tcctgattac tctgtcgtgc tgctgctgag acttgccaag    1140
```

```
acatatgaaa ccactctaga gaagtgctgt gccgctgcag atcctcatga atgctatgcc    1200
aaagtgttcg atgaatttaa acctcttgtg gaagagcctc agaatttaat caaacaaaat    1260
tgtgagcttt ttgagcagct tggagagtac aaattccaga atgcgctatt agttcgttac    1320
accaagaaag tacccccaagt gtcaactcca actcttgtag aggtctcaag aaacctagga    1380
aaagtgggca gcaaatgttg taaacatcct gaagcaaaaa gaatgccctg tgcagaagac    1440
tatctatccg tggtcctgaa ccagttatgt gtgttgcatg agaaaacgcc agtaagtgac    1500
agagtcacca aatgctgcac agaatccttg gtgaacaggc gaccatgctt ttcagctctg    1560
gaagtcgatg aaacatacgt tcccaaagag tttaatgctg aaacattcac cttccatgca    1620
gatatatgca cactttctga aaggagagag caaatcaaga aacaaactgc acttgttgag    1680
ctcgtgaaac acaagcccaa ggcaacaaaa gagcaactga agctgttat ggatgatttc    1740 gcagcttttg tagagaagtg ctgcaaggct gacgataagg agacctgctt tgccgaggag    1800
ggtaaaaaac ttgttgctgc aagtcaagct gccttaggct tatga                    1845

<210> SEQ ID NO 6
<211> LENGTH: 882
<212> TYPE: DNA
<213> ORGANISM: Homo sapiens

<400> SEQUENCE: 6
gatgcacaca agagtgaggt tgctcatcgg tttaaagatt tgggagaaga aaatttcaaa      60
gccttggtgt tgattgcctt tgctcagtat cttcagcagt gtccatttga agatcatgta    120
aaattagtga atgaagtaac tgaatttgca aaaacatgtg ttgctgatga gtcagctgaa    180
aattgtgaca aatcacttca tacccttttt ggagacaaat tatgcacagt tgcaactctt    240
cgtgaaacct atggtgaaat ggctgactgc tgtgcaaaac aagaacctga gaaaatgaa    300 tgcttcttgc aacacaaaga tgacaaccca aacctccccc gattggtgag accagaggtt    360
gatgtgatgt gcactgcttt tcatgacaat gaagagacat ttttgaaaaa atacttatat    420
gaaattgcca aagacatcc ttacttttat gccccggaac tcctttcctt tgctaaaagg    480
tataaagctg ctttacaga atgttgccaa gctgctgata agctgcctg cctgttgcca    540 aagctcgatg aacttcggga tgaagggaag gcttcgtctg ccaaacagag actcaagtgt    600
gccagtctcc aaaaatttgg agaaagagct ttcaaagcat gggcagtagc tcgcctgagc    660
cagagatttc ccaaagctga gtttgcagaa gtttccaagt tagtgacaga tcttaccaaa    720
gtccacacgg aatgctgcca tggagatctg cttgaatgtg ctgatgacag gcggaccttt    780
gccaagtata tctgtgaaaa tcaagattcg atctccagta aactgaagga atgctgtgaa    840
aaacctctgt tggaaaaatc ccactgcatt gccgaagtgt ga                       882

<210> SEQ ID NO 7
<211> LENGTH: 849
<212> TYPE: DNA
<213> ORGANISM: Homo sapiens

<400> SEQUENCE: 7
tcattagctg ctgattttgt tgaaagtaag gatgtttgca aaaactatgc tgaggcaaag      60
gatgtcttcc tgggcatgtt tttgtatgaa tatgcaagaa ggcatcctga ttactctgtc    120
gtgctgctgc tgagacttgc caagacatat gaaaccactc tagagaagtg ctgtgccgct    180
gcagatcctc atgaatgcta tgccaaagtg ttcgatgaat taaaacctct tgtggaagag    240
cctcagaatt taatcaaaca aaattgtgag cttttgagc agcttggaga gtacaaattc    300
```

-continued

```
cagaatgcgc tattagttcg ttacaccaag aaagtacccc aagtgtcaac tccaactctt     360
gtagaggtct caagaaacct aggaaaagtg ggcagcaaat gttgtaaaca tcctgaagca     420
aaaagaatgc cctgtgcaga agactatcta tccgtggtcc tgaaccagtt atgtgtgttg     480
catgagaaaa cgccagtaag tgacagagtc accaaatgct gcacagaatc cttggtgaac     540
aggcgaccat gcttttcagc tctggaagtc gatgaaacat acgttcccaa agagtttaat     600
gctgaaacat tcaccttcca tgcagatata tgcacacttt ctgagaagga gacaaatc      660 aagaaacaaa ctgcacttgt tgagctcgtg aaacacaagc ccaaggcaac aaaagagcaa     720
ctgaaagctg ttatggatga tttcgcagct tttgtagaga agtgctgcaa ggctgacgat     780
aaggagacct gctttgccga ggagggtaaa aaacttgttg ctgcaagtca agctgcctta     840
ggcttatga                                                              849
```

<210> SEQ ID NO 8
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide <400> SEQUENCE: 8

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255
```

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Ala

<210> SEQ ID NO 9
<211> LENGTH: 1014
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gatgcacaca agagtgaggt tgctcatcgg tttaaagatt tgggagaaga aaatttcaaa      60
gccttggtgt tgattgcctt tgctcagtat cttcagcagt gtccatttga agatcatgta     120
aaattagtga atgaagtaac tgaatttgca aaaacatgtg ttgctgatga gtcagctgaa     180
aattgtgaca atcacttca taccctttttt ggagacaaat tatgcacagt tgcaactctt     240
cgtgaaacct atggtgaaat ggctgactgc tgtgcaaaac aagaacctga gagaaatgaa     300
tgcttcttgc aacacaaaga tgacaaccca aacctccccc gattggtgag accagaggtt     360
gatgtgatgt gcactgcttt tcatgacaat gaagagacat ttttgaaaaa atacttatat     420
gaaattgcca aagacatcc ttacttttat gccccggaac tccttttctt tgctaaaagg     480
tataaagctg cttttacaga tgttgccaa gctgctgata agctgcctg cctgttgcca     540 aagctcgatg aacttcggga tgaagggaag gcttcgtctg ccaaacagag actcaagtgt     600
gccagtctcc aaaaatttgg agaaagagct ttcaaagcat gggcagtagc tcgcctgagc     660
cagagatttc ccaaagctga gtttgcagaa gtttccaagt tagtgacaga tcttaccaaa     720
gtccacacgg aatgctgcca tggagatctg cttgaatgtg ctgatgacag gcggaccttt     780
gccaagtata tctgtgaaaa tcaagattcg atctccagta aactgaagga atgctgtgaa     840
aaacctctgt tggaaaaatc ccactgcatt gccgaagtgg aaaatgatga gatgcctgct     900
gacttgcctt cattagctgc tgattttgtt gaaagtaagg atgttgcaa aaactatgct     960 gaggcaaagg atgtcttcct gggcatgttt ttgtatgaat atgcaagagc atga          1014

<210> SEQ ID NO 10
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Val Val Leu Leu Leu Arg Leu Ala Lys Thr Tyr Glu Thr Thr Leu
1               5                   10                  15

Glu Lys Cys Cys Ala Ala Ala Asp Pro His Glu Cys Tyr Ala Lys Val
            20                  25                  30
```

Phe Asp Glu Phe Lys Pro Leu Val Glu Glu Pro Gln Asn Leu Ile Lys
         35                  40                  45

Gln Asn Cys Glu Leu Phe Glu Gln Leu Gly Glu Tyr Lys Phe Gln Asn
 50                  55                  60

Ala Leu Leu Val Arg Tyr Thr Lys Lys Val Pro Gln Val Ser Thr Pro
 65                  70                  75                  80

Thr Leu Val Glu Val Ser Arg Asn Leu Gly Lys Val Gly Ser Lys Cys
                 85                  90                  95

Cys Lys His Pro Glu Ala Lys Arg Met Pro Cys Ala Glu Asp Tyr Leu
             100                 105                 110

Ser Val Val Leu Asn Gln Leu Cys Val Leu His Glu Lys Thr Pro Val
             115                 120                 125

Ser Asp Arg Val Thr Lys Cys Cys Thr Glu Ser Leu Val Asn Arg Arg
130                 135                 140

Pro Cys Phe Ser Ala Leu Glu Val Asp Glu Thr Tyr Val Pro Lys Glu
145                 150                 155                 160

Phe Asn Ala Glu Thr Phe Thr Phe His Ala Asp Ile Cys Thr Leu Ser
                 165                 170                 175

Glu Lys Glu Arg Gln Ile Lys Lys Gln Thr Ala Leu Val Glu Leu Val
             180                 185                 190

Lys His Lys Pro Lys Ala Thr Lys Glu Gln Leu Lys Ala Val Met Asp
             195                 200                 205

Asp Phe Ala Ala Phe Val Glu Lys Cys Cys Lys Ala Asp Asp Lys Glu
210                 215                 220

Thr Cys Phe Ala Glu Glu Gly Lys Lys Leu Val Ala Ala Ser Gln Ala
225                 230                 235                 240

Ala Leu Gly Leu

<210> SEQ ID NO 11
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
tctgtcgtgc tgctgctgag acttgccaag acatatgaaa ccactctaga gaagtgctgt        60
gccgctgcag atcctcatga atgctatgcc aaagtgttcg atgaatttaa acctcttgtg       120
gaagagcctc agaatttaat caaacaaaat tgtgagcttt ttgagcagct tggagagtac       180
aaattccaga tgcgctatt agttcgttac accaagaaag taccccaagt gtcaactcca       240
actcttgtag aggtctcaag aaacctagga aaagtgggca gcaaatgttg taaacatcct       300
gaagcaaaaa gaatgccctg tgcagaagac tatctatccg tggtcctgaa ccagttatgt       360
gtgttgcatg agaaaacgcc agtaagtgac agagtcacca atgctgcac agaatccttg        420 gtgaacaggc gaccatgctt ttcagctctg gaagtcgatg aaacatacgt tcccaaagag       480
tttaatgctg aaacattcac cttccatgca gatatatgca cactttctga aggagaga         540 caaatcaaga acaaaactgc acttgttgag ctcgtgaaac acaagcccaa ggcaacaaaa       600
gagcaactga agctgttat ggatgatttc gcagcttttg tagagaagtg ctgcaaggct        660
gacgataagg agacctgctt tgccgaggag ggtaaaaaac ttgttgctgc aagtcaagct       720
gccttaggct tatga                                                        735

<210> SEQ ID NO 12
<211> LENGTH: 31
<212> TYPE: PRT
<213> ORGANISM: Unknown
<220> FEATURE:
<223> OTHER INFORMATION: Description of Unknown: GLP-1 peptide

<400> SEQUENCE: 12

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 13
<211> LENGTH: 29
<212> TYPE: PRT
<213> ORGANISM: Unknown
<220> FEATURE:
<223> OTHER INFORMATION: Description of Unknown: Glucagon peptide

<400> SEQUENCE: 13

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 14
<211> LENGTH: 314
<212> TYPE: PRT
<213> ORGANISM: Homo sapiens

<400> SEQUENCE: 14

Gly Ser Ala Val Ser Pro Tyr Pro Thr Phe Asn Pro Ser Ser Asp Val
1               5                   10                  15

Ala Ala Leu His Lys Ala Ile Met Val Lys Gly Val Asp Glu Ala Thr
            20                  25                  30

Ile Ile Asp Ile Leu Thr Lys Arg Asn Asn Ala Gln Arg Gln Gln Ile
        35                  40                  45

Lys Ala Ala Tyr Leu Gln Glu Thr Gly Lys Pro Leu Asp Glu Thr Leu
    50                  55                  60

Lys Lys Ala Leu Thr Gly His Leu Glu Glu Val Val Leu Ala Leu Leu
65                  70                  75                  80

Lys Thr Pro Ala Gln Phe Asp Ala Asp Glu Leu Arg Ala Ala Met Lys
                85                  90                  95

Gly Leu Gly Thr Asp Glu Asp Thr Leu Ile Glu Ile Leu Ala Ser Arg
            100                 105                 110

Thr Asn Lys Glu Ile Arg Asp Ile Asn Arg Val Tyr Arg Glu Glu Leu
        115                 120                 125

Lys Arg Asp Leu Ala Lys Asp Ile Thr Ser Asp Thr Ser Gly Asp Phe
    130                 135                 140

Arg Asn Ala Leu Leu Ser Leu Ala Lys Gly Asp Arg Ser Glu Asp Phe
145                 150                 155                 160

Gly Val Asn Glu Asp Leu Ala Asp Ser Asp Ala Arg Ala Leu Tyr Glu
                165                 170                 175

Ala Gly Glu Arg Arg Lys Gly Thr Asp Val Asn Val Phe Asn Thr Ile
            180                 185                 190

Leu Thr Thr Arg Ser Tyr Pro Gln Leu Arg Arg Val Phe Gln Lys Tyr
        195                 200                 205

Thr Lys Tyr Ser Lys His Asp Met Asn Lys Val Leu Asp Leu Glu Leu
210                 215                 220

Lys Gly Asp Ile Glu Lys Cys Leu Thr Ala Ile Val Lys Cys Ala Thr
225                 230                 235                 240

Ser Lys Pro Ala Phe Phe Ala Glu Lys Leu His Gln Ala Met Lys Gly
                245                 250                 255

Val Gly Thr Arg His Lys Ala Leu Ile Arg Ile Met Val Ser Arg Ser
            260                 265                 270

Glu Ile Asp Met Asn Asp Ile Lys Ala Phe Tyr Gln Lys Met Tyr Gly
                275                 280                 285

Ile Ser Leu Cys Gln Ala Ile Leu Asp Glu Thr Lys Gly Asp Tyr Glu
            290                 295                 300

Lys Ile Leu Val Ala Leu Cys Gly Gly Asn
305                 310

<210> SEQ ID NO 15
<211> LENGTH: 153
<212> TYPE: PRT
<213> ORGANISM: Homo sapiens

<400> SEQUENCE: 15

Ser Ala Val Ser Pro Tyr Pro Thr Phe Asn Pro Ser Ser Asp Val Ala
1               5                   10                  15

Ala Leu His Lys Ala Ile Met Val Lys Gly Val Asp Glu Ala Thr Ile
            20                  25                  30

Ile Asp Ile Leu Thr Lys Arg Asn Asn Ala Gln Arg Gln Gln Ile Lys
        35                  40                  45

Ala Ala Tyr Leu Gln Glu Thr Gly Lys Pro Leu Asp Glu Thr Leu Lys
50                  55                  60

Lys Ala Leu Thr Gly His Leu Glu Glu Val Val Leu Ala Leu Leu Lys
65                  70                  75                  80

Thr Pro Ala Gln Phe Asp Ala Asp Glu Leu Arg Ala Ala Met Lys Gly
                85                  90                  95

Leu Gly Thr Asp Glu Asp Thr Leu Ile Glu Ile Leu Ala Ser Arg Thr
            100                 105                 110

Asn Lys Glu Ile Arg Asp Ile Asn Arg Val Tyr Arg Glu Glu Leu Lys
        115                 120                 125

Arg Asp Leu Ala Lys Asp Ile Thr Ser Asp Thr Ser Gly Asp Phe Arg
    130                 135                 140

Asn Ala Leu Leu Ser Leu Ala Lys Gly
145                 150

<210> SEQ ID NO 16
<211> LENGTH: 154
<212> TYPE: PRT
<213> ORGANISM: Homo sapiens

<400> SEQUENCE: 16

Gly Val Asn Glu Asp Leu Ala Asp Ser Asp Ala Arg Ala Leu Tyr Glu
1               5                   10                  15

Ala Gly Glu Arg Arg Lys Gly Thr Asp Val Asn Val Phe Asn Thr Ile
            20                  25                  30

Leu Thr Thr Arg Ser Tyr Pro Gln Leu Arg Arg Val Phe Gln Lys Tyr
        35                  40                  45

Thr Lys Tyr Ser Lys His Asp Met Asn Lys Val Leu Asp Leu Glu Leu
50                  55                  60

```
Lys Gly Asp Ile Glu Lys Cys Leu Thr Ala Ile Val Lys Cys Ala Thr
 65                  70                  75                  80

Ser Lys Pro Ala Phe Phe Ala Glu Lys Leu His Gln Ala Met Lys Gly
                 85                  90                  95

Val Gly Thr Arg His Lys Ala Leu Ile Arg Ile Met Val Ser Arg Ser
            100                 105                 110

Glu Ile Asp Met Asn Asp Ile Lys Ala Phe Tyr Gln Lys Met Tyr Gly
            115                 120                 125

Ile Ser Leu Cys Gln Ala Ile Leu Asp Glu Thr Lys Gly Asp Tyr Glu
130                 135                 140

Lys Ile Leu Val Ala Leu Cys Gly Gly Asn
145                 150

<210> SEQ ID NO 17
<211> LENGTH: 348
<212> TYPE: PRT
<213> ORGANISM: Homo sapiens

<400> SEQUENCE: 17

Met Arg Leu Ala Val Gly Ala Leu Leu Val Cys Ala Val Leu Gly Leu
 1               5                  10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
50                  55                  60

Leu Asp Cys Ile Arg Ala Ile Ala Ala Asn Glu Ala Asp Ala Val Thr
 65                  70                  75                  80

Leu Asp Ala Gly Leu Val Tyr Asp Ala Tyr Leu Ala Pro Asn Asn Leu
                 85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
            195                 200                 205

Gly Ala Phe Lys Cys Leu Lys Asp Gly Ala Gly Asp Val Ala Phe Val
210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
            275                 280                 285
```

```
Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly
            340                 345

<210> SEQ ID NO 18
<211> LENGTH: 342
<212> TYPE: PRT
<213> ORGANISM: Homo sapiens

<400> SEQUENCE: 18

Glu Cys Lys Pro Val Lys Trp Cys Ala Leu Ser His His Glu Arg Leu
1               5                   10                  15

Lys Cys Asp Glu Trp Ser Val Asn Ser Val Gly Lys Ile Glu Cys Val
            20                  25                  30

Ser Ala Glu Thr Thr Glu Asp Cys Ile Ala Lys Ile Met Asn Gly Glu
        35                  40                  45

Ala Asp Ala Met Ser Leu Asp Gly Gly Phe Val Tyr Ile Ala Gly Lys
    50                  55                  60

Cys Gly Leu Val Pro Val Leu Ala Glu Asn Tyr Asn Lys Ser Asp Asn
65                  70                  75                  80

Cys Glu Asp Thr Pro Glu Ala Gly Tyr Phe Ala Val Ala Val Val Lys
                85                  90                  95

Lys Ser Ala Ser Asp Leu Thr Trp Asp Asn Leu Lys Gly Lys Lys Ser
            100                 105                 110

Cys His Thr Ala Val Gly Arg Thr Ala Gly Trp Asn Ile Pro Met Gly
        115                 120                 125

Leu Leu Tyr Asn Lys Ile Asn His Cys Arg Phe Asp Glu Phe Phe Ser
    130                 135                 140

Glu Gly Cys Ala Pro Gly Ser Lys Lys Asp Ser Ser Leu Cys Lys Leu
145                 150                 155                 160

Cys Met Gly Ser Gly Leu Asn Leu Cys Glu Pro Asn Asn Lys Glu Gly
                165                 170                 175

Tyr Tyr Gly Tyr Thr Gly Ala Phe Arg Cys Leu Val Glu Lys Gly Asp
            180                 185                 190

Val Ala Phe Val Lys His Gln Thr Val Pro Gln Asn Thr Gly Gly Lys
        195                 200                 205

Asn Pro Asp Pro Trp Ala Lys Asn Leu Asn Glu Lys Asp Tyr Glu Leu
    210                 215                 220

Leu Cys Leu Asp Gly Thr Arg Lys Pro Val Glu Glu Tyr Ala Asn Cys
225                 230                 235                 240

His Leu Ala Arg Ala Pro Asn His Ala Val Val Thr Arg Lys Asp Lys
                245                 250                 255

Glu Ala Cys Val His Lys Ile Leu Arg Gln Gln Gln His Leu Phe Gly
            260                 265                 270

Ser Asn Val Thr Asp Cys Ser Gly Asn Phe Cys Leu Phe Arg Ser Glu
        275                 280                 285

Thr Lys Asp Leu Leu Phe Arg Asp Asp Thr Val Cys Leu Ala Lys Leu
    290                 295                 300

His Asp Arg Asn Thr Tyr Glu Lys Tyr Leu Gly Glu Glu Tyr Val Lys
```

```
305                 310                 315                 320
Ala Val Gly Asn Leu Arg Lys Cys Ser Thr Ser Ser Leu Leu Glu Ala
                325                 330                 335

Cys Thr Phe Arg Arg Pro
            340

<210> SEQ ID NO 19
<211> LENGTH: 698
<212> TYPE: PRT
<213> ORGANISM: Homo sapiens

<400> SEQUENCE: 19

Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
                20                  25                  30

His Glu Ala Thr Lys Cys Gln Ser Phe Arg Asp His Met Lys Ser Val
            35                  40                  45

Ile Pro Ser Asp Gly Pro Ser Val Ala Cys Val Lys Lys Ala Ser Tyr
        50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
                100                 105                 110

Phe Tyr Tyr Ala Val Ala Val Val Lys Lys Asp Ser Gly Phe Gln Met
            115                 120                 125

Asn Gln Leu Arg Gly Lys Lys Ser Cys His Thr Gly Leu Gly Arg Ser
130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335
```

Glu Tyr Val Thr Ala Ile Arg Asn Leu Arg Gly Thr Cys Pro Glu
                340                 345                 350

Ala Pro Thr Asp Glu Cys Lys Pro Val Lys Trp Cys Ala Leu Ser His
            355                 360                 365

His Glu Arg Leu Lys Cys Asp Glu Trp Ser Val Asn Ser Val Gly Lys
        370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
            420                 425                 430

Lys Ser Asp Asn Cys Glu Asp Thr Pro Glu Ala Gly Tyr Phe Ala Val
        435                 440                 445

Ala Val Val Lys Lys Ser Ala Ser Asp Leu Thr Trp Asp Asn Leu Lys
450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
            500                 505                 510

Leu Cys Lys Leu Cys Met Gly Ser Gly Leu Asn Leu Cys Glu Pro Asn
        515                 520                 525

Asn Lys Glu Gly Tyr Tyr Gly Tyr Thr Gly Ala Phe Arg Cys Leu Val
530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
            580                 585                 590

Tyr Ala Asn Cys His Leu Ala Arg Ala Pro Asn His Ala Val Val Thr
        595                 600                 605

Arg Lys Asp Lys Glu Ala Cys Val His Lys Ile Leu Arg Gln Gln Gln
610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
            660                 665                 670

Glu Tyr Val Lys Ala Val Gly Asn Leu Arg Lys Cys Ser Thr Ser Ser
        675                 680                 685

Leu Leu Glu Ala Cys Thr Phe Arg Arg Pro
            690                 695

<210> SEQ ID NO 20
<211> LENGTH: 29
<212> TYPE: PRT
<213> ORGANISM: Homo sapiens

<400> SEQUENCE: 20

Thr Cys Cys Cys Lys Ser Ser Cys Leu Arg Leu Ile Thr Ser His Leu
1               5                   10                  15

Lys Ala Ser Gln Pro Thr Met Arg Ile Arg Glu Arg Lys
            20                  25

<210> SEQ ID NO 21
<211> LENGTH: 17
<212> TYPE: PRT
<213> ORGANISM: Homo sapiens

<400> SEQUENCE: 21

Met Leu Gln Asn Ser Ala Val Leu Leu Leu Val Ile Ser Ala Ser
1               5                   10                  15

Ala

<210> SEQ ID NO 22
<211> LENGTH: 22
<212> TYPE: PRT
<213> ORGANISM: Artificial Sequence
<220> FEATURE:
<223> OTHER INFORMATION: Description of Artificial Sequence: Synthetic
      consensus signal sequence

<400> SEQUENCE: 22

Met Pro Thr Trp Ala Trp Trp Leu Phe Leu Val Leu Leu Ala Leu
1               5                   10                  15

Trp Ala Pro Ala Arg Gly
            20

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Ser Gly
1

<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Ser Gly Gly Ser Gly Gly Ser Gly Gly Ser Gly Gly
1               5                   10

<210> SEQ ID NO 25
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
tcaagcgagc tgacccagga ccccgccgtg agcgtcgcac tggggcagac cgtgcgcatc        60
acatgccagg gagatagcct gcgatcctac tatgcatctt ggtaccagca gaagccagga       120
caggcacctg tgctggtcat ctatgggaaa aacaataga c catcaggcat ccccgacagg      180

```
ttcagcggaa gctcctctgg caacacagct tctctgacca ttacaggcgc acaggccgag    240
gacgaagcag attactattg caacagtcgg gatagttcag ggaatcacgt ggtctttgga    300
ggaggaacta agctgaccgt gggaggagga tcaggaggag gaagcggagg aggcagcgga    360
ggaggatctg gaggaggaag tggagaggtg cagctggtcg aaagcggagg aggagtggtc    420
cgacctggag ggtcactgcg actgagctgt gcagcttccg gcttcacatt tgacgattac    480
gggatgtcat gggtgagaca ggccccaggg aaaggactgg aatgggtctc cggcatcaac    540
tggaatggag gctctactgg atacgccgac agtgtgaagg gcaggttcac catttcccgc    600
gataacgcta aaaattctct gtatctgcag atgaacagtc tgagggccga ggacactgcc    660
gtgtactatt gtgcccgggg cagatccctg ctgtttgatt actggggcca ggggacactg    720
gtgactgtct ctcgcggcag tgaaaatctg tatttcag                           759
```

<210> SEQ ID NO 26
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Ser Glu Asn Leu Tyr Phe Gln
                245                 250
```

<210> SEQ ID NO 27
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
gacatccaga tgacccagtc tccatcctcc ctgtctgcat ctgtaggaga cagagtcacc    60
atcacttgcc gggcaagtca ggacgttaac accgctgtag cttggtatca gcagaaacca   120
gggaaagccc ctaagctcct gatctattct gcatccttt tgtacagtgg ggtcccatca   180
aggttcagtg gcagtcgatc tgggacagat ttcactctca ccatcagcag tctgcaacct   240
gaagattttg caacttacta ctgtcaacag cattacacta ccccaccac tttcggccaa   300
gggaccaaag tggagatcaa aggtggttct ggtggtggtt ctggtggtgg ttctggtggt   360
ggttctggtg gtggttctgg tgaagtgcag ctggtggagt ctggggagg cttggtacag   420
cctggcgggt ccctgagact ctcctgtgca gcctctggat tcaacattaa agatacttat   480
atccactggg tccggcaagc tccagggaag ggcctgagt gggtcgcacg tatttatccc   540
acaaatggtt acacacggta tgcggactct gtgaagggcc gattcaccat ctccgcagac   600
acttccaaga acaccgcgta tctgcaaatg aacagtctga gagctgagga cacggccgtt   660
tattactgtt caagatgggg cggagacggt ttctacgcta tggactactg gggccaaggg   720
accctggtca ccgtctcctc aggcagcgag aacctgtatt ttcag                   765
```

<210> SEQ ID NO 28
<211> LENGTH: 255
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
```

```
            165                 170                 175
Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
            210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Ser Glu Asn Leu Tyr Phe Gln
                245                 250                 255
```

<210> SEQ ID NO 29
<211> LENGTH: 1767
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29

```
agtagcgaac tgacacagga ccccgcagtg agcgtcgcac tgggacagac agtgcgaatc      60
acttgccagg gggactcact gcggagctac tatgcctcct ggtaccagca gaaaccaggc     120
caggctcccg tgctggtcat ctatggcaag aacaataggc ctagtgggat tccagatcgc     180
ttttcaggga gctcctctgg aaacactgca gtctgaccat tacaggcgct caggcagag     240 gacgaagccg attactattg caacagcagg acagttcag ggaatcacgt ggtcttcgga     300
ggaggaacta agctgaccgt ggggaggaggc agcggaggag gatctggagg aggaagtgga     360
ggaggatcag gaggaggaag cggagaggtg cagctggtcg aaagcggagg aggagtggtc     420
cggccaggag ggtccctgag actgtcttgt gccgctagtg gattcacttt tgacgattac     480
ggaatgtcat gggtccggca ggcacctggc aagggactgg agtgggtgag cggcatcaac     540
tggaatggag gctccacagg gtacgctgat tctgtgaaag gacgctttac tattagccga     600
gacaacgcca agaacagcct gtatctgcag atgaactctc tgagagctga ggataccgca     660
gtgtactatt gcgccagggg ccgctctctg ctgttcgact actggggaca gggcacactg     720
gtgactgtct cacgcggggg aagcggggat gctcacaagt ccgaggtcgc acatcgattc     780
aaagacctgg agaggaaaaa ttttaaggcc ctggtgctga tcgccttcgc tcagtatctg     840
cagcagtgcc cttttgaaga ccacgtgaaa ctggtcaacg aggtgaccga gttcgccaag     900
acatgcgtgg ccgacgagag tgctgaaaat tgtgataaat cactgcatac cctgtttgga     960
gataagctgt gtaccgtggc cacactgcgg gagacatacg gcgaaatggc agactgctgt    1020
gccaaacagg agcctgaaag aaacgagtgc ttcctgcagc acaaggacga taaccccaat    1080
ctgcctcgac tggtgcggcc agaagtggac gtcatgtgta ctgctttcca cgataatgag    1140
gaaacctttc tgaagaaata cctgtatgag attgcccgga gacatccata cttttatgcc    1200
cccgaactgc tgttctttgc taagcgctat aaagcagcct tcaccgagtg ctgtcaggct    1260
gcagataagg ccgcttgcct gctgccaaaa ctggacgagc tgagagatga aggcaaagca    1320
agctccgcca agcagaggct gaaatgtgca agcctgcaga agttcggcga gagggccttt    1380
aaagcatggg ccgtggctag actgtctcag aggttcccca aggctgagtt tgcagaagtc    1440
agtaagctgg tgactgacct gaccaaagtg cacacagagt gctgtcatgg cgacctgctg    1500
gaatgcgccg acgatcgcgc cgatctggct aagtacatct gtgagaacca ggactccatt    1560
```

```
tctagtaagc tgaaagagtg ctgtgaaaag ccactgctgg agaaatctca ttgcatcgct   1620
gaggtggaaa atgacgaaat gcccgcagat ctgcctagcc tggcagccga cttcgtcgag   1680
tccaaggatg tgtgtaaaaa ctatgccgag gctaaagatg tgtttctggg aatgtttctg   1740
tatgagtatg caagagcatg aggatcc                                       1767
```

<210> SEQ ID NO 30
<211> LENGTH: 586
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Ser Gly Gly Gly Ser Gly
        115                 120                 125

Glu Val Gln Leu Val Glu Ser Gly Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320
```

Asp Lys Leu Cys Thr Val Ala Thr Leu Arg Glu Thr Tyr Gly Glu Met
             325                 330                 335

Ala Asp Cys Cys Ala Lys Gln Glu Pro Glu Arg Asn Glu Cys Phe Leu
         340                 345                 350

Gln His Lys Asp Asp Asn Pro Asn Leu Pro Arg Leu Val Arg Pro Glu
     355                 360                 365

Val Asp Val Met Cys Thr Ala Phe His Asp Asn Glu Glu Thr Phe Leu
370                 375                 380

Lys Lys Tyr Leu Tyr Glu Ile Ala Arg Arg His Pro Tyr Phe Tyr Ala
385                 390                 395                 400

Pro Glu Leu Leu Phe Phe Ala Lys Arg Tyr Lys Ala Ala Phe Thr Glu
             405                 410                 415

Cys Cys Gln Ala Ala Asp Lys Ala Ala Cys Leu Leu Pro Lys Leu Asp
         420                 425                 430

Glu Leu Arg Asp Glu Gly Lys Ala Ser Ser Ala Lys Gln Arg Leu Lys
     435                 440                 445

Cys Ala Ser Leu Gln Lys Phe Gly Glu Arg Ala Phe Lys Ala Trp Ala
450                 455                 460

Val Ala Arg Leu Ser Gln Arg Phe Pro Lys Ala Glu Phe Ala Glu Val
465                 470                 475                 480

Ser Lys Leu Val Thr Asp Leu Thr Lys Val His Thr Glu Cys Cys His
             485                 490                 495

Gly Asp Leu Leu Glu Cys Ala Asp Asp Arg Ala Asp Leu Ala Lys Tyr
         500                 505                 510

Ile Cys Glu Asn Gln Asp Ser Ile Ser Ser Lys Leu Lys Glu Cys Cys
     515                 520                 525

Glu Lys Pro Leu Leu Glu Lys Ser His Cys Ile Ala Glu Val Glu Asn
530                 535                 540

Asp Glu Met Pro Ala Asp Leu Pro Ser Leu Ala Ala Asp Phe Val Glu
545                 550                 555                 560

Ser Lys Asp Val Cys Lys Asn Tyr Ala Glu Ala Lys Asp Val Phe Leu
             565                 570                 575

Gly Met Phe Leu Tyr Glu Tyr Ala Arg Ala
         580                 585

<210> SEQ ID NO 31
<211> LENGTH: 1797
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
gatgctcata aatctgaggt cgctcaccgg ttcaaggatc tgggcgagga aaactttaaa      60
gcactggtgc tgatcgcttt cgcacagtac ctgcagcagt gccccttga ggaccacgtg      120 aagctggtca acgaggtgac agagttcgcc aaaacttgcg tcgccgacga gtctgctgaa     180
aattgtgata agagtctgca tacactgttt ggagataaac tgtgtactgt ggccaccctg     240
agagagactt atggcgaaat ggcagactgc tgtgccaagc aggagcctga aggaacgag      300 tgcttcctgc agcataaaga cgataacccc aatctgccta ggctggtgcg cccagaagtg    360
gacgtcatgt gtaccgcctt ccacgataat gaggaaacat ttctgaagaa atacctgtat    420
gagattgccc ggagacatcc atactttat gcacccgaac tgctgttctt tgccaagaga     480

```
tacaaagccg ctttcaccga gtgctgtcag gcagccgata aggctgcatg cctgctgcca    540
aaactggacg agctgcgaga tgaagggaag gccagctccg ctaagcagcg gctgaaatgt    600
gctagcctgc agaagttcgg agagcgagcc ttcaaggcat gggctgtggc acgactgtcc    660
cagcggttcc ccaaagcaga gtttgccgaa gtctctaagc tggtgacaga cctgactaaa    720
gtgcacaccg agtgctgtca tggcgacctg ctggaatgcg ccgacgatcg agctgatctg    780
gcaaagtaca tctgtgagaa tcaggacagc atttctagta agctgaaaga gtgctgtgaa    840
aagcctctgc tggagaaatc ccactgcatc gccgaggtgg aaaacgacga atgccagct    900 gatctgccct cactggccgc tgactttgtc gagagcaagg atgtgtgtaa aaattatgcc    960
gaagctaagg atgtgttcct gggcatgttt ctgtacgagt atgcaagggc aggagggtcc    1020
ggaggctctg gaggaagtgg agggtcagga ggctcaagcg aactgactca ggaccccgct    1080
gtgagcgtcg cactgggaca gactgtgagg atcacctgcc aggggacag cctgcgctcc     1140 tactatgcat cctggtacca gcagaagcct ggccaggccc cagtgctggt catctatggc    1200
aaaaacaatc ggccctcagg gattcctgat cggttcagcg gtcctctag tggaaacaca    1260 gcttctctga ccattacagg cgctcaggca gaggacgaag ccgattacta ttgcaacagc    1320
cgcgactcaa gcgggaatca tgtggtcttc ggaggaggaa ccaagctgac agtgggagga    1380
ggctctggag gaggcagtgg gggaggctca ggaggaggca gcggaggagg ctccggagag    1440
gtccagctgg tggaaagcgg aggaggagtg gtccgcccag gaggatctct gcgactgagt    1500
tgtgcagcct caggattcac ctttgacgat tacggaatga gttgggtccg gcaggcacct    1560
ggaaagggac tggagtgggt gagcggcatc aactggaatg gcgggagcac tgggtacgct    1620
gattccgtga agggaagatt caccatttcc agggacaacg ccaaaaattc tctgtatctg    1680
cagatgaata gtctgagagc cgaggacaca gctgtgtact attgcgccag ggggaggtct    1740
ctgctgttcg actactgggg gcagggcact ctggtcactg tgtcaagatg aggatcc      1797
```

<210> SEQ ID NO 32
<211> LENGTH: 596
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

```
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Ala Gly Gly Ser Gly Gly Ser Gly Gly Ser Gly Gly Ser Gly Gly Ser
                340                 345                 350

Ser Glu Leu Thr Gln Asp Pro Ala Val Ser Val Ala Leu Gly Gln Thr
            355                 360                 365

Val Arg Ile Thr Cys Gln Gly Asp Ser Leu Arg Ser Tyr Tyr Ala Ser
370                 375                 380

Trp Tyr Gln Gln Lys Pro Gly Gln Ala Pro Val Leu Val Ile Tyr Gly
385                 390                 395                 400

Lys Asn Asn Arg Pro Ser Gly Ile Pro Asp Arg Phe Ser Gly Ser Ser
                405                 410                 415

Ser Gly Asn Thr Ala Ser Leu Thr Ile Thr Gly Ala Gln Ala Glu Asp
                420                 425                 430

Glu Ala Asp Tyr Tyr Cys Asn Ser Arg Asp Ser Ser Gly Asn His Val
                435                 440                 445

Val Phe Gly Gly Gly Thr Lys Leu Thr Val Gly Gly Gly Ser Gly Gly
            450                 455                 460

Gly Ser Gly Gly Gly Ser Gly Gly Gly Ser Gly Gly Gly Ser Gly Glu
465                 470                 475                 480

Val Gln Leu Val Glu Ser Gly Gly Val Val Arg Pro Gly Gly Ser
                485                 490                 495

Leu Arg Leu Ser Cys Ala Ala Ser Gly Phe Thr Phe Asp Asp Tyr Gly
            500                 505                 510

Met Ser Trp Val Arg Gln Ala Pro Gly Lys Gly Leu Glu Trp Val Ser
            515                 520                 525

Gly Ile Asn Trp Asn Gly Gly Ser Thr Gly Tyr Ala Asp Ser Val Lys
530                 535                 540

Gly Arg Phe Thr Ile Ser Arg Asp Asn Ala Lys Asn Ser Leu Tyr Leu
```

```
                  545                 550                 555                 560
Gln Met Asn Ser Leu Arg Ala Glu Asp Thr Ala Val Tyr Tyr Cys Ala
                      565                 570                 575

Arg Gly Arg Ser Leu Leu Phe Asp Tyr Trp Gly Gln Gly Thr Leu Val
                  580                 585                 590

Thr Val Ser Arg
        595

<210> SEQ ID NO 33
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
```

| | | | | | |
|---|---|---|---|---|---|
| tcctccgagc | tgacccagga | ccctgccgtg | tccgtcgctc | tgggacagac | cgtgcggatc | 60 |
| acatgccagg | gagatagcct | gagatcctac | tatgctagct | ggtaccagca | gaaacccggc | 120 |
| caggcacctg | tgctggtcat | ctatgggaag | aacaatcgcc | catctggcat | ccccgaccga | 180 |
| ttcagtggaa | gctcctctgg | caacacagcc | tctctgacta | ttaccggcgc | tcaggcagag | 240 |
| gacgaagctg | attactattg | caacagcagg | gatagttcag | ggaatcacgt | ggtctttgga | 300 |
| ggaggaacta | agctgaccgt | gggaggagga | tctggaggag | aagtggcgg | gggatcagga | 360 |
| ggaggaagcg | aggaggcag | cggagaggtg | cagctggtcg | aaagcggagg | aggagtggtc | 420 |
| agaccaggag | gtctctgag | gctgagttgt | gccgcttcag | gcttcacctt | tgacgattac | 480 |
| ggaatgtctt | gggtgcggca | ggcacctgga | aagggactgg | agtgggtgag | tggcatcaac | 540 |
| tggaatggag | gcagcacagg | atacgcagac | tccgtgaaag | gccgattcac | tatttcacgg | 600 |
| gataacgcca | agaatagcct | gtatctgcag | atgaacagcc | tgagagcaga | ggacacagcc | 660 |
| gtgtactatt | gtgccagggg | ccgctctctg | ctgtttgatt | actgggggca | gggaacactg | 720 |
| gtgactgtca | gccgaggagg | atctggaggg | agtggaggct | caggaggaag | cggagggtcc | 780 |
| gtggtcctgc | tgctgcgact | ggctaaaact | tacgagacca | cactggaaaa | gtgctgtgca | 840 |
| gccgctgacc | cccatgagtg | ctatgcaaaa | gtgttcgatg | agttcaagcc | tctggtcgag | 900 |
| gaaccacaga | acctgatcaa | acagaattgt | gagctgttcg | aacagctggg | cgagtacaag | 960 |
| tttcagaacg | ccctgctggt | gagatatacc | aagaaagtgc | cccaggtctc | tacacctact | 1020 |
| ctggtggagt | cagtaggaa | tctgggcaaa | gtggggtcaa | aatgctgtaa | gcacccagag | 1080 |
| gctaagcgca | tgccctgcgc | agaagactac | ctgagcgtgg | tcctgaacca | gctgtgtgtg | 1140 |
| ctgcatgaga | aaactccagt | gtccgatagg | gtcactaagt | gctgtaccga | agcctggtg | 1200 |
| aaccggagac | cttgcttctc | cgccctggag | gtggacgaaa | cctatgtccc | aaaagagttt | 1260 |
| aatgccgaaa | ccttcacatt | tcacgctgat | atctgtaccc | tgtccgagaa | ggaacgccag | 1320 |
| attaagaaac | agacagctct | ggtggagctg | gtcaagcata | acccaaggc | aacaaaagaa | 1380 |
| cagctgaagg | ccgtgatgga | cgatttcgca | gcctttgtgg | agaaatgctg | taaggccgac | 1440 |
| gataaggaaa | cttgctttgc | tgaagaaggg | aagaaactgg | tcgccgcatc | acaggctgct | 1500 |
| ctgggactgt | gaggatcc | | | | | 1518 |

```
<210> SEQ ID NO 34
<211> LENGTH: 503
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 34

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Val Val Arg Pro Gly Gly
130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Gly Ser Gly Gly Ser Gly Gly
            245                 250                 255

Ser Gly Gly Ser Val Val Leu Leu Arg Leu Ala Lys Thr Tyr Glu
        260                 265                 270

Thr Thr Leu Glu Lys Cys Cys Ala Ala Ala Asp Pro His Glu Cys Tyr
    275                 280                 285

Ala Lys Val Phe Asp Glu Phe Lys Pro Leu Val Glu Glu Pro Gln Asn
290                 295                 300

Leu Ile Lys Gln Asn Cys Glu Leu Phe Glu Gln Leu Gly Glu Tyr Lys
305                 310                 315                 320

Phe Gln Asn Ala Leu Leu Val Arg Tyr Thr Lys Lys Val Pro Gln Val
                325                 330                 335

Ser Thr Pro Thr Leu Val Glu Val Ser Arg Asn Leu Gly Lys Val Gly
            340                 345                 350

Ser Lys Cys Cys Lys His Pro Glu Ala Lys Arg Met Pro Cys Ala Glu
        355                 360                 365

Asp Tyr Leu Ser Val Val Leu Asn Gln Leu Cys Val Leu His Glu Lys
    370                 375                 380

Thr Pro Val Ser Asp Arg Val Thr Lys Cys Cys Thr Glu Ser Leu Val
```

```
                385                 390                 395                 400
Asn Arg Arg Pro Cys Phe Ser Ala Leu Glu Val Asp Glu Thr Tyr Val
                    405                 410                 415

Pro Lys Glu Phe Asn Ala Glu Thr Phe Thr Phe His Ala Asp Ile Cys
                420                 425                 430

Thr Leu Ser Glu Lys Glu Arg Gln Ile Lys Lys Gln Thr Ala Leu Val
            435                 440                 445

Glu Leu Val Lys His Lys Pro Lys Ala Thr Lys Glu Gln Leu Lys Ala
        450                 455                 460

Val Met Asp Asp Phe Ala Ala Phe Val Glu Lys Cys Cys Lys Ala Asp
465                 470                 475                 480

Asp Lys Glu Thr Cys Phe Ala Glu Glu Gly Lys Lys Leu Val Ala Ala
                485                 490                 495

Ser Gln Ala Ala Leu Gly Leu
                500

<210> SEQ ID NO 35
<211> LENGTH: 1518
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
agcgtcgtcc tgctgctgag actggctaaa acatacgaga ccacactgga aaagtgctgt      60
gccgctgcag accctcacga gtgctatgcc aaagtgttcg atgagttcaa gcctctggtc    120
gaggaaccac agaacctgat caaacagaat tgtgagctgt tcgaacagct gggcgagtac    180
aagtttcaga acgccctgct ggtgaggtat actaagaaag tgccccaggt cagtactcct    240
accctggtgg aggtctcacg gaatctgggg aaagtgggaa gcaaatgctg taagcaccca    300
gaggcaaaga gaatgccctg cgccgaagac tacctgagcg tggtcctgaa ccagctgtgt    360
gtgctgcatg agaaaaactc cagtgagcga gggtcacaa gtgctgtac tgaatccctg     420 gtgaaccgga gaccttgctt ctctgccctg gaggtggacg aaacctatgt cccaaaggag    480
tttaatgctg aaacattcac ttttcacgca gatatctgta cactgagcga aggaacgc     540 cagattaaga acagactgc cctggtggag ctggtcaagc ataaacccaa ggccaccaaa     600
gaacagctga aggctgtgat ggacgatttc gccgcttttg tcgagaaatg ctgtaaggca    660
gacgataagg aaacatgctt cgccgaggaa gggaagaaac tggtggcagc aagccaggct    720
gcactgggac tgggagggtc tggaggcagt ggaggatcag gagggagcgg aggcagctcc    780
gagctgaccc caggaccccgc tgtgagcgtc gcactgggac agaccgtgcg catcacatgt    840
cagggcgatt ccctgcgatc ttactatgct tcctggtacc agcagaaacc cggccaggca    900
cctgtgctgg tcatctatgg aaagaacaat agaccaagtg gcattcccga caggttctca    960
ggctctagtt cagggaacac cgcctccctg accattacag cgcacaggc cgaggacgaa    1020 gctgattact attgcaactc tcgggatagc tccggcaatc atgtggtctt tggggaggc    1080 actaagctga ccgtgggggg aggcagtggg ggaggctcag gaggaggcag cggaggaggc    1140
tccggaggag gctctggcga ggtgcagctg gtcgaatccg gaggaggagt ggtccgacca    1200
ggaggaagtc tgcgactgtc atgtgccgct agcgggttca cctttgacga ttacggaatg    1260
agttgggtgc gacaggcacc tggaaaggga ctggagtggg tgtctggcat caactggaat    1320
ggcgggtcca ctggctacgc agactctgtg aagggaggt ttaccattag ccgcgataac    1380
```

```
gccaagaaca gcctgtatct gcagatgaac agcctgcgcg ccgaggacac agctgtgtac   1440
tattgcgcca gggggaggtc actgctgttt gattactggg gcagggggac tctggtcact   1500
gtgtcacggt gaggatcc                                                 1518
```

<210> SEQ ID NO 36
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Ser Val Val Leu Leu Arg Leu Ala Lys Thr Tyr Glu Thr Thr Leu
1               5                   10                  15

Glu Lys Cys Cys Ala Ala Ala Asp Pro His Glu Cys Tyr Ala Lys Val
            20                  25                  30

Phe Asp Glu Phe Lys Pro Leu Val Glu Glu Pro Gln Asn Leu Ile Lys
        35                  40                  45

Gln Asn Cys Glu Leu Phe Glu Gln Leu Gly Glu Tyr Lys Phe Gln Asn
    50                  55                  60

Ala Leu Leu Val Arg Tyr Thr Lys Lys Val Pro Gln Val Ser Thr Pro
65                  70                  75                  80

Thr Leu Val Glu Val Ser Arg Asn Leu Gly Lys Val Gly Ser Lys Cys
                85                  90                  95

Cys Lys His Pro Glu Ala Lys Arg Met Pro Cys Ala Glu Asp Tyr Leu
            100                 105                 110

Ser Val Val Leu Asn Gln Leu Cys Val Leu His Glu Lys Thr Pro Val
        115                 120                 125

Ser Asp Arg Val Thr Lys Cys Cys Thr Glu Ser Leu Val Asn Arg Arg
    130                 135                 140

Pro Cys Phe Ser Ala Leu Glu Val Asp Glu Thr Tyr Val Pro Lys Glu
145                 150                 155                 160

Phe Asn Ala Glu Thr Phe Thr Phe His Ala Asp Ile Cys Thr Leu Ser
                165                 170                 175

Glu Lys Glu Arg Gln Ile Lys Lys Gln Thr Ala Leu Val Glu Leu Val
            180                 185                 190

Lys His Lys Pro Lys Ala Thr Lys Glu Gln Leu Lys Ala Val Met Asp
        195                 200                 205

Asp Phe Ala Ala Phe Val Glu Lys Cys Cys Lys Ala Asp Asp Lys Glu
    210                 215                 220

Thr Cys Phe Ala Glu Glu Gly Lys Lys Leu Val Ala Ala Ser Gln Ala
225                 230                 235                 240

Ala Leu Gly Leu Gly Gly Ser Gly Gly Ser Gly Gly Ser Gly Gly Ser
                245                 250                 255

Gly Gly Ser Ser Glu Leu Thr Gln Asp Pro Ala Val Ser Val Ala Leu
            260                 265                 270

Gly Gln Thr Val Arg Ile Thr Cys Gln Gly Asp Ser Leu Arg Ser Tyr
        275                 280                 285

Tyr Ala Ser Trp Tyr Gln Gln Lys Pro Gly Gln Ala Pro Val Leu Val
    290                 295                 300

Ile Tyr Gly Lys Asn Asn Arg Pro Ser Gly Ile Pro Asp Arg Phe Ser
305                 310                 315                 320

Gly Ser Ser Ser Gly Asn Thr Ala Ser Leu Thr Ile Thr Gly Ala Gln
```

325                 330                 335
Ala Glu Asp Glu Ala Asp Tyr Tyr Cys Asn Ser Arg Asp Ser Ser Gly
            340                 345                 350

Asn His Val Val Phe Gly Gly Gly Thr Lys Leu Thr Val Gly Gly Gly
        355                 360                 365

Ser Gly Gly Gly Ser Gly Gly Gly Ser Gly Gly Ser Gly Gly Gly
    370                 375                 380

Ser Gly Glu Val Gln Leu Val Glu Ser Gly Gly Val Val Arg Pro
385                 390                 395                 400

Gly Gly Ser Leu Arg Leu Ser Cys Ala Ala Ser Gly Phe Thr Phe Asp
                405                 410                 415

Asp Tyr Gly Met Ser Trp Val Arg Gln Ala Pro Gly Lys Gly Leu Glu
            420                 425                 430

Trp Val Ser Gly Ile Asn Trp Asn Gly Gly Ser Thr Gly Tyr Ala Asp
            435                 440                 445

Ser Val Lys Gly Arg Phe Thr Ile Ser Arg Asp Asn Ala Lys Asn Ser
        450                 455                 460

Leu Tyr Leu Gln Met Asn Ser Leu Arg Ala Glu Asp Thr Ala Val Tyr
465                 470                 475                 480

Tyr Cys Ala Arg Gly Arg Ser Leu Leu Phe Asp Tyr Trp Gly Gln Gly
                485                 490                 495

Thr Leu Val Thr Val Ser Arg
            500

<210> SEQ ID NO 37
<211> LENGTH: 1773
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
gacattcaga tgacacagtc cccaagctcc ctgagcgctt ccgtcggcga tcgagtgact      60
atcacctgcc gagcctctca ggacgtcaac actgctgtgg catggtacca gcagaagcct    120
gggaaagcac caaagctgct gatctactct gccagttttc tgtattctgg agtgcccagt    180
agattctcag gaagcaggtc cggcaccgat tttacactga ctatctctag tctgcagcct    240
gaggacttcg ccacatacta ttgccagcag cactatacca cacccctac atttggacag    300
ggcactaaag tggaaattaa gggcgggtca ggcggaggga gcggaggagg gtccggagga    360
gggtctggag gagggagtgg agaggtgcag ctggtcgaat ccggaggagg actggtgcag    420
cctggaggct cactgaggct gagctgtgcc gcttccggct tcaacatcaa ggataccta c    480
attcattggg tcagacaggc tcctgggaaa ggactggagt gggtggcaag gatctatcca    540
accaatgggt acacacggta tgccgatagc gtgaagggaa gattcactat ttctgctgac    600
actagtaaaa acaccgcata cctgcagatg aatagcctga gggcagagga caccgccgtg    660
tactattgct cccgctgggg gggagacggc ttttacgcca tggattattg gggccagggg    720
accctggtga cagtctcaag cggcgggtca ggagatgcac acaaaagcga ggtcgcccat    780
cgcttcaagg acctgggcga ggaaaatttt aaagccctgg tgctgattgc cttcgctcag    840
tacctgcagc agtgcccatt cgaagaccac gtgaagctgg tcaacgaggt gaccgaattt    900
gccaaaacat gctcgctga cgagtccgca gaaaattgtg ataagtctct gcatacactg    960
ttcggcgata aactgtgtac tgtggccacc ctgcgcgaga cttatgggga aatggccgac   1020

-continued

```
tgctgtgcta agcaggagcc agaacgaaac gagtgctttc tgcagcacaa ggacgataac    1080
ccaaatctgc caaggctggt gcgcccagaa gtggacgtca tgtgtactgc tttccacgat    1140
aatgaggaaa cctttctgaa gaaataccctg tatgagatcg cccggagaca tccatacttc   1200
tatgcccccg aactgctgtt ctttgctaaa cggtacaagg cagcctttac cgagtgctgt    1260
caggctgcag ataaagccgc ttgcctgctg cctaagctgg acgagctgcg agatgaaggc    1320
aaggcatcct ctgccaaaca gcggctgaag tgtgccagcc tgcagaaatt cggggagcgg    1380
gcttttaagg catgggccgt ggctcgactg tctcagcggt cccaaaggc tgagtttgca     1440 gaagtcagta aactggtgac agacctgact aaggtgcaca cagagtgctg tcatggcgac    1500
ctgctggaat gcgccgacga tagagccgat ctggctaagt acatctgtga aaccaggac    1560 agcattagtt caaagctgaa agagtgctgt gaaaaacctc tgctggagaa gagccactgc   1620
atcgcagagg tggaaaatga cgaaatgccc gccgatctgc ctagtctggc agccgacttc   1680
gtcgagtcaa aagatgtgtg taagaactac gccgaagcaa aagatgtgtt tctgggaatg   1740
tttctgtatg agtatgcccg agcctgagga tcc                                1773
```

<210> SEQ ID NO 38
<211> LENGTH: 588
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 38

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220
```

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
            245                 250                 255

Glu Val Ala His Arg Phe Lys Asp Leu Gly Glu Glu Asn Phe Lys Ala
        260                 265                 270

Leu Val Leu Ile Ala Phe Ala Gln Tyr Leu Gln Gln Cys Pro Phe Glu
    275                 280                 285

Asp His Val Lys Leu Val Asn Glu Val Thr Glu Phe Ala Lys Thr Cys
    290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
            325                 330                 335

Glu Met Ala Asp Cys Cys Ala Lys Gln Glu Pro Glu Arg Asn Glu Cys
        340                 345                 350

Phe Leu Gln His Lys Asp Asp Asn Pro Asn Leu Pro Arg Leu Val Arg
    355                 360                 365

Pro Glu Val Asp Val Met Cys Thr Ala Phe His Asp Asn Glu Glu Thr
370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
            405                 410                 415

Thr Glu Cys Cys Gln Ala Ala Asp Lys Ala Ala Cys Leu Leu Pro Lys
        420                 425                 430

Leu Asp Glu Leu Arg Asp Glu Gly Lys Ala Ser Ser Ala Lys Gln Arg
    435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
            485                 490                 495

Cys His Gly Asp Leu Leu Glu Cys Ala Asp Asp Arg Ala Asp Leu Ala
        500                 505                 510

Lys Tyr Ile Cys Glu Asn Gln Asp Ser Ile Ser Ser Lys Leu Lys Glu
    515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
            565                 570                 575

Phe Leu Gly Met Phe Leu Tyr Glu Tyr Ala Arg Ala
        580                 585

<210> SEQ ID NO 39
<211> LENGTH: 1803
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 39

```
gacgcacata agtccgaggt cgctcacagg ttcaaagatc tgggcgagga aaactttaag      60
gccctggtgc tgatcgcttt cgcacagtac ctgcagcagt gcccattcga agaccacgtg     120
aaactggtca acgaagtgac tgaatttgcc aagacctgcg tcgccgacga gtccgctgaa     180
aattgtgata aatctctgca tactctgttc ggggataagc tgtgtaccgt ggccacactg     240
cgcgagacct atggagaaat ggcagactgc tgtgccaaac aggagccaga acgaaacgag     300
tgctttctgc agcataagga cgataaccca aatctgccaa ggctggtgcg cccagaagtg     360
gacgtcatgt gtaccgcctt ccacgataat gaggaaacat ttctgaagaa atacctgtat     420
gagattgccc ggagacatcc atacttctat gcccccgaac tgctgttctt tgctaagcgc     480
tacaaagccg cttttaccga gtgctgtcag gcagccgata agctgcatg cctgctgcct      540
aagctggacg agctgaggga tgaaggaaag gccagctccg ctaaacagcg cctgaagtgt     600
gcctctctgc agaaattcgg cgagcgggct tttaaggcat gggctgtcgc acgactgagc     660
cagcggttcc caaaggcaga gtttgccgaa gtctccaaac tggtgactga cctgaccaag     720
gtgcacaccg agtgctgtca tggcgacctg ctggaatgcg ccgacgatag agctgatctg     780
gcaaagtaca tctgtgagaa ccaggacagc atttctagta agctgaaaga gtgctgtgaa     840
aaaccctgc tggagaagag ccactgcatc gcagaggtgg aaaacgacga atgcctgcc      900
gatctgccaa gtctggccgc tgacttcgtc gagtcaaaag atgtgtgtaa gaattatgcc     960
gaagctaagg atgtgttcct gggcatgttt ctgtacgagt atgcacgagc aggagggagc    1020
ggaggctccg gaggatctgg cgggagtgga ggcgacatcc agatgactca gtccccttca    1080
agcctgagtg cttcagtcgg cgatcgcgtg actattacct gccgagcctc tcaggacgtc    1140
aatacagctg tggcatggta ccagcagaag cccggcaaag ctcctaagct gctgatctac    1200
agcgcatcct ttctgtattc aggggtgccc agcagattct ctggcagtag atcagggaca    1260
gattttacac tgactatttc ctctctgcag cctgaggact cgccacctta ctattgccag    1320
cagcactata ccacaccccc tacatttgga cagggcacta aagtggaaat caagggaggc    1380
agcggaggag atctggaggg aggaagtgga ggagatcag gaggaggaag cggagaggtc    1440
cagctggtgg aaagcggagg aggactggtg cagcctggag ggtccctgag actgtcttgt    1500
gcagccagtg gcttcaacat caaagatacc tacattcatt gggtcagaca ggctcctggg    1560
aagggactgg agtgggtggc aaggatctat ccaacaaatg gatacactcg gtatgccgat    1620
agcgtgaaag gccggttcac catttcagca gacaccagca gaacacagc ctacctgcag     1680
atgaacagcc tgcgagctga ggacacagca gtgtactatt gcagtcggtg ggcggcgat    1740
ggcttttacg ctatggacta ttggggcag gggacactgg tgactgtgag ttcttgagga    1800
tcc                                                                  1803
```

<210> SEQ ID NO 40
<211> LENGTH: 598
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 40

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
                20                  25                  30
Gln Cys Pro Phe Glu Asp His Val Lys Leu Val Asn Glu Val Thr Glu
             35                  40                  45
Phe Ala Lys Thr Cys Val Ala Asp Glu Ser Ala Glu Asn Cys Asp Lys
         50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
        210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Ala Gly Gly Ser Gly Gly Ser Gly Gly Ser Gly Gly Ser Gly Gly Asp
            340                 345                 350
Ile Gln Met Thr Gln Ser Pro Ser Ser Leu Ser Ala Ser Val Gly Asp
        355                 360                 365
Arg Val Thr Ile Thr Cys Arg Ala Ser Gln Asp Val Asn Thr Ala Val
        370                 375                 380
Ala Trp Tyr Gln Gln Lys Pro Gly Lys Ala Pro Lys Leu Leu Ile Tyr
385                 390                 395                 400
Ser Ala Ser Phe Leu Tyr Ser Gly Val Pro Ser Arg Phe Ser Gly Ser
                405                 410                 415
Arg Ser Gly Thr Asp Phe Thr Leu Thr Ile Ser Ser Leu Gln Pro Glu
            420                 425                 430
Asp Phe Ala Thr Tyr Tyr Cys Gln Gln His Tyr Thr Thr Pro Pro Thr
        435                 440                 445
```

```
Phe Gly Gln Gly Thr Lys Val Glu Ile Lys Gly Gly Gly
    450                 455                 460
Ser Gly Gly Gly Ser Gly Gly Ser Gly Gly Ser Gly Glu Val
465                 470                 475                 480
Gln Leu Val Glu Ser Gly Gly Leu Val Gln Pro Gly Gly Ser Leu
                    485                 490                 495
Arg Leu Ser Cys Ala Ala Ser Gly Phe Asn Ile Lys Asp Thr Tyr Ile
                500                 505                 510
His Trp Val Arg Gln Ala Pro Gly Lys Gly Leu Glu Trp Val Ala Arg
            515                 520                 525
Ile Tyr Pro Thr Asn Gly Tyr Thr Arg Tyr Ala Asp Ser Val Lys Gly
        530                 535                 540
Arg Phe Thr Ile Ser Ala Asp Thr Ser Lys Asn Thr Ala Tyr Leu Gln
545                 550                 555                 560
Met Asn Ser Leu Arg Ala Glu Asp Thr Ala Val Tyr Tyr Cys Ser Arg
                565                 570                 575
Trp Gly Gly Asp Gly Phe Tyr Ala Met Asp Tyr Trp Gly Gln Gly Thr
            580                 585                 590
Leu Val Thr Val Ser Ser
            595
```

```
<210> SEQ ID NO 41
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacattcaga tgacacagag cccaagctcc ctgtccgcat ctgtgggcga ccgagtcaca      60
atcacttgcc gggcctccca ggatgtgaac actgctgtcg catggtacca gcagaaacca     120
gggaaggctc ccaaactgct gatctacagt gcatcattcc tgtatagtgg cgtgccatca     180
aggtttagcg gctcccgatc tggaaccgac ttcaccctga caatctctag tctgcagccc     240
gaggattttg ccacatacta ttgccagcag cactatacca cacccctac tttcggcag      300
ggaccaagg tggagatcaa gggaggggagc ggaggagggt ccggaggagg gtctggaggc     360
gggagtggag gagggtcagg agaggtgcag ctggtcgaaa gcggaggagg actggtgcag     420
cctggaggca gcctgcgact gtcctgtgcc gcttctggct ttaacatcaa ggacacctac     480
attcattggg tgcggcaggc acctggcaaa ggactggagt gggtggctag aatctatcca     540
actaatggat acaccagata tgctgacagc gtgaagggca ggtttactat cagtgctgat     600
acatcaaaga acactgcata cctgcagatg aatagcctgc gcgccgagga taccgctgtg     660
tactattgta gccgatgggg gggagacggg ttctacgcca tggattattg gggacagggc     720
accctggtga cagtctcaag cggagggagt ggaggctcag gaggaagcgg agggtccgga     780
ggctctgtgg tcctgctgct gagactggct aagacctacg agactaccct ggaaaaatgc     840
tgtgcagccg ctgacccca cgagtgctat gcaaaggtgt tcgatgagtt caagcctctg     900
gtcgaggaac cacagaacct gatcaagcag aattgtgagc tgttcgaaca gctgggcgag    960
tacaagtttc agaacgccct gctggtgagg tatacaaaga agtgccccca ggtcagcact    1020
cctaccctgg tggaggtctc caggaatctg ggaaggtcg gatctaagtg ctgtaaacac    1080
ccagaggcaa aacgcatgcc ctgcgccgaa gactacctgt ccgtggtcct gaatcagctg    1140
```

```
tgtgtgctgc atgagaagac ccctgtgtct gatcgagtca ccaaatgctg tacagaaagt   1200
ctggtgaacc ggagaccctg cttttctgcc ctggaggtgg acgaaacata tgtccctaag   1260
gagttcaatg ccgaaacatt cactttcac gctgatatct gtacactgtc cgagaaggaa   1320
cgccagatta agaaacagac tgctctggtg gagctggtac agcataaacc aaaggcaacc   1380
aaggaacagc tgaaagccgt gatggacgat ttcgcagcct tgtcgagaa gtgctgtaaa   1440 gccgacgata aggaaacttg tttcgccgag gaaggcaaaa aactggtcgc agcatcacag   1500
gcagcactgg gactgtgagg atcc   1524
```

<210> SEQ ID NO 42
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Ser Gly Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Gly Ser
                245                 250                 255

Gly Gly Ser Gly Gly Ser Val Val Leu Leu Arg Leu Ala Lys Thr
        260                 265                 270

Tyr Glu Thr Thr Leu Glu Lys Cys Cys Ala Ala Ala Asp Pro His Glu
    275                 280                 285
```

```
Cys Tyr Ala Lys Val Phe Asp Glu Phe Lys Pro Leu Val Glu Glu Pro
            290                 295                 300

Gln Asn Leu Ile Lys Gln Asn Cys Glu Leu Phe Glu Gln Leu Gly Glu
305                 310                 315                 320

Tyr Lys Phe Gln Asn Ala Leu Leu Val Arg Tyr Thr Lys Lys Val Pro
                325                 330                 335

Gln Val Ser Thr Pro Thr Leu Val Glu Val Ser Arg Asn Leu Gly Lys
            340                 345                 350

Val Gly Ser Lys Cys Cys Lys His Pro Glu Ala Lys Arg Met Pro Cys
        355                 360                 365

Ala Glu Asp Tyr Leu Ser Val Val Leu Asn Gln Leu Cys Val Leu His
    370                 375                 380

Glu Lys Thr Pro Val Ser Asp Arg Val Thr Lys Cys Cys Thr Glu Ser
385                 390                 395                 400

Leu Val Asn Arg Arg Pro Cys Phe Ser Ala Leu Glu Val Asp Glu Thr
                405                 410                 415

Tyr Val Pro Lys Glu Phe Asn Ala Glu Thr Phe Thr Phe His Ala Asp
            420                 425                 430

Ile Cys Thr Leu Ser Glu Lys Glu Arg Gln Ile Lys Lys Gln Thr Ala
        435                 440                 445

Leu Val Glu Leu Val Lys His Lys Pro Lys Ala Thr Lys Glu Gln Leu
    450                 455                 460

Lys Ala Val Met Asp Asp Phe Ala Ala Phe Val Glu Lys Cys Cys Lys
465                 470                 475                 480

Ala Asp Asp Lys Glu Thr Cys Phe Ala Glu Glu Gly Lys Lys Leu Val
                485                 490                 495

Ala Ala Ser Gln Ala Ala Leu Gly Leu
            500                 505
```

<210> SEQ ID NO 43
<211> LENGTH: 1524
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
tccgtcgtcc tgctgctgag actggctaag acctacgaga ccacactgga aaaatgctgt     60
gccgctgcag accccacga gtgctatgcc aaggtgttcg atgagttcaa gcctctggtc    120
gaggaaccac agaacctgat caagcagaat tgtgagctgt cgaacagct gggcgagtac    180 aaatttcaga cgccctgct ggtgaggtat acaaagaaag tgccccaggt ctctacacct    240
actctggtgg aggtcagtag gaatctgggc aaggtcgggt caaaatgctg taagcaccca    300
gaggccaaac gcatgccctg cgctgaagac tacctgtctg tggtcctgaa ccagctgtgt    360
gtgctgcatg agaagacccc tgtgagcgat cgagtcacca aatgctgtac agaaagcctg    420
gtgaatcgga gaccctgctt tccgctctg gaggtggacg aaacatatgt ccctaaggag    480
ttcaatgcag aaaccttcac atttcacgcc gatatctgta ctctgtccga aggaacgc     540 cagattaaga aacagaccgc cctggtggag ctggtcaagc ataaaccaaa ggctactaag    600
gaacagctga agcagtgat ggacgatttc gccgcttttg tcgagaaatg ctgtaaggca    660
gacgataagg aaacctgctt tgccgaggaa ggcaagaaac tggtggcagc cagccaggct    720
gcactgggac tggagggtc cggaggctct ggaggaagtg gagggtcagg aggcgacatc    780
```

-continued

```
cagatgacac agagcccaag ctccctgtca gcaagcgtgg gcgaccgagt cactattacc    840
tgtcgggcct cccaggatgt gaatactgca gtcgcctggt accagcagaa accaggaaag    900
gctcccaaac tgctgatcta ctccgcatct ttcctgtata gcggcgtgcc atccaggttt    960
agtggatcac gcagcggcac agacttcaca ctgactattt ctagtctgca gcccgaggat   1020
tttgccactt actattgcca gcagcactat actacccccc ctaccttcgg acagggcaca   1080
aaggtggaga tcaagggagg atctggagga ggaagtggag gaggatcagg aggaggaagc   1140
ggaggaggca gcggagaggt gcagctggtc gaatctggag gaggactggt gcagcctgga   1200
gggtctctgc gactgagttg tgccgcttca ggctttaaca tcaaggacac ctacattcat   1260
tgggtgcggc aggcacctgg gaagggactg gagtgggtcg ctagaatcta tccaactaat   1320
gggtacacca gatatgccga cagcgtgaag gaaggttca ccattagcgc cgatacatcc    1380
aaaaacactg cttacctgca gatgaacagc ctgcgcgctg aggatacagc agtgtactat   1440
tgcagtcgat ggggcggcga tgggttctac gcaatggact actggggaca ggggactctg   1500
gtcaccgtca gcagctgagg atcc                                          1524
```

<210> SEQ ID NO 44
<211> LENGTH: 505
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Ser Val Val Leu Leu Arg Leu Ala Lys Thr Tyr Glu Thr Thr Leu
1               5                   10                  15

Glu Lys Cys Cys Ala Ala Asp Pro His Glu Cys Tyr Ala Lys Val
                20                  25                  30

Phe Asp Glu Phe Lys Pro Leu Val Glu Glu Pro Gln Asn Leu Ile Lys
            35                  40                  45

Gln Asn Cys Glu Leu Phe Glu Gln Leu Gly Glu Tyr Lys Phe Gln Asn
        50                  55                  60

Ala Leu Leu Val Arg Tyr Thr Lys Lys Val Pro Gln Val Ser Thr Pro
65                  70                  75                  80

Thr Leu Val Glu Val Ser Arg Asn Leu Gly Lys Val Gly Ser Lys Cys
                85                  90                  95

Cys Lys His Pro Glu Ala Lys Arg Met Pro Cys Ala Glu Asp Tyr Leu
            100                 105                 110

Ser Val Val Leu Asn Gln Leu Cys Val Leu His Glu Lys Thr Pro Val
        115                 120                 125

Ser Asp Arg Val Thr Lys Cys Cys Thr Glu Ser Leu Val Asn Arg Arg
    130                 135                 140

Pro Cys Phe Ser Ala Leu Glu Val Asp Glu Thr Tyr Val Pro Lys Glu
145                 150                 155                 160

Phe Asn Ala Glu Thr Phe Thr Phe His Ala Asp Ile Cys Thr Leu Ser
                165                 170                 175

Glu Lys Glu Arg Gln Ile Lys Lys Gln Thr Ala Leu Val Glu Leu Val
            180                 185                 190

Lys His Lys Pro Lys Ala Thr Lys Glu Gln Leu Lys Ala Val Met Asp
        195                 200                 205

Asp Phe Ala Ala Phe Val Glu Lys Cys Cys Lys Ala Asp Asp Lys Glu
    210                 215                 220
```

Thr Cys Phe Ala Glu Glu Gly Lys Lys Leu Val Ala Ala Ser Gln Ala
225                 230                 235                 240

Ala Leu Gly Leu Gly Gly Ser Gly Gly Ser Gly Gly Ser Gly Gly Ser
            245                 250                 255

Gly Gly Asp Ile Gln Met Thr Gln Ser Pro Ser Ser Leu Ser Ala Ser
        260                 265                 270

Val Gly Asp Arg Val Thr Ile Thr Cys Arg Ala Ser Gln Asp Val Asn
    275                 280                 285

Thr Ala Val Ala Trp Tyr Gln Gln Lys Pro Gly Lys Ala Pro Lys Leu
290                 295                 300

Leu Ile Tyr Ser Ala Ser Phe Leu Tyr Ser Gly Val Pro Ser Arg Phe
305                 310                 315                 320

Ser Gly Ser Arg Ser Gly Thr Asp Phe Thr Leu Thr Ile Ser Ser Leu
            325                 330                 335

Gln Pro Glu Asp Phe Ala Thr Tyr Tyr Cys Gln Gln His Tyr Thr Thr
        340                 345                 350

Pro Pro Thr Phe Gly Gln Gly Thr Lys Val Glu Ile Lys Gly Gly Ser
    355                 360                 365

Gly Gly Gly Ser Gly Gly Gly Ser Gly Gly Gly Ser Gly Gly Gly Ser
370                 375                 380

Gly Glu Val Gln Leu Val Glu Ser Gly Gly Gly Leu Val Gln Pro Gly
385                 390                 395                 400

Gly Ser Leu Arg Leu Ser Cys Ala Ala Ser Gly Phe Asn Ile Lys Asp
            405                 410                 415

Thr Tyr Ile His Trp Val Arg Gln Ala Pro Gly Lys Gly Leu Glu Trp
        420                 425                 430

Val Ala Arg Ile Tyr Pro Thr Asn Gly Tyr Thr Arg Tyr Ala Asp Ser
    435                 440                 445

Val Lys Gly Arg Phe Thr Ile Ser Ala Asp Thr Ser Lys Asn Thr Ala
450                 455                 460

Tyr Leu Gln Met Asn Ser Leu Arg Ala Glu Asp Thr Ala Val Tyr Tyr
465                 470                 475                 480

Cys Ser Arg Trp Gly Gly Asp Gly Phe Tyr Ala Met Asp Tyr Trp Gly
            485                 490                 495

Gln Gly Thr Leu Val Thr Val Ser Ser
        500                 505

<210> SEQ ID NO 45
<211> LENGTH: 2544
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45
tcaagcgaac tgactcagga ccccgctgtg agcgtcgcac tgggacagac tgtgcggatc     60
acctgccagg gggactccct gagatcttac tatgcctcct ggtaccagca gaaaccaggc    120
caggctcccg tgctggtcat ctatggcaag aacaatagac cttccgggat tccagatagg    180
ttttctggaa gctcctctgg caacacagct agcctgacca ttacaggagc ccaggctgag    240
gacgaagcag attactattg caactccagg gacagttcag caatcacgt ggtcttcggc    300 gggggaacaa agctgactgt ggaggaggga tcaggaggag gaagcggagg aggcagcgga    360
ggaggatctg gaggaggaag tggagaggtg cagctggtcg aaagcggagg aggagtggtc    420

```
aggcctggag ggtcactgcg actgagctgt gccgcttccg gattcacatt tgacgattac    480
ggaatgtctt gggtccggca ggcaccagga aagggactgg agtgggtgag tggcatcaac    540
tggaatggag gctctacagg gtacgctgat agtgtgaaag gacgctttac tattagtcga    600
gacaacgcca agaacagcct gtatctgcag atgaacagcc tgagagccga ggatactgct    660
gtgtactatt gtgccagggg ccgctccctg ctgttcgact actgggggca gggaaccctg    720
gtgacagtct ctaggggggg aagtggcgat gctcacaaga gcgaggtcgc acatcgcttc    780
aaagacctgg gggaggaaaa ttttaaggcc ctggtgctga tcgcattcgc ccagtatctg    840
cagcagtgcc cttttgaaga ccacgtgaaa ctggtcaacg aggtgaccga gttcgccaag    900
acatgcgtgg cagacgagtc cgccgaaaat tgtgataaat ctctgcatac tctgtttggg    960
gataagctgt gtactgtggc caccctgcgg gagacctacg agaaatggc tgactgctgt   1020 gcaaaacagg agccagaaag aaacgagtgc ttcctgcagc acaaggacga taaccccaat   1080
ctgcctcgac tggtgcggcc cgaagtggac gtcatgtgta ctgccttcca cgataatgag   1140
gaaacctttc tgaagaaata cctgtatgag attgcccgga gacatcccta cttttatgcc   1200
cctgaactgc tgttctttgc taagcggtac aaagcagcct tcaccgagtg ctgtcaggct   1260
gcagataagg ccgcttgcct gctgccaaaa ctggacgagc tgcgagatga agggaaagct   1320
agctccgcaa gcagagact gaaatgtgca agcctgcaga agttcggcga gagggccttt   1380
aaagcttggg cagtggccag actgagccag aggttcccca aggccgagtt tgctgaagtc   1440
tccaagctgg tgacagacct gactaaagtg cacaccgagt gctgtcatgg cgacctgctg   1500
gaatgcgccg acgatcgcgc agatctggcc aaatacatct gtgagaacca ggactctatt   1560
tctagtaagc tgaaagagtg ctgtgaaaag cctctgctgg agaaaagcca ctgcatcgct   1620
gaggtggaaa acgacgaaat gccccgcagat ctgcctagtc tggcagccga cttgtcgag   1680 tcaaaggatg tgtgtaaaaa ttatgctgaa gcaaaggatg tgttcctggg catgtttctg   1740
tacgagtatg cacgagctgg agggagtgga ggctcaggag gaagcggcgg gtccggaggc   1800
tcaagcgaac tgacccagga ccccgccgtg tctgtcgctc tgggacagac agtgaggatc   1860
acttgccagg gcgactctct gcgcagttac tatgcaagtt ggtatcagca gaagcctggc   1920
caggcccctg tcctggtcat ctatggcaag aataatcgcc ctagtgggat tccagatcga   1980
ttttcagggt cctctagtgg aaacacagct tctctgacta ttaccggcgc acaggccgag   2040
gacgaagccg attactattg caacagcaga gactcaagcg gcaatcatgt ggtcttcgga   2100
ggaggaacca agctgacagt ggggaggagc tcaggcggcg gcagcggagg aggctccggg   2160
ggaggctctg gaggaggcag tggagaggtc cagctggtgg aatccggagg aggagtggtc   2220
cgaccaggag gatcactgag actgtcctgt gctgcatccg gattcacctt cgatgattac   2280
ggaatgagct gggtcaggca ggcacctggc aagggcctgg aatgggtgtc cggcatcaac   2340
tggaatggcg ggtcaaccgg gtacgctgat agcgtgaaag gacggttcac aattagcagg   2400
gataatgcta agaacagctt atatctgcaa atgaacagcc tgcgcgcaga ggacacagcc   2460
gtgtactatt gcgccccggg gcggagcctg ctgtttgatt actgggggca gggcacactg   2520
gtgaccgtct ctcggtgagg atcc                                         2544
```

<210> SEQ ID NO 46
<211> LENGTH: 845
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 46

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
             20                  25                  30

Ser Trp Tyr Gln Gln Lys Pro Gly Gln Ala Pro Val Leu Val Ile Tyr
         35                  40                  45

Gly Lys Asn Asn Arg Pro Ser Gly Ile Pro Asp Arg Phe Ser Gly Ser
     50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320

Asp Lys Leu Cys Thr Val Ala Thr Leu Arg Glu Thr Tyr Gly Glu Met
                325                 330                 335

Ala Asp Cys Cys Ala Lys Gln Glu Pro Glu Arg Asn Glu Cys Phe Leu
            340                 345                 350

Gln His Lys Asp Asp Asn Pro Asn Leu Pro Arg Leu Val Arg Pro Glu
        355                 360                 365

Val Asp Val Met Cys Thr Ala Phe His Asp Asn Glu Glu Thr Phe Leu
    370                 375                 380

Lys Lys Tyr Leu Tyr Glu Ile Ala Arg Arg His Pro Tyr Phe Tyr Ala
385                 390                 395                 400
```

```
Pro Glu Leu Leu Phe Phe Ala Lys Arg Tyr Lys Ala Ala Phe Thr Glu
                405                 410                 415

Cys Cys Gln Ala Ala Asp Lys Ala Ala Cys Leu Leu Pro Lys Leu Asp
            420                 425                 430

Glu Leu Arg Asp Glu Gly Lys Ala Ser Ser Ala Lys Gln Arg Leu Lys
        435                 440                 445

Cys Ala Ser Leu Gln Lys Phe Gly Glu Arg Ala Phe Lys Ala Trp Ala
    450                 455                 460

Val Ala Arg Leu Ser Gln Arg Phe Pro Lys Ala Glu Phe Ala Glu Val
465                 470                 475                 480

Ser Lys Leu Val Thr Asp Leu Thr Lys Val His Thr Glu Cys Cys His
                485                 490                 495

Gly Asp Leu Leu Glu Cys Ala Asp Asp Arg Ala Asp Leu Ala Lys Tyr
            500                 505                 510

Ile Cys Glu Asn Gln Asp Ser Ile Ser Ser Lys Leu Lys Glu Cys Cys
        515                 520                 525

Glu Lys Pro Leu Leu Glu Lys Ser His Cys Ile Ala Glu Val Glu Asn
    530                 535                 540

Asp Glu Met Pro Ala Asp Leu Pro Ser Leu Ala Ala Asp Phe Val Glu
545                 550                 555                 560

Ser Lys Asp Val Cys Lys Asn Tyr Ala Glu Ala Lys Asp Val Phe Leu
                565                 570                 575

Gly Met Phe Leu Tyr Glu Tyr Ala Arg Ala Gly Gly Ser Gly Gly Ser
            580                 585                 590

Gly Gly Ser Gly Gly Ser Gly Ser Ser Glu Leu Thr Gln Asp Pro
        595                 600                 605

Ala Val Ser Val Ala Leu Gly Gln Thr Val Arg Ile Thr Cys Gln Gly
    610                 615                 620

Asp Ser Leu Arg Ser Tyr Tyr Ala Ser Trp Tyr Gln Gln Lys Pro Gly
625                 630                 635                 640

Gln Ala Pro Val Leu Val Ile Tyr Gly Lys Asn Asn Arg Pro Ser Gly
                645                 650                 655

Ile Pro Asp Arg Phe Ser Gly Ser Ser Ser Gly Asn Thr Ala Ser Leu
            660                 665                 670

Thr Ile Thr Gly Ala Gln Ala Glu Asp Glu Ala Asp Tyr Tyr Cys Asn
        675                 680                 685

Ser Arg Asp Ser Ser Gly Asn His Val Val Phe Gly Gly Gly Thr Lys
    690                 695                 700

Leu Thr Val Gly Gly Gly Ser Gly Gly Gly Ser Gly Gly Gly Ser Gly
705                 710                 715                 720

Gly Gly Ser Gly Gly Ser Gly Glu Val Gln Leu Val Glu Ser Gly
                725                 730                 735

Gly Gly Val Val Arg Pro Gly Gly Ser Leu Arg Leu Ser Cys Ala Ala
            740                 745                 750

Ser Gly Phe Thr Phe Asp Asp Tyr Gly Met Ser Trp Val Arg Gln Ala
        755                 760                 765

Pro Gly Lys Gly Leu Glu Trp Val Ser Gly Ile Asn Trp Asn Gly Gly
    770                 775                 780

Ser Thr Gly Tyr Ala Asp Ser Val Lys Gly Arg Phe Thr Ile Ser Arg
785                 790                 795                 800

Asp Asn Ala Lys Asn Ser Leu Tyr Leu Gln Met Asn Ser Leu Arg Ala
                805                 810                 815
```

```
Glu Asp Thr Ala Val Tyr Tyr Cys Ala Arg Gly Arg Ser Leu Leu Phe
                820                 825                 830

Asp Tyr Trp Gly Gln Gly Thr Leu Val Thr Val Ser Arg
        835                 840                 845

<210> SEQ ID NO 47
<211> LENGTH: 2295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
agtagcgaac tgacccagga ccccgcagtg agcgtcgcac tggggcagac agtgagaatc      60
acttgccagg gagattctct gaggagttac tatgcctcct ggtaccagca gaaacccggc    120
caggctcctg tgctggtcat ctatgggaag aacaataggc caagcggcat ccccgaccgc    180
ttctccggca gctcctctgg gaacacagct agcctgacta ttaccggcgc tcaggcagag    240
gacgaagcag attactattg caactccagg gatagttcag gcaatcacgt ggtctttggc    300
gggggaacaa agctgactgt gggaggagga agcggaggag gcagcggagg gggatctgga    360
ggaggaagtg gaggaggatc aggagaggtg cagctggtcg aaagcggagg aggagtggtc    420
cgccctggag ggagcctgcg actgtcctgt gccgcttctg gcttcacctt tgacgattac    480
ggaatgagct gggtgcggca ggcaccaggg aagggactgg agtgggtgtc cggcatcaac    540
tggaatggag ctccacagg atacgcagac tctgtgaaag ccgattcac tatttctcgg     600 gataacgcca agaatagtct gtatctgcag atgaacagcc tgagagctga ggacactgca    660
gtgtactatt gtgccagggg ccgcagcctg ctgtttgatt actggggcca gggaaccctg    720
gtgacagtct ccaggggagg atcaggaggg agcggaggct ccggaggatc tggagggagt    780
gtggtcctgc tgctgcgact ggctaaaacc tacgagacca cactggaaaa gtgctgtgca    840
gccgctgacc ctcatgagtg ctatgccaaa gtgttcgatg agttcaagcc actggtcgag    900
gaacccagag acctgatcaa acagaattgt gagctgttcg aacagctggg cgagtacaag    960
tttcagaacg ccctgctggt gcgctatacc aagaaagtgc ctcaggtcag cacaccaact   1020
ctggtggaag tctcccggaa tctggggaaa gtgggatcta aatgctgtaa gcaccccgag   1080
gctaagagaa tgccttgcgc agaagactac ctgtctgtgg tcctgaacca gctgtgtgtg   1140
ctgcatgaga aaacccccagt gagcgatagg gtcaccaagt gctgtacaga agtctggtg    1200 aaccggagac catgcttctc agccctggag gtggacgaaa catatgtccc caaagagttt   1260
aatgccgaaa ccttcacatt tcacgctgat atctgtactc tgtccgagaa ggaacgccag   1320
attaagaaac agaccgccct ggtggagctg gtcaagcata acccaaggc aacaaaagaa    1380 cagctgaagg ccgtgatgga cgatttcgca gcctttgtcg agaaatgctg taaggctgac   1440
gataaggaaa cttgcttcgc agaggaagga aagaaactgg tggctgcaag ccaggcagct   1500
ctgggactgg gaggctcagg aggaagcggc gggtccggag gctctggggg aagctccgag   1560
ctgacccagg acccagccgt gtctgtcgct ctgggccaga ctgtgcgcat cacctgtcag   1620
ggggatagtc tgcgatcata ctatgcaagt tggtatcagc agaaacctgg ccaggcccca   1680
gtcctggtca tctatgggaa gaataatcga ccttccggca tccccgaccg gttctccgga   1740
tctagttcag gcaacacagc ctctctgact attaccggcg cccaggctga ggacgaagct   1800
gattactatt gcaacagcag ggatagctcc ggaaaccacg tggtctttgg aggaggaact   1860
```

```
aagctgaccg tgggaggagg aagtggcggg ggatcaggcg gcggaagcgg cggcggcagc   1920
ggaggaggat ctggcgaagt gcagctggtc gaatctggcg gaggagtggt ccggccagga   1980
gggagtctga gactgtcatg tgcagccagc ggcttcacat tcgatgatta cggaatgtct   2040
tgggtgcggc aggcacctgg aaagggcctg aatgggtga gtggcatcaa ctggaacggc    2100
ggcagtaccg gatacgctga ctcagtgaaa ggcagattca caatttctag agacaatgct   2160
aagaatagtt tatatctgca aatgaacagc ctgagagcag aggacactgc cgtgtactat   2220
tgcgcccggg ggaggtcact gctgttcgat tactggggc agggcactct ggtcactgtg    2280
tcaaggtgag gatcc                                                    2295
```

<210> SEQ ID NO 48
<211> LENGTH: 762
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 48

```
Ser Ser Glu Leu Thr Gln Asp Pro Ala Val Ser Val Ala Leu Gly Gln
1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Gly Ser Gly Gly Ser Gly Gly
                245                 250                 255

Ser Gly Gly Ser Val Val Leu Leu Leu Arg Leu Ala Lys Thr Tyr Glu
            260                 265                 270

Thr Thr Leu Glu Lys Cys Cys Ala Ala Ala Asp Pro His Glu Cys Tyr
```

```
            275                 280                 285
Ala Lys Val Phe Asp Glu Phe Lys Pro Leu Val Glu Glu Pro Gln Asn
290                 295                 300
Leu Ile Lys Gln Asn Cys Glu Leu Phe Glu Gln Leu Gly Glu Tyr Lys
305                 310                 315                 320
Phe Gln Asn Ala Leu Leu Val Arg Tyr Thr Lys Lys Val Pro Gln Val
                325                 330                 335
Ser Thr Pro Thr Leu Val Glu Val Ser Arg Asn Leu Gly Lys Val Gly
            340                 345                 350
Ser Lys Cys Cys Lys His Pro Glu Ala Lys Arg Met Pro Cys Ala Glu
        355                 360                 365
Asp Tyr Leu Ser Val Val Leu Asn Gln Leu Cys Val Leu His Glu Lys
    370                 375                 380
Thr Pro Val Ser Asp Arg Val Thr Lys Cys Cys Thr Glu Ser Leu Val
385                 390                 395                 400
Asn Arg Arg Pro Cys Phe Ser Ala Leu Glu Val Asp Glu Thr Tyr Val
                405                 410                 415
Pro Lys Glu Phe Asn Ala Glu Thr Phe Thr Phe His Ala Asp Ile Cys
                420                 425                 430
Thr Leu Ser Glu Lys Glu Arg Gln Ile Lys Lys Gln Thr Ala Leu Val
            435                 440                 445
Glu Leu Val Lys His Lys Pro Lys Ala Thr Lys Glu Gln Leu Lys Ala
450                 455                 460
Val Met Asp Asp Phe Ala Ala Phe Val Glu Lys Cys Cys Lys Ala Asp
465                 470                 475                 480
Asp Lys Glu Thr Cys Phe Ala Glu Glu Gly Lys Lys Leu Val Ala Ala
                485                 490                 495
Ser Gln Ala Ala Leu Gly Leu Gly Gly Ser Gly Gly Ser Gly Gly Ser
                500                 505                 510
Gly Gly Ser Gly Gly Ser Ser Glu Leu Thr Gln Asp Pro Ala Val Ser
        515                 520                 525
Val Ala Leu Gly Gln Thr Val Arg Ile Thr Cys Gln Gly Asp Ser Leu
    530                 535                 540
Arg Ser Tyr Tyr Ala Ser Trp Tyr Gln Gln Lys Pro Gly Gln Ala Pro
545                 550                 555                 560
Val Leu Val Ile Tyr Gly Lys Asn Asn Arg Pro Ser Gly Ile Pro Asp
                565                 570                 575
Arg Phe Ser Gly Ser Ser Ser Gly Asn Thr Ala Ser Leu Thr Ile Thr
                580                 585                 590
Gly Ala Gln Ala Glu Asp Glu Ala Asp Tyr Tyr Cys Asn Ser Arg Asp
                595                 600                 605
Ser Ser Gly Asn His Val Val Phe Gly Gly Gly Thr Lys Leu Thr Val
        610                 615                 620
Gly Gly Gly Ser Gly Gly Gly Ser Gly Gly Gly Ser Gly Gly Gly Ser
625                 630                 635                 640
Gly Gly Gly Ser Gly Glu Val Gln Leu Val Glu Ser Gly Gly Gly Val
                645                 650                 655
Val Arg Pro Gly Gly Ser Leu Arg Leu Ser Cys Ala Ala Ser Gly Phe
                660                 665                 670
Thr Phe Asp Asp Tyr Gly Met Ser Trp Val Arg Gln Ala Pro Gly Lys
            675                 680                 685
Gly Leu Glu Trp Val Ser Gly Ile Asn Trp Asn Gly Gly Ser Thr Gly
690                 695                 700
```

```
Tyr Ala Asp Ser Val Lys Gly Arg Phe Thr Ile Ser Arg Asp Asn Ala
705                 710                 715                 720

Lys Asn Ser Leu Tyr Leu Gln Met Asn Ser Leu Arg Ala Glu Asp Thr
            725                 730                 735

Ala Val Tyr Tyr Cys Ala Arg Gly Arg Ser Leu Leu Phe Asp Tyr Trp
        740                 745                 750

Gly Gln Gly Thr Leu Val Thr Val Ser Arg
        755                 760

<210> SEQ ID NO 49
<211> LENGTH: 2556
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
gatattcaga tgactcagtc tcctagctcc ctgtcagcta gcgtcggcga tcgggtgaca      60
atcacttgca gagccagcca ggacgtcaac acagccgtgg cttggtacca gcagaagccc     120
ggaaaagcac ctaagctgct gatctactcc gcctcttttc tgtattctgg cgtgcccagt     180
agattcagtg gatcaaggag cggcaccgat tttaccctga caatctctag tctgcagcct     240
gaggactttg ccacatacta ttgccagcag cactatacca caccccctac tttcgggcag     300
ggaaccaagg tggaaatcaa aggcgggtca ggcggaggga gcggaggagg gtccggagga     360
gggtctggag agggagtggg agaggtgcag ctggtcgaat ctggaggagg actggtgcag     420
ccaggaggct cactgcggct gagctgtgcc gcttccggct caacatcaa agatacctac      480 attcattggg tccgacaggc caccaggcaag ggactggagt gggtggctag aatctatccc     540
accaatggct acacacgata tgccgatagc gtgaagggc ggtttacaat ttctgcagac      600
actagtaaga acaccgccta cctgcagatg aacagcctgc gcgctgagga cactgcagtg     660
tactattgta gtcgatgggg gggagacggc ttctacgcca tggattattg gggacagggc     720
accctggtga cagtctcaag cggagggtcc ggcgatgcac acaagtctga ggtcgctcat     780
agattcaaag acctggggga ggaaaatttt aaggccctgg tgctgattgc attcgcccag     840
tacctgcagc agtgcccctt tgaagaccac gtgaactgg tcaacgaggt gacagagttc     900
gccaagactt gcgtcgccga cgagagtgct gaaaattgtg ataaatcact gcatacactg     960
tttggggata gctgtgtac tgtggccacc ctgcgggaga cttatggaga aatggcagac    1020
tgctgtgcca aacaggagcc tgaaagaaac gagtgcttcc tgcagcacaa ggacgataac    1080
cctaatctgc caaggctggt gcgcccagaa gtggacgtca tgtgtactgc cttccacgat    1140
aatgaggaaa cctttctgaa gaaatacctg tatgagatcg cccggagaca tccctacttt    1200
tatgctcctg aactgctgtt ctttgcaaaa cggtacaagg cagccttcac cgagtgctgt    1260
caggctgcag ataaggccgc ttgcctgctg cccaaactgg acgagctgcg ggatgaaggc    1320
aaggcttcct ctgcaaagca gagactgaaa tgtgcaagcc tgcagaagtt cggggagagg    1380
gcctttaaag cttgggcagt cgcacgactg agccagcgat tccctaaggc cgagtttgct    1440
gaagtctcca gctggtgac agacctgact aaagtgcaca ccgagtgctg tcatggcgac    1500
ctgctggaat gcgccgacga tcgcgcagat ctggccaagt acatctgtga gaaccaggac    1560
agcattagtt caaagctgaa agagtgctgt gaaaagccac tgctggagaa atcccactgc    1620
attgctgagg tggaaaacga cgaaatgcca gcagatctgc ccagcctggc agccgacttc    1680
```

```
gtcgagtcca aggatgtgtg taaaaattat gctgaagcaa aggatgtgtt cctgggcatg    1740
tttctgtacg agtatgccag ggctggaggc agtggaggat caggagggag cggaggctcc    1800
ggaggagaca tccagatgac ccagagccca agctccctgt ccgcttctgt cggcgatagg    1860
gtgactatta cctgccgcgc ctcccaggac gtcaatacag cagtggcctg gtaccagcag    1920
aaacctggga aggctccaaa actgctgatc tacagtgcat cattcctgta ttcaggagtg    1980
ccaagccgct ttagcgggtc ccgatctgga actgatttca cactgactat ctctagtctg    2040
cagcccgagg actttgccac ctattactgc cagcagcact acactacccc acccaccttc    2100
gggcagggaa caaggtgga aatcaaaggg gggtccggcg gcgggtctgg cggagggagt    2160
ggaggagggt caggcggcgg gagcggcgag gtccagctgg tggaatccgg cggcggcctg    2220
gtgcagcctg gaggctccct gcgactgtct tgtgctgcaa gtggctttaa catcaaggac    2280
acttacattc attgggtcag gcaggctcct ggcaagggcc tggaatgggt ggcacgaatc    2340
tatccaacaa atggatacac taggtacgcc gatagcgtga aaggcaggtt caccatttca    2400
gccgacacca gcaagaacac agcttacctg caaatgaaca gcctgagggc tgaggacaca    2460
gcagtgtact attgcagccg ctggggcggg gacgggttct atgctatgga ctattggggg    2520
cagggcactc tggtcactgt gtcaagctga ggatcc                              2556
```

<210> SEQ ID NO 50  
<211> LENGTH: 849  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
```

-continued

```
            195                 200                 205
Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
                245                 250                 255

Glu Val Ala His Arg Phe Lys Asp Leu Gly Glu Glu Asn Phe Lys Ala
                260                 265                 270

Leu Val Leu Ile Ala Phe Ala Gln Tyr Leu Gln Gln Cys Pro Phe Glu
            275                 280                 285

Asp His Val Lys Leu Val Asn Glu Val Thr Glu Phe Ala Lys Thr Cys
        290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
                340                 345                 350

Phe Leu Gln His Lys Asp Asp Asn Pro Asn Leu Pro Arg Leu Val Arg
            355                 360                 365

Pro Glu Val Asp Val Met Cys Thr Ala Phe His Asp Asn Glu Glu Thr
370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
                420                 425                 430

Leu Asp Glu Leu Arg Asp Glu Gly Lys Ala Ser Ser Ala Lys Gln Arg
            435                 440                 445

Leu Lys Cys Ala Ser Leu Gln Lys Phe Gly Glu Arg Ala Phe Lys Ala
        450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
                500                 505                 510

Lys Tyr Ile Cys Glu Asn Gln Asp Ser Ile Ser Ser Lys Leu Lys Glu
            515                 520                 525

Cys Cys Glu Lys Pro Leu Leu Glu Lys Ser His Cys Ile Ala Glu Val
        530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Ala Gly Gly Ser Gly
                580                 585                 590

Gly Ser Gly Gly Ser Gly Gly Ser Gly Gly Asp Ile Gln Met Thr Gln
            595                 600                 605

Ser Pro Ser Ser Leu Ser Ala Ser Val Gly Asp Arg Val Thr Ile Thr
        610                 615                 620
```

Cys Arg Ala Ser Gln Asp Val Asn Thr Ala Val Ala Trp Tyr Gln Gln
625                 630                 635                 640

Lys Pro Gly Lys Ala Pro Lys Leu Leu Ile Tyr Ser Ala Ser Phe Leu
            645                 650                 655

Tyr Ser Gly Val Pro Ser Arg Phe Ser Gly Ser Arg Ser Gly Thr Asp
            660                 665                 670

Phe Thr Leu Thr Ile Ser Ser Leu Gln Pro Glu Asp Phe Ala Thr Tyr
        675                 680                 685

Tyr Cys Gln Gln His Tyr Thr Thr Pro Pro Thr Phe Gly Gln Gly Thr
    690                 695                 700

Lys Val Glu Ile Lys Gly Gly Ser Gly Gly Ser Gly Gly Gly Gly Ser
705                 710                 715                 720

Gly Gly Gly Ser Gly Gly Ser Gly Glu Val Gln Leu Val Glu Ser
            725                 730                 735

Gly Gly Gly Leu Val Gln Pro Gly Gly Ser Leu Arg Leu Ser Cys Ala
            740                 745                 750

Ala Ser Gly Phe Asn Ile Lys Asp Thr Tyr Ile His Trp Val Arg Gln
            755                 760                 765

Ala Pro Gly Lys Gly Leu Glu Trp Val Ala Arg Ile Tyr Pro Thr Asn
770                 775                 780

Gly Tyr Thr Arg Tyr Ala Asp Ser Val Lys Gly Arg Phe Thr Ile Ser
785                 790                 795                 800

Ala Asp Thr Ser Lys Asn Thr Ala Tyr Leu Gln Met Asn Ser Leu Arg
            805                 810                 815

Ala Glu Asp Thr Ala Val Tyr Tyr Cys Ser Arg Trp Gly Gly Asp Gly
            820                 825                 830

Phe Tyr Ala Met Asp Tyr Trp Gly Gln Gly Thr Leu Val Thr Val Ser
        835                 840                 845

Ser

<210> SEQ ID NO 51
<211> LENGTH: 2307
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gacattcaga tgactcagag cccaagctcc ctgagcgcat ccgtgggcga cagagtcacc      60
atcacatgca gggcctccca ggatgtgaac accgctgtcg catggtacca gcagaaacct     120
gggaaggctc caaaactgct gatctactct gcaagtttcc tgtatagtgg agtgccatca     180
aggttttcag gcagccgctc cgggaccgac ttcactctga ccatctctag tctgcagccc     240
gaggatttcg ccacatacta ttgccagcag cactatacca cccccctac ctttggccag      300 gggacaaaag tggaaattaa gggagggagc ggaggagggt ccggaggagg gtctggaggc     360
gggagtggag gagggtcagg agaggtgcag ctggtcgaat ccggaggagg actggtgcag     420
ccaggaggca gctgcgcgct gtcctgtgcc gcttctggct tcaacatcaa agacacctac     480
attcattggg tgcgccaggc tccaggaaag ggactggagt gggtcgcacg aatctatccc     540
actaatgggt acacccggta tgccgattcc gtgaaaggaa gattcacaat tagtgcagat     600
acatcaaaga acactgccta cctgcagatg aacagcctgc gagcagagga tactgccgtg     660
tactattgta gtcggtgggg gggagacggc ttttacgcca tggattattg ggggcaggga     720

```
acctggtga  cagtctcaag  cggagggtca  ggaggcagcg  gaggcagcgg  agggtctgga    780
ggcagtgtgg  tcctgctgct  gaggctggct  aaaacctacg  agactaccct  ggaaaagtgc    840
tgtgcagccg  ctgacccca   cgagtgctat  gccaaagtgt  tcgatgagtt  caagccactg    900
gtcgaggaac  cccagaacct  gatcaaacag  aattgtgagc  tgttcgaaca  gctgggcgag    960
tacaagtttc  agaacgccct  gctggtgcgc  tataccaaga  aagtgcctca  ggtctctaca   1020
ccaactctgg  tggaggtcag  taggaatctg  gggaaagtgg  gatcaaagtg  ctgtaaacac   1080
cccgaggcca  agcgcatgcc  ttgcgctgaa  gactacctgt  ctgtggtcct  gaaccagctg   1140
tgtgtgctgc  atgagaaaac  ccccgtgagc  gatcgggtca  ccaagtgctg  tacagaaagc   1200
ctggtgaacc  ggagaccctg  cttctccgct  ctggaggtgg  acgaaacata  tgtccctaag   1260
gagtttaatg  ctgaaacctt  cacatttcac  gcagatatct  gtacactgtc  cgagaaggaa   1320
agacagatta  agaaacagac  tgccctggtg  gagctggtca  agcataaacc  taaggccaca   1380
aaagaacagc  tgaaggctgt  gatggacgat  ttcgcagcct  ttgtcgagaa  gtgctgtaaa   1440
gccgacgata  aggaaacttg  cttcgctgag  gaaggaaaga  actggtggc   tgcaagccag   1500 gcagctctgg  gcctgggagg  atcaggaggg  agcggaggct  ccggaggatc  tggaggggac   1560
atccagatga  cccagtctcc  ttcctctctg  tctgctagtg  tgggcgaccg  cgtcactatt   1620
acctgtcgag  ccagccagga  tgtgaataca  gccgtcgctt  ggtaccagca  gaagcccggc   1680
aaagcaccta  agctgctgat  ctactcagcc  agctttctgt  atagcggggt  gccttcccga   1740
ttctccggat  ctcggagtgg  cactgactt   acactgacta  tcagttcact  gcagccagag   1800
gatttcgcca  cctattactg  ccagcagcac  tacacaactc  cacccacttt  tggccagggg   1860
accaaagtgg  aaatcaaggg  aggctctgga  ggaggcagtg  gaggaggctc  aggaggaggc   1920
agcggaggag  gctccggcga  agtgcagctg  gtcgaatctg  gcggcggcct  ggtccagcca   1980
ggaggatctc  tgaggctgag  ttgtgcagcc  tcaggcttca  acatcaagga  tacttacatt   2040
cattgggtgc  ggcaggcacc  tggaaagggc  ctggaatggg  tcgctagaat  ctatccaact   2100
aatggctaca  ccagatatgc  cgacagcgtg  aaagggcgct  taccattag   cgcagataca   2160 tccaaaaata  ccgcttacct  gcagatgaat  agcctgagag  ctgaggatac  agcagtgtac   2220
tattgctcca  gatggggcgg  cgatgggttt  tacgcaatgg  actactgggg  acagggaaca   2280
ctggtcaccg  tctcttcttg  aggatcc                                           2307
```

<210> SEQ ID NO 52
<211> LENGTH: 766
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
                    65                  70                  75                  80
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Gly Ser Gly Gly Ser
                245                 250                 255

Gly Gly Ser Gly Gly Ser Val Val Leu Leu Arg Leu Ala Lys Thr
        260                 265                 270

Tyr Glu Thr Thr Leu Glu Lys Cys Cys Ala Ala Ala Asp Pro His Glu
    275                 280                 285

Cys Tyr Ala Lys Val Phe Asp Glu Phe Lys Pro Leu Val Glu Glu Pro
            290                 295                 300

Gln Asn Leu Ile Lys Gln Asn Cys Glu Leu Phe Glu Gln Leu Gly Glu
305                 310                 315                 320

Tyr Lys Phe Gln Asn Ala Leu Leu Val Arg Tyr Thr Lys Lys Val Pro
                325                 330                 335

Gln Val Ser Thr Pro Thr Leu Val Glu Val Ser Arg Asn Leu Gly Lys
            340                 345                 350

Val Gly Ser Lys Cys Cys Lys His Pro Glu Ala Lys Arg Met Pro Cys
        355                 360                 365

Ala Glu Asp Tyr Leu Ser Val Val Leu Asn Gln Leu Cys Val Leu His
    370                 375                 380

Glu Lys Thr Pro Val Ser Asp Arg Val Thr Lys Cys Cys Thr Glu Ser
385                 390                 395                 400

Leu Val Asn Arg Arg Pro Cys Phe Ser Ala Leu Glu Val Asp Glu Thr
                405                 410                 415

Tyr Val Pro Lys Glu Phe Asn Ala Glu Thr Phe Thr Phe His Ala Asp
            420                 425                 430

Ile Cys Thr Leu Ser Glu Lys Glu Arg Gln Ile Lys Lys Gln Thr Ala
        435                 440                 445

Leu Val Glu Leu Val Lys His Lys Pro Lys Ala Thr Lys Glu Gln Leu
    450                 455                 460

Lys Ala Val Met Asp Asp Phe Ala Ala Phe Val Glu Lys Cys Cys Lys
465                 470                 475                 480

Ala Asp Asp Lys Glu Thr Cys Phe Ala Glu Glu Gly Lys Lys Leu Val
                485                 490                 495
```

```
Ala Ala Ser Gln Ala Ala Leu Gly Leu Gly Gly Ser Gly Gly Ser Gly
                500                 505                 510
Gly Ser Gly Gly Ser Gly Gly Asp Ile Gln Met Thr Gln Ser Pro Ser
            515                 520                 525
Ser Leu Ser Ala Ser Val Gly Asp Arg Val Thr Ile Thr Cys Arg Ala
        530                 535                 540
Ser Gln Asp Val Asn Thr Ala Val Ala Trp Tyr Gln Gln Lys Pro Gly
545                 550                 555                 560
Lys Ala Pro Lys Leu Leu Ile Tyr Ser Ala Ser Phe Leu Tyr Ser Gly
                565                 570                 575
Val Pro Ser Arg Phe Ser Gly Ser Arg Ser Gly Thr Asp Phe Thr Leu
            580                 585                 590
Thr Ile Ser Ser Leu Gln Pro Glu Asp Phe Ala Thr Tyr Tyr Cys Gln
        595                 600                 605
Gln His Tyr Thr Thr Pro Pro Thr Phe Gly Gln Gly Thr Lys Val Glu
610                 615                 620
Ile Lys Gly Gly Ser Gly Gly Ser Gly Gly Ser Gly Gly Gly
625                 630                 635                 640
Ser Gly Gly Ser Gly Glu Val Gln Leu Val Glu Ser Gly Gly
                645                 650                 655
Leu Val Gln Pro Gly Gly Ser Leu Arg Leu Ser Cys Ala Ala Ser Gly
                660                 665                 670
Phe Asn Ile Lys Asp Thr Tyr Ile His Trp Val Arg Gln Ala Pro Gly
                675                 680                 685
Lys Gly Leu Glu Trp Val Ala Arg Ile Tyr Pro Thr Asn Gly Tyr Thr
            690                 695                 700
Arg Tyr Ala Asp Ser Val Lys Gly Arg Phe Thr Ile Ser Ala Asp Thr
705                 710                 715                 720
Ser Lys Asn Thr Ala Tyr Leu Gln Met Asn Ser Leu Arg Ala Glu Asp
                725                 730                 735
Thr Ala Val Tyr Tyr Cys Ser Arg Trp Gly Gly Asp Gly Phe Tyr Ala
            740                 745                 750
Met Asp Tyr Trp Gly Gln Gly Thr Leu Val Thr Val Ser Ser
        755                 760                 765

<210> SEQ ID NO 53
<211> LENGTH: 2550
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
agttctgagc tgacccagga ccccgctgtg agcgtcgcac tgggacagac agtgcggatc      60
acttgccagg gcgacagcct gagatcctac tatgctagct ggtaccagca gaagcctggc     120
caggcaccag tgctggtcat ctatggaaaa aacaatagac ccagcggcat tcctgatagg     180
ttctccggga gctcctctgg aaacacagct agcctgacta ttaccggcgc ccaggctgag     240
gacgaagccg attactattg caacagcagg gacagttcag ggaatcacgt ggtctttgga     300
ggaggaacta agctgaccgt gggaggaggc agcggaggag atctggagg aggaagtgga     360 ggaggatcag gaggaggaag cggagaggtg cagctggtcg aaagcggagg aggagtggtc     420
aggccaggag ggtccctgcg actgtcttgt gccgctagtg ggttcactt tgacgattac     480
```

-continued

```
ggaatgagtt gggtcaggca ggcaccagga aagggactgg agtgggtgag cggcatcaac    540
tggaatggag gcagtacagg ctacgctgat tcagtgaagg ggcgcttcac tatttctcga    600
gacaacgcca aaaatagtct gtatctgcag atgaactcac tgcgcgccga ggatacagct    660
gtgtactatt gcgccagggg ccgctccctg ctgtttgact actgggggca gggaacactg    720
gtgactgtct cacgggggg aagcggagat gcacacaaat ctgaggtcgc ccatagattc    780
aaggacctgg gcgaggaaaa ttttaaagcc ctggtgctga tcgcattcgc ccagtatctg    840
cagcagtgcc ctttcgaaga ccacgtgaag ctggtcaacg aggtgacaga atttgccaaa    900
acttgcgtcg cagacgagag cgccgaaaat tgtgataagt ccctgcatac cctgttcggc    960
gataaactgt gtaccgtggc cacactgagg gagacatacg gggaaatggc tgactgctgt   1020
gcaaagcagg agcccgaacg caacgagtgc tttctgcagc acaaagacga taacccaaat   1080
ctgccccgac tggtgcggcc tgaagtggac gtcatgtgta ctgccttcca cgataatgag   1140
gaaacctttc tgaagaaata cctgtatgag attgcccgga gacatcccta cttctatgct   1200
cctgaactgc tgttctttgc aaagcggtac aaagcagcct ttaccgagtg ctgtcaggct   1260
gcagataaag ccgcttgcct gctgcctaag ctggacgagc tgagggatga aggcaaggct   1320
agctccgcaa aacagcgcct gaagtgtgct agcctgcaga aattcggcga gcgggccttc   1380
aaggcttggg cagtggccag actgtcacag aggttcccaa aggccgagtt tgctgaagtc   1440
agcaaactgg tgactgacct gaccaaggtg cacaccgagt gctgtcatgg cgacctgctg   1500
gaatgcgccg acgatagagc agatctggcc aagtacatct gtgagaacca ggactccatt   1560
tctagtaagc tgaaagagtg ctgtgaaaaa cccctgctgg agaagtctca ttgcatcgcc   1620
gaggtggaaa acgacgaaat gccagctgat ctgccctctc tggcagccga cttcgtcgag   1680
agtaaagatg tgtgtaagaa ttatgctgaa gcaaaggatg tgttcctggg catgtttctg   1740
tacgagtatg cacgagctgg agggtctgga ggcagtggag gatcaggagg gagcggaggc   1800
gacatccaga tgacccagtc cccttcaagc ctgagtgctt cagtcggcga tcgagtgaca   1860
attacttgcc gggcctctca ggacgtcaat acagcagtgg cttggtatca gcagaagcct   1920
gggaaagcac caaagctgct gatctacagc gcctcctttc tgtattccgg agtgccttct   1980
cggttctctg gcagtagatc agggactgat tttaccctga caatttcctc tctgcagcca   2040
gaggacttcg ccacctacta ttgccagcag cactatacca caccccctac ctttggccag   2100
gggacaaaag tggaaatcaa ggggggaagt ggcgggggat caggcggcgg aagcggcggc   2160
ggcagcggcg gcggatctgg agaggtccag ctggtggaaa gcggaggagg actggtgcag   2220
ccaggaggga gtctgagact gtcatgtgct gcaagcggct tcaacatcaa ggatacctac   2280
attcactggg tcaggcaggc cccaggaaaa ggcctggagt gggtggcccg catctatccc   2340
accaatgggt acacacgcta tgccgattcc gtgaagggac gattcacaat ttccgccgac   2400
acttctaaaa acaccgctta cctgcagatg aacagcctgc gagccgagga cactgctgtg   2460
tactattgtt ctagatgggg cggggacggg ttttacgcaa tggactactg ggggcagggg   2520
actctggtca ctgtcagcag ctgaggatcc                                    2550
```

<210> SEQ ID NO 54
<211> LENGTH: 847
<212> TYPE: PRT
<213> ORGANISM: Artificial Sequence
<220> FEATURE:
<223> OTHER INFORMATION: Description of Artificial Sequence: Synthetic polypeptide -continued

```
<400> SEQUENCE: 54

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Ser Gly Gly Gly Ser Gly
        115                 120                 125

Glu Val Gln Leu Val Glu Ser Gly Gly Gly Val Val Arg Pro Gly Gly
130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

Lys Gly Arg Phe Thr Ile Ser Arg Asp Asn Ala Lys Asn Ser Leu Tyr
        195                 200                 205

Leu Gln Met Asn Ser Leu Arg Ala Glu Asp Thr Ala Val Tyr Tyr Cys
    210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Asp Ala His Lys Ser Glu Val
                245                 250                 255

Ala His Arg Phe Lys Asp Leu Gly Glu Glu Asn Phe Lys Ala Leu Val
            260                 265                 270

Leu Ile Ala Phe Ala Gln Tyr Leu Gln Gln Cys Pro Phe Glu Asp His
        275                 280                 285

Val Lys Leu Val Asn Glu Val Thr Glu Phe Ala Lys Thr Cys Val Ala
    290                 295                 300

Asp Glu Ser Ala Glu Asn Cys Asp Lys Ser Leu His Thr Leu Phe Gly
305                 310                 315                 320

Asp Lys Leu Cys Thr Val Ala Thr Leu Arg Glu Thr Tyr Gly Glu Met
                325                 330                 335

Ala Asp Cys Cys Ala Lys Gln Glu Pro Glu Arg Asn Glu Cys Phe Leu
            340                 345                 350

Gln His Lys Asp Asp Asn Pro Asn Leu Pro Arg Leu Val Arg Pro Glu
        355                 360                 365

Val Asp Val Met Cys Thr Ala Phe His Asp Asn Glu Glu Thr Phe Leu
    370                 375                 380

Lys Lys Tyr Leu Tyr Glu Ile Ala Arg Arg His Pro Tyr Phe Tyr Ala
385                 390                 395                 400

Pro Glu Leu Leu Phe Phe Ala Lys Arg Tyr Lys Ala Ala Phe Thr Glu
                405                 410                 415
```

```
Cys Cys Gln Ala Ala Asp Lys Ala Ala Cys Leu Leu Pro Lys Leu Asp
            420                 425                 430

Glu Leu Arg Asp Glu Gly Lys Ala Ser Ser Ala Lys Gln Arg Leu Lys
            435                 440                 445

Cys Ala Ser Leu Gln Lys Phe Gly Glu Arg Ala Phe Lys Ala Trp Ala
450                 455                 460

Val Ala Arg Leu Ser Gln Arg Phe Pro Lys Ala Glu Phe Ala Glu Val
465                 470                 475                 480

Ser Lys Leu Val Thr Asp Leu Thr Lys Val His Thr Glu Cys Cys His
                485                 490                 495

Gly Asp Leu Leu Glu Cys Ala Asp Asp Arg Ala Asp Leu Ala Lys Tyr
                500                 505                 510

Ile Cys Glu Asn Gln Asp Ser Ile Ser Ser Lys Leu Lys Glu Cys Cys
            515                 520                 525

Glu Lys Pro Leu Leu Glu Lys Ser His Cys Ile Ala Glu Val Glu Asn
            530                 535                 540

Asp Glu Met Pro Ala Asp Leu Pro Ser Leu Ala Ala Asp Phe Val Glu
545                 550                 555                 560

Ser Lys Asp Val Cys Lys Asn Tyr Ala Glu Ala Lys Asp Val Phe Leu
                565                 570                 575

Gly Met Phe Leu Tyr Glu Tyr Ala Arg Ala Gly Gly Ser Gly Gly Ser
                580                 585                 590

Gly Gly Ser Gly Gly Ser Gly Gly Asp Ile Gln Met Thr Gln Ser Pro
            595                 600                 605

Ser Ser Leu Ser Ala Ser Val Gly Asp Arg Val Thr Ile Thr Cys Arg
            610                 615                 620

Ala Ser Gln Asp Val Asn Thr Ala Val Ala Trp Tyr Gln Gln Lys Pro
625                 630                 635                 640

Gly Lys Ala Pro Lys Leu Leu Ile Tyr Ser Ala Ser Phe Leu Tyr Ser
                645                 650                 655

Gly Val Pro Ser Arg Phe Ser Gly Ser Arg Ser Gly Thr Asp Phe Thr
                660                 665                 670

Leu Thr Ile Ser Ser Leu Gln Pro Glu Asp Phe Ala Thr Tyr Tyr Cys
            675                 680                 685

Gln Gln His Tyr Thr Thr Pro Pro Thr Phe Gly Gln Gly Thr Lys Val
            690                 695                 700

Glu Ile Lys Gly Gly Ser Gly Gly Ser Gly Gly Ser Gly Gly Ser Gly
705                 710                 715                 720

Gly Ser Gly Gly Ser Gly Glu Val Gln Leu Val Glu Ser Gly Gly Gly
                725                 730                 735

Gly Leu Val Gln Pro Gly Gly Ser Leu Arg Leu Ser Cys Ala Ala Ser
                740                 745                 750

Gly Phe Asn Ile Lys Asp Thr Tyr Ile His Trp Val Arg Gln Ala Pro
            755                 760                 765

Gly Lys Gly Leu Glu Trp Val Ala Arg Ile Tyr Pro Thr Asn Gly Tyr
            770                 775                 780

Thr Arg Tyr Ala Asp Ser Val Lys Gly Arg Phe Thr Ile Ser Ala Asp
785                 790                 795                 800

Thr Ser Lys Asn Thr Ala Tyr Leu Gln Met Asn Ser Leu Arg Ala Glu
                805                 810                 815

Asp Thr Ala Val Tyr Tyr Cys Ser Arg Trp Gly Gly Asp Gly Phe Tyr
                820                 825                 830
```

Ala Met Asp Tyr Trp Gly Gln Gly Thr Leu Val Thr Val Ser Ser
    835                 840                 845

<210> SEQ ID NO 55
<211> LENGTH: 2550
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

| | | | | | |
|---|---|---|---|---|---|
| gacattcaga | tgacccagtc | cccaagctcc | ctgtctgcta | gtgtcggcga | tcgggtgact | 60 |
| atcacctgca | gagcctctca | ggacgtcaac | acagccgtgg | cttggtacca | gcagaagcct | 120 |
| ggcaaagcac | caaagctgct | gatctactca | gccagctttc | tgtatagcgg | ggtgccttcc | 180 |
| agattctccg | gctctaggag | tgggactgat | tttacactga | ctatctctag | tctgcagcca | 240 |
| gaggacttcg | ccacctacta | ttgccagcag | cactatacca | cccccctac | atttgggcag | 300 |
| ggaactaaag | tggaaattaa | gggagggtct | ggaggaggga | gtggaggagg | gtcaggcgga | 360 |
| gggagcggag | gagggtccgg | cgaggtgcag | ctggtcgaaa | gcggaggagg | actggtgcag | 420 |
| cctggaggct | ctctgaggct | gagttgtgcc | gcttcaggct | tcaacatcaa | ggatacctac | 480 |
| attcattggg | tccgacaggc | tccaggcaaa | gggctggagt | gggtggcaag | aatctatccc | 540 |
| acaaatggct | acactagata | tgccgatagc | gtgaagggga | ggttcacaat | tagcgctgac | 600 |
| acctccaaaa | acacagcata | cctgcagatg | aatagtctgc | gggctgagga | cactgcagtg | 660 |
| tactattgta | gcagatgggg | gggagacggc | ttttacgcca | tggattattg | gggacagggc | 720 |
| actctggtga | ccgtctcaag | cggagggagc | ggggatgcac | acaaatccga | ggtcgcccat | 780 |
| cgcttcaagg | acctgggaga | ggaaaatttt | aaagccctgg | tgctgattgc | attcgcccag | 840 |
| tacctgcagc | agtgccccct | cgaagaccac | gtgaagctgg | tcaacgaggt | gaccgaattt | 900 |
| gccaaaacat | gctcgccga | cgagtcagct | gaaaattgtg | ataagagcct | gcatacctg | 960 |
| ttcggagata | aactgtgtac | agtggccact | ctgagggaga | catatggcga | aatggcagac | 1020 |
| tgctgtgcca | gcaggagcc | cgaacgcaac | gagtgctttc | tgcagcacaa | agacgataac | 1080 |
| ccaaatctgc | ccaggctggt | gcgccctgaa | gtggacgtca | tgtgtactgc | cttccacgat | 1140 |
| aatgaggaaa | cctttctgaa | gaaataacctg | tatgagatcg | cccggagaca | tcctacttc | 1200 |
| tatgcccctg | aactgctgtt | ctttgctaaa | cggtacaagg | cagcctttac | cgagtgctgt | 1260 |
| caggctgcag | ataaagccgc | ttgcctgctg | cctaagctgg | acgagctgag | ggatgaagga | 1320 |
| aaggcttcct | ctgcaaaaca | gcgcctgaag | tgtgcctccc | tgcagaaatt | cggcgagcgg | 1380 |
| gcttttaagg | cttgggcagt | ggcacgactg | tcccagcgat | tcccaaaggc | cgagtttgct | 1440 |
| gaagtctcta | aactggtgac | cgacctgaca | aaggtgcaca | ccgagtgctg | tcatggcgac | 1500 |
| ctgctggaat | gcgccgacga | tagagcagat | ctggccaagt | acatctgtga | aaaccaggac | 1560 |
| tccattagtt | caaagctgaa | agagtgctgt | gaaaaacccc | tgctggagaa | gtctcactgc | 1620 |
| atcgcagagg | tggaaaacga | cgaaatgcca | gcagatctgc | cttccctggc | agcagacttc | 1680 |
| gtcgagtcta | agatgtgtg | taagaattat | gctgaagcaa | aggatgtgtt | cctgggcatg | 1740 |
| tttctgtacg | agtatgcacg | agctggaggc | tcaggaggaa | gcggagggtc | cggaggctct | 1800 |
| gggggaagct | ccgaactgac | ccaggacccc | gctgtgagcg | tcgcactggg | acagactgtg | 1860 |
| cgcattacct | gccagggaga | cagtctgcga | tcatactatg | cttcctggta | ccagcagaag | 1920 |
| ccaggccagg | caccccgtgct | ggtcatctat | gggaaaaaca | atcgaccttc | cggcatcccc | 1980 |

```
gatcggttct ctggatctag ttcaggcaac acagctagcc tgaccatcac aggggcacag    2040
gccgaggacg aagccgatta ctattgcaac agcagagaca gctccggcaa tcatgtggtc    2100
tttggaggag gaactaagct gaccgtggga ggaggatctg gaggaggaag tggcggggga    2160
tcaggaggag gaagcggagg aggcagcgga gaggtccagc tggtggaaag cggaggagga    2220
gtggtcaggc caggagggtc tctgcgactg agttgtgctg catcaggctt cacttttgac    2280
gattacggaa tgagctgggt caggcaggca ccagggaagg gactggagtg ggtgagcggc    2340
atcaactgga atggaggctc tacaggatac gctgatagtg tgaagggccg cttcactatt    2400
agtcgagaca acgccaaaaa ttcactgtat ctgcagatga atagcctgcg cgccgaggac    2460
acagctgtgt actattgcgc cagaggaagg tcactgctgt tgattattg ggggcagggc    2520 acactggtca ccgtctcccg ctgaggatcc                                    2550
```

<210> SEQ ID NO 56
<211> LENGTH: 847
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
                245                 250                 255

```
Glu Val Ala His Arg Phe Lys Asp Leu Gly Glu Asn Phe Lys Ala
            260                 265                 270

Leu Val Leu Ile Ala Phe Ala Gln Tyr Leu Gln Gln Cys Pro Phe Glu
        275                 280                 285

Asp His Val Lys Leu Val Asn Glu Val Thr Glu Phe Ala Lys Thr Cys
290                 295                 300

Val Ala Asp Glu Ser Ala Glu Asn Cys Asp Lys Ser Leu His Thr Leu
305                 310                 315                 320

Phe Gly Asp Lys Leu Cys Thr Val Ala Thr Leu Arg Glu Thr Tyr Gly
                325                 330                 335

Glu Met Ala Asp Cys Cys Ala Lys Gln Glu Pro Glu Arg Asn Glu Cys
            340                 345                 350

Phe Leu Gln His Lys Asp Asp Asn Pro Asn Leu Pro Arg Leu Val Arg
        355                 360                 365

Pro Glu Val Asp Val Met Cys Thr Ala Phe His Asp Asn Glu Glu Thr
    370                 375                 380

Phe Leu Lys Lys Tyr Leu Tyr Glu Ile Ala Arg Arg His Pro Tyr Phe
385                 390                 395                 400

Tyr Ala Pro Glu Leu Leu Phe Phe Ala Lys Arg Tyr Lys Ala Ala Phe
                405                 410                 415

Thr Glu Cys Cys Gln Ala Ala Asp Lys Ala Ala Cys Leu Leu Pro Lys
            420                 425                 430

Leu Asp Glu Leu Arg Asp Glu Gly Lys Ala Ser Ser Ala Lys Gln Arg
        435                 440                 445

Leu Lys Cys Ala Ser Leu Gln Lys Phe Gly Glu Arg Ala Phe Lys Ala
    450                 455                 460

Trp Ala Val Ala Arg Leu Ser Gln Arg Phe Pro Lys Ala Glu Phe Ala
465                 470                 475                 480

Glu Val Ser Lys Leu Val Thr Asp Leu Thr Lys Val His Thr Glu Cys
                485                 490                 495

Cys His Gly Asp Leu Leu Glu Cys Ala Asp Asp Arg Ala Asp Leu Ala
            500                 505                 510

Lys Tyr Ile Cys Glu Asn Gln Asp Ser Ile Ser Ser Lys Leu Lys Glu
        515                 520                 525

Cys Cys Glu Lys Pro Leu Leu Glu Lys Ser His Cys Ile Ala Glu Val
    530                 535                 540

Glu Asn Asp Glu Met Pro Ala Asp Leu Pro Ser Leu Ala Ala Asp Phe
545                 550                 555                 560

Val Glu Ser Lys Asp Val Cys Lys Asn Tyr Ala Glu Ala Lys Asp Val
                565                 570                 575

Phe Leu Gly Met Phe Leu Tyr Glu Tyr Ala Arg Ala Gly Gly Ser Gly
            580                 585                 590

Gly Ser Gly Gly Ser Gly Gly Ser Gly Gly Ser Ser Glu Leu Thr Gln
        595                 600                 605

Asp Pro Ala Val Ser Val Ala Leu Gly Gln Thr Val Arg Ile Thr Cys
    610                 615                 620

Gln Gly Asp Ser Leu Arg Ser Tyr Tyr Ala Ser Trp Tyr Gln Gln Lys
625                 630                 635                 640

Pro Gly Gln Ala Pro Val Leu Val Ile Tyr Gly Lys Asn Asn Arg Pro
                645                 650                 655

Ser Gly Ile Pro Asp Arg Phe Ser Gly Ser Ser Gly Asn Thr Ala
            660                 665                 670
```

```
Ser Leu Thr Ile Thr Gly Ala Gln Ala Glu Asp Glu Ala Asp Tyr Tyr
            675                 680                 685

Cys Asn Ser Arg Asp Ser Ser Gly Asn His Val Val Phe Gly Gly Gly
        690                 695                 700

Thr Lys Leu Thr Val Gly Gly Ser Gly Gly Gly Ser Gly Gly Gly
705                 710                 715                 720

Ser Gly Gly Gly Ser Gly Gly Ser Gly Glu Val Gln Leu Val Glu
                725                 730                 735

Ser Gly Gly Gly Val Val Arg Pro Gly Ser Leu Arg Leu Ser Cys
                740                 745                 750

Ala Ala Ser Gly Phe Thr Phe Asp Asp Tyr Gly Met Ser Trp Val Arg
            755                 760                 765

Gln Ala Pro Gly Lys Gly Leu Glu Trp Val Ser Gly Ile Asn Trp Asn
        770                 775                 780

Gly Gly Ser Thr Gly Tyr Ala Asp Ser Val Lys Gly Arg Phe Thr Ile
785                 790                 795                 800

Ser Arg Asp Asn Ala Lys Asn Ser Leu Tyr Leu Gln Met Asn Ser Leu
                805                 810                 815

Arg Ala Glu Asp Thr Ala Val Tyr Tyr Cys Ala Arg Gly Arg Ser Leu
            820                 825                 830

Leu Phe Asp Tyr Trp Gly Gln Gly Thr Leu Val Thr Val Ser Arg
        835                 840                 845

<210> SEQ ID NO 57
<211> LENGTH: 2301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
tcttcagaac tgacccagga ccccgcagtg agcgtcgcac tgggccagac cgtgagaatc      60
acatgccagg gggattccct gaggtcttac tatgctagct ggtaccagca gaagccaggc     120
caggcacccg tgctggtcat ctatggcaaa acaataggc cttcagggat tccagaccgc      180
tttagcggaa gctcctctgg caacacagca agcctgacaa ttactggcgc tcaggcagag     240
gacgaagccg attactattg caacagcagg gatagttcag gcaatcacgt ggtcttcgga     300
ggaggaacta agctgaccgt gggaggagga tctggaggag aagtggcgg gggatcagga     360 ggaggaagcg gaggaggcag cggagaggtg cagctggtcg aaagcggagg aggagtggtc     420
cgcccaggag ggtctctgcg actgagttgt gccgcttcag gattcacctt tgacgattac     480
ggaatgtcct gggtgaggca ggcaccaggg aagggactgg agtgggtctc tggcatcaac     540
tggaatggag gctctacagg gtacgctgac agtgtgaagg gacggttcac catttcccgg     600
gataacgcca aaaattctct gtatctgcag atgaatagtc tgcgcgctga ggacaccgca     660
gtgtactatt gtgccagggg ccgcagtctg ctgttcgatt actggggcca gggaacactg     720
gtgactgtca gccgaggagg aagtggaggg tcaggaggca gcggaggcag cggagggtct     780
gtggtcctgc tgctgagact ggctaagaca tacgagacca cactggaaaa atgctgtgca     840
gccgctgacc cccatgagtg ctatgccaag gtgttcgatg agttcaagcc actggtcgag     900
gaacccagag acctgatcaa gcagaattgt gagctgttcg aacagctggg cgagtacaaa     960
tttcagaacg ccctgctggt gcgctatacc aagaaagtgc ctcaggtctc aaccccaaca    1020
ctggtggagg tcagcaggaa tctgggcaag gtcgggtcca aatgctgtaa gcaccccgag    1080
```

```
gcaaaacgca tgccttgcgc cgaagactac ctgtccgtgg tcctgaacca gctgtgtgtg    1140
ctgcatgaga agacacctgt gtctgatcgg gtcactaaat gctgtaccga atctctggtg    1200
aaccggagac cttgctttag tgccctggag gtggacgaaa cttatgtccc aaaggagttc    1260
aatgctgaaa ctttcacctt tcacgcagat atctgtaccc tgagcgagaa ggaaagacag    1320
attaagaaac agacagccct ggtggagctg gtcaagcata aaccaaaggc caccaaggaa    1380
cagctgaaag ctgtgatgga cgatttcgca gcctttgtcg agaaatgctg taaggctgac    1440
gataaggaaa catgcttcgc agaggaaggg aagaaactgg tggctgcatc ccaggcagct    1500
ctgggactgg gaggcagtgg aggatcagga gggagcggag gctccggagg agacatccag    1560
atgactcagt ccccaagctc cctgtcagca agcgtgggcg accgggtcac aattacttgt    1620
agagcttctc aggatgtgaa taccgccgtc gcttggtacc agcagaaacc cggcaaggcc    1680
cctaaactgc tgatctactc cgcttctttc ctgtatagcg gagtgccatc ccggttcagc    1740
gggtcaagga gcggaactga cttcacccta caatttctaa gtctgcagcc tgaggatttt    1800
gccacctact attgccagca gcactatact accccccccta ctttcggaca gggcaccaag    1860
gtggaaatca aggagggtc tggaggaggg agtggaggag ggtcaggcgg agggagcgga    1920
ggagggtccg gcgaagtcca gctggtcgaa tccggaggag actggtgca gcctggaggc    1980 tctctgaggc tgagttgtgc agcctcaggc tttaacatca aggacaccta cattcattgg    2040
gtgcggcagg caccagggaa aggactggag tgggtggcca gaatctatcc cacaaatgga    2100
tacactcgat atgccgactc tgtgaagggc cggttcacaa ttagcgcaga tacctccaaa    2160
aacacagcct acctgcagat gaacagcctg cgcgccgagg atactgctgt gtactattgc    2220
agccgatggg gcggggacgg cttctacgct atggactatt ggggggcaggg gactctggtg    2280 acagtgagca gctgaggatc c                                              2301
```

<210> SEQ ID NO 58
<211> LENGTH: 764
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Gly Val Val Arg Pro Gly Gly
```

```
            130                 135                 140
Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Ser Thr Gly Tyr Ala Asp Ser Val
            180                 185                 190

Lys Gly Arg Phe Thr Ile Ser Arg Asp Asn Ala Lys Asn Ser Leu Tyr
                195                 200                 205

Leu Gln Met Asn Ser Leu Arg Ala Glu Asp Thr Ala Val Tyr Tyr Cys
        210                 215                 220

Ala Arg Gly Arg Ser Leu Leu Phe Asp Tyr Trp Gly Gln Gly Thr Leu
225                 230                 235                 240

Val Thr Val Ser Arg Gly Gly Ser Gly Gly Ser Gly Gly
                245                 250                 255

Ser Gly Gly Ser Val Val Leu Leu Arg Leu Ala Lys Thr Tyr Glu
            260                 265                 270

Thr Thr Leu Glu Lys Cys Cys Ala Ala Ala Asp Pro His Glu Cys Tyr
        275                 280                 285

Ala Lys Val Phe Asp Glu Phe Lys Pro Leu Val Glu Glu Pro Gln Asn
        290                 295                 300

Leu Ile Lys Gln Asn Cys Glu Leu Phe Glu Gln Leu Gly Glu Tyr Lys
305                 310                 315                 320

Phe Gln Asn Ala Leu Leu Val Arg Tyr Thr Lys Lys Val Pro Gln Val
                325                 330                 335

Ser Thr Pro Thr Leu Val Glu Val Ser Arg Asn Leu Gly Lys Val Gly
                340                 345                 350

Ser Lys Cys Cys Lys His Pro Glu Ala Lys Arg Met Pro Cys Ala Glu
            355                 360                 365

Asp Tyr Leu Ser Val Val Leu Asn Gln Leu Cys Val Leu His Glu Lys
        370                 375                 380

Thr Pro Val Ser Asp Arg Val Thr Lys Cys Cys Thr Glu Ser Leu Val
385                 390                 395                 400

Asn Arg Arg Pro Cys Phe Ser Ala Leu Glu Val Asp Glu Thr Tyr Val
                405                 410                 415

Pro Lys Glu Phe Asn Ala Glu Thr Phe Thr Phe His Ala Asp Ile Cys
                420                 425                 430

Thr Leu Ser Glu Lys Glu Arg Gln Ile Lys Lys Gln Thr Ala Leu Val
        435                 440                 445

Glu Leu Val Lys His Lys Pro Lys Ala Thr Lys Glu Gln Leu Lys Ala
        450                 455                 460

Val Met Asp Asp Phe Ala Ala Phe Val Glu Lys Cys Cys Lys Ala Asp
465                 470                 475                 480

Asp Lys Glu Thr Cys Phe Ala Glu Glu Gly Lys Lys Leu Val Ala Ala
                485                 490                 495

Ser Gln Ala Ala Leu Gly Leu Gly Gly Ser Gly Gly Ser Gly Gly Ser
                500                 505                 510

Gly Gly Ser Gly Gly Asp Ile Gln Met Thr Gln Ser Pro Ser Ser Leu
            515                 520                 525

Ser Ala Ser Val Gly Asp Arg Val Thr Ile Thr Cys Arg Ala Ser Gln
        530                 535                 540

Asp Val Asn Thr Ala Val Ala Trp Tyr Gln Gln Lys Pro Gly Lys Ala
545                 550                 555                 560
```

```
Pro Lys Leu Leu Ile Tyr Ser Ala Ser Phe Leu Tyr Ser Gly Val Pro
                565                 570                 575

Ser Arg Phe Ser Gly Ser Arg Ser Gly Thr Asp Phe Thr Leu Thr Ile
            580                 585                 590

Ser Ser Leu Gln Pro Glu Asp Phe Ala Thr Tyr Tyr Cys Gln Gln His
        595                 600                 605

Tyr Thr Thr Pro Pro Thr Phe Gly Gln Gly Thr Lys Val Glu Ile Lys
    610                 615                 620

Gly Gly Ser Gly Gly Ser Gly Gly Ser Gly Gly Ser Gly
625                 630                 635                 640

Gly Gly Ser Gly Glu Val Gln Leu Val Glu Ser Gly Gly Leu Val
                645                 650                 655

Gln Pro Gly Gly Ser Leu Arg Leu Ser Cys Ala Ala Ser Gly Phe Asn
            660                 665                 670

Ile Lys Asp Thr Tyr Ile His Trp Val Arg Gln Ala Pro Gly Lys Gly
        675                 680                 685

Leu Glu Trp Val Ala Arg Ile Tyr Pro Thr Asn Gly Tyr Thr Arg Tyr
    690                 695                 700

Ala Asp Ser Val Lys Gly Arg Phe Thr Ile Ser Ala Asp Thr Ser Lys
705                 710                 715                 720

Asn Thr Ala Tyr Leu Gln Met Asn Ser Leu Arg Ala Glu Asp Thr Ala
                725                 730                 735

Val Tyr Tyr Cys Ser Arg Trp Gly Gly Asp Gly Phe Tyr Ala Met Asp
            740                 745                 750

Tyr Trp Gly Gln Gly Thr Leu Val Thr Val Ser Ser
        755                 760

<210> SEQ ID NO 59
<211> LENGTH: 2301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gatattcaga tgacccagag cccaagctcc ctgagtgcat cagtgggcga cagagtcaca      60
atcacttgca gggctagcca ggatgtgaac acagctgtcg catggtacca gcagaaacca     120
ggcaaggctc ccaaactgct gatctacagc gcatccttcc tgtattccgg cgtgccctct     180
aggttttctg gagtcgctc aggaactgac ttcaccctga caatctctag tctgcagcct     240
gaggattttg ccacctacta ttgccagcag cactacacca cccccctac tttcggccag     300 gggaccaagg tggagatcaa gggcgggagt ggaggcgggt caggcggagg gagcggagga     360
gggtccggag gagggtctgg cgaggtgcag ctggtcgaaa gcggaggagg actggtgcag     420
cctggaggca gtctgcggct gtcatgtgcc gctagcggct caacatcaa ggacacctac     480 attcattggg tgcgccaggc accaggaaaa ggcctggagt gggtcgcccg aatctatccc     540
accaatgggt acacaagata tgccgactcc gtgaagggac gctttacaat ttccgctgat     600
acttctaaaa acaccgcata cctgcagatg aatagtctga gagcagagga tactgccgtg     660
tactattgta gcagatgggg gggagacggc ttctacgcca tggactactg gggccagggc     720
actctggtga ccgtctcaag cggagggagc ggaggctccg gaggatctgg agggagtgga     780
ggctcagtgg tcctgctgct gaggctggct aagacctacg agactaccct ggaaaaatgc     840
```

```
tgtgcagccg ctgacccca cgagtgctat gccaaggtgt tcgatgagtt caagccactg    900
gtcgaggaac cccagaacct gatcaagcag aattgtgagc tgttcgaaca gctgggcgag    960
tacaaatttc agaacgccct gctggtgcgc tatacaaaga aagtgcctca ggtcagtact   1020
ccaaccctgg tggaagtctc acggaatctg gaaaggtcg gcagcaagtg ctgtaaacac   1080
cccgaggcaa aagaatgcc ttgcgccgaa gactacctga gcgtggtcct gaatcagctg   1140
tgtgtgctgc atgagaagac acctgtgagc gatagggtca caaaatgctg tactgaatcc   1200
ctggtgaacc ggagaccttg cttttctgct ctggaggtgg acgaaactta tgtcccaaag   1260
gagttcaatg ccgaaacatt cacttttcac gctgatatct gtaccctgag cgagaaggaa   1320
cgccagatta gaaacagac agccctggtg gagctggtca agcataaacc aaaggcaact   1380
aaggaacagc tgaaagccgt gatggacgat ttcgcagcct ttgtcgagaa gtgctgtaaa   1440
gccgacgata aggaaacctg ctttgctgag gaaggcaaga aactggtggc tgcaagccag   1500
gcagctctgg gactgggagg aagcggaggg tccggaggct ctgggggaag tggagggtcc   1560
tctgagctga cccaggaccc cgctgtgtcc gtcgcactgg gacagaccgt gcgaattaca   1620
tgtcagggcg attcactgcg gagctactat gcttcttggt accagcagaa gcctggccag   1680
gcaccagtgc tggtcatcta tggaaaaaac aatcggccca gtggcattcc tgacagattt   1740
tcaggcagtt caagcgggaa caccgcatcc ctgaccatca caggcgccca ggctgaggac   1800
gaagccgatt actattgcaa ctctaggat cctctggca atcatgtggt cttcggaggc   1860
gggacaaagc tgactgtggg aggagggagt ggcggagggt caggcggcgg gagcggcggc   1920
gggtccggcg gcgggtctgg agaagtgcag ctggtcgaat ccggaggagg agtggtccgc   1980
ccaggaggca gtctgcgact gtcatgtgca gccagcgggt tcacctttga cgattacgga   2040
atgtcctggg tgcggcaggc accaggcaag ggactggagt gggtgtctgg catcaactgg   2100
aatgggggca gcacaggcta cgctgactct gtgaaggggc gattcactat tagccgggat   2160
aacgccaaaa attccctgta tctgcagatg aacagcctga gagccgagga cacagctgtg   2220
tactattgcg ccagggggcg gtcactgctg tttgattatt gggggcaggg aactctggtc   2280
actgtctcta ggtgaggatc c                                             2301
```

<210> SEQ ID NO 60
<211> LENGTH: 764
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

```
Thr Phe Gly Gln Gly Thr Lys Val Glu Ile Lys Gly Gly
            100                 105                 110
Gly Ser Gly Gly Ser Gly Gly Gly Ser Gly Gly Ser Gly Glu
            115                 120                 125
Val Gln Leu Val Glu Ser Gly Gly Gly Leu Val Gln Pro Gly Gly Ser
    130                 135                 140
Leu Arg Leu Ser Cys Ala Ala Ser Gly Phe Asn Ile Lys Asp Thr Tyr
145                 150                 155                 160
Ile His Trp Val Arg Gln Ala Pro Gly Lys Gly Leu Glu Trp Val Ala
                165                 170                 175
Arg Ile Tyr Pro Thr Asn Gly Tyr Thr Arg Tyr Ala Asp Ser Val Lys
            180                 185                 190
Gly Arg Phe Thr Ile Ser Ala Asp Thr Ser Lys Asn Thr Ala Tyr Leu
        195                 200                 205
Gln Met Asn Ser Leu Arg Ala Glu Asp Thr Ala Val Tyr Tyr Cys Ser
    210                 215                 220
Arg Trp Gly Gly Asp Gly Phe Tyr Ala Met Asp Tyr Trp Gly Gln Gly
225                 230                 235                 240
Thr Leu Val Thr Val Ser Ser Gly Gly Ser Gly Gly Ser Gly Gly Ser
                245                 250                 255
Gly Gly Ser Gly Gly Ser Val Val Leu Leu Arg Leu Ala Lys Thr
            260                 265                 270
Tyr Glu Thr Thr Leu Glu Lys Cys Cys Ala Ala Ala Asp Pro His Glu
        275                 280                 285
Cys Tyr Ala Lys Val Phe Asp Glu Phe Lys Pro Leu Val Glu Glu Pro
    290                 295                 300
Gln Asn Leu Ile Lys Gln Asn Cys Glu Leu Phe Glu Gln Leu Gly Glu
305                 310                 315                 320
Tyr Lys Phe Gln Asn Ala Leu Leu Val Arg Tyr Thr Lys Lys Val Pro
                325                 330                 335
Gln Val Ser Thr Pro Thr Leu Val Glu Val Ser Arg Asn Leu Gly Lys
            340                 345                 350
Val Gly Ser Lys Cys Cys Lys His Pro Glu Ala Lys Arg Met Pro Cys
        355                 360                 365
Ala Glu Asp Tyr Leu Ser Val Val Leu Asn Gln Leu Cys Val Leu His
    370                 375                 380
Glu Lys Thr Pro Val Ser Asp Arg Val Thr Lys Cys Cys Thr Glu Ser
385                 390                 395                 400
Leu Val Asn Arg Arg Pro Cys Phe Ser Ala Leu Glu Val Asp Glu Thr
                405                 410                 415
Tyr Val Pro Lys Glu Phe Asn Ala Glu Thr Phe Thr Phe His Ala Asp
            420                 425                 430
Ile Cys Thr Leu Ser Glu Lys Glu Arg Gln Ile Lys Lys Gln Thr Ala
        435                 440                 445
Leu Val Glu Leu Val Lys His Lys Pro Lys Ala Thr Lys Glu Gln Leu
    450                 455                 460
Lys Ala Val Met Asp Asp Phe Ala Ala Phe Val Glu Lys Cys Cys Lys
465                 470                 475                 480
Ala Asp Asp Lys Glu Thr Cys Phe Ala Glu Glu Gly Lys Lys Leu Val
                485                 490                 495
Ala Ala Ser Gln Ala Ala Leu Gly Leu Gly Gly Ser Gly Gly Ser Gly
            500                 505                 510
Gly Ser Gly Gly Ser Gly Gly Ser Ser Glu Leu Thr Gln Asp Pro Ala
```

Val Ser Val Ala Leu Gly Gln Thr Val Arg Ile Thr Cys Gln Gly Asp
515                 520                 525
                530                 535                 540

Ser Leu Arg Ser Tyr Tyr Ala Ser Trp Tyr Gln Gln Lys Pro Gly Gln
545                 550                 555                 560

Ala Pro Val Leu Val Ile Tyr Gly Lys Asn Asn Arg Pro Ser Gly Ile
                565                 570                 575

Pro Asp Arg Phe Ser Gly Ser Ser Gly Asn Thr Ala Ser Leu Thr
            580                 585                 590

Ile Thr Gly Ala Gln Ala Glu Asp Glu Ala Asp Tyr Tyr Cys Asn Ser
            595                 600                 605

Arg Asp Ser Ser Gly Asn His Val Val Phe Gly Gly Gly Thr Lys Leu
            610                 615                 620

Thr Val Gly Gly Gly Ser Gly Gly Gly Ser Gly Gly Gly Ser Gly Gly
625                 630                 635                 640

Gly Ser Gly Gly Gly Ser Gly Glu Val Gln Leu Val Glu Ser Gly Gly
                645                 650                 655

Gly Val Val Arg Pro Gly Gly Ser Leu Arg Leu Ser Cys Ala Ala Ser
            660                 665                 670

Gly Phe Thr Phe Asp Asp Tyr Gly Met Ser Trp Val Arg Gln Ala Pro
            675                 680                 685

Gly Lys Gly Leu Glu Trp Val Ser Gly Ile Asn Trp Asn Gly Gly Ser
690                 695                 700

Thr Gly Tyr Ala Asp Ser Val Lys Gly Arg Phe Thr Ile Ser Arg Asp
705                 710                 715                 720

Asn Ala Lys Asn Ser Leu Tyr Leu Gln Met Asn Ser Leu Arg Ala Glu
                725                 730                 735

Asp Thr Ala Val Tyr Tyr Cys Ala Arg Gly Arg Ser Leu Leu Phe Asp
            740                 745                 750

Tyr Trp Gly Gln Gly Thr Leu Val Thr Val Ser Arg
            755                 760

<210> SEQ ID NO 61
<211> LENGTH: 3294
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
gacattcaga tgacacagag cccaagctcc ctgtctgcaa gtgtcggcga tcgagtgaca      60
atcacttgcc gggcttccca ggacgtcaac actgccgtgg cttggtacca gcagaaacct     120
gggaaggccc caaaactgct gatctactca gctagctttc tgtatagcgg agtgccctcc     180
cggttctccg gatctagaag tggcaccgat tttaccctga caatctctag tctgcagcct     240
gaggacttcg ccacatacta ttgccagcag cactatacca caccccctac ctttgggcag     300
ggaacaaagg tggaaatcaa aggagggtct ggaggaggga gtggaggagg gtcaggcgga     360
gggagcggag gagggtccgg cgaggtgcag ctggtcgaaa gcggaggagg actggtgcag     420
cctggaggct ctctgaggct gagttgtgcc gcttcaggct tcaacatcaa agatacctac     480
attcattggg tccgccaggc tccaggcaag ggactggagt gggtggcacg aatctatccc     540
acaaatggat acactcggta tgccgattcc gtgaaaggca gattcactat tagcgctgac     600
acctccaaga acacagcata cctgcagatg aatagtctgc gagcagagga caccgccgtg     660

```
tactattgct cacggtgggg gggagacggc ttttacgcca tggattattg gggacagggc      720
actctggtga ccgtctcaag cggagggagc ggagatgcac acaagtccga ggtcgctcat      780
cgcttcaaag acctgggcga ggaaaacttt aaggccctgg tgctgattgc attcgcccag      840
tacctgcagc agtgcccatt cgaggaccac gtgaaactgg tcaacgaagt gactgaattt      900
gccaagacct gcgtggctga cgagtcagca gaaaattgtg ataaaagcct gcatacactg      960
ttcggcgata agctgtgtac agtggccact ctgagggaga cttatgggga aatgccgac     1020 tgctgtgcta acaggagcc agaacgcaac gagtgctttc tgcagcacaa ggacgataac     1080
ccaaatctgc ccagactggt gaggcccgaa gtggacgtca tgtgtacagc cttccacgat     1140
aatgaggaaa ctttctgaa gaaataccg tatgagatcg ctcggagaca tccctacttc     1200
tatgcccctg aactgctgtt ctttgctaag aggtacaaag cagcctttac cgagtgctgt     1260
caggctgcag ataaggccgc ttgcctgctg ccaaaactgg acgagctgag agatgaaggc     1320
aaggcatcct ctgccaagca gaggctgaaa tgtgcctccc tgcagaagtt cggggagagg     1380
gcttttaaag cttgggcagt ggcacgactg agccagcgat tcccaaaggc tgagtttgca     1440
gaagtctcca gctggtgac cgacctgaca aaagtgcaca ccgagtgctg tcatggcgac     1500
ctgctggaat gcgccgacga tcgcgccgat ctggctaagt acatctgtga gaaccaggac     1560
agcattagtt caaagctgaa agagtgctgt gaaaagcctc tgctggagaa atcccactgc     1620
attgcagagg tggaaaacga cgaaatgcca gcagatctgc cttccctggc agcagacttc     1680
gtcgagtcta aggatgtgtg taaaaattac gctgaagcaa aggatgtgtt cctgggcatg     1740
tttctgtacg agtatgccag gcgccaccct gactacagcg tggtcctgct gctgcggctg     1800
gctaaaacct atgagactac cctggaaaag tgctgtgctg cagccgatcc acatgagtgc     1860
tatgccaagg tcttcgacga gttcaagcca ctggtggagg aaccccagaa cctgatcaaa     1920
cagaattgtg agctgtttga acagctgggc gagtacaagt tccagaacgc cctgctggtg     1980
agatatacaa agaaagtccc tcaggtgagt actccaaccc tggtggaagt ctcacggaat     2040
ctgggcaaag tggggagcaa gtgctgtaaa cacccccgagg caaagagaat gccttgcgcc     2100
gaagattacc tgtctgtggt cctgaatcag ctgtgtgtgc tgcatgagaa aactcctgtc     2160
agcgaccggg tgactaagtg ctgtaccgaa tccctggtga accgacggcc ttgcttctct     2220
gccctggagg tcgatgaaac atatgtgcca aaggagttta tgcagaaaac attcactttt     2280
cacgccgaca tctgtactct gagcgagaag gaaagacaga ttaagaaaca gaccgccctg     2340
gtcgagctgg tgaagcataa accaaaggct accaaggaac agctgaaagc agtcatggac     2400
gatttcgctg catttgtgga gaagtgctgt aaagcagacg ataaggaaac atgcttcgcc     2460
gaggaaggga gaaactggt ggcagctagc caggcagcac tgggactggg aggctcagga     2520
ggaagcggag ggtccggagg ctctggagga agctccgagc tgacccagga ccccgcagtg     2580
tctgtcgcac tgggacagac agtgaggatt acttgtcagg ggacagtct gcgctcatac     2640 tatgctagct ggtaccagca gaaaccaggc caggcacccg tgctggtcat ctatggcaag     2700
aacaatcgcc cttccgggat tccagatcga ttctctgggt ctagttcagg aaacaccgca     2760
tctctgacca tcacaggcgc ccaggctgag gacgaagctg attactattg caacagcaga     2820
gacagctccg gcaatcacgt ggtctttgga ggaggaacta agctgaccgt gggaggagga     2880
tctggaggag gaagtggcgg gggatcagga ggaagcg gaggaggcag cggagaggtc     2940
cagctggtgg aaagcggagg aggcgtggtc agaccaggag ggtctctgag actgtcctgt     3000
```

```
gctgcatcag gattcacctt tgacgattac ggcatgtctt gggtcaggca ggcacctggg    3060
aagggcctgg aatgggtgag tggcatcaac tggaatggag gctctaccgg gtacgccgat    3120
agtgtgaaag gaaggttcac aattagtcgc gacaacgcta agaacagcct gtatctgcag    3180
atgaatagcc tgcgcgctga ggacacagca gtgtactatt gcgccagggg gaggtcactg    3240
ctgtttgatt attgggggca gggaactctg gtcactgtgt cacggtgagg atcc          3294
```

<210> SEQ ID NO 62
<211> LENGTH: 1095
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Gly Ser Gly Gly
            100                 105                 110

Gly Ser Gly Gly Gly Ser Gly Gly Gly Ser Gly Gly Ser Gly Glu
        115                 120                 125

Val Gln Leu Val Glu Ser Gly Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Gly Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Ser Gly Asp Ala His Lys Ser
                245                 250                 255

Glu Val Ala His Arg Phe Lys Asp Leu Gly Glu Glu Asn Phe Lys Ala
            260                 265                 270

Leu Val Leu Ile Ala Phe Ala Gln Tyr Leu Gln Gln Cys Pro Phe Glu
        275                 280                 285

Asp His Val Lys Leu Val Asn Glu Val Thr Glu Phe Ala Lys Thr Cys
    290                 295                 300

Val Ala Asp Glu Ser Ala Glu Asn Cys Asp Lys Ser Leu His Thr Leu
```

```
            305                 310                 315                 320
        Phe Gly Asp Lys Leu Cys Thr Val Ala Thr Leu Arg Glu Thr Tyr Gly
                        325                 330                 335

Glu Met Ala Asp Cys Cys Ala Lys Gln Glu Pro Arg Asn Glu Cys
                        340                 345                 350

Phe Leu Gln His Lys Asp Asp Asn Pro Asn Leu Pro Arg Leu Val Arg
                        355                 360                 365

Pro Glu Val Asp Val Met Cys Thr Ala Phe His Asp Asn Glu Glu Thr
                370                 375                 380

Phe Leu Lys Lys Tyr Leu Tyr Glu Ile Ala Arg Arg His Pro Tyr Phe
        385                 390                 395                 400

Tyr Ala Pro Glu Leu Leu Phe Phe Ala Lys Arg Tyr Lys Ala Ala Phe
                        405                 410                 415

Thr Glu Cys Cys Gln Ala Ala Asp Lys Ala Ala Cys Leu Leu Pro Lys
                        420                 425                 430

Leu Asp Glu Leu Arg Asp Glu Gly Lys Ala Ser Ser Ala Lys Gln Arg
                        435                 440                 445

Leu Lys Cys Ala Ser Leu Gln Lys Phe Gly Glu Arg Ala Phe Lys Ala
                        450                 455                 460

Trp Ala Val Ala Arg Leu Ser Gln Arg Phe Pro Lys Ala Glu Phe Ala
        465                 470                 475                 480

Glu Val Ser Lys Leu Val Thr Asp Leu Thr Lys Val His Thr Glu Cys
                        485                 490                 495

Cys His Gly Asp Leu Leu Glu Cys Ala Asp Asp Arg Ala Asp Leu Ala
                        500                 505                 510

Lys Tyr Ile Cys Glu Asn Gln Asp Ser Ile Ser Ser Lys Leu Lys Glu
                        515                 520                 525

Cys Cys Glu Lys Pro Leu Leu Glu Lys Ser His Cys Ile Ala Glu Val
                        530                 535                 540

Glu Asn Asp Glu Met Pro Ala Asp Leu Pro Ser Leu Ala Ala Asp Phe
        545                 550                 555                 560

Val Glu Ser Lys Asp Val Cys Lys Asn Tyr Ala Glu Ala Lys Asp Val
                        565                 570                 575

Phe Leu Gly Met Phe Leu Tyr Glu Tyr Ala Arg Arg His Pro Asp Tyr
                        580                 585                 590

Ser Val Val Leu Leu Leu Arg Leu Ala Lys Thr Tyr Glu Thr Thr Leu
                        595                 600                 605

Glu Lys Cys Cys Ala Ala Ala Asp Pro His Glu Cys Tyr Ala Lys Val
                        610                 615                 620

Phe Asp Glu Phe Lys Pro Leu Val Glu Glu Pro Gln Asn Leu Ile Lys
        625                 630                 635                 640

Gln Asn Cys Glu Leu Phe Glu Gln Leu Gly Glu Tyr Lys Phe Gln Asn
                        645                 650                 655

Ala Leu Leu Val Arg Tyr Thr Lys Lys Val Pro Gln Val Ser Thr Pro
                        660                 665                 670

Thr Leu Val Glu Val Ser Arg Asn Leu Gly Lys Val Gly Ser Lys Cys
                        675                 680                 685

Cys Lys His Pro Glu Ala Lys Arg Met Pro Cys Ala Glu Asp Tyr Leu
                        690                 695                 700

Ser Val Val Leu Asn Gln Leu Cys Val Leu His Glu Lys Thr Pro Val
        705                 710                 715                 720

Ser Asp Arg Val Thr Lys Cys Cys Thr Glu Ser Leu Val Asn Arg Arg
                        725                 730                 735
```

Pro Cys Phe Ser Ala Leu Glu Val Asp Glu Thr Tyr Val Pro Lys Glu
            740                 745                 750

Phe Asn Ala Glu Thr Phe Thr Phe His Ala Asp Ile Cys Thr Leu Ser
        755                 760                 765

Glu Lys Glu Arg Gln Ile Lys Lys Gln Thr Ala Leu Val Glu Leu Val
770                 775                 780

Lys His Lys Pro Lys Ala Thr Lys Glu Gln Leu Lys Ala Val Met Asp
785                 790                 795                 800

Asp Phe Ala Ala Phe Val Glu Lys Cys Cys Lys Ala Asp Asp Lys Glu
                805                 810                 815

Thr Cys Phe Ala Glu Glu Gly Lys Lys Leu Val Ala Ala Ser Gln Ala
            820                 825                 830

Ala Leu Gly Leu Gly Gly Ser Gly Gly Ser Gly Gly Ser Gly Gly Ser
            835                 840                 845

Gly Gly Ser Ser Glu Leu Thr Gln Asp Pro Ala Val Ser Val Ala Leu
850                 855                 860

Gly Gln Thr Val Arg Ile Thr Cys Gln Gly Asp Ser Leu Arg Ser Tyr
865                 870                 875                 880

Tyr Ala Ser Trp Tyr Gln Gln Lys Pro Gly Gln Ala Pro Val Leu Val
                885                 890                 895

Ile Tyr Gly Lys Asn Asn Arg Pro Ser Gly Ile Pro Asp Arg Phe Ser
            900                 905                 910

Gly Ser Ser Ser Gly Asn Thr Ala Ser Leu Thr Ile Thr Gly Ala Gln
            915                 920                 925

Ala Glu Asp Glu Ala Asp Tyr Tyr Cys Asn Ser Arg Asp Ser Ser Gly
930                 935                 940

Asn His Val Val Phe Gly Gly Gly Thr Lys Leu Thr Val Gly Gly Gly
945                 950                 955                 960

Ser Gly Gly Gly Ser Gly Gly Gly Ser Gly Gly Ser Gly Gly Gly
                965                 970                 975

Ser Gly Glu Val Gln Leu Val Glu Ser Gly Gly Val Val Arg Pro
            980                 985                 990

Gly Gly Ser Leu Arg Leu Ser Cys Ala Ala Ser Gly Phe Thr Phe Asp
            995                 1000                1005

Asp Tyr Gly Met Ser Trp Val Arg Gln Ala Pro Gly Lys Gly Leu
    1010                1015                1020

Glu Trp Val Ser Gly Ile Asn Trp Asn Gly Gly Ser Thr Gly Tyr
    1025                1030                1035

Ala Asp Ser Val Lys Gly Arg Phe Thr Ile Ser Arg Asp Asn Ala
    1040                1045                1050

Lys Asn Ser Leu Tyr Leu Gln Met Asn Ser Leu Arg Ala Glu Asp
    1055                1060                1065

Thr Ala Val Tyr Tyr Cys Ala Arg Gly Arg Ser Leu Leu Phe Asp
    1070                1075                1080

Tyr Trp Gly Gln Gly Thr Leu Val Thr Val Ser Arg
    1085                1090                1095

<210> SEQ ID NO 63
<211> LENGTH: 3294
<212> TYPE: DNA
<213> ORGANISM: Artificial Sequence
<220> FEATURE:
<223> OTHER INFORMATION: Description of Artificial Sequence: Synthetic
      polynucleotide -continued

```
<400> SEQUENCE: 63
agtagcgaac tgacccagga ccccgcagtg agcgtcgcac tggggcagac agtgcgaatc      60
acttgccagg gagacagcct gcggtcctac tatgcttcct ggtaccagca gaaacctggc     120
caggcaccag tgctggtcat ctatgggaag aacaatcggc ccagcggcat ccccgataga     180
ttctccggca gctcctctgg gaacaccgcc tctctgacaa ttactggggc ccaggctgag     240
gacgaagctg attactattg caacagcagg gacagttcag gaaatcacgt ggtctttgga     300
ggaggaacta agctgaccgt ggggaggaggc agcggaggag gatctggagg aggaagtgga     360
ggaggatcag gaggaggaag cggagaggtg cagctggtcg aaagcggagg aggagtggtc     420
agacctggag ggtccctgag gctgtcttgt gccgctagtg gcttcacctt tgacgattac     480
ggaatgagtt gggtccggca ggcaccagga aagggactgg agtgggtgtc aggcatcaac     540
tggaatggag gcagtaccgg atacgccgat tcagtgaaag gcaggttcac aatttctcgc     600
gacaacgcta agaatagtct gtatctgcag atgaactcac tgagagctga ggatacagca     660
gtgtactatt gcgccagagg caggtctctg ctgtttgact actgggggca gggaacactg     720
gtgactgtct cacgaggagg aagcggcgat gcacacaagt ccgaggtcgc tcatagattc     780
aaagacctgg gggaggaaaa ttttaaggcc ctggtgctga tcgcattcgc ccagtatctg     840
cagcagtgcc cattcgagga ccacgtgaaa ctggtcaacg aggtgaccga atttgccaag     900
acatgcgtgg ccgacgagag cgctgaaaat tgtgataaat ccctgcatac actgttcggg     960
gataagctgt gtaccgtggc cacactgagg gagacttacg agaaatggca gactgctgt    1020 gccaaacagg agccagaacg caacgagtgc tttctgcagc acaaggacga taacccaaat    1080
ctgccacgac tggtgcgacc agaagtggac gtcatgtgta cagccttcca cgataatgag    1140
gaaacttttc tgaagaaata cctgtatgag atcgcccgga gacatcccta cttctatgct    1200
cctgaactgc tgttctttgc aaaacggtac aaggcagcct ttaccgagtg ctgtcaggct    1260
gcagataagg ccgcttgcct gctgccaaaa ctggacgagc tgagagatga aggcaaggca    1320
agctccgcca agcagaggct gaaatgtgct agcctgcaga agttcgggga gagggccttc    1380
aaggcttggg cagtggcacg actgtcacag agattcccca aggctgagtt tgcagaagtc    1440
agcaagctgg tgactgacct gaccaaagtg cacaccgagt gctgtcatgg cgacctgctg    1500
gaatgcgccg acgatcgcgc cgatctggct aagtacatct gtgagaacca ggacagcatt    1560
tctagtaagc tgaaagagtg ctgtgaaaag cctctgctgg agaaatccca ctgcatcgcc    1620
gaggtggaaa acgacgaaat gccagctgat ctgccctctc tggcagccga cttcgtcgag    1680
agtaaggatg tgtgtaaaaa ttacgctgaa gcaaaggatg tgttcctggg catgtttctg    1740
tacgagtatg caaggcgaca cccagactac tccgtggtcc tgctgctgcg gctggctaaa    1800
acctatgaga ccacactgga aaagtgctgt gctgcagccg atcctcatga gtgctatgcc    1860
aaggtcttcg acgagttcaa gccactggtg gaggaacccc agaacctgat caagcagaat    1920
tgtgagctgt ttgaacagct gggcgagtac aagttccaga acgccctgct ggtgagatat    1980
acaaagaaag tccctcaggt gtcaaccccca acactggtgg aggtcagccg gaatctgggg    2040
aaagtgggca gcaaatgctg taagcacccc gaggcaaaga aatgccttg cgccgaagat    2100 tacctgtctg tggtcctgaa ccagctgtgt gtgctgcatg agaaaactcc tgtcagtgac    2160
agggtgacca agtgctgtac agaatctctg gtgaaccgac ggcttgctt cagtgccctg    2220 gaggtcgatg aaacatatgt gccaaaggag tttaatgccg aaactttcac cttctcacgct    2280 gacatctgta ctctgagcga gaaggaacgc cagattaaga acagaccgc cctggtcgag    2340
```

```
ctggtgaagc ataaaccaaa ggcaacaaag gaacagctga aagccgtcat ggacgatttc    2400
gctgcatttg tggagaaatg ctgtaaggcc gacgataagg aaacttgctt cgctgaggaa    2460
ggaaagaaac tggtggcagc ttcccaggca gcactgggac tgggagggtc tggaggcagt    2520
ggaggatcag gagggagcgg aggcgacatc cagatgaccc agtcccctc aagcctgagt    2580 gcctcagtcg gcgatcgcgt gacaattact tgtcgagctt ctcaggacgt caatacagcc    2640
gtggcttggt atcagcagaa gcctggaaag gcaccaaaac tgctgatcta cagcgcctcc    2700
tttctgtatt ccggcgtgcc ctctcgattc tctggaagtc ggtcaggcac cgattttacc    2760
ctgacaattt cctctctgca gcctgaggac ttcgccacat actattgcca gcagcactat    2820 actaccccc ctacttttgg ccaggggacc aaggtggaaa tcaaggggg aagtggcggg    2880 ggatcaggcg gcggaagcgg cggcggcagc ggcggcggat ctggagaggt ccagctggtg    2940
gaaagcggag gaggactggt gcagcctgga gggagtctgc gactgtcatg tgctgcaagc    3000
ggcttcaaca tcaaagatac ctacattcat tgggtcaggc aggcccctgg aaagggcctg    3060
gaatgggtgg cacgaatcta tcccactaat ggctacacca gatatgccga ttccgtgaaa    3120
gggcgcttca ctatttccgc tgacacatct aagaacactg catacctgca gatgaacagc    3180
ctgcgcgctg aggacaccgc agtgtactat tgctctcgat ggggcggcga cggcttctac    3240
gcaatggact actgggggca ggggacactg gtgactgtga gcagctgagg atcc          3294
```

<210> SEQ ID NO 64
<211> LENGTH: 1095
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Gly Gly Gly Ser Gly
            100                 105                 110

Gly Gly Ser Gly Gly Gly Ser Gly Gly Gly Ser Gly Gly Gly Ser Gly
        115                 120                 125

Glu Val Gln Leu Val Glu Ser Gly Gly Val Val Arg Pro Gly Gly
    130                 135                 140

Ser Leu Arg Leu Ser Cys Ala Ala Ser Gly Phe Thr Phe Asp Asp Tyr
145                 150                 155                 160

Gly Met Ser Trp Val Arg Gln Ala Pro Gly Lys Gly Leu Glu Trp Val
                165                 170                 175

Ser Gly Ile Asn Trp Asn Gly Gly Ser Thr Gly Tyr Ala Asp Ser Val
            180                 185                 190

-continued

```
Lys Gly Arg Phe Thr Ile Ser Arg Asp Asn Ala Lys Asn Ser Leu Tyr
        195                 200                 205
Leu Gln Met Asn Ser Leu Arg Ala Glu Asp Thr Ala Val Tyr Tyr Cys
        210                 215                 220
Ala Arg Gly Arg Ser Leu Leu Phe Asp Tyr Trp Gly Gln Gly Thr Leu
225                 230                 235                 240
Val Thr Val Ser Arg Gly Gly Ser Gly Asp Ala His Lys Ser Glu Val
            245                 250                 255
Ala His Arg Phe Lys Asp Leu Gly Glu Glu Asn Phe Lys Ala Leu Val
            260                 265                 270
Leu Ile Ala Phe Ala Gln Tyr Leu Gln Gln Cys Pro Phe Glu Asp His
        275                 280                 285
Val Lys Leu Val Asn Glu Val Thr Glu Phe Ala Lys Thr Cys Val Ala
        290                 295                 300
Asp Glu Ser Ala Glu Asn Cys Asp Lys Ser Leu His Thr Leu Phe Gly
305                 310                 315                 320
Asp Lys Leu Cys Thr Val Ala Thr Leu Arg Glu Thr Tyr Gly Glu Met
                325                 330                 335
Ala Asp Cys Cys Ala Lys Gln Glu Pro Glu Arg Asn Glu Cys Phe Leu
            340                 345                 350
Gln His Lys Asp Asp Asn Pro Asn Leu Pro Arg Leu Val Arg Pro Glu
            355                 360                 365
Val Asp Val Met Cys Thr Ala Phe His Asp Asn Glu Glu Thr Phe Leu
        370                 375                 380
Lys Lys Tyr Leu Tyr Glu Ile Ala Arg Arg His Pro Tyr Phe Tyr Ala
385                 390                 395                 400
Pro Glu Leu Leu Phe Phe Ala Lys Arg Tyr Lys Ala Ala Phe Thr Glu
                405                 410                 415
Cys Cys Gln Ala Ala Asp Lys Ala Ala Cys Leu Leu Pro Lys Leu Asp
            420                 425                 430
Glu Leu Arg Asp Glu Gly Lys Ala Ser Ser Ala Lys Gln Arg Leu Lys
            435                 440                 445
Cys Ala Ser Leu Gln Lys Phe Gly Glu Arg Ala Phe Lys Ala Trp Ala
        450                 455                 460
Val Ala Arg Leu Ser Gln Arg Phe Pro Lys Ala Glu Phe Ala Glu Val
465                 470                 475                 480
Ser Lys Leu Val Thr Asp Leu Thr Lys Val His Thr Glu Cys Cys His
                485                 490                 495
Gly Asp Leu Leu Glu Cys Ala Asp Asp Arg Ala Asp Leu Ala Lys Tyr
            500                 505                 510
Ile Cys Glu Asn Gln Asp Ser Ile Ser Ser Lys Leu Lys Glu Cys Cys
            515                 520                 525
Glu Lys Pro Leu Leu Glu Lys Ser His Cys Ile Ala Glu Val Glu Asn
        530                 535                 540
Asp Glu Met Pro Ala Asp Leu Pro Ser Leu Ala Ala Asp Phe Val Glu
545                 550                 555                 560
Ser Lys Asp Val Cys Lys Asn Tyr Ala Glu Ala Lys Asp Val Phe Leu
                565                 570                 575
Gly Met Phe Leu Tyr Glu Tyr Ala Arg Arg His Pro Asp Tyr Ser Val
            580                 585                 590
Val Leu Leu Leu Arg Leu Ala Lys Thr Tyr Glu Thr Thr Leu Glu Lys
            595                 600                 605
```

-continued

```
Cys Cys Ala Ala Ala Asp Pro His Glu Cys Tyr Ala Lys Val Phe Asp
    610                 615                 620

Glu Phe Lys Pro Leu Val Glu Pro Gln Asn Leu Ile Lys Gln Asn
625                 630                 635                 640

Cys Glu Leu Phe Glu Gln Leu Gly Glu Tyr Lys Phe Gln Asn Ala Leu
                    645                 650                 655

Leu Val Arg Tyr Thr Lys Lys Val Pro Gln Val Ser Thr Pro Thr Leu
                660                 665                 670

Val Glu Val Ser Arg Asn Leu Gly Lys Val Gly Ser Lys Cys Cys Lys
            675                 680                 685

His Pro Glu Ala Lys Arg Met Pro Cys Ala Glu Asp Tyr Leu Ser Val
690                 695                 700

Val Leu Asn Gln Leu Cys Val Leu His Glu Lys Thr Pro Val Ser Asp
705                 710                 715                 720

Arg Val Thr Lys Cys Cys Thr Glu Ser Leu Val Asn Arg Arg Pro Cys
                725                 730                 735

Phe Ser Ala Leu Glu Val Asp Glu Thr Tyr Val Pro Lys Glu Phe Asn
                740                 745                 750

Ala Glu Thr Phe Thr Phe His Ala Asp Ile Cys Thr Leu Ser Glu Lys
                755                 760                 765

Glu Arg Gln Ile Lys Lys Gln Thr Ala Leu Val Glu Leu Val Lys His
    770                 775                 780

Lys Pro Lys Ala Thr Lys Glu Gln Leu Lys Ala Val Met Asp Asp Phe
785                 790                 795                 800

Ala Ala Phe Val Glu Lys Cys Cys Lys Ala Asp Asp Lys Glu Thr Cys
                805                 810                 815

Phe Ala Glu Glu Gly Lys Lys Leu Val Ala Ala Ser Gln Ala Ala Leu
                820                 825                 830

Gly Leu Gly Gly Ser Gly Gly Ser Gly Gly Ser Gly Gly
    835                 840                 845

Asp Ile Gln Met Thr Gln Ser Pro Ser Ser Leu Ser Ala Ser Val Gly
    850                 855                 860

Asp Arg Val Thr Ile Thr Cys Arg Ala Ser Gln Asp Val Asn Thr Ala
865                 870                 875                 880

Val Ala Trp Tyr Gln Gln Lys Pro Gly Lys Ala Pro Lys Leu Leu Ile
                885                 890                 895

Tyr Ser Ala Ser Phe Leu Tyr Ser Gly Val Pro Ser Arg Phe Ser Gly
                900                 905                 910

Ser Arg Ser Gly Thr Asp Phe Thr Leu Thr Ile Ser Ser Leu Gln Pro
    915                 920                 925

Glu Asp Phe Ala Thr Tyr Tyr Cys Gln Gln His Tyr Thr Thr Pro Pro
    930                 935                 940

Thr Phe Gly Gln Gly Thr Lys Val Glu Ile Lys Gly Gly Ser Gly Gly
945                 950                 955                 960

Gly Ser Gly Gly Gly Ser Gly Gly Gly Ser Gly Glu
                965                 970                 975

Val Gln Leu Val Glu Ser Gly Gly Leu Val Gln Pro Gly Gly Ser
            980                 985                 990

Leu Arg Leu Ser Cys Ala Ala Ser Gly Phe Asn Ile Lys Asp Thr Tyr
                995                 1000                1005

Ile His Trp Val Arg Gln Ala Pro Gly Lys Gly Leu Glu Trp Val
    1010                1015                1020

Ala Arg Ile Tyr Pro Thr Asn Gly Tyr Thr Arg Tyr Ala Asp Ser
```

```
            1025                1030                1035

Val Lys Gly Arg Phe Thr Ile Ser Ala Asp Thr Ser Lys Asn Thr
        1040                1045                1050

Ala Tyr Leu Gln Met Asn Ser Leu Arg Ala Glu Asp Thr Ala Val
        1055                1060                1065

Tyr Tyr Cys Ser Arg Trp Gly Gly Asp Gly Phe Tyr Ala Met Asp
        1070                1075                1080

Tyr Trp Gly Gln Gly Thr Leu Val Thr Val Ser Ser
        1085                1090                1095

<210> SEQ ID NO 65
<211> LENGTH: 614
<212> TYPE: PRT
<213> ORGANISM: Homo sapiens

<400> SEQUENCE: 65

Glu Phe Ala Thr Met Ala Val Met Ala Pro Arg Thr Leu Val Leu Leu
1               5                   10                  15

Leu Ser Gly Ala Leu Ala Leu Thr Gln Thr Trp Ala Gly Asp Ala His
            20                  25                  30

Lys Ser Glu Val Ala His Arg Phe Lys Asp Leu Gly Glu Glu Asn Phe
        35                  40                  45

Lys Ala Leu Val Leu Ile Ala Phe Ala Gln Tyr Leu Gln Gln Cys Pro
    50                  55                  60

Phe Glu Asp His Val Lys Leu Val Asn Glu Val Thr Glu Phe Ala Lys
65                  70                  75                  80

Thr Cys Val Ala Asp Glu Ser Ala Glu Asn Cys Asp Lys Ser Leu His
                85                  90                  95

Thr Leu Phe Gly Asp Lys Leu Cys Thr Val Ala Thr Leu Arg Glu Thr
            100                 105                 110

Tyr Gly Glu Met Ala Asp Cys Cys Ala Lys Gln Glu Pro Glu Arg Asn
        115                 120                 125

Glu Cys Phe Leu Gln His Lys Asp Asp Asn Pro Asn Leu Pro Arg Leu
    130                 135                 140

Val Arg Pro Glu Val Asp Val Met Cys Thr Ala Phe His Asp Asn Glu
145                 150                 155                 160

Glu Thr Phe Leu Lys Lys Tyr Leu Tyr Glu Ile Ala Arg Arg His Pro
                165                 170                 175

Tyr Phe Tyr Ala Pro Glu Leu Leu Phe Phe Ala Lys Arg Tyr Lys Ala
            180                 185                 190

Ala Phe Thr Glu Cys Cys Gln Ala Ala Asp Lys Ala Ala Cys Leu Leu
        195                 200                 205

Pro Lys Leu Asp Glu Leu Arg Asp Glu Gly Lys Ala Ser Ser Ala Lys
    210                 215                 220

Gln Arg Leu Lys Cys Ala Ser Leu Gln Lys Phe Gly Glu Arg Ala Phe
225                 230                 235                 240

Lys Ala Trp Ala Val Ala Arg Leu Ser Gln Arg Phe Pro Lys Ala Glu
                245                 250                 255

Phe Ala Glu Val Ser Lys Leu Val Thr Asp Leu Thr Lys Val His Thr
            260                 265                 270

Glu Cys Cys His Gly Asp Leu Leu Glu Cys Ala Asp Asp Arg Ala Asp
        275                 280                 285

Leu Ala Lys Tyr Ile Cys Glu Asn Gln Asp Ser Ile Ser Ser Lys Leu
    290                 295                 300
```

-continued

```
Lys Glu Cys Cys Glu Lys Pro Leu Leu Glu Lys Ser His Cys Ile Ala
305             310                 315                 320

Glu Val Glu Asn Asp Glu Met Pro Ala Asp Leu Pro Ser Leu Ala Ala
                325                 330                 335

Asp Phe Val Glu Ser Lys Asp Val Cys Lys Asn Tyr Ala Glu Ala Lys
                340                 345                 350

Asp Val Phe Leu Gly Met Phe Leu Tyr Glu Tyr Ala Arg Arg His Pro
                355                 360                 365

Asp Tyr Ser Val Val Leu Leu Leu Arg Leu Ala Lys Thr Tyr Glu Thr
        370                 375                 380

Thr Leu Glu Lys Cys Cys Ala Ala Ala Asp Pro His Glu Cys Tyr Ala
385                 390                 395                 400

Lys Val Phe Asp Glu Phe Lys Pro Leu Val Glu Glu Pro Gln Asn Leu
                405                 410                 415

Ile Lys Gln Asn Cys Glu Leu Phe Glu Gln Leu Gly Glu Tyr Lys Phe
                420                 425                 430

Gln Asn Ala Leu Leu Val Arg Tyr Thr Lys Lys Val Pro Gln Val Ser
            435                 440                 445

Thr Pro Thr Leu Val Glu Val Ser Arg Asn Leu Gly Lys Val Gly Ser
    450                 455                 460

Lys Cys Cys Lys His Pro Glu Ala Lys Arg Met Pro Cys Ala Glu Asp
465                 470                 475                 480

Tyr Leu Ser Val Val Leu Asn Gln Leu Cys Val Leu His Glu Lys Thr
                485                 490                 495

Pro Val Ser Asp Arg Val Thr Lys Cys Cys Thr Glu Ser Leu Val Asn
            500                 505                 510

Arg Arg Pro Cys Phe Ser Ala Leu Glu Val Asp Glu Thr Tyr Val Pro
            515                 520                 525

Lys Glu Phe Asn Ala Glu Thr Phe Thr Phe His Ala Asp Ile Cys Thr
    530                 535                 540

Leu Ser Glu Lys Glu Arg Gln Ile Lys Lys Gln Thr Ala Leu Val Glu
545                 550                 555                 560

Leu Val Lys His Lys Pro Lys Ala Thr Lys Glu Gln Leu Lys Ala Val
                565                 570                 575

Met Asp Asp Phe Ala Ala Phe Val Glu Lys Cys Cys Lys Ala Asp Asp
                580                 585                 590

Lys Glu Thr Cys Phe Ala Glu Glu Gly Lys Lys Leu Val Ala Ala Ser
            595                 600                 605

Gln Ala Ala Leu Gly Leu
    610
```